US011879133B2

(12) United States Patent
Bennett et al.

(10) Patent No.: US 11,879,133 B2
(45) Date of Patent: Jan. 23, 2024

(54) GENE THERAPY FOR OCULAR DISORDERS

(71) Applicant: The Trustees of the University of Pennsylvania, Philadelphia, PA (US)

(72) Inventors: Jean Bennett, Bryn Mawr, PA (US); Junwei Sun, Philadelphia, PA (US); Kenneth Shindler, Havertown, PA (US); Devin McDougald, Philadelphia, PA (US); Ahmara Gibbons Ross, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 985 days.

(21) Appl. No.: 16/607,834

(22) PCT Filed: Apr. 24, 2018

(86) PCT No.: PCT/US2018/029167
§ 371 (c)(1),
(2) Date: Oct. 24, 2019

(87) PCT Pub. No.: WO2018/200542
PCT Pub. Date: Nov. 1, 2018

(65) Prior Publication Data

US 2020/0131532 A1 Apr. 30, 2020

Related U.S. Application Data

(60) Provisional application No. 62/488,989, filed on Apr. 24, 2017.

(51) Int. Cl.
*C12N 15/86* (2006.01)
*A61K 9/00* (2006.01)
*A61P 27/02* (2006.01)
*A61K 48/00* (2006.01)

(52) U.S. Cl.
CPC ............ *C12N 15/86* (2013.01); *A61K 9/0048* (2013.01); *A61P 27/02* (2018.01); *A61K 48/00* (2013.01); *C12N 2710/10043* (2013.01)

(58) Field of Classification Search
CPC .......... C12N 15/86; C12N 2710/10043; A61P 27/02; A61K 9/0048; A61K 48/00
See application file for complete search history.

(56) References Cited

U.S. PATENT DOCUMENTS

| | | | |
|---|---|---|---|
| 5,139,941 | A | 8/1992 | Muzyczka et al. |
| 5,478,745 | A | 12/1995 | Samulski et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |
| 7,588,772 | B2 | 9/2009 | Kay et al. |
| 7,629,322 | B2 | 12/2009 | Kleinschmidt et al. |
| 7,790,449 | B2 | 9/2010 | Gao et al. |
| 7,906,111 | B2 | 3/2011 | Wilson et al. |
| 8,147,823 | B2 | 4/2012 | Acland et al. |
| 2006/0136184 | A1 | 6/2006 | Gustafsson et al. |
| 2007/0036760 | A1 | 2/2007 | Wilson et al. |
| 2009/0197338 | A1 | 8/2009 | Vandenberghe et al. |
| 2014/0032186 | A1 | 1/2014 | Gustafsson et al. |
| 2016/0354489 | A1 | 12/2016 | Tubert et al. |

FOREIGN PATENT DOCUMENTS

| | | |
|---|---|---|
| EP | 1310571 | 2/2006 |
| WO | WO 2003/042397 | 5/2003 |
| WO | WO 2005/033321 | 4/2005 |
| WO | WO 2006/001982 A2 | 1/2006 |
| WO | WO 2006/110689 | 10/2006 |
| WO | WO 2010/053572 | 5/2010 |
| WO | WO 2011/126808 | 10/2011 |
| WO | WO 2012/158757 | 11/2012 |
| WO | WO 2012/170930 | 12/2012 |
| WO | WO 2013/049493 | 4/2013 |
| WO | WO 2013/182683 | 12/2013 |
| WO | WO 2014/011210 | 1/2014 |
| WO | WO 2015/012924 | 1/2015 |

OTHER PUBLICATIONS

Patrício et al. Inclusion of the Woodchuck Hepatitis Virus Post-transcriptional Regulatory Element Enhances AAV2-Driven Transduction of Mouse and Human Retina. Molecular Therapy: Nucleic Acids. Mar. 2017; 6: 198-208. (Year: 2017).*
Supplementary Search Report and Written Opinion issued in corresponding European Patent Application No. 18791759.6, dated Aug. 11, 2021.
Nakagami, Y, Nrf2 Is an Attractive Therapeutic Target for Retinal Diseases, Oxid Med Cell Longev. 2016;2016:7469326.
Tang et al., An Optic Nerve Crush Injury Murine Model to Study Retinal Ganglion Cell Survival, Journal of Visualized Experiments, (50):265, Apr. 2011.

(Continued)

*Primary Examiner* — Arthur S Leonard
*Assistant Examiner* — Jianjian Zhu
(74) *Attorney, Agent, or Firm* — Howson & Howson LLC; Colleen M. Schaller; Francis J. Coffey

(57) ABSTRACT

Compositions and methods are provided for treating ocular neuropathy in a subject. In one aspect, a recombinant adeno-associated viral vector is provided which includes a nucleic acid molecule comprising a sequence encoding NRF2. In another aspect, a recombinant adeno-associated viral vector is provided which includes a nucleic acid molecule comprising a sequence encoding SIRT1. In desired embodiments, the subject is human, cat, dog, sheep, or non-human primate.

21 Claims, 30 Drawing Sheets

Specification includes a Sequence Listing.

(56) References Cited

OTHER PUBLICATIONS

Supplementary Search Report issued in corresponding European Patent Application No. 18791759.6, dated May 4, 2021.
Beck RW, et al. A randomized, controlled trial of corticosteroids in the treatment of acute optic neuritis. The Optic Neuritis Study Group. N Engl J Med. Feb. 27, 1992;326(9):581-8.
Beltran WA, et al., rAAV2/5 gene-targeting to rods:dose-dependent efficiency and complications associated with different promoters. Gene Ther. Sep. 2010;17(9):1162-74. doi: 10.1038/gt.2010.56. Epub Apr. 29, 2010.
Bennett J, et al. Safety and durability of effect of contralateral-eye administration of AAV2 gene therapy in patients with childhood-onset blindness caused by RPE65 mutations: a follow-on phase 1 trial. Lancet. Aug. 13, 2016;388(10045):661-72. doi: 10.1016/S0140-6736(16)30371-3. Epub Jun. 30, 2016.
Bennicelli J, et al. Reversal of blindness in animal models of Leber congenital amaurosis using optimized AAV2-mediated gene transfer. Mol Ther. Mar. 2008;16(3):458-65. doi: 10.4038/sj.mt.6300389. Epub Jan. 22, 2008.
Buning H, et al. Recent developments in adeno-associated virus vector technology. J Gene Med. Jul. 2008;10(7):717-33. doi: 10.1002/jgm.1205.
Cai et al., A 350 bp region of the proximal promoter of Rds drives cell-type specific gene expression. Exp Eye Res. Aug. 2010;91(2):186-94. doi: 10.1016/j.exer.2010.04.017. Epub May 4, 2010.
Cearley CN, et al. Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Chaffiol A, et al. A New Promoter Allows Optogenetic Vision Restoration with Enhanced Sensitivity in Macaque Retina. Mol Ther. Nov. 1, 2017;25(11):2546-2560. doi: 10.1016/j.ymthe.2017.07.011. Epub Jul. 20, 2017.
Choudhury SR, et al. In vivo selection yields AAV-B1 capsid for central nervous system and muscle gene therapy. Mol Ther. Aug. 2016;24(7):1247-57. doi: 10.1038/mt.2016.84. Epub Apr. 27, 2016.
Costello F, et al. Quntifying axonal loss after optic neuritis with optical coherence tomography. Ann Neurol. Jun. 2006;59(6):963-9.
Cronin T, et al. Efficient transduction and optogenetic stimulation of retinal bipolar cells by a synthetic adeno-associated virus capsid and promoter. EMBO Mol Med. Sep. 2014;6(9):1175-90. doi: 10.15252/emmm.201404077.
Daber R, Lewis M. A novel molecular switch. J Mol Biol. Aug. 28, 2009;391(4):661-70. doi: 10.1016/j.jmb.2009.06.039. Epub Jun. 21, 2009.
Dalkara D, et al. In vivo-directed evolution of a new adeno-associated virus for therapeutic outer retinal gene delivery from the vitreous. Sci transl Med. Jun. 12, 2013;5(189):189ra76. doi: 10.1126/scitranslmed.3005708.
Damdindorj L, et al. A comparative analysis of constitutive promoters located in adeno-associated viral vectors. PLoS One. Aug. 29, 2014;9(8):e106472. doi: 10.1371/journal.pone.0106472. eCollection 2014.
David et al., Recombinant adeno-associated virus-mediated in utero gene transfer gives therapeutic transgene expression in the sheep. Hum Gene Ther. Apr. 2011;22(4):419-26. doi: 10.1089/hum.2010.007. Epub Feb. 2, 2011.
Delzor A, et al. Restricted transgene expression in the brain with cell-type specific neuronal promoters. Hum Gene Ther Methods. Aug. 2012;23(4):242-54. doi: 10.1089/hgtb.2012.073. Epub Aug. 30, 2012.
Dendrou CA et al. Immunopathology of multiple sclerosis. Nat Rev Immunol. Sep. 15, 2015;15(9):545-58. doi: 10.1038/nri3871. Epub Aug. 7, 2015.
Deverman BE, et al. Cre-dependent selction yields AAV variants for widespread gene transfer to the adult brain. Nat Biotechnol. Feb. 2016;34(2):204-9. doi: 10.1038/nbt.3440. Epub Feb. 1, 2016.
Diehl KH, et al. A good practice guide to the administration of substances and removal of blood, including routes and volumes. J Appl Toxicol. Jan.-Feb. 2001;21(1):15-23.
Ding YW, et al. SIRT1 exerts protective effects against paraquat-induced injury in mouse type II alveolar epithelial cells by deacetylating NRF2 in vitro. Int J Mol Med. Apr. 2016,37(4):1049-58. doi: 10.3892/ijmm.2016.2503. Epub Feb. 25, 2016.
Dinkova-Kostova AT, et al. Direct evidence of sulfhydryl groups of KEAP1 are the sensors regulating induction of phase 2 enzymes that protect against carcinogens and oxidants. Proc Natl Acad Sci U S A. Sep. 3, 2002,99(18):11908-13. Epub Aug. 22, 2002.
Dudus L, et al. Persistent transgene product in retina, optic nerve and brain after intraocular injection of rAAV. Vision Res. Jul. 1999;39(15):2545-53.
Fisher JB, et al. Relation of visual function to retinal nerve fiber layer thickness in multiple sclerosis. Ophthalmology. Ophthalmology. Feb. 2006;113(2):324-32. Epub Jan. 10, 2006.
Fisher KJ, et al. Transduction with recombinant adeno-associated virus for gene therapy is limited b leading-strand synthesis. J Virol. Jan. 1996;70(1):520-32.
Fonseca-Kelly Z, et al. Resveratrol neuroprotection in a chronic mouse model of multiple sclerosis. Front Neurol. May 24, 2012,3:84. doi: 10.3389/fneur.2012.00084. eCollection 2012.
Fujita K, et al. Spatially and Temporally Regulated NRF2 Gene Therapy Using Mcp-1 Promoter in Retinal Ganglion Cell Injury. Mol Ther Methods Clin Dev. Apr. 19, 2017;5:130-141. doi: 10.1016/j.omtm.2017.04.003. eCollection Jun. 16, 2017.
Genbank: AY327580.1, *Homo sapiens* rhodopsin kinase gene, promoter region, exon 1 and oartial cds, Jul. 26, 2016.
Genbank: BC011558.1, *Homo sapiens* nuclear factor (erythroid-derived 2)-like 2, Jul. 15, 2006
Grieger JC and Samulski RJ. Adeno-associated virus as a gene therapy vector: vector development, production and clinical applications. Adv Biochem Eng Biotechnol. 2005;99:119-45.
Hioki, H et al. Efficient gene transduction of neurons by lentivirus with enhanced neuron-specific promoters. Gene Ther. Jun. 2007;14(11):872-82. Epub Mar. 15, 2007.
Holehonnur R et al., Adeno-associated viral serotypes produce differing titers and differentially transduce neurons within the rat basal and lateral amygdala. BMC Neurosci. Feb. 18, 2014;15:28. doi: 10.1186/1471-2202-15-28.
Itoh K, et al. Keap1 regulates both cytoplasmic-nuclear shuttling and degradation of NRF2 in response to electrophiles. Genes Cells. Apr. 2003;8(4):379-91.
Jeong H, et al. Sirt1 mediates neuroprotection from mutant huntingtin by activation of the TORC1 and CREB transcriptional pathway. Nat Med. Dec. 18, 2011;18(1):159-65. doi: 10.1038/nm.2559.
Johnson DA & Johnson JA. Nrf2—a therapeutic target for the treatment of neurodegenerative diseases. Free Radic Biol Med. Nov. 2015;88(Pt B):253-267. doi: 10.1016/.freeradbiomed.2015.07.147. Epub Aug. 14, 2015.
Johnson DA, et al. The absence of the pro-antioxidant transcription factor Nrf2 exacerbates experimental autoimmune encephalomyelitis. Toxicol Sci. Apr. 2010;114(2):237-46. doi: 10.1093/toxsci/kfp274. Epub Nov. 12, 2009.
Kachi S, et al. Equine infectious anemia viral vector-mediated codelivery of endostatin and angiostatin driven by retinal pigmented epithelium-specific VMD2 promoter inhibits choroidal neovascularization. Hum Gene Ther. Jan. 2009;20(1):31-9. doi: 10.1089/hum.2008.046.
Kay CN, et al. Targeting Photoreceptors via Intravitreal Delivery Using Novel, Capsid-Mutated AAV Vectors, PLoS One. Apr. 26, 2013;8(4):e62097. doi: 10.1371/journal.pone.0062097. Print 2013.
Khan RS, et al. SIRT1 activating compounds reduce oxidative stress and prevent cell death in neuronal cells. Front Cell Neurosci. Dec. 31, 2012;6:63. doi: 10.3389/fncel.2012.00063. eCollection 2012.
Khan RS, et al. SIRT1 activating compounds reduce oxidative stress mediated neuronal loss in viral induced CNS demyelinating disease. Acta Neuropathol Commun. Jan. 2, 2014,2:3. doi: 10.1186/2051-5960-2-3.
Kim D, et al. SIRT1 deacetylase protects against neurodegeneration in models for Alzheimer's disease and amyotrophic lateral sclerosis. EMBO J. Jul. 11, 2007;26(13):3169-79. Epub Jun. 21, 2007.

(56) References Cited

OTHER PUBLICATIONS

Kimura A, et al. Targeting Oxidative Stress for Treatment of Glaucoma and Optic Neuritis. Oxid Med Cell Longev. 2017,2017:2817252. doi: 10.1155/2017/2817252. Epub Feb. 8, 2017.
Lambard S, et al. Expression of rod-derived cone viability factor: dual role of CRX in regulating promoter activity and cell-type specificity. PLoS One. Oct. 7, 2010,5(10):e13075. doi: 10.1371/journal.pone.0013075.
Larabee CM, et al. Loss of Nrf2 exacerbates the visual deficits and optic neuritis elicited by experimental autoimmune encephalomyelitis. Toxicol Sci. Apr. 2010,114(2):237-46. Mol Vis. Dec. 30, 2016;22:1503-1513. eCollection 2016.
Lassmann H, et al. Progressive multiple sclerosis: pathology and pathogenesis. Nat Rev Neurol. Nov. 5, 2012;8(11):647-56. doi: 10.1038/nrneurol.2012.168. Epub Sep. 25, 2012.
Li B, et al. Sulforaphane ameliorates the development of experimental autoimmune encephalomyelitis by antagonizing oxidative stress and Th17-related inflammation in mice. Exp Neurol. Dec. 2013;250:239-49. doi: 10.1016/j.expneurol.2013.10.002. Epub Oct. 9, 2013.
Liang KJ, et al. AAV-NRF2 promotes protection and recovery in animal models of oxidative stress. Mol Ther. Mar. 1, 2017;25(3):765-779. doi: 10.1016/j.ymthe.2016.12.016.
Linker RA, et al. Fumaric acid esters exert neuroprotective effects in neuroinflammation via activation of the Nrf2 antioxidant pathway. Brain. Mar. 2011;134(Pt 3):678-92. doi: 10.1093/brain/awq386.
Lock M, et al. Absolute determination of single-stranded and self-complementary adeno-associated viral vector genome titers by droplet digital PCR. Hum Gene Ther Methods. Apr. 2014;25(2):115-25. doi: 10.1089/hgtb.2013.131. Epub Feb. 14, 2014.
Luo J, et al. Negative control of p53 by Sir2alpha promotes cell survival under stress. Cell. Oct. 19, 2001;107(2):137-48.
Maguire AM, et al. Safety and efficacy of gene transfer for Leber's congenital amaurosis. N Engl J Med. May 22, 2008;358(21):2240-8. doi: 10.1056/NEJMoa0802315. Epub Apr. 27, 2008.
Martin A, et al. Role of SIRT1 in autoimmune demyelination and neurodegeneration. Immunol Res. Mar. 2015;61(3):187-97. doi: 10.1007/s12026-014-8557-5.
McCarty DM, et al. Self-complementary recombinant adeno-associated virus (scAAV) vectors promote eff1cient transduction independently of DNA synthesis. Gene Ther. Aug. 2001;8(16):1248-54.
McDougald DS, et al. SIRT1 and NRF2 Gene Transfer Mediate Distinct Neuroprotective Effects Upon Retinal Ganglion Cell Survival and Function in Experimental Optic Neuritis. Invest Ophthalmol Vis Sci. Mar. 1, 2018;59(3):1212-1220. doi: 10.1167/iovs.17-22972.
McLaughlin SK, et al. Adeno-associated virus general transduction vectors: analysis of proviral structures. J Virol. Jun. 1988;62(6):1963-73.
McMahon M, et al. Keapl-dependent proteasomal degradation of transcription factor NRF2 contributes to negative regulation of antioxidant response element-driven gene expression. J Biol Chem. Jun. 13, 2003;278(24):21592-600. Epub Apr. 7, 2003.
Morrissey ME, et al. PRE-1, a cis element sufficient to enhance cone- and rod-specific expression in differentiating zebraf1sh photoreceptors. BMC Dev Biol. Jan. 24, 2011;11:3. doi: 10.1186/1471-213X-11-3.
Mowat FM, et al. Tyrosiune capsid-murtant AAV vectors for gene delivery to the canine ratina from a subretinal or intravitreal approach. Gene Ther. Jan. 2014;21(1):96-105. doi: 10.1038/gt.2013.64. Epub Nov. 14, 2013.
Mussolino C, et al. AAV-mediated photoreceptor transduction of the pig cone-enriched retina. Gene Ther. Jul. 2011;18(7):637-45. doi: 10.1038/gt.2011.3. Epub Mar. 17, 2011.
Nathans J & Hogness DS. Isolation and nucleotide sequence of the gene encoding human rhodopsin. Proc Natl Acad Sci U S A. Aug. 1984;81(15):4851-5.
Nemoto S, et al. SIRT1 functionally interacts with the metabolic regulator and transcriptional coactivator PGC-1α. J Biol Chem. Apr. 22, 2005;280(16):16456-60. Epub Feb. 16, 2005.
Nicoud M, et al. Development of photoreceptor-specific promoters and their utility to investigate EIAV lentiviral vector mediated gene transfer to photoreceptors. J Gene Med. Dec. 2007;9(12):1015-23.
Nimmagadda VK, et al. Overexpression of SIRT1 protein in neurons protects agains experimental autoimmune encephalomyelitis through activation of multiple SIRT1 targets. J Immunol. 2013; 190: 4595-4607.
Passini MA, et al. CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Petrosyan HA et al., Transduction efficiency of neurons and glial cells by AAV-1, -5, -9, -rh10 and -hu11 serotypes in raty spinal cord following contusion injury. Gene Ther. Dec. 2014;21(12):991-1000. doi: 10.1038/gt.2014.74. Epub Aug. 14, 2014.
Pierce EA, Bennett J. The status of the RPE65 gene therapy trials: safety and efficacy. Cold Spring Harb Perspect Med. Jan. 29, 2015;5(9):a017285. doi: 10.1101/cshperspect.a017285.
Prusky GT, et al. Rapid quantification of adult and developing mouse spatial vision using a virtual optomotor system. Invest Ophthalmol Vis Sci. Dec. 2004;45(12):4611-6.
Qgueta SB, et al. The human cGMP-PDE beta-subunit promoter region directs expression of the gene to mouse photoreceptors. Invest Ophthalmol Vis Sci. Dec. 2000;41(13):4059-63.
Qi X, et al. Dual gene therapy with extracellular superoxide dismutase and catalase attenuates experimental optic neuritis. Mol Vis. Mol Vis. Jan. 5, 2007;13:1-11.
Qi X, et al. Suppression of mitochondrial oxidative stress provides long-term neuroprotection in experimental optic neuritis. Invest Ophthalmol Vis Sci. Feb. 2007;48(2):681-91.
Quinn TA, et al. Optic neuritis and retinal ganglion cell loss in a chronic murine model of multiple sclerosis. Front Neurol. Aug. 2, 2011;2:50. doi: 10.3389/fneur.2011.0050. eCollection 2011.
Royo NC, et al. Specific AAV serotypes stably transduce primary hippocampal and cortical cultures with high efficiency and low toxicity. Brain Res. Jan. 23, 2008;1190:15-22. Epub Nov. 17, 2007.
Shindler KS, et al. Oral resveratrol reduces neuronal damage in a model of multiple sclerosis. J Neuroophthalmol. Dec. 2010;30(4):328-39. doi: 10.1097/WNO.0b013e3181f7f833.
Shindler KS, et al. Retinal ganglion cell loss induced by acute optic neuritis in a relapsing model of multiple sclerosis. Mult Scler. Oct. 2006;12(5):526-32.
Shindler KS, et al. SIRT1 activation confers neuroprotection in experimental optic neuritis. Invest Ophthalmol Vis Sci. Aug. 2007;48(8):3602-9.
Shu X, et al. Functional characterization of the human RPGR proximal promoter. Invest Ophthalmol Vis Sci. Jun. 26, 2012;53(7):3951-8. doi: 10.1167/iovs.11-8811.
Sochor MA, et al. An Autogenously Regulated Expression System for Gene Therapeutic Ocular Applications. Sci Rep. Nov. 24, 2015;5:17105. doi: 10.1038/srep17105.
Su X, et al. In vitro and in vivo mRNA delivery using lipid-enveloped pH-responsive polymer nanoparticles. Mol Pharm. Jun. 6, 2011;8(3):774-87. doi: 10.1021/mp100390w. Epub Apr. 1, 2011.
Sugita Y, et al. Contributions of retinal direction-selective ganglion cells to optokinetic responses in mice. Eur J Neurosci. Eur J Neurosci. Sep. 2013;38(6):2823-31. doi: 10.1111/ejn.12284. Epub Jun. 12, 2013.
Sun X, et al. Gene Therapy with a Promoter Targeting Both Rods and Cones Rescues Retinal Degeneration Caused by AIPL1 Mutations. Gene Ther. Jan. 2010;17(1):117-31. doi: 10.1038/gt.2009.104. Epub Aug. 27, 2009.
Talla V, et al. Complex I subunit gene therapy with NDUFA6 ameliorates neurodegeneration in EAE. Invest Ophthalmol Vis Sci. Jan. 22, 2015;56(2):1129-40. doi: 10.1167/iovs.14-15950.
Talla V, et al. Gene therapy with mitochondiral heat shock protein 70 suppresses visual loss and optic atrophy in experimental autoimmune encephalomyelitis. Invest Ophthalmol Vis Sci. Jul. 11, 2014;55(8):5214-26. doi: 10.1167/iovs.14-14688.

(56) References Cited

OTHER PUBLICATIONS

Talla V, et al. NADH-dehydrogenase type-2 suppresses irreversible visual loss and neurogeneration in the EAE animal model of MS. Mol Ther. Oct. 2013;21(10):1876-88. doi: 10.1038/mt.2013.104. Epub Jun. 11, 2013.
Thompson JD, et al. A comprehensive comparison of multiple sequence alignment programs. Nucleic Acids Res. Jul. 1, 1999;27(13):2682-90.
Trip SA, et al. Retinal nerve fiber layer axonal loss and visual dysfunction in optic neuritis. Ann Neurol. Sep. 2005;58(3):383-91.
Xia X, et al. NFAT5 protects astrocytes against oxygen-glucose-serum deprivation/restoration damage via the SIRT1/Nrf2 pathway. J Mol Neurosci. Jan. 2017;61(1):96-104. doi: 10.1007/s12031-016-0849-x. Epub Nov. 12, 2016.
Xiong et al., NRF2 promotes neuronal survival in neurodegeneration and acute nerve damage. J Clin Invest. Apr. 2015;125(4):1433-45. doi: 10.1172/JCI79735. Epub Mar. 23, 2015.
Zhang H, et al. Adenovirus-adeno-associated virus hybrid for large-scale recombinant adeno-associated virus production. Hum Gene Ther. Sep. 2009;20(9):922-9. doi: 10.1089/hum.2009.125.
Zhang P, et al. Resveratyrol ameliorated vascular calcification by regulating Sirt-1 and Nrf2. Transplant Proc. Dec. 2016;48(10):3378-3386. doi: 10.1016/j.transproceed.2016.10.023.
Zinn E, et al. In silico reconsrtuction of the viral evolutionary lineage yields a potent gene therapy vector. Cell Rep. Aug. 11, 2015;12(6):1056-68. doi: 10.1016/j.celrep.2015.07.019. Epub Jul. 20, 2015.
Zuo L, et al. SIRT1 promotes RGC survival and delays loss of function following optic nerve crush. Invest Ophthalmol Vis Sci. Jul. 26, 2013;54(7):5097-102. doi: 10.1167/iovs.13-12157.
International Search Report in International Patent Application No. PCT/US2018/029167, dated Oct. 1, 2018.
Written Opinion in International Patent Application No. PCT/US2018/029167, dated Oct. 1, 2018.

* cited by examiner

FIG 9A

```
hNRF_native      atgatggacttggagctgccgccgccgggactcccgtcccagcaggacatggatttgatt
hNRF_co          ATGATGGACCTCGAACTGCCGCCGCCTGGCCTCCCAAGCCAACAGGATATGGACCTGATT
                 ********* * ** *********** ** *****   *** ***** *****  *****

hNRF_native      gacatactttggaggcaagatatagatcttggagtaagtcgagaagtatttgacttcagt
hNRF_co          GACATCCTGTGGCGGCAGGACATTGATCTGGGTGTCAGCCGCGAGGTGTTCGATTTCTCG
                 ***** ** *** **** ** ** ***** ** ** ** ** ** ** ** ** ***

hNRF_native      cagcgacggaaagagtatgagctggaaaaacagaaaaaacttgaaaaggaaagacaagaa
hNRF_co          CAACGCCGGAAGGAATACGAACTCGAGAAGCAGAAGAAGCTCGAGAAAGAGCGGCAGGAA
                 ** ** ***** ** ** ** ** ** ** ***** ** ** ** ** **  * ** ***

hNRF_native      caactccaaaaggagcaagagaaagcctttttcgctcagttacaactagatgaagagaca
hNRF_co          CAGCTCCAGAAGGAACAGGAAAAGGCCTTCTTCGCACAACTTCAGCTGGACGAGGAAACC
                 ** ***** ***** ** ** ** ***** ***** **  * ** ** ** ** ** **

hNRF_native      ggtgaatttctcccaattcagccagcccagcacatccagtcagaaaccagtggatctgcc
hNRF_co          GGCGAATTCCTGCCTATTCAACCAGCCCAGCACATCCAGAGCGAAACCTCCGGCAGCGCC
                 ** ***** ** ** ***** ******************   ******   **    ***

hNRF_native      aactactcccaggttgcccacattcccaaatcagatgctttgtactttgatgactgcatg
hNRF_co          AACTATTCCCAAGTGGCTCACATCCCGAAGTCCGACGCCCTGTACTTTGACGATTGTATG
                 ***** ***** ** ** ***** ** ** ** ** ** ** ********** ** ** ***

hNRF_native      cagcttttggcgcagacattcccgtttgtagatgacaatgaggtttcttcggctacgttt
hNRF_co          CAGCTGCTGGCACAGACCTTCCCCTTCGTCGATGATAACGAGGTGTCCTCCGCGACGTTT
                 *****  **** ***** ***** ** ** ***** ** ***** ** ** ** ******

hNRF_native      cagtcacttgttcctgatattcccggtcacatcgagagcccagtcttcattgctactaat
hNRF_co          CAGTCGCTGGTCCCCGACATCCCCGGTCATATCGAGAGCCCTGTGTTCATCGCCACCAAC
                 ***** ** ** ** ** ** ******** *********** ** ***** ** ** **

hNRF_native      caggctcagtcacctgaaacttctgttgctcaggtagcccctgttgatttagacggtatg
hNRF_co          CAGGCTCAGTCCCCCGAAACCTCAGTGGCACAAGTGGCGCCGGTGGACTTGGACGGCATG
                 *********** ** ***** ** ** ** ** ** ** ** ** ** ** ***** ***

hNRF_native      caacaggacattgagcaagtttgggaggagctattatccattcctgagttacagtgtctt
hNRF_co          CAGCAAGACATCGAACAAGTCTGGGAGGAGCTTCTGTCCATCCCCGAGCTGCAATGCCTC
                 ** ** ***** ** ***** ***********  * ***** ** *** * ** ** **

hNRF_native      aatattgaaaatgacaagctggttgagactaccatggttccaagtccagaagccaaactg
hNRF_co          AACATCGAGAATGACAAGCTCGTGGAGACTACTATGGTCCCGTCCCCGGAAGCTAAGCTG
                 ** ** ** *********** ** ******** ***** **    ** ***** ** ***

hNRF_native      acagaagttgacaattatcatttttactcatctataccctcaatggaaaaagaagtaggt
hNRF_co          ACCGAGGTCGACAACTACCATTTCTACTCCTCAATCCCCTCCATGGAAAAGGAAGTCGGA
                 ** ** ** ***** ** ***** ***** ** ** ***** ******** ***** **

hNRF_native      aactgtagtccacattttcttaatgcttttgaggattccttcagcagcatcctctccaca
hNRF_co          AACTGCTCGCCTCATTTCCTCAACGCCTTCGAGGACTCCTTCTCGTCAATTCTGTCCACT
                 *****    ** ***** ** ** ** ** ***** ******      ** ** *****

hNRF_native      gaagaccccaaccagttgacagtgaactcattaaattcagatgccacagtcaacacagat
hNRF_co          GAGGACCCCAACCAGCTGACCGTCAATTCCTTGAACTCGGATGCCACTGTGAACACCGAC
                 ** ************ **** ** ** ** ** ** ** ******** ** ***** **

hNRF_native      tttggtgatgaattttattctgctttcatagctgagcccagtatcagcaacagcatgccc
hNRF_co          TTCGGCGACGAATTCTACAGCGCGTTCATCGCCGAACCGAGCATCTCGAACTCCATGCCC
                 ** ** ** ***** **    ** ***** ** ** ** ** ***   ***  *******
```

FIG 9B

```
hNRF_native     tcacctgctactttaagccattcactctctgaacttctaaatgg(
hNRF_co         TCGCCCGCCACCTTGTCACATTCCCTGTCTGAGCTGCTGAACGGGCCGATTGACGTGTCA
                ** ** ** ** **    ***** ** ***** ** ** ** ***** ***** ** **

hNRF_native     gatctatcactttgcaaagctttcaaccaaaaccaccctgaaagcacagcagaattcaat
hNRF_co         GACCTGAGCCTGTGTAAAGCCTTCAACCAGAATCACCCGGAGTCGACTGCCGAATTCAAC
                ** **    ** ** ***** ******** ** ***** **    ** ** ********

hNRF_native     gattctgactccggcatttcactaaacacaagtcccagtgtggcatcaccagaacactca
hNRF_co         GACTCGGACTCCGGGATCTCACTGAACACTAGCCCTAGCGTGGCCTCGCCCGAACACTCC
                ** ** ******** ** ***** ***** ** ** ** ***** ** ** ********

hNRF_native     gtggaatcttccagctatggagacacactacttggcctcagtgattctgaagtggaagag
hNRF_co         GTGGAGTCCAGCTCCTATGGCGATACTCTTCTGGGTCTGTCCGACTCCGAAGTGGAAGAA
                ***** **   *  ****** ** ** ** ** ** **    ** ** ***********

hNRF_native     ctagatagtgcccctggaagtgtcaaacagaatggtcctaaaacaccagtacattcttct
hNRF_co         CTGGACTCTGCCCCCGGAAGCGTGAAACAGAACGGACCTAAGACCCCAGTGCACTCCTCC
                ** **   ****** ***** ** ******** ** ***** ** ***** ** ** **

hNRF_native     ggggatatggtacaacccttgtcaccatctcaggggcagagcactcacgtgcatgatgcc
hNRF_co         GGGGATATGGTGCAGCCGTTGTCACCGAGCCAGGGGCAATCCACCCACGTGCATGACGCT
                *********** ** ** ********    ********   *** *********** **

hNRF_native     caatgtgagaacacaccagagaaagaattgcctgtaagtcctggtcatcggaaaacccca
hNRF_co         CAGTGCGAGAACACCCCCGAGAAAGAACTCCCAGTGTCCCCCGGACACCGAAAGACCCCG
                ** ** ******** ** ********* * ** **    ** ** ** ** ** *****

hNRF_native     ttcacaaaagacaaacattcaagccgcttggaggctcatctcacaagagatgaacttagg
hNRF_co         TTTACCAAGGACAAGCACTCCTCACGGCTGGAAGCACACCTTACTCGGGATGAACTCAGA
                ** ** ** ***** ** **    **  **** ** ** ** **  * ******** **

hNRF_native     gcaaaagctctccatatcccattccctgtagaaaaaatcattaacctccctgttgttgac
hNRF_co         GCCAAGGCCCTCCACATTCCTTTCCCCGTGGAGAAGATTATCAATCTCCCTGTGGTGGAT
                ** ** ** ***** ** ** ***** ** ** ** ** ** ** ******** ** **

hNRF_native     ttcaacgaaatgatgtccaaagagcagttcaatgaagctcaacttgcattaattcgggat
hNRF_co         TTCAACGAGATGATGAGCAAGGAACAGTTCAACGAAGCGCAGCTGGCGCTGATCAGGGAC
                ******** ******  *** ** ******** ***** ** ** **  * **  ****

hNRF_native     atacgtaggaggggtaagaataaagtggctgctcagaattgcagaaaaagaaaactggaa
hNRF_co         ATCAGGCGCAGAGGAAAGAACAAAGTGGCCGCCCAAAACTGCCGGAAGAGAAAGCTCGAA
                **  *  * ** ** ***** ******** ** ** ** *** * ** ***** ** ***

hNRF_native     aatatagtagaactagagcaagatttagatcatttgaaagatgaaaaagaaaaattgctc
hNRF_co         AACATCGTGGAGCTCGAACAGGACTTGGACCACCTGAAGGATGAAAAAGAAAAGCTGCTG
                ** ** ** ** ** ** ** ** ** ** **  **** **************  ****

hNRF_native     aaagaaaaaggagaaaatgacaaaagccttcacctactgaaaaaacaactcagcacctta
hNRF_co         AAGGAGAAGGGAGAGAACGACAAGTCCCTCCATCTGCTGAAGAAGCAGCTGAGCACACTG
                ** ** ** ***** ** *****   *** ** ** ***** ** ** ** *****  *

hNRF_native     tatctcgaagttttcagcatgctacgtgatgaagatggaaaaccttattctcctagtgaa
hNRF_co         TACCTCGAAGTGTTTTCCATGCTGCGCGATGAGGATGGAAAGCCGTACTCCCCGTCCGAA
                ** ******** **   ****** ** ***** ******** ** ** ** **    ***

hNRF_native     tactccctgcagcaaacaagagatggcaatgttttccttgttcccaaaagtaagaagcca
hNRF_co         TACTCGCTGCAACAGACGCGCGACGGAAACGTGTTCCTCGTGCCAAAGTCCAAGAAGCCT
                ***** ***** ** **  * ** ** ** ** ***** ** ** **    ********

hNRF_native     gatgttaagaaaaac---
hNRF_co         GACGTGAAGAAGAACTGA
                ** ** ***** ***
```

| Sham (N=10) | EAE (N=10) | EAE (N=25) |
|---|---|---|
| OD = AAV2-eGFP | OD = AAV2-eGFP | OD = AAV2-NRF2 |
| OS = Vehicle | OS = Vehicle | OS = AAV2-SIRT1 |

SEQUENCE LISTING

```
<160> NUMBER OF SEQ ID NOS: 28

<210> SEQ ID NO 1
<211> LENGTH: 747
<212> TYPE: PRT
<213> ORGANISM: Homo sapiens

<400> SEQUENCE: 1

Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Ala Leu Trp Arg Glu Ala Glu
65                  70                  75                  80

Ala Glu Ala Ala Ala Ala Gly Gly Glu Gln Glu Ala Gln Ala Thr Ala
                85                  90                  95
```

```
Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Glu Ala Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365

Ala Ser Cys Leu Ile Cys Lys Tyr Lys Val Asp Cys Glu Ala Val Arg
    370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510
```

-continued

```
Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745
```

<210> SEQ ID NO 2
<211> LENGTH: 2241
<212> TYPE: DNA
<213> ORGANISM: Homo sapiens

<400> SEQUENCE: 2

```
atggcggacg aggcggccct cgcccttcag cccggcggct ccccctcggc ggcgggggcc      60

gacagggagg ccgcgtcgtc ccccgccggg gagccgctcc gcaagaggcc gcggagagat     120

ggtcccggcc tcgagcggag cccgggcgag cccggtgggg cggccccaga gcgtgaggtg     180

ccggcggcgg ccaggggctg cccgggtgcg gcggcggcgg cgctgtggcg ggaggcggag     240

gcagaggcgg cggcggcagg cggggagcaa gaggcccagg cgactgcggc ggctggggaa     300

ggagacaatg ggccgggcct gcagggccca tctcgggagc caccgctggc cgacaacttg     360

tacgacgaag acgacgacga cgagggcgag gaggaggaag aggcggcggc ggcggcgatt     420

gggtaccgag ataaccttct gttcggtgat gaaattatca ctaatggttt tcattcctgt     480

gaaagtgatg aggaggatag agcctcacat gcaagctcta gtgactggac tccaaggcca     540

cggataggtc catatacttt tgttcagcaa catcttatga ttggcacaga tcctcgaaca     600

attcttaaag atttattgcc ggaaacaata cctccacctg agttggatga tatgacactg     660

tggcagattg ttattaatat cctttcagaa ccaccaaaaa ggaaaaaaag aaaagatatt     720

aatacaattg aagatgctgt gaaattactg caagagtgca aaaaaattat agttctaact     780
```

-continued

```
ggagctgggg tgtctgtttc atgtggaata cctgacttca ggtcaaggga tggtatttat    840

gctcgccttg ctgtagactt cccagatctt ccagatcctc aagcgatgtt tgatattgaa    900

tatttcagaa aagatccaag accattcttc aagtttgcaa aggaaatata tcctggacaa    960

ttccagccat ctctctgtca caaattcata gccttgtcag ataaggaagg aaaactactt   1020

cgcaactata cccagaacat agacacgctg gaacaggttg cgggaatcca aaggataatt   1080

cagtgtcatg gttcctttgc aacagcatct tgcctgattt gtaaatacaa agttgactgt   1140

gaagctgtac gaggagatat ttttaatcag gtagttcctc gatgtcctag gtgcccagct   1200

gatgaaccgc ttgctatcat gaaaccagag attgtgtttt ttggtgaaaa tttaccagaa   1260

cagtttcata gagccatgaa gtatgacaaa gatgaagttg acctcctcat tgttattggg   1320

tcttccctca aagtaagacc agtagcacta attccaagtt ccataccccca tgaagtgcct   1380

cagatattaa ttaatagaga acctttgcct catctgcatt ttgatgtaga gcttcttgga   1440

gactgtgatg tcataattaa tgaattgtgt cataggttag gtggtgaata tgccaaactt   1500

tgctgtaacc ctgtaaagct ttcagaaatt actgaaaaac ctccacgaac acaaaaagaa   1560

ttggcttatt tgtcagagtt gccacccaca cctcttcatg tttcagaaga ctcaagttca   1620

ccagaaagaa cttcaccacc agattcttca gtgattgtca cacttttaga ccaagcagct   1680

aagagtaatg atgatttaga tgtgtctgaa tcaaaaggtt gtatggaaga aaaaccacag   1740

gaagtacaaa cttctaggaa tgttgaaagt attgctgaac agatggaaaa tccggatttg   1800

aagaatgttg gttctagtac tggggagaaa aatgaaagaa cttcagtggc tggaacagtg   1860

agaaaatgct ggcctaatag agtggcaaag gagcagatta gtaggcggct tgatggtaat   1920

cagtatctgt tttgccacc aaatcgttac attttccatg gcgctgaggt atattcagac   1980

tctgaagatg acgtcttatc ctctagttct tgtggcagta acagtgatag tgggacatgc   2040

cagagtccaa gtttagaaga acccatggag gatgaaagtg aaattgaaga attctacaat   2100

ggcttagaag atgagcctga tgttccagag agagctggag gagctggatt tgggactgat   2160

ggagatgatc aagaggcaat taatgaagct atatctgtga aacaggaagt aacagacatg   2220

aactatccat caaacaaatc a                                               2241
```

<210> SEQ ID NO 3
<211> LENGTH: 605
<212> TYPE: PRT
<213> ORGANISM: Homo sapiens

<400> SEQUENCE: 3

```
Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln His Ile Gln Ser Glu Thr
                85                  90                  95

Ser Gly Ser Ala Asn Tyr Ser Gln Val Ala His Ile Pro Lys Ser Asp
            100                 105                 110
```

-continued

```
Ala Leu Tyr Phe Asp Asp Cys Met Gln Leu Leu Ala Gln Thr Phe Pro
        115                 120                 125

Phe Val Asp Asp Asn Glu Val Ser Ser Ala Thr Phe Gln Ser Leu Val
    130                 135                 140

Pro Asp Ile Pro Gly His Ile Glu Ser Pro Val Phe Ile Ala Thr Asn
145                 150                 155                 160

Gln Ala Gln Ser Pro Glu Thr Ser Val Ala Gln Val Ala Pro Val Asp
                165                 170                 175

Leu Asp Gly Met Gln Gln Asp Ile Glu Gln Val Trp Glu Glu Leu Leu
            180                 185                 190

Ser Ile Pro Glu Leu Gln Cys Leu Asn Ile Glu Asn Asp Lys Leu Val
        195                 200                 205

Glu Thr Thr Met Val Pro Ser Pro Glu Ala Lys Leu Thr Glu Val Asp
    210                 215                 220

Asn Tyr His Phe Tyr Ser Ser Ile Pro Ser Met Glu Lys Glu Val Gly
225                 230                 235                 240

Asn Cys Ser Pro His Phe Leu Asn Ala Phe Glu Asp Ser Phe Ser Ser
                245                 250                 255

Ile Leu Ser Thr Glu Asp Pro Asn Gln Leu Thr Val Asn Ser Leu Asn
            260                 265                 270

Ser Asp Ala Thr Val Asn Thr Asp Phe Gly Asp Glu Phe Tyr Ser Ala
        275                 280                 285

Phe Ile Ala Glu Pro Ser Ile Ser Asn Ser Met Pro Ser Pro Ala Thr
    290                 295                 300

Leu Ser His Ser Leu Ser Glu Leu Leu Asn Gly Pro Ile Asp Val Ser
305                 310                 315                 320

Asp Leu Ser Leu Cys Lys Ala Phe Asn Gln Asn His Pro Glu Ser Thr
                325                 330                 335

Ala Glu Phe Asn Asp Ser Asp Ser Gly Ile Ser Leu Asn Thr Ser Pro
            340                 345                 350

Ser Val Ala Ser Pro Glu His Ser Val Glu Ser Ser Ser Tyr Gly Asp
        355                 360                 365

Thr Leu Leu Gly Leu Ser Asp Ser Glu Val Glu Glu Leu Asp Ser Ala
    370                 375                 380

Pro Gly Ser Val Lys Gln Asn Gly Pro Lys Thr Pro Val His Ser Ser
385                 390                 395                 400

Gly Asp Met Val Gln Pro Leu Ser Pro Ser Gln Gly Gln Ser Thr His
                405                 410                 415

Val His Asp Ala Gln Cys Glu Asn Thr Pro Glu Lys Glu Leu Pro Val
            420                 425                 430

Ser Pro Gly His Arg Lys Thr Pro Phe Thr Lys Asp Lys His Ser Ser
        435                 440                 445

Arg Leu Glu Ala His Leu Thr Arg Asp Glu Leu Arg Ala Lys Ala Leu
    450                 455                 460

His Ile Pro Phe Pro Val Glu Lys Ile Ile Asn Leu Pro Val Val Asp
465                 470                 475                 480

Phe Asn Glu Met Met Ser Lys Glu Gln Phe Asn Glu Ala Gln Leu Ala
                485                 490                 495

Leu Ile Arg Asp Ile Arg Arg Arg Gly Lys Asn Lys Val Ala Ala Gln
            500                 505                 510

Asn Cys Arg Lys Arg Lys Leu Glu Asn Ile Val Glu Leu Glu Gln Asp
        515                 520                 525

Leu Asp His Leu Lys Asp Glu Lys Glu Lys Leu Leu Lys Glu Lys Gly
```

-continued

```
    530                 535                 540

Glu Asn Asp Lys Ser Leu His Leu Leu Lys Lys Gln Leu Ser Thr Leu
545                 550                 555                 560

Tyr Leu Glu Val Phe Ser Met Leu Arg Asp Glu Asp Gly Lys Pro Tyr
                565                 570                 575

Ser Pro Ser Glu Tyr Ser Leu Gln Gln Thr Arg Asp Gly Asn Val Phe
            580                 585                 590

Leu Val Pro Lys Ser Lys Lys Pro Asp Val Lys Lys Asn
        595                 600                 605


<210> SEQ ID NO 4
<211> LENGTH: 1815
<212> TYPE: DNA
<213> ORGANISM: Homo sapiens

<400> SEQUENCE: 4

atgatggact tggagctgcc gccgccggga ctcccgtccc agcaggacat ggatttgatt     60

gacatacttt ggaggcaaga tatagatctt ggagtaagtc gagaagtatt tgacttcagt    120

cagcgacgga aagagtatga gctggaaaaa cagaaaaaac ttgaaaagga aagacaagaa    180

caactccaaa aggagcaaga gaaagccttt ttcgctcagt tacaactaga tgaagagaca    240

ggtgaatttc tcccaattca gccagcccag cacatccagt cagaaaccag tggatctgcc    300

aactactccc aggttgccca cattcccaaa tcagatgctt tgtactttga tgactgcatg    360

cagcttttgg cgcagacatt cccgtttgta gatgacaatg aggtttcttc ggctacgttt    420

cagtcacttg ttcctgatat tcccggtcac atcgagagcc cagtcttcat tgctactaat    480

caggctcagt cacctgaaac ttctgttgct caggtagccc ctgttgattt agacggtatg    540

caacaggaca ttgagcaagt ttgggaggag ctattatcca ttcctgagtt acagtgtctt    600

aatattgaaa atgacaagct ggttgagact accatggttc caagtccaga agccaaactg    660

acagaagttg acaattatca tttttactca tctataccct caatggaaaa agaagtaggt    720

aactgtagtc cacattttct taatgctttt gaggattcct tcagcagcat cctctccaca    780

gaagacccca accagttgac agtgaactca ttaaattcag atgccacagt caacacagat    840

tttggtgatg aattttattc tgctttcata gctgagccca gtatcagcaa cagcatgccc    900

tcacctgcta ctttaagcca ttcactctct gaacttctaa atgggcccat tgatgtttct    960

gatctatcac tttgcaaagc tttcaaccaa aaccaccctg aaagcacagc agaattcaat   1020

gattctgact ccggcatttc actaaacaca agtcccagtg tggcatcacc agaacactca   1080

gtggaatctt ccagctatgg agacacacta cttggcctca gtgattctga agtggaagag   1140

ctagatagtg cccctggaag tgtcaaacag aatggtccta aaacaccagt acattcttct   1200

ggggatatgg tacaaccctt gtcaccatct caggggcaga gcactcacgt gcatgatgcc   1260

caatgtgaga acacaccaga gaaagaattg cctgtaagtc ctggtcatcg gaaaacccca   1320

ttcacaaaag acaaacattc aagccgcttg gaggctcatc tcacaagaga tgaacttagg   1380

gcaaaagctc tccatatccc attccctgta gaaaaaatca ttaacctccc tgttgttgac   1440

ttcaacgaaa tgatgtccaa agagcagttc aatgaagctc aacttgcatt aattcgggat   1500

atacgtagga ggggtaagaa taaagtggct gctcagaatt gcagaaaaag aaaactggaa   1560

aatatagtag aactagagca agatttagat catttgaaag atgaaaaaga aaaattgctc   1620

aaagaaaaag gagaaaatga caaaagcctt cacctactga aaaaacaact cagcacctta   1680

tatctcgaag ttttcagcat gctacgtgat gaagatggaa aaccttattc tcctagtgaa   1740
```

-continued

```
tactccctgc agcaaacaag agatggcaat gttttccttg ttcccaaaag taagaagcca   1800

gatgttaaga aaaac                                                    1815


<210> SEQ ID NO 5
<211> LENGTH: 12025
<212> TYPE: DNA
<213> ORGANISM: Artificial Sequence
<220> FEATURE:
<223> OTHER INFORMATION: constructed sequence

<400> SEQUENCE: 5

tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720

ttatcgcgag cccatttata cccatataaa tcagcatcca tgttggaatt taatcgcggc    780

ctcgacgttt cccgttgaat atggctcata ttcttccttt ttcaatatta ttgaagcatt    840

tatcagggtt attgtctcat gagcggatac atatttgaat gtatttagaa aaataaacaa    900

ataggggtca gtgttacaac caattaacca attctgaaca ttatcgcgag cccatttata    960

cctgaatatg gctcataaca ccccttgttt gcctggcggc agtagcgcgg tggtcccacc   1020

tgaccccatg ccgaactcag aagtgaaacg ccgtagcgcc gatggtagtg tggggactcc   1080

ccatgcgaga gtagggaact gccaggcatc aaataaaacg aaaggctcag tcgaaagact   1140

gggcctttcg cccgggctaa ttagggggtg tcgcccttat tcgactctat agtgaagttc   1200

ctattctcta gaaagtatag gaacttctga agtggggtcg acttaattaa ggctgcgcgc   1260

tcgctcgctc actgaggccg cccgggcaaa gcccgggcgt cgggcgacct ttggtcgccc   1320

ggcctcagtg agcgagcgag cgcgcagaga gggagtggcc aactccatca ctaggggttc   1380

cttgtagtta atgattaacc cgccatgcta cttatctacg tagcaagcta gctagttatt   1440

aatagtaatc aattacgggg tcattagttc atagcccata tatggagttc cgcgttacat   1500

aacttacggt aaatggcccg cctggctgac cgcccaacga cccccgccca ttgacgtcaa   1560

taatgacgta tgttcccata gtaacgccaa tagggacttt ccattgacgt caatgggtgg   1620

agtatttacg gtaaactgcc cacttggcag tacatcaagt gtatcatatg ccaagtacgc   1680

cccctattga cgtcaatgac ggtaaatggc ccgcctggca ttatgcccag tacatgacct   1740

tatgggactt tcctacttgg cagtacatct acgtattagt catcgctatt aacatggtcg   1800

aggtgagccc cacgttctgc ttcactctcc ccatctcccc cccctcccca cccccaattt   1860

tgtatttatt tattttttaa ttattttgtg cagcgatggg ggcggggggg gggggggggc   1920
```

-continued

```
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatga   3120
tggacttgga gctgccgccg ccgggactcc cgtcccagca ggacatggat ttgattgaca   3180
tactttggag gcaagatata gatcttggag taagtcgaga agtatttgac ttcagtcagc   3240
gacggaaaga gtatgagctg gaaaaacaga aaaaacttga aaaggaaaga caagaacaac   3300
tccaaaagga gcaagagaaa gcctttttcg ctcagttaca actagatgaa gagacaggtg   3360
aatttctccc aattcagcca gcccagcaca tccagtcaga aaccagtgga tctgccaact   3420
actcccaggt tgcccacatt cccaaatcag atgctttgta ctttgatgac tgcatgcagc   3480
ttttggcgca gacattcccg tttgtagatg acaatgaggt ttcttcggct acgtttcagt   3540
cacttgttcc tgatattccc ggtcacatcg agagcccagt cttcattgct actaatcagg   3600
ctcagtcacc tgaaacttct gttgctcagg tagcccctgt tgatttagac ggtatgcaac   3660
aggacattga gcaagtttgg gaggagctat tatccattcc tgagttacag tgtcttaata   3720
ttgaaaatga caagctggtt gagactacca tggttccaag tccagaagcc aaactgacag   3780
aagttgacaa ttatcatttt tactcatcta taccctcaat ggaaaaagaa gtaggtaact   3840
gtagtccaca ttttcttaat gcttttgagg attccttcag cagcatcctc tccacagaag   3900
accccaacca gttgacagtg aactcattaa attcagatgc cacagtcaac acagattttg   3960
gtgatgaatt ttattctgct ttcatagctg agcccagtat cagcaacagc atgccctcac   4020
ctgctacttt aagccattca ctctctgaac ttctaaatgg gcccattgat gtttctgatc   4080
tatcactttg caaagctttc aaccaaaacc accctgaaag cacagcagaa ttcaatgatt   4140
ctgactccgg catttcacta aacacaagtc ccagtgtggc atcaccagaa cactcagtgg   4200
aatcttccag ctatggagac acactacttg gcctcagtga ttctgaagtg gaagagctag   4260
atagtgcccc tggaagtgtc aaacagaatg gtcctaaaac accagtacat tcttctgggg   4320
```

```
atatggtaca acccttgtca ccatctcagg ggcagagcac tcacgtgcat gatgcccaat   4380
gtgagaacac accagagaaa gaattgcctg taagtcctgg tcatcggaaa accccattca   4440
caaaagacaa acattcaagc cgcttggagg ctcatctcac aagagatgaa cttagggcaa   4500
aagctctcca tatcccattc cctgtagaaa aaatcattaa cctccctgtt gttgacttca   4560
acgaaatgat gtccaaagag cagttcaatg aagctcaact tgcattaatt cgggatatac   4620
gtaggagggg taagaataaa gtggctgctc agaattgcag aaaaagaaaa ctggaaaata   4680
tagtagaact agagcaagat ttagatcatt tgaaagatga aaaagaaaaa ttgctcaaag   4740
aaaaaggaga aaatgacaaa agccttcacc tactgaaaaa acaactcagc accttatatc   4800
tcgaagtttt cagcatgcta cgtgatgaag atggaaaacc ttattctcct agtgaatact   4860
ccctgcagca aacaagagat ggcaatgttt tccttgttcc caaaagtaag aagccagatg   4920
ttaagaaaaa cgactacaaa gaccatgacg gtgattataa agatcatgac atcgattaca   4980
aggatgacga tgacaagtga ggccgcatag tactgcggat cctgcagatc tgcctcgact   5040
gtgccttcta gttgccagcc atctgttgtt tgcccctccc ccgtgccttc cttgaccctg   5100
gaaggtgcca ctcccactgt cctttcctaa taaaatgagg aaattgcatc gcattgtctg   5160
agtaggtgtc attctattct ggggggtggg gtggggcagg acagcaaggg ggaggattgg   5220
gaagacaata gcaggcatgc tggggactcg agttctacgt agataagtag catggcgggt   5280
taatcattaa ctacaaggaa cccctagtga tggagttggc cactccctct ctgcgcgctc   5340
gctcgctcac tgaggccggg cgaccaaagg tcgcccgacg cccgggcttt gcccgggcgg   5400
cctcagtgag cgagcgagcg cgcagcctta attaacctaa ggaaaatgaa gtgaagttcc   5460
tatactttct agagaatagg aacttctata gtgagtcgaa taagggcgac acaaaattta   5520
ttctaaatgc ataataaata ctgataacat cttatagttt gtattatatt ttgtattatc   5580
gttgacatgt ataattttga tatcaaaaac tgattttccc tttattattt tcgagattta   5640
ttttcttaat tctctttaac aaactagaaa tattgtatat acaaaaaatc ataaataata   5700
gatgaatagt ttaattatag gtgttcatca atcgaaaaag caacgtatct tatttaaagt   5760
gcgttgcttt tttctcattt ataaggttaa ataattctca tatatcaagc aaagtgacag   5820
gcgcccttaa atattctgac aaatgctctt tccctaaact ccccccataa aaaaacccgc   5880
cgaagcgggt ttttacgtta tttgcggatt aacgattact cgttatcaga accgcccagg   5940
gggcccgagc ttaacctttt tatttggggg agagggaagt catgaaaaaa ctaacctttg   6000
aaattcgatc tccagcacat cagcaaaacg ctattcacgc agtacagcaa atccttccag   6060
acccaaccaa accaatcgta gtaaccattc aggaacgcaa ccgcagctta gaccaaaaca   6120
ggaagctatg ggcctgctta ggtgacgtct ctcgtcaggt tgaatggcat ggtcgctggc   6180
tggatgcaga aagctggaag tgtgtgttta ccgcagcatt aaagcagcag gatgttgttc   6240
ctaaccttgc cgggaatggc tttgtggtaa taggccagtc aaccagcagg atgcgtgtag   6300
gcgaatttgc ggagctatta gagcttatac aggcattcgg tacagagcgt ggcgttaagt   6360
ggtcagacga agcgagactg gctctggagt ggaaagcgag atggggagac agggctgcat   6420
gataaatgtc gttagtttct ccggtggcag gacgtcagca tatttgctct ggctaatgga   6480
gcaaaagcga cgggcaggta aagacgtgca ttacgttttc atggatacag gttgtgaaca   6540
tccaatgaca tatcggtttg tcagggaagt tgtgaagttc tgggatatac cgctcaccgt   6600
attgcaggtt gatatcaacc cggagcttgg acagccaaat ggttatacgg tatgggaacc   6660
```

-continued

```
aaaggatatt cagacgcgaa tgcctgttct gaagccattt atcgatatgg taaagaaata   6720
tggcactcca tacgtcggcg gcgcgttctg cactgacaga ttaaaactcg ttcccttcac   6780
caaatactgt gatgaccatt tcgggcgagg gaattacacc acgtggattg gcatcagagc   6840
tgatgaaccg aagcggctaa agccaaagcc tggaatcaga tatcttgctg aactgtcaga   6900
ctttgagaag gaagatatcc tcgcatggtg gaagcaacaa ccattcgatt tgcaaatacc   6960
ggaacatctc ggtaactgca tattctgcat taaaaaatca acgcaaaaaa tcggacttgc   7020
ctgcaaagat gaggagggat tgcagcgtgt ttttaatgag gtcatcacgg gatcccatgt   7080
gcgtgacgga catcgggaaa cgccaaagga gattatgtac cgaggaagaa tgtcgctgga   7140
cggtatcgcg aaaatgtatt cagaaaatga ttatcaagcc ctgtatcagg acatggtacg   7200
agctaaaaga ttcgataccg gctcttgttc tgagtcatgc gaaatatttg gagggcagct   7260
tgatttcgac ttcgggaggg aagctgcatg atgcgatgtt atcggtgcgg tgaatgcaaa   7320
gaagataacc gcttccgacc aaatcaacct tactggaatc gatggtgtct ccggtgtgaa   7380
agaacaccaa caggggtgtt accactaccg caggaaaagg aggacgtgtg gcgagacagc   7440
gacgaagtat caccgacata atctgcgaaa actgcaaata ccttccaacg aaacgcacca   7500
gaaataaacc caagccaatc ccaaaagaat ctgacgtaaa aaccttcaac tacacggctc   7560
acctgtggga tatccggtgg ctaagacgtc gtgcgaggaa aacaaggtga ttgaccaaaa   7620
tcgaagttac gaacaagaaa gcgtcgagcg agctttaacg tgcgctaact gcggtcagaa   7680
gctgcatgtg ctggaagttc acgtgtgtga gcactgctgc gcagaactga tgagcgatcc   7740
gaatagctcg atgcacgagg aagaagatga tggctaaacc agcgcgaaga cgatgtaaaa   7800
acgatgaatg ccgggaatgg tttcaccctg cattcgctaa tcagtggtgg tgctctccag   7860
agtgtggaac caagatagca ctcgaacgac gaagtaaaga acgcgaaaaa gcggaaaaag   7920
cagcagagaa gaaacgacga cgagaggagc agaaacagaa agataaactt aagattcgaa   7980
aactcgcctt aaagccccgc agttactgga ttaaacaagc ccaacaagcc gtaaacgcct   8040
tcatcagaga aagagaccgc gacttaccat gtatctcgtg cggaacgctc acgtctgctc   8100
agtgggatgc cggacattac cggacaactg ctgcggcacc tcaactccga tttaatgaac   8160
gcaatattca caagcaatgc gtggtgtgca accagcacaa aagcggaaat ctcgttccgt   8220
atcgcgtcga actgattagc cgcatcgggc aggaagcagt agacgaaatc gaatcaaacc   8280
ataaccgcca tcgctggact atcgaagagt gcaaggcgat caaggcagag taccaacaga   8340
aactcaaaga cctgcgaaat agcagaagtg aggccgcatg acgttctcag taaaaaccat   8400
tccagacatg ctcgttgaag catacggaaa tcagacagaa gtagcacgca gactgaaatg   8460
tagtcgcggt acggtcagaa aatacgttga tgataaagac gggaaaatgc acgccatcgt   8520
caacgacgtt ctcatggttc atcgcggatg gagtgaaaga gatgcgctat tacgaaaaaa   8580
ttgatggcag caaataccga aatatttggg tagttggcga tctgcacgga tgctacacga   8640
acctgatgaa caaactggat acgattggat tcgacaacaa aaaagacctg cttatctcgg   8700
tgggcgattt ggttgatcgt ggtgcagaga acgttgaatg cctggaatta atcacattcc   8760
cctggttcag agctgtacgt ggaaaccatg agcaaatgat gattgatggc ttatcagagc   8820
gtggaaacgt taatcactgg ctgcttaatg gcggtggctg gttctttaat ctcgattacg   8880
acaaagaaat tctggctaaa gctcttgccc ataaagcaga tgaacttccg ttaatcatcg   8940
aactggtgag caaagataaa aaatatgtta tctgccacgc cgattatccc tttgacgaat   9000
acgagtttgg aaagccagtt gatcatcagc aggtaatctg gaaccgcgaa cgaatcagca   9060
```

```
actcacaaaa cgggatcgtg aaagaaatca aaggcgcgga cacgttcatc tttggtcata   9120
cgccagcagt gaaaccactc aagtttgcca accaaatgta tatcgatacc ggcgcagtgt   9180
tctgcggaaa cctaacattg attcaggtac agggagaagg cgcatgagac tcgaaagcgt   9240
agctaaattt cattcgccaa aaagcccgat gatgagcgac tcaccacggg ccacggcttc   9300
tgactctctt tccggtactg atgtgatggc tgctatgggg atggcgcaat cacaagccgg   9360
attcggtatg gctgcattct gcggtaagca cgaactcagc cagaacgaca aacaaaaggc   9420
tatcaactat ctgatgcaat ttgcacacaa ggtatcgggg aaataccgtg gtgtggcaaa   9480
gcttgaagga aatactaagg caaaggtact gcaagtgctc gcaacattcg cttatgcgga   9540
ttattgccgt agtgccgcga cgccgggggc aagatgcaga gattgccatg gtacaggccg   9600
tgcggttgat attgccaaaa cagagctgtg ggggagagtt gtcgagaaag agtgcggaag   9660
atgcaaaggc gtcggctatt caaggatgcc agcaagcgca gcatatcgcg ctgtgacgat   9720
gctaatccca aaccttaccc aacccacctg gtcacgcact gttaagccgc tgtatgacgc   9780
tctggtggtg caatgccaca aagaagagtc aatcgcagac aacattttga atgcggtcac   9840
acgttagcag catgattgcc acggatggca acatattaac ggcatgatat tgacttattg   9900
aataaaattg ggtaaatttg actcaacgat gggttaattc gctcgttgtg gtagtgagat   9960
gaaaagaggc ggcgcttact accgattccg cctagttggt cacttcgacg tatcgtctgg  10020
aactccaacc atcgcaggca gagaggtctg caaaatgcaa tcccgaaaca gttcgcaggt  10080
aatagttaga gcctgcataa cggtttcggg atttttttata tctgcacaac aggtaagagc  10140
attgagtcga taatcgtgaa gagtcggcga gcctggttag ccagtgctct ttccgttgtg  10200
ctgaattaag cgaataccgg aagcagaacc ggatcaccaa atgcgtacag gcgtcatcgc  10260
cgcccagcaa cagcacaacc caaactgagc cgtagccact gtctgtcctg aattcattag  10320
taatagttac gctgcggcct tttacacatg accttcgtga aagcgggtgg caggaggtcg  10380
cgctaacaac ctcctgccgt tttgcccgtg catatcggtc acgaacaaat ctgattacta  10440
aacacagtag cctggatttg ttctatcagt aatcgacctt attcctaatt aaatagagca  10500
aatcccctta ttgggggtaa gacatgaaga tgccagaaaa acatgacctg ttggccgcca  10560
ttctcgcggc aaaggaacaa ggcatcgggg caatccttgc gtttgcaatg gcgtaccttc  10620
gcggcagata taatggcggt gcgtttacaa aaacagtaat cgacgcaacg atgtgcgcca  10680
ttatcgcctg gttcattcgt gaccttctcg acttcgccgg actaagtagc aatctcgctt  10740
atataacgag cgtgtttatc ggctacatcg gtactgactc gattggttcg cttatcaaac  10800
gcttcgctgc taaaaaagcc ggagtagaag atggtagaaa tcaataatca acgtaaggcg  10860
ttcctcgata tgctggcgtg gtcggaggga actgataacg gacgtcagaa aaccagaaat  10920
catggttatg acgtcattgt aggcggagag ctatttactg attactccga tcaccctcgc  10980
aaacttgtca cgctaaaccc aaaactcaaa tcaacaggcg cttaagactg gccgtcgttt  11040
tacaacacag aaagagtttg tagaaacgca aaaaggccat ccgtcagggg ccttctgctt  11100
agtttgatgc ctggcagttc cctactctcg ccttccgctt cctcgctcac tgactcgctg  11160
cgctcggtcg ttcggctgcg gcgagcggta tcagctcact caaaggcggt aatacggtta  11220
tccacagaat caggggataa cgcaggaaag aacatgtgag caaaaggcca gcaaaaggcc  11280
aggaaccgta aaaaggccgc gttgctggcg tttttccata ggctccgccc ccctgacgag  11340
catcacaaaa atcgacgctc aagtcagagg tggcgaaacc cgacaggact ataaagatac  11400
```

caggcgtttc cccctggaag ctccctcgtg cgctctcctg ttccgaccct gccgcttacc 11460
ggatacctgt ccgcctttct cccttcggga agcgtggcgc tttctcatag ctcacgctgt 11520
aggtatctca gttcggtgta ggtcgttcgc tccaagctgg gctgtgtgca cgaacccccc 11580
gttcagcccg accgctgcgc cttatccggt aactatcgtc ttgagtccaa cccggtaaga 11640
cacgacttat cgccactggc agcagccact ggtaacagga ttagcagagc gaggtatgta 11700
ggcggtgcta cagagttctt gaagtggtgg gctaactacg gctacactag aagaacagta 11760
tttggtatct gcgctctgct gaagccagtt accttcggaa aaagagttgg tagctcttga 11820
tccggcaaac aaaccaccgc tggtagcggt ggtttttttg tttgcaagca gcagattacg 11880
cgcagaaaaa aaggatctca agaagatcct ttgatctttt ctacggggtc tgacgctcag 11940
tggaacgacg cgcgcgtaac tcacgttaag ggattttggt catgagcttg cgccgtcccg 12000
tcaagtcagc gtaatgctct gcttt 12025

<210> SEQ ID NO 6
<211> LENGTH: 12454
<212> TYPE: DNA
<213> ORGANISM: Artificial Sequence
<220> FEATURE:
<223> OTHER INFORMATION: constructed sequence

<400> SEQUENCE: 6
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320
ggcctcagtg agcgagcgag cgcgcagaga gggagtggcc aactccatca ctaggggttc 1380
cttgtagtta atgattaacc cgccatgcta cttatctacg tagcaagcta gctagttatt 1440

-continued

```
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tatttttttaa ttattttgtg cagcgatggg ggcggggggg ggggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc gggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatgg   3120
cggacgaggc ggccctcgcc cttcagcccg gcggctcccc ctcggcggcg ggggccgaca   3180
gggaggccgc gtcgtccccc gccggggagc cgctccgcaa gaggccgcgg agagatggtc   3240
ccggcctcga gcggagcccg ggcgagcccg gtggggcggc cccagagcgt gaggtgccgg   3300
cggcggccag gggctgcccg ggtgcggcgg cggcggcgct gtggcgggag gcggaggcag   3360
aggcggcggc ggcaggcggg gagcaagagg cccaggcgac tgcggcggct ggggaaggag   3420
acaatgggcc gggcctgcag ggcccatctc gggagccacc gctggccgac aacttgtacg   3480
acgaagacga cgacgacgag ggcgaggagg aggaagaggc ggcggcggcg gcgattgggt   3540
accgagataa ccttctgttc ggtgatgaaa ttatcactaa tggttttcat tcctgtgaaa   3600
gtgatgagga ggatagagcc tcacatgcaa gctctagtga ctggactcca aggccacgga   3660
taggtccata tacttttgtt cagcaacatc ttatgattgg cacagatcct cgaacaattc   3720
ttaaagattt attgccggaa acaatacctc cacctgagtt ggatgatatg acactgtggc   3780
```

-continued

```
agattgttat taatatcctt tcagaaccac caaaaaggaa aaaaagaaaa gatattaata   3840
caattgaaga tgctgtgaaa ttactgcaag agtgcaaaaa aattatagtt ctaactggag   3900
ctggggtgtc tgtttcatgt ggaatacctg acttcaggtc aagggatggt atttatgctc   3960
gccttgctgt agacttccca gatcttccag atcctcaagc gatgtttgat attgaatatt   4020
tcagaaaaga tccaagacca ttcttcaagt ttgcaaagga aatatatcct ggacaattcc   4080
agccatctct ctgtcacaaa ttcatagcct tgtcagataa ggaaggaaaa ctacttcgca   4140
actataccca gaacatagac acgctggaac aggttgcggg aatccaaagg ataattcagt   4200
gtcatggttc ctttgcaaca gcatcttgcc tgatttgtaa atacaaagtt gactgtgaag   4260
ctgtacgagg agatattttt aatcaggtag ttcctcgatg tcctaggtgc ccagctgatg   4320
aaccgcttgc tatcatgaaa ccagagattg tgtttttgg tgaaaattta ccagaacagt   4380
ttcatagagc catgaagtat gacaaagatg aagttgacct cctcattgtt attgggtctt   4440
ccctcaaagt aagaccagta gcactaattc caagttccat accccatgaa gtgcctcaga   4500
tattaattaa tagagaacct ttgcctcatc tgcattttga tgtagagctt cttggagact   4560
gtgatgtcat aattaatgaa ttgtgtcata ggttaggtgg tgaatatgcc aaactttgct   4620
gtaaccctgt aaagctttca gaaattactg aaaaacctcc acgaacacaa aaagaattgg   4680
cttatttgtc agagttgcca cccacacctc ttcatgtttc agaagactca agttcaccag   4740
aaagaacttc accaccagat tcttcagtga ttgtcacact tttagaccaa gcagctaaga   4800
gtaatgatga tttagatgtg tctgaatcaa aaggttgtat ggaagaaaaa ccacaggaag   4860
tacaaacttc taggaatgtt gaaagtattg ctgaacagat ggaaaatccg gatttgaaga   4920
atgttggttc tagtactggg gagaaaaatg aaagaacttc agtggctgga acagtgagaa   4980
aatgctggcc taatagagtg gcaaaggagc agattagtag gcggcttgat ggtaatcagt   5040
atctgttttt gccaccaaat cgttacattt tccatggcgc tgaggtatat tcagactctg   5100
aagatgacgt cttatcctct agttcttgtg gcagtaacag tgatagtggg acatgccaga   5160
gtccaagttt agaagaaccc atggaggatg aaagtgaaat tgaagaattc tacaatggct   5220
tagaagatga gcctgatgtt ccagagagag ctggaggagc tggatttggg actgatggag   5280
atgatcaaga ggcaattaat gaagctatat ctgtgaaaca ggaagtaaca gacatgaact   5340
atccatcaaa caaatcagac tacaaagacc atgacggtga ttataaagat catgacatcg   5400
attacaagga tgacgatgac aagtgatgag gccgcatagt actgcggatc ctgcagatct   5460
gcctcgactg tgccttctag ttgccagcca tctgttgttt gcccctcccc cgtgccttcc   5520
ttgaccctgg aaggtgccac tcccactgtc ctttcctaat aaaatgagga aattgcatcg   5580
cattgtctga gtaggtgtca ttctattctg gggggtgggg tggggcagga cagcaagggg   5640
gaggattggg aagacaatag caggcatgct ggggactcga gttctacgta gataagtagc   5700
atggcgggtt aatcattaac tacaaggaac ccctagtgat ggagttggcc actccctctc   5760
tgcgcgctcg ctcgctcact gaggccgggc gaccaaaggt cgcccgacgc ccgggctttg   5820
cccgggcggc ctcagtgagc gagcgagcgc gcagccttaa ttaacctaag gaaaatgaag   5880
tgaagttcct atactttcta gagaatagga acttctatag tgagtcgaat aagggcgaca   5940
caaaatttat tctaaatgca taataaatac tgataacatc ttatagtttg tattatattt   6000
tgtattatcg ttgacatgta taattttgat atcaaaaact gattttccct ttattatttt   6060
cgagatttat tttcttaatt ctctttaaca aactagaaat attgtatata caaaaaatca   6120
taaataatag atgaatagtt taattatagg tgttcatcaa tcgaaaaagc aacgtatctt   6180
```

-continued

```
atttaaagtg cgttgctttt ttctcattta taaggttaaa taattctcat atatcaagca   6240
aagtgacagg cgcccttaaa tattctgaca aatgctcttt ccctaaactc cccccataaa   6300
aaaacccgcc gaagcgggtt tttacgttat ttgcggatta acgattactc gttatcagaa   6360
ccgcccaggg ggcccgagct taaccttttt atttggggga gagggaagtc atgaaaaaac   6420
taacctttga aattcgatct ccagcacatc agcaaaacgc tattcacgca gtacagcaaa   6480
tccttccaga cccaaccaaa ccaatcgtag taaccattca ggaacgcaac cgcagcttag   6540
accaaaacag gaagctatgg gcctgcttag gtgacgtctc tcgtcaggtt gaatggcatg   6600
gtcgctggct ggatgcagaa agctggaagt gtgtgtttac cgcagcatta aagcagcagg   6660
atgttgttcc taaccttgcc gggaatggct ttgtggtaat aggccagtca accagcagga   6720
tgcgtgtagg cgaatttgcg gagctattag agcttataca ggcattcggt acagagcgtg   6780
gcgttaagtg gtcagacgaa gcgagactgg ctctggagtg gaaagcgaga tggggagaca   6840
gggctgcatg ataaatgtcg ttagtttctc cggtggcagg acgtcagcat atttgctctg   6900
gctaatggag caaaagcgac gggcaggtaa agacgtgcat tacgttttca tggatacagg   6960
ttgtgaacat ccaatgacat atcggtttgt cagggaagtt gtgaagttct gggatatacc   7020
gctcaccgta ttgcaggttg atatcaaccc ggagcttgga cagccaaatg gttatacggt   7080
atgggaacca aaggatattc agacgcgaat gcctgttctg aagccattta tcgatatggt   7140
aaagaaatat ggcactccat acgtcggcgg cgcgttctgc actgacagat taaaactcgt   7200
tcccttcacc aaatactgtg atgaccattt cgggcgaggg aattacacca cgtggattgg   7260
catcagagct gatgaaccga agcggctaaa gccaaagcct ggaatcagat atcttgctga   7320
actgtcagac tttgagaagg aagatatcct cgcatggtgg aagcaacaac cattcgattt   7380
gcaaataccg gaacatctcg gtaactgcat attctgcatt aaaaaatcaa cgcaaaaaat   7440
cggacttgcc tgcaaagatg aggagggatt gcagcgtgtt tttaatgagg tcatcacggg   7500
atcccatgtg cgtgacggac atcgggaaac gccaaaggag attatgtacc gaggaagaat   7560
gtcgctggac ggtatcgcga aaatgtattc agaaaatgat tatcaagccc tgtatcagga   7620
catggtacga gctaaaagat tcgataccgg ctcttgttct gagtcatgcg aaatatttgg   7680
agggcagctt gatttcgact tcgggaggga agctgcatga tgcgatgtta tcggtgcggt   7740
gaatgcaaag aagataaccg cttccgacca aatcaacctt actggaatcg atggtgtctc   7800
cggtgtgaaa gaacaccaac aggggtgtta ccactaccgc aggaaaagga ggacgtgtgg   7860
cgagacagcg acgaagtatc accgacataa tctgcgaaaa ctgcaaatac cttccaacga   7920
aacgcaccag aaataaaccc aagccaatcc caaaagaatc tgacgtaaaa accttcaact   7980
acacggctca cctgtgggat atccggtggc taagacgtcg tgcgaggaaa acaaggtgat   8040
tgaccaaaat cgaagttacg aacaagaaag cgtcgagcga gctttaacgt gcgctaactg   8100
cggtcagaag ctgcatgtgc tggaagttca cgtgtgtgag cactgctgcg cagaactgat   8160
gagcgatccg aatagctcga tgcacgagga agaagatgat ggctaaacca gcgcgaagac   8220
gatgtaaaaa cgatgaatgc cgggaatggt ttcaccctgc attcgctaat cagtggtggt   8280
gctctccaga gtgtggaacc aagatagcac tcgaacgacg aagtaaagaa cgcgaaaaag   8340
cggaaaaagc agcagagaag aaacgacgac gagaggagca gaaacagaaa gataaactta   8400
agattcgaaa actcgcctta aagccccgca gttactggat taaacaagcc caacaagccg   8460
taaacgcctt catcagagaa agagaccgcg acttaccatg tatctcgtgc ggaacgctca   8520
```

-continued

```
cgtctgctca gtgggatgcc ggacattacc ggacaactgc tgcggcacct caactccgat   8580
ttaatgaacg caatattcac aagcaatgcg tggtgtgcaa ccagcacaaa agcggaaatc   8640
tcgttccgta tcgcgtcgaa ctgattagcc gcatcgggca ggaagcagta gacgaaatcg   8700
aatcaaacca taaccgccat cgctggacta tcgaagagtg caaggcgatc aaggcagagt   8760
accaacagaa actcaaagac ctgcgaaata gcagaagtga ggccgcatga cgttctcagt   8820
aaaaaccatt ccagacatgc tcgttgaagc atacggaaat cagacagaag tagcacgcag   8880
actgaaatgt agtcgcggta cggtcagaaa atacgttgat gataaagacg ggaaaatgca   8940
cgccatcgtc aacgacgttc tcatggttca tcgcggatgg agtgaaagag atgcgctatt   9000
acgaaaaaat tgatggcagc aaataccgaa atatttgggt agttggcgat ctgcacggat   9060
gctacacgaa cctgatgaac aaactggata cgattggatt cgacaacaaa aaagacctgc   9120
ttatctcggt gggcgatttg gttgatcgtg gtgcagagaa cgttgaatgc ctggaattaa   9180
tcacattccc ctggttcaga gctgtacgtg gaaaccatga gcaaatgatg attgatggct   9240
tatcagagcg tggaaacgtt aatcactggc tgcttaatgg cggtggctgg ttctttaatc   9300
tcgattacga caaagaaatt ctggctaaag ctcttgccca taaagcagat gaacttccgt   9360
taatcatcga actggtgagc aaagataaaa aatatgttat ctgccacgcc gattatccct   9420
ttgacgaata cgagtttgga aagccagttg atcatcagca ggtaatctgg aaccgcgaac   9480
gaatcagcaa ctcacaaaac gggatcgtga aagaaatcaa aggcgcggac acgttcatct   9540
ttggtcatac gccagcagtg aaaccactca agtttgccaa ccaaatgtat atcgataccg   9600
gcgcagtgtt ctgcggaaac ctaacattga ttcaggtaca gggagaaggc gcatgagact   9660
cgaaagcgta gctaaatttc attcgccaaa aagcccgatg atgagcgact caccacgggc   9720
cacggcttct gactctcttt ccggtactga tgtgatggct gctatgggga tggcgcaatc   9780
acaagccgga ttcggtatgg ctgcattctg cggtaagcac gaactcagcc agaacgacaa   9840
acaaaaggct atcaactatc tgatgcaatt tgcacacaag gtatcgggga aataccgtgg   9900
tgtggcaaag cttgaaggaa atactaaggc aaaggtactg caagtgctcg caacattcgc   9960
ttatgcggat tattgccgta gtgccgcgac gccgggggca agatgcagag attgccatgg  10020
tacaggccgt gcggttgata ttgccaaaac agagctgtgg gggagagttg tcgagaaaga  10080
gtgcggaaga tgcaaaggcg tcggctattc aaggatgcca gcaagcgcag catatcgcgc  10140
tgtgacgatg ctaatcccaa accttaccca acccacctgg tcacgcactg ttaagccgct  10200
gtatgacgct ctggtggtgc aatgccacaa agaagagtca atcgcagaca acattttgaa  10260
tgcggtcaca cgttagcagc atgattgcca cggatggcaa catattaacg gcatgatatt  10320
gacttattga ataaaattgg gtaaatttga ctcaacgatg ggttaattcg ctcgttgtgg  10380
tagtgagatg aaaagaggcg gcgcttacta ccgattccgc ctagttggtc acttcgacgt  10440
atcgtctgga actccaacca tcgcaggcag agaggtctgc aaaatgcaat cccgaaacag  10500
ttcgcaggta atagttagag cctgcataac ggtttcggga tttttatat ctgcacaaca  10560
ggtaagagca ttgagtcgat aatcgtgaag agtcggcgag cctggttagc cagtgctctt  10620
tccgttgtgc tgaattaagc gaataccgga agcagaaccg gatcaccaaa tgcgtacagg  10680
cgtcatcgcc gcccagcaac agcacaaccc aaactgagcc gtagccactg tctgtcctga  10740
attcattagt aatagttacg ctgcggcctt ttacacatga ccttcgtgaa agcgggtggc  10800
aggaggtcgc gctaacaacc tcctgccgtt ttgcccgtgc atatcggtca cgaacaaatc  10860
tgattactaa acacagtagc ctggatttgt tctatcagta atcgacctta ttcctaatta  10920
```

aatagagcaa atccccttat tgggggtaag acatgaagat gccagaaaaa catgacctgt 10980
tggccgccat tctcgcggca aaggaacaag gcatcggggc aatccttgcg tttgcaatgg 11040
cgtaccttcg cggcagatat aatggcggtg cgtttacaaa aacagtaatc gacgcaacga 11100
tgtgcgccat tatcgcctgg ttcattcgtg accttctcga cttcgccgga ctaagtagca 11160
atctcgctta tataacgagc gtgtttatcg gctacatcgg tactgactcg attggttcgc 11220
ttatcaaacg cttcgctgct aaaaaagccg gagtagaaga tggtagaaat caataatcaa 11280
cgtaaggcgt tcctcgatat gctggcgtgg tcggagggaa ctgataacgg acgtcagaaa 11340
accagaaatc atggttatga cgtcattgta ggcggagagc tatttactga ttactccgat 11400
caccctcgca aacttgtcac gctaaaccca aaactcaaat caacaggcgc ttaagactgg 11460
ccgtcgtttt acaacacaga aagagtttgt agaaacgcaa aaaggccatc cgtcaggggc 11520
cttctgctta gtttgatgcc tggcagttcc ctactctcgc cttccgcttc ctcgctcact 11580
gactcgctgc gctcggtcgt tcggctgcgg cgagcggtat cagctcactc aaaggcggta 11640
atacggttat ccacagaatc aggggataac gcaggaaaga acatgtgagc aaaaggccag 11700
caaaaggcca ggaaccgtaa aaaggccgcg ttgctggcgt ttttccatag gctccgcccc 11760
cctgacgagc atcacaaaaa tcgacgctca agtcagaggt ggcgaaaccc gacaggacta 11820
taaagatacc aggcgtttcc ccctggaagc tccctcgtgc gctctcctgt tccgaccctg 11880
ccgcttaccg gatacctgtc cgcctttctc ccttcgggaa gcgtggcgct ttctcatagc 11940
tcacgctgta ggtatctcag ttcggtgtag gtcgttcgct ccaagctggg ctgtgtgcac 12000
gaaccccccg ttcagcccga ccgctgcgcc ttatccggta actatcgtct tgagtccaac 12060
ccggtaagac acgacttatc gccactggca gcagccactg gtaacaggat tagcagagcg 12120
aggtatgtag gcggtgctac agagttcttg aagtggtggg ctaactacgg ctacactaga 12180
agaacagtat ttggtatctg cgctctgctg aagccagtta ccttcggaaa aagagttggt 12240
agctcttgat ccggcaaaca aaccaccgct ggtagcggtg gtttttttgt ttgcaagcag 12300
cagattacgc gcagaaaaaa aggatctcaa gaagatcctt tgatcttttc tacggggtct 12360
gacgctcagt ggaacgacgc gcgcgtaact cacgttaagg gattttggtc atgagcttgc 12420
gccgtcccgt caagtcagcg taatgctctg cttt 12454

<210> SEQ ID NO 7
<211> LENGTH: 1815
<212> TYPE: DNA
<213> ORGANISM: Artificial Sequence
<220> FEATURE:
<223> OTHER INFORMATION: constructed sequence

<400> SEQUENCE: 7
atgatggacc tcgaactgcc gccgcctggc ctcccaagcc aacaggatat ggacctgatt 60
gacatcctgt ggcggcagga cattgatctg ggtgtcagcc gcgaggtgtt cgatttctcg 120
caacgccgga aggaatacga actcgagaag cagaagaagc tcgagaaaga gcggcaggaa 180
cagctccaga aggaacagga aaaggccttc ttcgcacaac ttcagctgga cgaggaaacc 240
ggcgaattcc tgcctattca accagcccag cacatccaga gcgaaacctc cggcagcgcc 300
aactattccc aagtggctca catcccgaag tccgacgccc tgtactttga cgattgtatg 360
cagctgctgg cacagacctt ccccttcgtc gatgataacg aggtgtcctc cgcgacgttt 420
cagtcgctgg tccccgacat ccccggtcat atcgagagcc ctgtgttcat cgccaccaac 480

-continued

```
caggctcagt cccccgaaac ctcagtggca caagtggcgc cggtggactt ggacggcatg    540

cagcaagaca tcgaacaagt ctgggaggag cttctgtcca tccccgagct gcaatgcctc    600

aacatcgaga atgacaagct cgtggagact actatggtcc cgtccccgga agctaagctg    660

accgaggtcg acaactacca tttctactcc tcaatcccct ccatggaaaa ggaagtcgga    720

aactgctcgc ctcatttcct caacgccttc gaggactcct tctcgtcaat tctgtccact    780

gaggacccca accagctgac cgtcaattcc ttgaactcgg atgccactgt gaacaccgac    840

ttcggcgacg aattctacag cgcgttcatc gccgaaccga gcatctcgaa ctccatgccc    900

tcgcccgcca ccttgtcaca ttccctgtct gagctgctga acgggccgat tgacgtgtca    960

gacctgagcc tgtgtaaagc cttcaaccag aatcacccgg agtcgactgc cgaattcaac   1020

gactcggact ccgggatctc actgaacact agccctagcg tggcctcgcc cgaacactcc   1080

gtggagtcca gctcctatgg cgatactctt ctgggtctgt ccgactccga agtggaagaa   1140

ctggactctg cccccggaag cgtgaaacag aacggaccta agaccccagt gcactcctcc   1200

ggggatatgg tgcagccgtt gtcaccgagc caggggcaat ccacccacgt gcatgacgct   1260

cagtgcgaga acacccccga gaaagaactc ccagtgtccc ccggacaccg aaagaccccg   1320

tttaccaagg acaagcactc ctcacggctg gaagcacacc ttactcggga tgaactcaga   1380

gccaaggccc tccacattcc tttccccgtg gagaagatta tcaatctccc tgtggtggat   1440

ttcaacgaga tgatgagcaa ggaacagttc aacgaagcgc agctggcgct gatcagggac   1500

atcaggcgca gaggaaagaa caaagtggcc gcccaaaact gccggaagag aaagctcgaa   1560

aacatcgtgg agctcgaaca ggacttggac cacctgaagg atgaaaaaga aaagctgctg   1620

aaggagaagg gagagaacga caagtccctc catctgctga agaagcagct gagcacactg   1680

tacctcgaag tgttttccat gctgcgcgat gaggatggaa agccgtactc cccgtccgaa   1740

tactcgctgc aacagacgcg cgacggaaac gtgttcctcg tgccaaagtc caagaagcct   1800

gacgtgaaga agaac                                                    1815
```

<210> SEQ ID NO 8
<211> LENGTH: 11951
<212> TYPE: DNA
<213> ORGANISM: Artificial Sequence
<220> FEATURE:
<223> OTHER INFORMATION: constructed sequence

<400> SEQUENCE: 8

```
tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720
```

```
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tattttttaa ttattttgtg cagcgatggg ggcggggggg ggggggggggc  1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cgggggtgg cggcaggtgg gggtgccggg cggggcgggg ccgcctcggg ccggggaggg    2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
```

-continued

```
ctaaccttct tctctttcct ctcctgacag gttggtgtac actagcggcc gccaccatga   3120
tggacctcga actgccgccg cctggcctcc caagccaaca ggatatggac ctgattgaca   3180
tcctgtggcg gcaggacatt gatctgggtg tcagccgcga ggtgttcgat ttctcgcaac   3240
gccggaagga atacgaactc gagaagcaga agaagctcga gaaagagcgg caggaacagc   3300
tccagaagga acaggaaaag gccttcttcg cacaacttca gctggacgag gaaaccggcg   3360
aattcctgcc tattcaacca gcccagcaca tccagagcga aacctccggc agcgccaact   3420
attcccaagt ggctcacatc ccgaagtccg acgccctgta ctttgacgat tgtatgcagc   3480
tgctggcaca gaccttcccc ttcgtcgatg ataacgaggt gtcctccgcg acgtttcagt   3540
cgctggtccc cgacatcccc ggtcatatcg agagccctgt gttcatcgcc accaaccagg   3600
ctcagtcccc cgaaacctca gtggcacaag tggcgccggt ggacttggac ggcatgcagc   3660
aagacatcga acaagtctgg gaggagcttc tgtccatccc cgagctgcaa tgcctcaaca   3720
tcgagaatga caagctcgtg gagactacta tggtcccgtc cccggaagct aagctgaccg   3780
aggtcgacaa ctaccatttc tactcctcaa tcccctccat ggaaaaggaa gtcggaaact   3840
gctcgcctca tttcctcaac gccttcgagg actccttctc gtcaattctg tccactgagg   3900
accccaacca gctgaccgtc aattccttga actcggatgc cactgtgaac accgacttcg   3960
gcgacgaatt ctacagcgcg ttcatcgccg aaccgagcat ctcgaactcc atgccctcgc   4020
ccgccacctt gtcacattcc ctgtctgagc tgctgaacgg gccgattgac gtgtcagacc   4080
tgagcctgtg taaagccttc aaccagaatc acccggagtc gactgccgaa ttcaacgact   4140
cggactccgg gatctcactg aacactagcc ctagcgtggc ctcgcccgaa cactccgtgg   4200
agtccagctc ctatggcgat actcttctgg gtctgtccga ctccgaagtg gaagaactgg   4260
actctgcccc cggaagcgtg aaacagaacg gacctaagac cccagtgcac tcctccgggg   4320
atatggtgca gccgttgtca ccgagccagg ggcaatccac ccacgtgcat gacgctcagt   4380
gcgagaacac ccccgagaaa gaactcccag tgtcccccgg acaccgaaag accccgttta   4440
ccaaggacaa gcactcctca cggctggaag cacaccttac tcgggatgaa ctcagagcca   4500
aggccctcca cattcctttc cccgtggaga agattatcaa tctccctgtg gtggatttca   4560
acgagatgat gagcaaggaa cagttcaacg aagcgcagct ggcgctgatc agggacatca   4620
ggcgcagagg aaagaacaaa gtggccgccc aaaactgccg gaagagaaag ctcgaaaaca   4680
tcgtggagct cgaacaggac ttggaccacc tgaaggatga aaaagaaaag ctgctgaagg   4740
agaagggaga gaacgacaag tccctccatc tgctgaagaa gcagctgagc acactgtacc   4800
tcgaagtgtt ttccatgctg cgcgatgagg atggaaagcc gtactccccg tccgaatact   4860
cgctgcaaca gacgcgcgac ggaaacgtgt tcctcgtgcc aaagtccaag aagcctgacg   4920
tgaagaagaa ctgaagtact gcggatcctg cagatctgcc tcgactgtgc cttctagttg   4980
ccagccatct gttgtttgcc cctcccccgt gccttccttg accctggaag gtgccactcc   5040
cactgtcctt tcctaataaa atgaggaaat tgcatcgcat tgtctgagta ggtgtcattc   5100
tattctgggg ggtggggtgg ggcaggacag caagggggag gattgggaag acaatagcag   5160
gcatgctggg gactcgagtt ctacgtagat aagtagcatg gcgggttaat cattaactac   5220
aaggaacccc tagtgatgga gttggccact ccctctctgc gcgctcgctc gctcactgag   5280
gccgggcgac caaaggtcgc ccgacgcccg ggctttgccc gggcggcctc agtgagcgag   5340
cgagcgcgca gccttaatta acctaaggaa aatgaagtga agttcctata ctttctagag   5400
aataggaact tctatagtga gtcgaataag ggcgacacaa aatttattct aaatgcataa   5460
```

-continued

```
taaatactga taacatctta tagtttgtat tatattttgt attatcgttg acatgtataa   5520
ttttgatatc aaaaactgat tttcccttta ttattttcga gatttatttt cttaattctc   5580
tttaacaaac tagaaatatt gtatatacaa aaaatcataa ataatagatg aatagtttaa   5640
ttataggtgt tcatcaatcg aaaaagcaac gtatcttatt taaagtgcgt tgcttttttc   5700
tcatttataa ggttaaataa ttctcatata tcaagcaaag tgacaggcgc ccttaaatat   5760
tctgacaaat gctctttccc taaactcccc ccataaaaaa acccgccgaa gcgggttttt   5820
acgttatttg cggattaacg attactcgtt atcagaaccg cccagggggc ccgagcttaa   5880
cctttttatt tgggggagag ggaagtcatg aaaaaactaa cctttgaaat tcgatctcca   5940
gcacatcagc aaaacgctat tcacgcagta cagcaaatcc ttccagaccc aaccaaacca   6000
atcgtagtaa ccattcagga acgcaaccgc agcttagacc aaaacaggaa gctatgggcc   6060
tgcttaggtg acgtctctcg tcaggttgaa tggcatggtc gctggctgga tgcagaaagc   6120
tggaagtgtg tgtttaccgc agcattaaag cagcaggatg ttgttcctaa ccttgccggg   6180
aatggctttg tggtaatagg ccagtcaacc agcaggatgc gtgtaggcga atttgcggag   6240
ctattagagc ttatacaggc attcggtaca gagcgtggcg ttaagtggtc agacgaagcg   6300
agactggctc tggagtggaa agcgagatgg ggagacaggg ctgcatgata aatgtcgtta   6360
gtttctccgg tggcaggacg tcagcatatt tgctctggct aatggagcaa aagcgacggg   6420
caggtaaaga cgtgcattac gttttcatgg atacaggttg tgaacatcca atgacatatc   6480
ggtttgtcag ggaagttgtg aagttctggg atataccgct caccgtattg caggttgata   6540
tcaacccgga gcttggacag ccaaatggtt atacggtatg ggaaccaaag gatattcaga   6600
cgcgaatgcc tgttctgaag ccatttatcg atatggtaaa gaaatatggc actccatacg   6660
tcggcggcgc gttctgcact gacagattaa aactcgttcc cttcaccaaa tactgtgatg   6720
accatttcgg gcgagggaat tacaccacgt ggattggcat cagagctgat gaaccgaagc   6780
ggctaaagcc aaagcctgga atcagatatc ttgctgaact gtcagacttt gagaaggaag   6840
atatcctcgc atggtggaag caacaaccat tcgatttgca aataccggaa catctcggta   6900
actgcatatt ctgcattaaa aaatcaacgc aaaaaatcgg acttgcctgc aaagatgagg   6960
agggattgca gcgtgttttt aatgaggtca tcacgggatc ccatgtgcgt gacggacatc   7020
gggaaacgcc aaaggagatt atgtaccgag gaagaatgtc gctggacggt atcgcgaaaa   7080
tgtattcaga aaatgattat caagccctgt atcaggacat ggtacgagct aaaagattcg   7140
ataccggctc ttgttctgag tcatgcgaaa tatttggagg gcagcttgat ttcgacttcg   7200
ggagggaagc tgcatgatgc gatgttatcg gtgcggtgaa tgcaaagaag ataaccgctt   7260
ccgaccaaat caaccttact ggaatcgatg gtgtctccgg tgtgaaagaa caccaacagg   7320
ggtgttacca ctaccgcagg aaaaggagga cgtgtggcga gacagcgacg aagtatcacc   7380
gacataatct gcgaaaactg caaatacctt ccaacgaaac gcaccagaaa taaacccaag   7440
ccaatcccaa aagaatctga cgtaaaaacc ttcaactaca cggctcacct gtgggatatc   7500
cggtggctaa gacgtcgtgc gaggaaaaca aggtgattga ccaaaatcga agttacgaac   7560
aagaaagcgt cgagcgagct ttaacgtgcg ctaactgcgg tcagaagctg catgtgctgg   7620
aagttcacgt gtgtgagcac tgctgcgcag aactgatgag cgatccgaat agctcgatgc   7680
acgaggaaga agatgatggc taaaccagcg cgaagacgat gtaaaaacga tgaatgccgg   7740
gaatggtttc accctgcatt cgctaatcag tggtggtgct ctccagagtg tggaaccaag   7800
```

atagcactcg aacgacgaag taaagaacgc gaaaaagcgg aaaaagcagc agagaagaaa 7860
cgacgacgag aggagcagaa acagaaagat aaacttaaga ttcgaaaact cgccttaaag 7920
ccccgcagtt actggattaa acaagcccaa caagccgtaa acgccttcat cagagaaaga 7980
gaccgcgact taccatgtat ctcgtgcgga acgctcacgt ctgctcagtg ggatgccgga 8040
cattaccgga caactgctgc ggcacctcaa ctccgattta atgaacgcaa tattcacaag 8100
caatgcgtgg tgtgcaacca gcacaaaagc ggaaatctcg ttccgtatcg cgtcgaactg 8160
attagccgca tcgggcagga agcagtagac gaaatcgaat caaaccataa ccgccatcgc 8220
tggactatcg aagagtgcaa ggcgatcaag gcagagtacc aacagaaact caaagacctg 8280
cgaaatagca gaagtgaggc cgcatgacgt tctcagtaaa aaccattcca gacatgctcg 8340
ttgaagcata cggaaatcag acagaagtag cacgcagact gaaatgtagt cgcggtacgg 8400
tcagaaaata cgttgatgat aaagacggga aaatgcacgc catcgtcaac gacgttctca 8460
tggttcatcg cggatggagt gaaagagatg cgctattacg aaaaaattga tggcagcaaa 8520
taccgaaata tttgggtagt tggcgatctg cacggatgct acacgaacct gatgaacaaa 8580
ctggatacga ttggattcga caacaaaaaa gacctgctta tctcggtggg cgatttggtt 8640
gatcgtggtg cagagaacgt tgaatgcctg gaattaatca cattcccctg gttcagagct 8700
gtacgtggaa accatgagca aatgatgatt gatggcttat cagagcgtgg aaacgttaat 8760
cactggctgc ttaatggcgg tggctggttc tttaatctcg attacgacaa agaaattctg 8820
gctaaagctc ttgcccataa agcagatgaa cttccgttaa tcatcgaact ggtgagcaaa 8880
gataaaaaat atgttatctg ccacgccgat tatccctttg acgaatacga gtttggaaag 8940
ccagttgatc atcagcaggt aatctggaac cgcgaacgaa tcagcaactc acaaaacggg 9000
atcgtgaaag aaatcaaagg cgcggacacg ttcatctttg gtcatacgcc agcagtgaaa 9060
ccactcaagt ttgccaacca aatgtatatc gataccggcg cagtgttctg cggaaaccta 9120
acattgattc aggtacaggg agaaggcgca tgagactcga aagcgtagct aaatttcatt 9180
cgccaaaaag cccgatgatg agcgactcac cacgggccac ggcttctgac tctctttccg 9240
gtactgatgt gatggctgct atggggatgg cgcaatcaca agccggattc ggtatggctg 9300
cattctgcgg taagcacgaa ctcagccaga acgacaaaca aaaggctatc aactatctga 9360
tgcaatttgc acacaaggta tcggggaaat accgtggtgt ggcaaagctt gaaggaaata 9420
ctaaggcaaa ggtactgcaa gtgctcgcaa cattcgctta tgcggattat tgccgtagtg 9480
ccgcgacgcc gggggcaaga tgcagagatt gccatggtac aggccgtgcg gttgatattg 9540
ccaaaacaga gctgtggggg agagttgtcg agaaagagtg cggaagatgc aaaggcgtcg 9600
gctattcaag gatgccagca agcgcagcat atcgcgctgt gacgatgcta atcccaaacc 9660
ttacccaacc cacctggtca cgcactgtta agccgctgta tgacgctctg gtggtgcaat 9720
gccacaaaga agagtcaatc gcagacaaca ttttgaatgc ggtcacacgt tagcagcatg 9780
attgccacgg atggcaacat attaacggca tgatattgac ttattgaata aaattgggta 9840
aatttgactc aacgatgggt taattcgctc gttgtggtag tgagatgaaa agaggcggcg 9900
cttactaccg attccgccta gttggtcact tcgacgtatc gtctggaact ccaaccatcg 9960
caggcagaga ggtctgcaaa atgcaatccc gaaacagttc gcaggtaata gttagagcct 10020
gcataacggt ttcgggattt tttatatctg cacaacaggt aagagcattg agtcgataat 10080
cgtgaagagt cggcgagcct ggttagccag tgctctttcc gttgtgctga attaagcgaa 10140
taccggaagc agaaccggat caccaaatgc gtacaggcgt catcgccgcc cagcaacagc 10200

```
acaacccaaa ctgagccgta gccactgtct gtcctgaatt cattagtaat agttacgctg  10260

cggcctttta cacatgacct tcgtgaaagc gggtggcagg aggtcgcgct aacaacctcc  10320

tgccgttttg cccgtgcata tcggtcacga acaaatctga ttactaaaca cagtagcctg  10380

gatttgttct atcagtaatc gaccttattc ctaattaaat agagcaaatc cccttattgg  10440

gggtaagaca tgaagatgcc agaaaaacat gacctgttgg ccgccattct cgcggcaaag  10500

gaacaaggca tcggggcaat ccttgcgttt gcaatggcgt accttcgcgg cagatataat  10560

ggcggtgcgt ttacaaaaac agtaatcgac gcaacgatgt gcgccattat cgcctggttc  10620

attcgtgacc ttctcgactt cgccggacta agtagcaatc tcgcttatat aacgagcgtg  10680

tttatcggct acatcggtac tgactcgatt ggttcgctta tcaaacgctt cgctgctaaa  10740

aaagccggag tagaagatgg tagaaatcaa taatcaacgt aaggcgttcc tcgatatgct  10800

ggcgtggtcg gagggaactg ataacggacg tcagaaaacc agaaatcatg gttatgacgt  10860

cattgtaggc ggagagctat ttactgatta ctccgatcac cctcgcaaac ttgtcacgct  10920

aaacccaaaa ctcaaatcaa caggcgctta agactggccg tcgttttaca acacagaaag  10980

agtttgtaga aacgcaaaaa ggccatccgt caggggcctt ctgcttagtt tgatgcctgg  11040

cagttcccta ctctcgcctt ccgcttcctc gctcactgac tcgctgcgct cggtcgttcg  11100

gctgcggcga gcggtatcag ctcactcaaa ggcggtaata cggttatcca cagaatcagg  11160

ggataacgca ggaaagaaca tgtgagcaaa aggccagcaa aaggccagga accgtaaaaa  11220

ggccgcgttg ctggcgtttt tccataggct ccgcccccct gacgagcatc acaaaaatcg  11280

acgctcaagt cagaggtggc gaaacccgac aggactataa agataccagg cgtttccccc  11340

tggaagctcc ctcgtgcgct ctcctgttcc gaccctgccg cttaccggat acctgtccgc  11400

ctttctccct tcgggaagcg tggcgctttc tcatagctca cgctgtaggt atctcagttc  11460

ggtgtaggtc gttcgctcca agctgggctg tgtgcacgaa ccccccgttc agcccgaccg  11520

ctgcgcctta tccggtaact atcgtcttga gtccaacccg gtaagacacg acttatcgcc  11580

actggcagca gccactggta acaggattag cagagcgagg tatgtaggcg gtgctacaga  11640

gttcttgaag tggtgggcta actacggcta cactagaaga acagtatttg gtatctgcgc  11700

tctgctgaag ccagttacct tcggaaaaag agttggtagc tcttgatccg gcaaacaaac  11760

caccgctggt agcggtggtt tttttgtttg caagcagcag attacgcgca gaaaaaaagg  11820

atctcaagaa gatcctttga tcttttctac ggggtctgac gctcagtgga acgacgcgcg  11880

cgtaactcac gttaagggat tttggtcatg agcttgcgcc gtcccgtcaa gtcagcgtaa  11940

tgctctgctt t                                                      11951
```

<210> SEQ ID NO 9
<211> LENGTH: 12388
<212> TYPE: DNA
<213> ORGANISM: Artificial Sequence
<220> FEATURE:
<223> OTHER INFORMATION: constructed sequence

<400> SEQUENCE: 9

```
tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240
```

-continued

```
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tatttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
```

-continued cgggggtgg cggcaggtgg gggtgccggg cggggcgggg ccgcctcggg ccggggaggg 2700
ctcgggggag gggcgcggcg gcccccggag cgccggcggc tgtcgaggcg cggcgagccg 2760
cagccattgc cttttatggt aatcgtgcga gagggcgcag ggacttcctt tgtcccaaat 2820
ctgtgcggag ccgaaatctg ggaggcgccg ccgcaccccc tctagcgggc gcggggcgaa 2880
gcggtgcggc gccggcagga aggaaatggg cggggagggc cttcgtgcgt cgccgcgccg 2940
ccgtcccctt ctccctctcc agcctcgggg ctgtccgcgg ggggacggct gccttcgggg 3000
gggacggggc agggcggggt tcggcttctg gcgtgtgacc ggcggctcta gacaattgta 3060
ctaaccttct tctctttcct ctcctgacag gttggtgtac actagcggcc gccaccatgg 3120
cggacgaggc ggccctcgcc cttcagcccg gcggctcccc ctcggcggcg ggggccgaca 3180
gggaggccgc gtcgtccccc gccggggagc cgctccgcaa gaggccgcgg agagatggtc 3240
ccggcctcga gcggagcccg ggcgagcccg gtggggcggc cccagagcgt gaggtgccgg 3300
cggcggccag gggctgcccg ggtgcggcgg cggcggcgct gtggcgggag gcggaggcag 3360
aggcggcggc ggcaggcggg gagcaagagg cccaggcgac tgcggcggct ggggaaggag 3420
acaatgggcc gggcctgcag ggcccatctc gggagccacc gctggccgac aacttgtacg 3480
acgaagacga cgacgacgag ggcgaggagg aggaagaggc ggcggcggcg gcgattgggt 3540
accgagataa ccttctgttc ggtgatgaaa ttatcactaa tggttttcat tcctgtgaaa 3600
gtgatgagga ggatagagcc tcacatgcaa gctctagtga ctggactcca aggccacgga 3660
taggtccata tacttttgtt cagcaacatc ttatgattgg cacagatcct cgaacaattc 3720
ttaaagattt attgccggaa acaatacctc cacctgagtt ggatgatatg acactgtggc 3780
agattgttat taatatcctt tcagaaccac caaaaaggaa aaaaagaaaa gatattaata 3840
caattgaaga tgctgtgaaa ttactgcaag agtgcaaaaa aattatagtt ctaactggag 3900
ctggggtgtc tgtttcatgt ggaatacctg acttcaggtc aagggatggt atttatgctc 3960
gccttgctgt agacttccca gatcttccag atcctcaagc gatgtttgat attgaatatt 4020
tcagaaaaga tccaagacca ttcttcaagt ttgcaaagga aatatatcct ggacaattcc 4080
agccatctct ctgtcacaaa ttcatagcct tgtcagataa ggaaggaaaa ctacttcgca 4140
actataccca gaacatagac acgctggaac aggttgcggg aatccaaagg ataattcagt 4200
gtcatggttc ctttgcaaca gcatcttgcc tgatttgtaa atacaaagtt gactgtgaag 4260
ctgtacgagg agatattttt aatcaggtag ttcctcgatg tcctaggtgc ccagctgatg 4320
aaccgcttgc tatcatgaaa ccagagattg tgttttttgg tgaaaattta ccagaacagt 4380
ttcatagagc catgaagtat gacaaagatg aagttgacct cctcattgtt attgggtctt 4440
ccctcaaagt aagaccagta gcactaattc caagttccat accccatgaa gtgcctcaga 4500
tattaattaa tagagaacct ttgcctcatc tgcattttga tgtagagctt cttggagact 4560
gtgatgtcat aattaatgaa ttgtgtcata ggttaggtgg tgaatatgcc aaactttgct 4620
gtaaccctgt aaagctttca gaaattactg aaaaacctcc acgaacacaa aaagaattgg 4680
cttatttgtc agagttgcca cccacacctc ttcatgtttc agaagactca agttcaccag 4740
aaagaacttc accaccagat tcttcagtga ttgtcacact tttagaccaa gcagctaaga 4800
gtaatgatga tttagatgtg tctgaatcaa aaggttgtat ggaagaaaaa ccacaggaag 4860
tacaaacttc taggaatgtt gaaagtattg ctgaacagat ggaaaatccg gatttgaaga 4920
atgttggttc tagtactggg gagaaaaatg aaagaacttc agtggctgga acagtgagaa 4980

-continued

```
aatgctggcc taatagagtg gcaaaggagc agattagtag gcggcttgat ggtaatcagt   5040
atctgttttt gccaccaaat cgttacattt tccatggcgc tgaggtatat tcagactctg   5100
aagatgacgt cttatcctct agttcttgtg gcagtaacag tgatagtggg acatgccaga   5160
gtccaagttt agaagaaccc atggaggatg aaagtgaaat tgaagaattc tacaatggct   5220
tagaagatga gcctgatgtt ccagagagag ctggaggagc tggatttggg actgatggag   5280
atgatcaaga ggcaattaat gaagctatat ctgtgaaaca ggaagtaaca gacatgaact   5340
atccatcaaa caaatcatga tgaggccgca tagtactgcg gatcctgcag atctgcctcg   5400
actgtgcctt ctagttgcca gccatctgtt gtttgcccct cccccgtgcc ttccttgacc   5460
ctggaaggtg ccactcccac tgtcctttcc taataaaatg aggaaattgc atcgcattgt   5520
ctgagtaggt gtcattctat tctggggggt ggggtggggc aggacagcaa gggggaggat   5580
tgggaagaca atagcaggca tgctggggac tcgagttcta cgtagataag tagcatggcg   5640
ggttaatcat taactacaag gaacccctag tgatggagtt ggccactccc tctctgcgcg   5700
ctcgctcgct cactgaggcc gggcgaccaa aggtcgcccg acgcccgggc tttgcccggg   5760
cggcctcagt gagcgagcga gcgcgcagcc ttaattaacc taaggaaaat gaagtgaagt   5820
tcctatactt tctagagaat aggaacttct atagtgagtc gaataagggc gacacaaaat   5880
ttattctaaa tgcataataa atactgataa catcttatag tttgtattat attttgtatt   5940
atcgttgaca tgtataattt tgatatcaaa aactgatttt ccctttatta ttttcgagat   6000
ttattttctt aattctcttt aacaaactag aaatattgta tatacaaaaa atcataaata   6060
atagatgaat agtttaatta taggtgttca tcaatcgaaa aagcaacgta tcttatttaa   6120
agtgcgttgc tttttttctca tttataaggt taaataattc tcatatatca agcaaagtga   6180
caggcgccct taaatattct gacaaatgct ctttccctaa actcccccca taaaaaaacc   6240
cgccgaagcg ggtttttacg ttatttgcgg attaacgatt actcgttatc agaaccgccc   6300
agggggcccg agcttaacct ttttatttgg gggagaggga agtcatgaaa aaactaacct   6360
ttgaaattcg atctccagca catcagcaaa acgctattca cgcagtacag caaatccttc   6420
cagacccaac caaaccaatc gtagtaacca ttcaggaacg caaccgcagc ttagaccaaa   6480
acaggaagct atgggcctgc ttaggtgacg tctctcgtca ggttgaatgg catggtcgct   6540
ggctggatgc agaaagctgg aagtgtgtgt ttaccgcagc attaaagcag caggatgttg   6600
ttcctaacct tgccgggaat ggctttgtgg taataggcca gtcaaccagc aggatgcgtg   6660
taggcgaatt tgcggagcta ttagagctta tacaggcatt cggtacagag cgtggcgtta   6720
agtggtcaga cgaagcgaga ctggctctgg agtggaaagc gagatgggga gacagggctg   6780
catgataaat gtcgttagtt tctccggtgg caggacgtca gcatatttgc tctggctaat   6840
ggagcaaaag cgacgggcag gtaaagacgt gcattacgtt ttcatggata caggttgtga   6900
acatccaatg acatatcggt ttgtcaggga agttgtgaag ttctgggata taccgctcac   6960
cgtattgcag gttgatatca acccggagct tggacagcca aatggttata cggtatggga   7020
accaaaggat attcagacgc gaatgcctgt tctgaagcca tttatcgata tggtaaagaa   7080
atatggcact ccatacgtcg gcggcgcgtt ctgcactgac agattaaaac tcgttccctt   7140
caccaaatac tgtgatgacc atttcgggcg agggaattac accacgtgga ttggcatcag   7200
agctgatgaa ccgaagcggc taaagccaaa gcctggaatc agatatcttg ctgaactgtc   7260
agactttgag aaggaagata tcctcgcatg gtggaagcaa caaccattcg atttgcaaat   7320
accggaacat ctcggtaact gcatattctg cattaaaaaa tcaacgcaaa aaatcggact   7380
```

tgcctgcaaa gatgaggagg gattgcagcg tgtttttaat gaggtcatca cgggatccca 7440
tgtgcgtgac ggacatcggg aaacgccaaa ggagattatg taccgaggaa gaatgtcgct 7500
ggacggtatc gcgaaaatgt attcagaaaa tgattatcaa gccctgtatc aggacatggt 7560
acgagctaaa agattcgata ccggctcttg ttctgagtca tgcgaaatat ttggagggca 7620
gcttgatttc gacttcggga gggaagctgc atgatgcgat gttatcggtg cggtgaatgc 7680
aaagaagata accgcttccg accaaatcaa ccttactgga atcgatggtg tctccggtgt 7740
gaaagaacac caacaggggt gttaccacta ccgcaggaaa aggaggacgt gtggcgagac 7800
agcgacgaag tatcaccgac ataatctgcg aaaactgcaa ataccttcca acgaaacgca 7860
ccagaaataa acccaagcca atcccaaaag aatctgacgt aaaaaccttc aactacacgg 7920
ctcacctgtg ggatatccgg tggctaagac gtcgtgcgag gaaaacaagg tgattgacca 7980
aaatcgaagt tacgaacaag aaagcgtcga gcgagcttta acgtgcgcta actgcggtca 8040
gaagctgcat gtgctggaag ttcacgtgtg tgagcactgc tgcgcagaac tgatgagcga 8100
tccgaatagc tcgatgcacg aggaagaaga tgatggctaa accagcgcga agacgatgta 8160
aaaacgatga atgccgggaa tggtttcacc ctgcattcgc taatcagtgg tggtgctctc 8220
cagagtgtgg aaccaagata gcactcgaac gacgaagtaa agaacgcgaa aaagcggaaa 8280
aagcagcaga gaagaaacga cgacgagagg agcagaaaca gaaagataaa cttaagattc 8340
gaaaactcgc cttaaagccc cgcagttact ggattaaaca agcccaacaa gccgtaaacg 8400
ccttcatcag agaaagagac cgcgacttac catgtatctc gtgcggaacg ctcacgtctg 8460
ctcagtggga tgccggacat taccggacaa ctgctgcggc acctcaactc cgatttaatg 8520
aacgcaatat tcacaagcaa tgcgtggtgt gcaaccagca caaaagcgga aatctcgttc 8580
cgtatcgcgt cgaactgatt agccgcatcg ggcaggaagc agtagacgaa atcgaatcaa 8640
accataaccg ccatcgctgg actatcgaag agtgcaaggc gatcaaggca gagtaccaac 8700
agaaactcaa agacctgcga aatagcagaa gtgaggccgc atgacgttct cagtaaaaac 8760
cattccagac atgctcgttg aagcatacgg aaatcagaca gaagtagcac gcagactgaa 8820
atgtagtcgc ggtacggtca gaaaatacgt tgatgataaa gacgggaaaa tgcacgccat 8880
cgtcaacgac gttctcatgg ttcatcgcgg atggagtgaa agagatgcgc tattacgaaa 8940
aaattgatgg cagcaaatac cgaaatattt gggtagttgg cgatctgcac ggatgctaca 9000
cgaacctgat gaacaaactg gatacgattg gattcgacaa caaaaaagac ctgcttatct 9060
cggtgggcga tttggttgat cgtggtgcag agaacgttga atgcctggaa ttaatcacat 9120
tcccctggtt cagagctgta cgtggaaacc atgagcaaat gatgattgat ggcttatcag 9180
agcgtggaaa cgttaatcac tggctgctta atggcggtgg ctggttcttt aatctcgatt 9240
acgacaaaga aattctggct aaagctcttg cccataaagc agatgaactt ccgttaatca 9300
tcgaactggt gagcaaagat aaaaaatatg ttatctgcca cgccgattat ccctttgacg 9360
aatacgagtt tggaaagcca gttgatcatc agcaggtaat ctggaaccgc gaacgaatca 9420
gcaactcaca aaacgggatc gtgaaagaaa tcaaaggcgc ggacacgttc atctttggtc 9480
atacgccagc agtgaaacca ctcaagtttg ccaaccaaat gtatatcgat accggcgcag 9540
tgttctgcgg aaacctaaca ttgattcagg tacagggaga aggcgcatga gactcgaaag 9600
cgtagctaaa tttcattcgc caaaaagccc gatgatgagc gactcaccac gggccacggc 9660
ttctgactct ctttccggta ctgatgtgat ggctgctatg ggatggcgc aatcacaagc 9720

-continued

```
cggattcggt atggctgcat tctgcggtaa gcacgaactc agccagaacg acaaacaaaa    9780
ggctatcaac tatctgatgc aatttgcaca caaggtatcg gggaaatacc gtggtgtggc    9840
aaagcttgaa ggaaatacta aggcaaaggt actgcaagtg ctcgcaacat tcgcttatgc    9900
ggattattgc cgtagtgccg cgacgccggg ggcaagatgc agagattgcc atggtacagg    9960
ccgtgcggtt gatattgcca aaacagagct gtgggggaga gttgtcgaga aagagtgcgg   10020
aagatgcaaa ggcgtcggct attcaaggat gccagcaagc gcagcatatc gcgctgtgac   10080
gatgctaatc ccaaacctta cccaacccac ctggtcacgc actgttaagc cgctgtatga   10140
cgctctggtg gtgcaatgcc acaaagaaga gtcaatcgca gacaacattt tgaatgcggt   10200
cacacgttag cagcatgatt gccacggatg gcaacatatt aacggcatga tattgactta   10260
ttgaataaaa ttgggtaaat ttgactcaac gatgggttaa ttcgctcgtt gtggtagtga   10320
gatgaaaaga ggcggcgctt actaccgatt ccgcctagtt ggtcacttcg acgtatcgtc   10380
tggaactcca accatcgcag gcagagaggt ctgcaaaatg caatcccgaa acagttcgca   10440
ggtaatagtt agagcctgca taacggtttc gggatttttt atatctgcac aacaggtaag   10500
agcattgagt cgataatcgt gaagagtcgg cgagcctggt tagccagtgc tctttccgtt   10560
gtgctgaatt aagcgaatac cggaagcaga accggatcac caaatgcgta caggcgtcat   10620
cgccgcccag caacagcaca acccaaactg agccgtagcc actgtctgtc ctgaattcat   10680
tagtaatagt tacgctgcgg ccttttacac atgaccttcg tgaaagcggg tggcaggagg   10740
tcgcgctaac aacctcctgc cgttttgccc gtgcatatcg gtcacgaaca aatctgatta   10800
ctaaacacag tagcctggat ttgttctatc agtaatcgac cttattccta attaaataga   10860
gcaaatcccc ttattggggg taagacatga agatgccaga aaaacatgac ctgttggccg   10920
ccattctcgc ggcaaaggaa caaggcatcg gggcaatcct tgcgtttgca atggcgtacc   10980
ttcgcggcag atataatggc ggtgcgttta caaaaacagt aatcgacgca acgatgtgcg   11040
ccattatcgc ctggttcatt cgtgaccttc tcgacttcgc cggactaagt agcaatctcg   11100
cttatataac gagcgtgttt atcggctaca tcggtactga ctcgattggt tcgcttatca   11160
aacgcttcgc tgctaaaaaa gccggagtag aagatggtag aaatcaataa tcaacgtaag   11220
gcgttcctcg atatgctggc gtggtcggag ggaactgata acggacgtca gaaaaccaga   11280
aatcatggtt atgacgtcat tgtaggcgga gagctattta ctgattactc cgatcaccct   11340
cgcaaacttg tcacgctaaa cccaaaactc aaatcaacag gcgcttaaga ctggccgtcg   11400
ttttacaaca cagaaagagt ttgtagaaac gcaaaaaggc catccgtcag gggccttctg   11460
cttagtttga tgcctggcag ttccctactc tcgccttccg cttcctcgct cactgactcg   11520
ctgcgctcgg tcgttcggct gcggcgagcg gtatcagctc actcaaaggc ggtaatacgg   11580
ttatccacag aatcagggga taacgcagga aagaacatgt gagcaaaagg ccagcaaaag   11640
gccaggaacc gtaaaaaggc cgcgttgctg gcgtttttcc ataggctccg cccccctgac   11700
gagcatcaca aaaatcgacg ctcaagtcag aggtggcgaa acccgacagg actataaaga   11760
taccaggcgt ttccccctgg aagctccctc gtgcgctctc ctgttccgac cctgccgctt   11820
accggatacc tgtccgcctt tctcccttcg ggaagcgtgg cgctttctca tagctcacgc   11880
tgtaggtatc tcagttcggt gtaggtcgtt cgctccaagc tgggctgtgt gcacgaaccc   11940
cccgttcagc ccgaccgctg cgccttatcc ggtaactatc gtcttgagtc caacccggta   12000
agacacgact tatcgccact ggcagcagcc actggtaaca ggattagcag agcgaggtat   12060
gtaggcggtg ctacagagtt cttgaagtgg tgggctaact acggctacac tagaagaaca   12120
```

```
gtatttggta tctgcgctct gctgaagcca gttaccttcg gaaaaagagt tggtagctct  12180

tgatccggca aacaaaccac cgctggtagc ggtggttttt ttgtttgcaa gcagcagatt  12240

acgcgcagaa aaaaaggatc tcaagaagat cctttgatct tttctacggg gtctgacgct  12300

cagtggaacg acgcgcgcgt aactcacgtt aagggatttt ggtcatgagc ttgcgccgtc  12360

ccgtcaagtc agcgtaatgc tctgcttt                                     12388


<210> SEQ ID NO 10
<211> LENGTH: 11959
<212> TYPE: DNA
<213> ORGANISM: Artificial Sequence
<220> FEATURE:
<223> OTHER INFORMATION: constructed sequence

<400> SEQUENCE: 10

tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720

ttatcgcgag cccatttata cccatataaa tcagcatcca tgttggaatt taatcgcggc    780

ctcgacgttt cccgttgaat atggctcata ttcttccttt ttcaatatta ttgaagcatt    840

tatcagggtt attgtctcat gagcggatac atatttgaat gtatttagaa aaataaacaa    900

ataggggtca gtgttacaac caattaacca attctgaaca ttatcgcgag cccatttata    960

cctgaatatg gctcataaca ccccttgttt gcctggcggc agtagcgcgg tggtcccacc   1020

tgaccccatg ccgaactcag aagtgaaacg ccgtagcgcc gatggtagtg tggggactcc   1080

ccatgcgaga gtagggaact gccaggcatc aaataaaacg aaaggctcag tcgaaagact   1140

gggcctttcg cccgggctaa ttagggggtg tcgcccttat tcgactctat agtgaagttc   1200

ctattctcta gaaagtatag gaacttctga agtggggtcg acttaattaa ggctgcgcgc   1260

tcgctcgctc actgaggccg cccgggcaaa gcccgggcgt cgggcgacct ttggtcgccc   1320

ggcctcagtg agcgagcgag cgcgcagaga gggagtggcc aactccatca ctaggggttc   1380

cttgtagtta atgattaacc cgccatgcta cttatctacg tagcaagcta gctagttatt   1440

aatagtaatc aattacgggg tcattagttc atagcccata tatggagttc cgcgttacat   1500

aacttacggt aaatggcccg cctggctgac cgcccaacga cccccgccca ttgacgtcaa   1560

taatgacgta tgttcccata gtaacgccaa tagggacttt ccattgacgt caatgggtgg   1620

agtatttacg gtaaactgcc cacttggcag tacatcaagt gtatcatatg ccaagtacgc   1680

cccctattga cgtcaatgac ggtaaatggc ccgcctggca ttatgcccag tacatgacct   1740
```

-continued

```
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tatttttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cgggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatga   3120
tggacttgga gctgccgccg ccgggactcc cgtcccagca ggacatggat ttgattgaca   3180
tactttggag gcaagatata gatcttggag taagtcgaga agtatttgac ttcagtcagc   3240
gacggaaaga gtatgagctg gaaaaacaga aaaaacttga aaaggaaaga caagaacaac   3300
tccaaaagga gcaagagaaa gcctttttcg ctcagttaca actagatgaa gagacaggtg   3360
aatttctccc aattcagcca gcccagcaca tccagtcaga aaccagtgga tctgccaact   3420
actcccaggt tgcccacatt cccaaatcag atgctttgta ctttgatgac tgcatgcagc   3480
ttttggcgca gacattcccg tttgtagatg acaatgaggt ttcttcggct acgtttcagt   3540
cacttgttcc tgatattccc ggtcacatcg agagcccagt cttcattgct actaatcagg   3600
ctcagtcacc tgaaacttct gttgctcagg tagcccctgt tgatttagac ggtatgcaac   3660
aggacattga gcaagtttgg gaggagctat tatccattcc tgagttacag tgtcttaata   3720
ttgaaaatga caagctggtt gagactacca tggttccaag tccagaagcc aaactgacag   3780
aagttgacaa ttatcatttt tactcatcta taccctcaat ggaaaaagaa gtaggtaact   3840
gtagtccaca ttttcttaat gcttttgagg attccttcag cagcatcctc tccacagaag   3900
accccaacca gttgacagtg aactcattaa attcagatgc cacagtcaac acagattttg   3960
gtgatgaatt ttattctgct ttcatagctg agcccagtat cagcaacagc atgccctcac   4020
ctgctacttt aagccattca ctctctgaac ttctaaatgg gcccattgat gtttctgatc   4080
tatcactttg caaagctttc aaccaaaacc accctgaaag cacagcagaa ttcaatgatt   4140
```

-continued

```
ctgactccgg catttcacta aacacaagtc ccagtgtggc atcaccagaa cactcagtgg   4200
aatcttccag ctatggagac acactacttg gcctcagtga ttctgaagtg gaagagctag   4260
atagtgcccc tggaagtgtc aaacagaatg gtcctaaaac accagtacat tcttctgggg   4320
atatggtaca acccttgtca ccatctcagg ggcagagcac tcacgtgcat gatgcccaat   4380
gtgagaacac accagagaaa gaattgcctg taagtcctgg tcatcggaaa accccattca   4440
caaaagacaa acattcaagc cgcttggagg ctcatctcac aagagatgaa cttagggcaa   4500
aagctctcca tatcccattc cctgtagaaa aaatcattaa cctccctgtt gttgacttca   4560
acgaaatgat gtccaaagag cagttcaatg aagctcaact tgcattaatt cgggatatac   4620
gtaggagggg taagaataaa gtggctgctc agaattgcag aaaaagaaaa ctggaaaata   4680
tagtagaact agagcaagat ttagatcatt tgaaagatga aaaagaaaaa ttgctcaaag   4740
aaaaaggaga aaatgacaaa agccttcacc tactgaaaaa acaactcagc accttatatc   4800
tcgaagtttt cagcatgcta cgtgatgaag atggaaaacc ttattctcct agtgaatact   4860
ccctgcagca aacaagagat ggcaatgttt tccttgttcc caaaagtaag aagccagatg   4920
ttaagaaaaa ctgaggccgc atagtactgc ggatcctgca gatctgcctc gactgtgcct   4980
tctagttgcc agccatctgt tgtttgcccc tcccccgtgc cttccttgac cctggaaggt   5040
gccactccca ctgtcctttc ctaataaaat gaggaaattg catcgcattg tctgagtagg   5100
tgtcattcta ttctgggggg tggggtgggg caggacagca agggggagga ttgggaagac   5160
aatagcaggc atgctgggga ctcgagttct acgtagataa gtagcatggc gggttaatca   5220
ttaactacaa ggaaccccta gtgatggagt tggccactcc ctctctgcgc gctcgctcgc   5280
tcactgaggc cgggcgacca aaggtcgccc gacgcccggg ctttgcccgg gcggcctcag   5340
tgagcgagcg agcgcgcagc cttaattaac ctaaggaaaa tgaagtgaag ttcctatact   5400
ttctagagaa taggaacttc tatagtgagt cgaataaggg cgacacaaaa tttattctaa   5460
atgcataata aatactgata acatcttata gtttgtatta tattttgtat tatcgttgac   5520
atgtataatt ttgatatcaa aaactgattt tccctttatt attttcgaga tttatttttct   5580
taattctctt taacaaacta gaaatattgt atatacaaaa aatcataaat aatagatgaa   5640
tagtttaatt ataggtgttc atcaatcgaa aaagcaacgt atcttattta aagtgcgttg   5700
ctttttttctc atttataagg ttaaataatt ctcatatatc aagcaaagtg acaggcgccc   5760
ttaaatattc tgacaaatgc tctttcccta aactcccccc ataaaaaaac ccgccgaagc   5820
gggtttttac gttatttgcg gattaacgat tactcgttat cagaaccgcc cagggggccc   5880
gagcttaacc tttttatttg gggggagaggg aagtcatgaa aaaactaacc tttgaaattc   5940
gatctccagc acatcagcaa aacgctattc acgcagtaca gcaaatcctt ccagacccaa   6000
ccaaaccaat cgtagtaacc attcaggaac gcaaccgcag cttagaccaa aacaggaagc   6060
tatgggcctg cttaggtgac gtctctcgtc aggttgaatg gcatggtcgc tggctggatg   6120
cagaaagctg gaagtgtgtg tttaccgcag cattaaagca gcaggatgtt gttcctaacc   6180
ttgccgggaa tggctttgtg gtaataggcc agtcaaccag caggatgcgt gtaggcgaat   6240
ttgcggagct attagagctt atacaggcat tcggtacaga gcgtggcgtt aagtggtcag   6300
acgaagcgag actggctctg gagtggaaag cgagatgggg agacagggct gcatgataaa   6360
tgtcgttagt ttctccggtg gcaggacgtc agcatatttg ctctggctaa tggagcaaaa   6420
gcgacgggca ggtaaagacg tgcattacgt tttcatggat acaggttgtg aacatccaat   6480
```

-continued

```
gacatatcgg tttgtcaggg aagttgtgaa gttctgggat ataccgctca ccgtattgca   6540
ggttgatatc aacccggagc ttggacagcc aaatggttat acggtatggg aaccaaagga   6600
tattcagacg cgaatgcctg ttctgaagcc atttatcgat atggtaaaga aatatggcac   6660
tccatacgtc ggcggcgcgt tctgcactga cagattaaaa ctcgttccct tcaccaaata   6720
ctgtgatgac catttcgggc gagggaatta caccacgtgg attggcatca gagctgatga   6780
accgaagcgg ctaaagccaa agcctggaat cagatatctt gctgaactgt cagactttga   6840
gaaggaagat atcctcgcat ggtggaagca acaaccattc gatttgcaaa taccggaaca   6900
tctcggtaac tgcatattct gcattaaaaa atcaacgcaa aaaatcggac ttgcctgcaa   6960
agatgaggag ggattgcagc gtgtttttaa tgaggtcatc acgggatccc atgtgcgtga   7020
cggacatcgg gaaacgccaa aggagattat gtaccgagga agaatgtcgc tggacggtat   7080
cgcgaaaatg tattcagaaa atgattatca agccctgtat caggacatgg tacgagctaa   7140
aagattcgat accggctctt gttctgagtc atgcgaaata tttggagggc agcttgattt   7200
cgacttcggg agggaagctg catgatgcga tgttatcggt gcggtgaatg caaagaagat   7260
aaccgcttcc gaccaaatca accttactgg aatcgatggt gtctccggtg tgaaagaaca   7320
ccaacagggg tgttaccact accgcaggaa aaggaggacg tgtggcgaga cagcgacgaa   7380
gtatcaccga cataatctgc gaaaactgca aataccttcc aacgaaacgc accagaaata   7440
aacccaagcc aatcccaaaa gaatctgacg taaaaacctt caactacacg gctcacctgt   7500
gggatatccg gtggctaaga cgtcgtgcga ggaaaacaag gtgattgacc aaaatcgaag   7560
ttacgaacaa gaaagcgtcg agcgagcttt aacgtgcgct aactgcggtc agaagctgca   7620
tgtgctggaa gttcacgtgt gtgagcactg ctgcgcagaa ctgatgagcg atccgaatag   7680
ctcgatgcac gaggaagaag atgatggcta aaccagcgcg aagacgatgt aaaaacgatg   7740
aatgccggga atggtttcac cctgcattcg ctaatcagtg gtggtgctct ccagagtgtg   7800
gaaccaagat agcactcgaa cgacgaagta aagaacgcga aaaagcggaa aaagcagcag   7860
agaagaaacg acgacgagag gagcagaaac agaaagataa acttaagatt cgaaaactcg   7920
ccttaaagcc ccgcagttac tggattaaac aagcccaaca agccgtaaac gccttcatca   7980
gagaaagaga ccgcgactta ccatgtatct cgtgcggaac gctcacgtct gctcagtggg   8040
atgccggaca ttaccggaca actgctgcgg cacctcaact ccgatttaat gaacgcaata   8100
ttcacaagca atgcgtggtg tgcaaccagc acaaaagcgg aaatctcgtt ccgtatcgcg   8160
tcgaactgat tagccgcatc gggcaggaag cagtagacga aatcgaatca aaccataacc   8220
gccatcgctg gactatcgaa gagtgcaagg cgatcaaggc agagtaccaa cagaaactca   8280
aagacctgcg aaatagcaga agtgaggccg catgacgttc tcagtaaaaa ccattccaga   8340
catgctcgtt gaagcatacg gaaatcagac agaagtagca cgcagactga aatgtagtcg   8400
cggtacggtc agaaaatacg ttgatgataa agacgggaaa atgcacgcca tcgtcaacga   8460
cgttctcatg gttcatcgcg gatggagtga aagagatgcg ctattacgaa aaaattgatg   8520
gcagcaaata ccgaaatatt tgggtagttg gcgatctgca cggatgctac acgaacctga   8580
tgaacaaact ggatacgatt ggattcgaca acaaaaaaga cctgcttatc tcggtgggcg   8640
atttggttga tcgtggtgca gagaacgttg aatgcctgga attaatcaca ttcccctggt   8700
tcagagctgt acgtggaaac catgagcaaa tgatgattga tggcttatca gagcgtggaa   8760
acgttaatca ctggctgctt aatggcggtg gctggttctt taatctcgat tacgacaaag   8820
aaattctggc taaagctctt gcccataaag cagatgaact tccgttaatc atcgaactgg   8880
```

```
tgagcaaaga taaaaaatat gttatctgcc acgccgatta tccctttgac gaatacgagt   8940
ttggaaagcc agttgatcat cagcaggtaa tctggaaccg cgaacgaatc agcaactcac   9000
aaaacgggat cgtgaaagaa atcaaaggcg cggacacgtt catctttggt catacgccag   9060
cagtgaaacc actcaagttt gccaaccaaa tgtatatcga taccggcgca gtgttctgcg   9120
gaaacctaac attgattcag gtacagggag aaggcgcatg agactcgaaa gcgtagctaa   9180
atttcattcg ccaaaaagcc cgatgatgag cgactcacca cgggccacgg cttctgactc   9240
tctttccggt actgatgtga tggctgctat ggggatggcg caatcacaag ccggattcgg   9300
tatggctgca ttctgcggta agcacgaact cagccagaac gacaaacaaa aggctatcaa   9360
ctatctgatg caatttgcac acaaggtatc ggggaaatac cgtggtgtgg caaagcttga   9420
aggaaatact aaggcaaagg tactgcaagt gctcgcaaca ttcgcttatg cggattattg   9480
ccgtagtgcc gcgacgccgg gggcaagatg cagagattgc catggtacag gccgtgcggt   9540
tgatattgcc aaaacagagc tgtgggggag agttgtcgag aaagagtgcg gaagatgcaa   9600
aggcgtcggc tattcaagga tgccagcaag cgcagcatat cgcgctgtga cgatgctaat   9660
cccaaacctt acccaaccca cctggtcacg cactgttaag ccgctgtatg acgctctggt   9720
ggtgcaatgc cacaaagaag agtcaatcgc agacaacatt ttgaatgcgg tcacacgtta   9780
gcagcatgat tgccacggat ggcaacatat taacggcatg atattgactt attgaataaa   9840
attgggtaaa tttgactcaa cgatgggtta attcgctcgt tgtggtagtg agatgaaaag   9900
aggcggcgct tactaccgat tccgcctagt tggtcacttc gacgtatcgt ctggaactcc   9960
aaccatcgca ggcagagagg tctgcaaaat gcaatcccga aacagttcgc aggtaatagt  10020
tagagcctgc ataacggttt cgggattttt tatatctgca caacaggtaa gagcattgag  10080
tcgataatcg tgaagagtcg gcgagcctgg ttagccagtg ctctttccgt tgtgctgaat  10140
taagcgaata ccggaagcag aaccggatca ccaaatgcgt acaggcgtca tcgccgccca  10200
gcaacagcac aacccaaact gagccgtagc cactgtctgt cctgaattca ttagtaatag  10260
ttacgctgcg gccttttaca catgaccttc gtgaaagcgg gtggcaggag gtcgcgctaa  10320
caacctcctg ccgttttgcc cgtgcatatc ggtcacgaac aaatctgatt actaaacaca  10380
gtagcctgga tttgttctat cagtaatcga ccttattcct aattaaatag agcaaatccc  10440
cttattgggg gtaagacatg aagatgccag aaaaacatga cctgttggcc gccattctcg  10500
cggcaaagga acaaggcatc ggggcaatcc ttgcgtttgc aatggcgtac cttcgcggca  10560
gatataatgg cggtgcgttt acaaaaaacag taatcgacgc aacgatgtgc gccattatcg  10620
cctggttcat tcgtgacctt ctcgacttcg ccggactaag tagcaatctc gcttatataa  10680
cgagcgtgtt tatcggctac atcggtactg actcgattgg ttcgcttatc aaacgcttcg  10740
ctgctaaaaa agccggagta gaagatggta gaaatcaata atcaacgtaa ggcgttcctc  10800
gatatgctgg cgtggtcgga gggaactgat aacggacgtc agaaaaccag aaatcatggt  10860
tatgacgtca ttgtaggcgg agagctattt actgattact ccgatcaccc tcgcaaactt  10920
gtcacgctaa acccaaaact caaatcaaca ggcgcttaag actggccgtc gttttacaac  10980
acagaaagag tttgtagaaa cgcaaaaagg ccatccgtca ggggccttct gcttagtttg  11040
atgcctggca gttccctact ctcgccttcc gcttcctcgc tcactgactc gctgcgctcg  11100
gtcgttcggc tgcggcgagc ggtatcagct cactcaaagg cggtaatacg gttatccaca  11160
gaatcagggg ataacgcagg aaagaacatg tgagcaaaag gccagcaaaa ggccaggaac  11220
```

cgtaaaaagg ccgcgttgct ggcgtttttc cataggctcc gcccccctga cgagcatcac 11280
aaaaatcgac gctcaagtca gaggtggcga aacccgacag gactataaag ataccaggcg 11340
tttccccctg gaagctccct cgtgcgctct cctgttccga ccctgccgct taccggatac 11400
ctgtccgcct ttctcccttc gggaagcgtg gcgctttctc atagctcacg ctgtaggtat 11460
ctcagttcgg tgtaggtcgt tcgctccaag ctgggctgtg tgcacgaacc ccccgttcag 11520
cccgaccgct gcgccttatc cggtaactat cgtcttgagt ccaacccggt aagacacgac 11580
ttatcgccac tggcagcagc cactggtaac aggattagca gagcgaggta tgtaggcggt 11640
gctacagagt tcttgaagtg gtggcctaac tacggctaca ctagaagaac agtatttggt 11700
atctgcgctc tgctgaagcc agttaccttc ggaaaaagag ttggtagctc ttgatccggc 11760
aaacaaacca ccgctggtag cggtggtttt tttgtttgca agcagcagat tacgcgcaga 11820
aaaaaaggat ctcaagaaga tcctttgatc ttttctacgg ggtctgacgc tcagtggaac 11880
gacgcgcgcg taactcacgt taagggattt tggtcatgag cttgcgccgt cccgtcaagt 11940
cagcgtaatg ctctgcttt 11959

<210> SEQ ID NO 11
<211> LENGTH: 12392
<212> TYPE: DNA
<213> ORGANISM: Artificial Sequence
<220> FEATURE:
<223> OTHER INFORMATION: constructed sequence

<400> SEQUENCE: 11
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900 atagggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320

-continued

```
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tattttttaa ttattttgtg cagcgatggg ggcggggggg ggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gcgccgccac   3120
catggcggac gaggcggccc tcgcccttca gcccggcggc tccccctcgg cggcgggggc   3180
cgacagggag gccgcgtcgt cccccgccgg ggagccgctc cgcaagaggc cgcggagaga   3240
tggtcccggc ctcgagcgga gcccgggcga gcccggtggg gcggccccag agcgtgaggt   3300
gccggcggcg gccaggggct gcccgggtgc ggcggcggcg gcgctgtggc gggaggcgga   3360
ggcagaggcg gcggcggcag gcggggagca agaggcccag gcgactgcgg cggctgggga   3420
aggagacaat gggccgggcc tgcagggccc atctcgggag ccaccgctgg ccgacaactt   3480
gtacgacgaa gacgacgacg acgagggcga ggaggaggaa gaggcggcgg cggcggcgat   3540
tgggtaccga gataaccttc tgttcggtga tgaaattatc actaatggtt ttcattcctg   3600
tgaaagtgat gaggaggata gagcctcaca tgcaagctct agtgactgga ctccaaggcc   3660
```

-continued

```
acggataggt ccatatactt ttgttcagca acatcttatg attggcacag atcctcgaac   3720
aattcttaaa gatttattgc cggaaacaat acctccacct gagttggatg atatgacact   3780
gtggcagatt gttattaata tcctttcaga accaccaaaa aggaaaaaaa gaaaagatat   3840
taatacaatt gaagatgctg tgaaattact gcaagagtgc aaaaaaatta tagttctaac   3900
tggagctggg gtgtctgttt catgtggaat acctgacttc aggtcaaggg atggtattta   3960
tgctcgcctt gctgtagact tcccagatct tccagatcct caagcgatgt ttgatattga   4020
atatttcaga aaagatccaa gaccattctt caagtttgca aaggaaatat atcctggaca   4080
attccagcca tctctctgtc acaaattcat agccttgtca gataaggaag gaaaactact   4140
tcgcaactat acccagaaca tagacacgct ggaacaggtt gcgggaatcc aaaggataat   4200
tcagtgtcat ggttcctttg caacagcatc ttgcctgatt tgtaaataca aagttgactg   4260
tgaagctgta cgaggagata tttttaatca ggtagttcct cgatgtccta ggtgcccagc   4320
tgatgaaccg cttgctatca tgaaaccaga gattgtgttt tttggtgaaa atttaccaga   4380
acagtttcat agagccatga agtatgacaa agatgaagtt gacctcctca ttgttattgg   4440
gtcttccctc aaagtaagac cagtagcact aattccaagt tccatacccc atgaagtgcc   4500
tcagatatta attaatagag aacctttgcc tcatctgcat tttgatgtag agcttcttgg   4560
agactgtgat gtcataatta atgaattgtg tcataggtta ggtggtgaat atgccaaact   4620
ttgctgtaac cctgtaaagc tttcagaaat tactgaaaaa cctccacgaa cacaaaaaga   4680
attggcttat ttgtcagagt tgccacccac acctcttcat gtttcagaag actcaagttc   4740
accagaaaga acttcaccac cagattcttc agtgattgtc acacttttag accaagcagc   4800
taagagtaat gatgatttag atgtgtctga atcaaaaggt tgtatggaag aaaaaccaca   4860
ggaagtacaa acttctagga atgttgaaag tattgctgaa cagatggaaa atccggattt   4920
gaagaatgtt ggttctagta ctggggagaa aaatgaaaga acttcagtgg ctggaacagt   4980
gagaaaatgc tggcctaata gagtggcaaa ggagcagatt agtaggcggc ttgatggtaa   5040
tcagtatctg tttttgccac caaatcgtta cattttccat ggcgctgagg tatattcaga   5100
ctctgaagat gacgtcttat cctctagttc ttgtggcagt aacagtgata gtgggacatg   5160
ccagagtcca agtttagaag aacccatgga ggatgaaagt gaaattgaag aattctacaa   5220
tggcttagaa gatgagcctg atgttccaga gagagctgga ggagctggat ttgggactga   5280
tggagatgat caagaggcaa ttaatgaagc tatatctgtg aaacaggaag taacagacat   5340
gaactatcca tcaaacaaat catgagcggc cgcatagtac tgcggatcct gcagatctgc   5400
ctcgactgtg ccttctagtt gccagccatc tgttgtttgc ccctcccccg tgccttcctt   5460
gaccctggaa ggtgccactc ccactgtcct ttcctaataa aatgaggaaa ttgcatcgca   5520
ttgtctgagt aggtgtcatt ctattctggg gggtggggtg gggcaggaca gcaaggggga   5580
ggattgggaa gacaatagca ggcatgctgg ggactcgagt tctacgtaga taagtagcat   5640
ggcgggttaa tcattaacta caaggaaccc ctagtgatgg agttggccac tccctctctg   5700
cgcgctcgct cgctcactga ggccgggcga ccaaaggtcg cccgacgccc gggctttgcc   5760
cgggcggcct cagtgagcga gcgagcgcgc agccttaatt aacctaagga aaatgaagtg   5820
aagttcctat actttctaga gaataggaac ttctatagtg agtcgaataa gggcgacaca   5880
aaatttattc taaatgcata ataaatactg ataacatctt atagtttgta ttatattttg   5940
tattatcgtt gacatgtata attttgatat caaaaactga ttttcccttt attattttcg   6000
agatttattt tcttaattct ctttaacaaa ctagaaatat tgtatataca aaaaatcata   6060
```

```
aataatagat gaatagttta attataggtg ttcatcaatc gaaaaagcaa cgtatcttat   6120
ttaaagtgcg ttgctttttt ctcatttata aggttaaata attctcatat atcaagcaaa   6180
gtgacaggcg cccttaaata ttctgacaaa tgctctttcc ctaaactccc cccataaaaa   6240
aacccgccga agcgggtttt tacgttattt gcggattaac gattactcgt tatcagaacc   6300
gcccaggggg cccgagctta accttttat ttgggggaga gggaagtcat gaaaaaacta   6360
acctttgaaa ttcgatctcc agcacatcag caaaacgcta ttcacgcagt acagcaaatc   6420
cttccagacc caaccaaacc aatcgtagta accattcagg aacgcaaccg cagcttagac   6480
caaaacagga agctatgggc ctgcttaggt gacgtctctc gtcaggttga atggcatggt   6540
cgctggctgg atgcagaaag ctggaagtgt gtgtttaccg cagcattaaa gcagcaggat   6600
gttgttccta accttgccgg gaatggcttt gtggtaatag gccagtcaac cagcaggatg   6660
cgtgtaggcg aatttgcgga gctattagag cttatacagg cattcggtac agagcgtggc   6720
gttaagtggt cagacgaagc gagactggct ctggagtgga aagcgagatg gggagacagg   6780
gctgcatgat aaatgtcgtt agtttctccg gtggcaggac gtcagcatat ttgctctggc   6840
taatggagca aaagcgacgg gcaggtaaag acgtgcatta cgttttcatg gatacaggtt   6900
gtgaacatcc aatgacatat cggtttgtca gggaagttgt gaagttctgg gatataccgc   6960
tcaccgtatt gcaggttgat atcaacccgg agcttggaca gccaaatggt tatacggtat   7020
gggaaccaaa ggatattcag acgcgaatgc ctgttctgaa gccatttatc gatatggtaa   7080
agaaatatgg cactccatac gtcggcggcg cgttctgcac tgacagatta aaactcgttc   7140
ccttcaccaa atactgtgat gaccatttcg ggcgagggaa ttacaccacg tggattggca   7200
tcagagctga tgaaccgaag cggctaaagc caaagcctgg aatcagatat cttgctgaac   7260
tgtcagactt tgagaaggaa gatatcctcg catggtggaa gcaacaacca ttcgatttgc   7320
aaataccgga acatctcggt aactgcatat tctgcattaa aaaatcaacg caaaaaatcg   7380
gacttgcctg caaagatgag gagggattgc agcgtgtttt taatgaggtc atcacgggat   7440
cccatgtgcg tgacggacat cgggaaacgc caaaggagat tatgtaccga ggaagaatgt   7500
cgctggacgg tatcgcgaaa atgtattcag aaaatgatta tcaagccctg tatcaggaca   7560
tggtacgagc taaaagattc gataccggct cttgttctga gtcatgcgaa atatttggag   7620
ggcagcttga tttcgacttc gggagggaag ctgcatgatg cgatgttatc ggtgcggtga   7680
atgcaaagaa gataaccgct tccgaccaaa tcaaccttac tggaatcgat ggtgtctccg   7740
gtgtgaaaga acaccaacag ggtgttacc actaccgcag gaaaaggagg acgtgtggcg   7800
agacagcgac gaagtatcac cgacataatc tgcgaaaact gcaaatacct tccaacgaaa   7860
cgcaccagaa ataaacccaa gccaatccca aaagaatctg acgtaaaaac cttcaactac   7920
acggctcacc tgtgggatat ccggtggcta agacgtcgtg cgaggaaaac aaggtgattg   7980
accaaaatcg aagttacgaa caagaaagcg tcgagcgagc tttaacgtgc gctaactgcg   8040
gtcagaagct gcatgtgctg gaagttcacg tgtgtgagca ctgctgcgca gaactgatga   8100
gcgatccgaa tagctcgatg cacgaggaag aagatgatgg ctaaaccagc gcgaagacga   8160
tgtaaaaacg atgaatgccg ggaatggttt caccctgcat tcgctaatca gtggtggtgc   8220
tctccagagt gtggaaccaa gatagcactc gaacgacgaa gtaaagaacg cgaaaaagcg   8280
gaaaaagcag cagagaagaa acgacgacga gaggagcaga aacagaaaga taaacttaag   8340
attcgaaaac tcgccttaaa gccccgcagt tactggatta aacaagccca acaagccgta   8400
```

-continued

```
aacgccttca tcagagaaag agaccgcgac ttaccatgta tctcgtgcgg aacgctcacg   8460
tctgctcagt gggatgccgg acattaccgg acaactgctg cggcacctca actccgattt   8520
aatgaacgca atattcacaa gcaatgcgtg gtgtgcaacc agcacaaaag cggaaatctc   8580
gttccgtatc gcgtcgaact gattagccgc atcgggcagg aagcagtaga cgaaatcgaa   8640
tcaaaccata accgccatcg ctggactatc gaagagtgca aggcgatcaa ggcagagtac   8700
caacagaaac tcaaagacct gcgaaatagc agaagtgagg ccgcatgacg ttctcagtaa   8760
aaaccattcc agacatgctc gttgaagcat acggaaatca gacagaagta gcacgcagac   8820
tgaaatgtag tcgcggtacg gtcagaaaat acgttgatga taaagacggg aaaatgcacg   8880
ccatcgtcaa cgacgttctc atggttcatc gcggatggag tgaaagagat gcgctattac   8940
gaaaaaattg atggcagcaa ataccgaaat atttgggtag ttggcgatct gcacggatgc   9000
tacacgaacc tgatgaacaa actggatacg attggattcg acaacaaaaa agacctgctt   9060
atctcggtgg gcgatttggt tgatcgtggt gcagagaacg ttgaatgcct ggaattaatc   9120
acattcccct ggttcagagc tgtacgtgga aaccatgagc aaatgatgat tgatggctta   9180
tcagagcgtg gaaacgttaa tcactggctg cttaatggcg gtggctggtt ctttaatctc   9240
gattacgaca aagaaattct ggctaaagct cttgcccata aagcagatga acttccgtta   9300
atcatcgaac tggtgagcaa agataaaaaa tatgttatct gccacgccga ttatcccttt   9360
gacgaatacg agtttggaaa gccagttgat catcagcagg taatctggaa ccgcgaacga   9420
atcagcaact cacaaaacgg gatcgtgaaa gaaatcaaag gcgcggacac gttcatcttt   9480
ggtcatacgc cagcagtgaa accactcaag tttgccaacc aaatgtatat cgataccggc   9540
gcagtgttct gcggaaacct aacattgatt caggtacagg gagaaggcgc atgagactcg   9600
aaagcgtagc taaatttcat tcgccaaaaa gcccgatgat gagcgactca ccacgggcca   9660
cggcttctga ctctctttcc ggtactgatg tgatggctgc tatggggatg gcgcaatcac   9720
aagccggatt cggtatggct gcattctgcg gtaagcacga actcagccag aacgacaaac   9780
aaaaggctat caactatctg atgcaatttg cacacaaggt atcggggaaa taccgtggtg   9840
tggcaaagct tgaaggaaat actaaggcaa aggtactgca agtgctcgca acattcgctt   9900
atgcggatta ttgccgtagt gccgcgacgc cgggggcaag atgcagagat tgccatggta   9960
caggccgtgc ggttgatatt gccaaaacag agctgtgggg gagagttgtc gagaaagagt  10020
gcggaagatg caaaggcgtc ggctattcaa ggatgccagc aagcgcagca tatcgcgctg  10080
tgacgatgct aatcccaaac cttacccaac ccacctggtc acgcactgtt aagccgctgt  10140
atgacgctct ggtggtgcaa tgccacaaag aagagtcaat cgcagacaac attttgaatg  10200
cggtcacacg ttagcagcat gattgccacg gatggcaaca tattaacggc atgatattga  10260
cttattgaat aaaattgggt aaatttgact caacgatggg ttaattcgct cgttgtggta  10320
gtgagatgaa aagaggcggc gcttactacc gattccgcct agttggtcac ttcgacgtat  10380
cgtctggaac tccaaccatc gcaggcagag aggtctgcaa aatgcaatcc cgaaacagtt  10440
cgcaggtaat agttagagcc tgcataacgg tttcgggatt ttttatatct gcacaacagg  10500
taagagcatt gagtcgataa tcgtgaagag tcggcgagcc tggttagcca gtgctctttc  10560
cgttgtgctg aattaagcga ataccggaag cagaaccgga tcaccaaatg cgtacaggcg  10620
tcatcgccgc ccagcaacag cacaacccaa actgagccgt agccactgtc tgtcctgaat  10680
tcattagtaa tagttacgct gcggcctttt acacatgacc ttcgtgaaag cgggtggcag  10740
gaggtcgcgc taacaacctc ctgccgtttt gcccgtgcat atcggtcacg aacaaatctg  10800
```

attactaaac acagtagcct ggatttgttc tatcagtaat cgaccttatt cctaattaaa 10860
tagagcaaat ccccttattg ggggtaagac atgaagatgc cagaaaaaca tgacctgttg 10920
gccgccattc tcgcggcaaa ggaacaaggc atcggggcaa tccttgcgtt tgcaatggcg 10980
taccttcgcg gcagatataa tggcggtgcg tttacaaaaa cagtaatcga cgcaacgatg 11040
tgcgccatta tcgcctggtt cattcgtgac cttctcgact tcgccggact aagtagcaat 11100
ctcgcttata taacgagcgt gtttatcggc tacatcggta ctgactcgat tggttcgctt 11160
atcaaacgct tcgctgctaa aaaagccgga gtagaagatg gtagaaatca ataatcaacg 11220
taaggcgttc ctcgatatgc tggcgtggtc ggagggaact gataacggac gtcagaaaac 11280
cagaaatcat ggttatgacg tcattgtagg cggagagcta tttactgatt actccgatca 11340
ccctcgcaaa cttgtcacgc taaacccaaa actcaaatca acaggcgctt aagactggcc 11400
gtcgttttac aacacagaaa gagtttgtag aaacgcaaaa aggccatccg tcaggggcct 11460
tctgcttagt ttgatgcctg gcagttccct actctcgcct tccgcttcct cgctcactga 11520
ctcgctgcgc tcggtcgttc ggctgcggcg agcggtatca gctcactcaa aggcggtaat 11580
acggttatcc acagaatcag gggataacgc aggaaagaac atgtgagcaa aaggccagca 11640
aaaggccagg aaccgtaaaa aggccgcgtt gctggcgttt ttccataggc tccgcccccc 11700
tgacgagcat cacaaaaatc gacgctcaag tcagaggtgg cgaaacccga caggactata 11760
aagataccag gcgtttcccc ctggaagctc cctcgtgcgc tctcctgttc cgaccctgcc 11820
gcttaccgga tacctgtccg cctttctccc ttcgggaagc gtggcgcttt ctcatagctc 11880
acgctgtagg tatctcagtt cggtgtaggt cgttcgctcc aagctgggct gtgtgcacga 11940
accccccgtt cagcccgacc gctgcgcctt atccggtaac tatcgtcttg agtccaaccc 12000
ggtaagacac gacttatcgc cactggcagc agccactggt aacaggatta gcagagcgag 12060
gtatgtaggc ggtgctacag agttcttgaa gtggtgggct aactacggct acactagaag 12120
aacagtattt ggtatctgcg ctctgctgaa gccagttacc ttcggaaaaa gagttggtag 12180
ctcttgatcc ggcaaacaaa ccaccgctgg tagcggtggt ttttttgttt gcaagcagca 12240
gattacgcgc agaaaaaaag gatctcaaga agatcctttg atcttttcta cggggtctga 12300
cgctcagtgg aacgacgcgc gcgtaactca cgttaaggga ttttggtcat gagcttgcgc 12360
cgtcccgtca agtcagcgta atgctctgct tt 12392

<210> SEQ ID NO 12
<211> LENGTH: 2241
<212> TYPE: DNA
<213> ORGANISM: Artificial Sequence
<220> FEATURE:
<223> OTHER INFORMATION: constructed sequence

<400> SEQUENCE: 12
atggccgacg aagccgcact cgcgctgcaa ccagggggtt ccccgtctgc agcaggcgcc 60
gatagagaag cagccagctc gccagcagga gaaccgctcc ggaagcgacc caggagagat 120
ggcccaggcc tggaacgctc accgggtgaa ccaggaggtg ccgctcctga acgggaagtg 180
cccgcagctg ctaggggctg tccaggagca gccgcagcag cactctggcg cgaagccgaa 240
gccgaggctg ctgcagccgg aggagaacaa gaagcccaag cgaccgctgc agcaggagag 300
ggcgacaacg gacccggcct gcaaggaccg tcccgcgaac ctccgctggc cgacaatctg 360
tacgacgagg acgatgatga tgagggcgaa gaagaagagg aagccgccgc tgctgctatt 420
ggatacagag acaaccttct cttcggcgac gagatcatca ccaatggatt ccactcctgt 480
gaatctgacg aagaagatcg ggcctcccat gctagcagct ctgactggac gccacggcca 540
aggatcggtc cgtacacctt cgtgcagcag cacctgatga tcggcacaga tccccgcacc 600
attctgaagg atctgctgcc cgagactatc ccaccccctg agctggacga catgactctg 660
tggcagattg tgatcaacat cctttccgag cccccaaagc ggaagaagcg caaggatatt 720
aacaccatcg aggacgccgt gaagcttctg caggagtgca aaaagatcat cgtgctgact 780
ggtgcagggg tgtccgtgtc ctgcggcatt ccggatttca gaagccgcga cggaatctac 840
gccagactcg cggtcgactt tcccgatctg cctgaccctc aggccatgtt cgatattgaa 900
tacttccgca aggacccgag gccgttcttt aagttcgcca aggagatcta ccctgggcag 960
ttccaaccct ccctctgcca taagttcatt gcgctgagcg ataaggaagg aaagctgctg 1020
cggaactaca cccagaacat cgacactctt gagcaagtgg cgggtatcca gagaatcatc 1080
caatgccacg gctccttcgc cactgcctcc tgcctgatct gcaagtacaa ggtcgattgt 1140
gaagccgtca ggggcgatat cttcaaccaa gtggtcccgc gatgcccaag atgcccggcg 1200
gatgaaccct tggccatcat gaagcctgaa atcgtgttct tcggggaaaa cctccccgaa 1260
cagtttcacc gcgccatgaa gtacgacaag gacgaagtgg atctcctgat tgtgattggt 1320
tccagcttga aagtccggcc agtggccttg atcccctcct cgattccaca cgaagtgcct 1380
caaatcctta ttaaccggga accactgccg catcttcact tcgatgtgga actgctggga 1440
gactgcgacg tgattattaa cgaactgtgt caccgcttgg gtggcgaata cgccaagctg 1500
tgctgcaacc ctgtgaaact gtcggagatc accgaaaagc cgcccagaac tcaaaaagag 1560
ctggcctacc tgtccgagct ccctccgact ccgctgcatg tgtccgagga ttcgtcgtcc 1620
ccggaaagga cttcgcctcc ggactcctcc gtgatcgtga ccctgctcga ccaagccgcc 1680
aagtcgaacg acgatctgga cgtgtcggaa tccaagggct gcatggaaga aaagcctcaa 1740
gaggtgcaga cttcacggaa cgtggagtcc atcgccgaac agatggaaaa cccggacctg 1800
aagaacgtgg gaagcagcac tggcgaaaag aacgagagaa cctccgtggc cggtactgtc 1860
cggaagtgct ggccgaacag ggtggccaag gaacagatat cccggagact tgacggcaac 1920
cagtacctct tcctccccc taaccgctat atttttcacg gggccgaggt gtacagcgac 1980
tccgaggacg atgtgctgtc atcctcatca tgcggttcca attccgactc cggaacctgt 2040
cagagcccct ccctggagga acctatggag gacgaatccg agatcgagga attctacaac 2100
ggtctggagg acgagcctga tgtcccggaa cgcgctggag gagctggctt cggaaccgac 2160
ggggacgacc aggaagccat caacgaggcc atctcggtga agcaggaagt gaccgatatg 2220
aactacccgt ccaacaagtc c 2241

<210> SEQ ID NO 13
<211> LENGTH: 12377
<212> TYPE: DNA
<213> ORGANISM: Artificial Sequence
<220> FEATURE:
<223> OTHER INFORMATION: constructed sequence

<400> SEQUENCE: 13
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240

-continued

```
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tatttttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
```

-continued

```
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatgg   3120
cggacgaggc ggccctcgcc cttcagcccg gcggctcccc ctcggcggcg gggggccgaca   3180
gggaggccgc gtcgtccccc gccggggagc cgctccgcaa gaggccgcgg agagatggtc   3240
ccggcctcga gcggagcccg ggcgagcccg gtggggcggc cccagagcgt gaggtgccgg   3300
cggcggccag gggctgcccg ggtgcggcgg cggcggcgct gtggcgggag gcggaggcag   3360
aggcggcggc ggcaggcggg gagcaagagg cccaggcgac tgcggcggct ggggaaggag   3420
acaatgggcc gggcctgcag ggcccatctc gggagccacc gctggccgac aacttgtacg   3480
acgaagacga cgacgacgag ggcgaggagg aggaagaggc ggcggcggcg gcgattgggt   3540
accgagataa ccttctgttc ggtgatgaaa ttatcactaa tggttttcat tcctgtgaaa   3600
gtgatgagga ggatagagcc tcacatgcaa gctctagtga ctggactcca aggccacgga   3660
taggtccata tacttttgtt cagcaacatc ttatgattgg cacagatcct cgaacaattc   3720
ttaaagattt attgccggaa acaatacctc cacctgagtt ggatgatatg acactgtggc   3780
agattgttat taatatcctt tcagaaccac caaaaaggaa aaaaagaaaa gatattaata   3840
caattgaaga tgctgtgaaa ttactgcaag agtgcaaaaa aattatagtt ctaactggag   3900
ctggggtgtc tgtttcatgt ggaatacctg acttcaggtc aagggatggt atttatgctc   3960
gccttgctgt agacttccca gatcttccag atcctcaagc gatgtttgat attgaatatt   4020
tcagaaaaga tccaagacca ttcttcaagt ttgcaaagga aatatatcct ggacaattcc   4080
agccatctct ctgtcacaaa ttcatagcct tgtcagataa ggaaggaaaa ctacttcgca   4140
actataccca gaacatagac acgctggaac aggttgcggg aatccaaagg ataattcagt   4200
gtcatggttc ctttgcaaca gcatcttgcc tgatttgtaa atacaaagtt gactgtgaag   4260
ctgtacgagg agatattttt aatcaggtag ttcctcgatg tcctaggtgc ccagctgatg   4320
aaccgcttgc tatcatgaaa ccagagattg tgtttttttgg tgaaaattta ccagaacagt   4380
ttcatagagc catgaagtat gacaaagatg aagttgacct cctcattgtt attgggtctt   4440
ccctcaaagt aagaccagta gcactaattc caagttccat accccatgaa gtgcctcaga   4500
tattaattaa tagagaacct ttgcctcatc tgcattttga tgtagagctt cttggagact   4560
gtgatgtcat aattaatgaa ttgtgtcata ggttaggtgg tgaatatgcc aaactttgct   4620
gtaaccctgt aaagctttca gaaattactg aaaaacctcc acgaacacaa aaagaattgg   4680
cttatttgtc agagttgcca cccacacctc ttcatgtttc agaagactca agttcaccag   4740
aaagaacttc accaccagat tcttcagtga ttgtcacact tttagaccaa gcagctaaga   4800
gtaatgatga tttagatgtg tctgaatcaa aaggttgtat ggaagaaaaa ccacaggaag   4860
tacaaacttc taggaatgtt gaaagtattg ctgaacagat ggaaaatccg gatttgaaga   4920
atgttggttc tagtactggg gagaaaaatg aaagaacttc agtggctgga acagtgagaa   4980
```

```
aatgctggcc taatagagtg gcaaaggagc agattagtag gcggcttgat ggtaatcagt   5040
atctgttttt gccaccaaat cgttacattt tccatggcgc tgaggtatat tcagactctg   5100
aagatgacgt cttatcctct agttcttgtg gcagtaacag tgatagtggg acatgccaga   5160
gtccaagttt agaagaaccc atggaggatg aaagtgaaat tgaagaattc tacaatggct   5220
tagaagatga gcctgatgtt ccagagagag ctggaggagc tggatttggg actgatggag   5280
atgatcaaga ggcaattaat gaagctatat ctgtgaaaca ggaagtaaca gacatgaact   5340
atccatcaaa caaatcatga agtactgcgg atcctgcaga tctgcctcga ctgtgccttc   5400
tagttgccag ccatctgttg tttgcccctc ccccgtgcct tccttgaccc tggaaggtgc   5460
cactcccact gtcctttcct aataaaatga ggaaattgca tcgcattgtc tgagtaggtg   5520
tcattctatt ctggggggtg gggtggggca ggacagcaag ggggaggatt gggaagacaa   5580
tagcaggcat gctggggact cgagttctac gtagataagt agcatggcgg gttaatcatt   5640
aactacaagg aacccctagt gatggagttg gccactccct ctctgcgcgc tcgctcgctc   5700
actgaggccg ggcgaccaaa ggtcgcccga cgcccgggct ttgcccgggc ggcctcagtg   5760
agcgagcgag cgcgcagcct taattaacct aaggaaaatg aagtgaagtt cctatacttt   5820
ctagagaata ggaacttcta tagtgagtcg aataagggcg acacaaaatt tattctaaat   5880
gcataataaa tactgataac atcttatagt ttgtattata ttttgtatta tcgttgacat   5940
gtataatttt gatatcaaaa actgatttc cctttattat tttcgagatt tatttctta    6000
attctcttta acaaactaga aatattgtat atacaaaaaa tcataaataa tagatgaata   6060
gtttaattat aggtgttcat caatcgaaaa agcaacgtat cttatttaaa gtgcgttgct   6120
tttttctcat ttataaggtt aaataattct catatatcaa gcaaagtgac aggcgccctt   6180
aaatattctg acaaatgctc tttccctaaa ctccccccat aaaaaaaccc gccgaagcgg   6240
gtttttacgt tatttgcgga ttaacgatta ctcgttatca gaaccgccca gggggcccga   6300
gcttaacctt tttatttggg ggagagggaa gtcatgaaaa aactaacctt tgaaattcga   6360
tctccagcac atcagcaaaa cgctattcac gcagtacagc aaatccttcc agacccaacc   6420
aaaccaatcg tagtaaccat tcaggaacgc aaccgcagct tagaccaaaa caggaagcta   6480
tgggcctgct taggtgacgt ctctcgtcag gttgaatggc atggtcgctg gctggatgca   6540
gaaagctgga agtgtgtgtt taccgcagca ttaaagcagc aggatgttgt tcctaacctt   6600
gccgggaatg gctttgtggt aataggccag tcaaccagca ggatgcgtgt aggcgaattt   6660
gcggagctat tagagcttat acaggcattc ggtacagagc gtggcgttaa gtggtcagac   6720
gaagcgagac tggctctgga gtggaaagcg agatggggag acagggctgc atgataaatg   6780
tcgttagttt ctccggtggc aggacgtcag catatttgct ctggctaatg gagcaaaagc   6840
gacgggcagg taaagacgtg cattacgttt tcatggatac aggttgtgaa catccaatga   6900
catatcggtt tgtcagggaa gttgtgaagt tctgggatat accgctcacc gtattgcagg   6960
ttgatatcaa cccggagctt ggacagccaa atggttatac ggtatgggaa ccaaaggata   7020
ttcagacgcg aatgcctgtt ctgaagccat ttatcgatat ggtaaagaaa tatggcactc   7080
catacgtcgg cggcgcgttc tgcactgaca gattaaaact cgttcccttc accaaatact   7140
gtgatgacca tttcgggcga gggaattaca ccacgtggat tggcatcaga gctgatgaac   7200
cgaagcggct aaagccaaag cctggaatca gatatcttgc tgaactgtca gactttgaga   7260
aggaagatat cctcgcatgg tggaagcaac aaccattcga tttgcaaata ccggaacatc   7320
```

-continued tcggtaactg catattctgc attaaaaaat caacgcaaaa aatcggactt gcctgcaaag 7380
atgaggaggg attgcagcgt gtttttaatg aggtcatcac gggatcccat gtgcgtgacg 7440
gacatcggga aacgccaaag gagattatgt accgaggaag aatgtcgctg gacggtatcg 7500
cgaaaatgta ttcagaaaat gattatcaag ccctgtatca ggacatggta cgagctaaaa 7560
gattcgatac cggctcttgt tctgagtcat gcgaaatatt tggagggcag cttgatttcg 7620
acttcgggag ggaagctgca tgatgcgatg ttatcggtgc ggtgaatgca aagaagataa 7680
ccgcttccga ccaaatcaac cttactggaa tcgatggtgt ctccggtgtg aaagaacacc 7740
aacaggggtg ttaccactac cgcaggaaaa ggaggacgtg tggcgagaca gcgacgaagt 7800
atcaccgaca taatctgcga aaactgcaaa taccttccaa cgaaacgcac cagaaataaa 7860
cccaagccaa tcccaaaaga atctgacgta aaaaccttca actacacggc tcacctgtgg 7920
gatatccggt ggctaagacg tcgtgcgagg aaaacaaggt gattgaccaa aatcgaagtt 7980
acgaacaaga aagcgtcgag cgagctttaa cgtgcgctaa ctgcggtcag aagctgcatg 8040
tgctggaagt tcacgtgtgt gagcactgct gcgcagaact gatgagcgat ccgaatagct 8100
cgatgcacga ggaagaagat gatggctaaa ccagcgcgaa gacgatgtaa aaacgatgaa 8160
tgccgggaat ggtttcaccc tgcattcgct aatcagtggt ggtgctctcc agagtgtgga 8220
accaagatag cactcgaacg acgaagtaaa gaacgcgaaa aagcggaaaa agcagcagag 8280
aagaaacgac gacgagagga gcagaaacag aaagataaac ttaagattcg aaaactcgcc 8340
ttaaagcccc gcagttactg gattaaacaa gcccaacaag ccgtaaacgc cttcatcaga 8400
gaaagagacc gcgacttacc atgtatctcg tgcggaacgc tcacgtctgc tcagtgggat 8460
gccggacatt accggacaac tgctgcggca cctcaactcc gatttaatga acgcaatatt 8520
cacaagcaat gcgtggtgtg caaccagcac aaaagcggaa atctcgttcc gtatcgcgtc 8580
gaactgatta gccgcatcgg gcaggaagca gtagacgaaa tcgaatcaaa ccataaccgc 8640
catcgctgga ctatcgaaga gtgcaaggcg atcaaggcag agtaccaaca gaaactcaaa 8700
gacctgcgaa atagcagaag tgaggccgca tgacgttctc agtaaaaacc attccagaca 8760
tgctcgttga agcatacgga aatcagacag aagtagcacg cagactgaaa tgtagtcgcg 8820
gtacggtcag aaaatacgtt gatgataaag acgggaaaat gcacgccatc gtcaacgacg 8880
ttctcatggt tcatcgcgga tggagtgaaa gagatgcgct attacgaaaa aattgatggc 8940
agcaaatacc gaaatatttg ggtagttggc gatctgcacg gatgctacac gaacctgatg 9000
aacaaactgg atacgattgg attcgacaac aaaaaagacc tgcttatctc ggtgggcgat 9060
ttggttgatc gtggtgcaga gaacgttgaa tgcctggaat taatcacatt cccctggttc 9120
agagctgtac gtggaaacca tgagcaaatg atgattgatg gcttatcaga gcgtggaaac 9180
gttaatcact ggctgcttaa tggcggtggc tggttcttta atctcgatta cgacaaagaa 9240
attctggcta aagctcttgc ccataaagca gatgaacttc cgttaatcat cgaactggtg 9300
agcaaagata aaaaatatgt tatctgccac gccgattatc cctttgacga atacgagttt 9360
ggaaagccag ttgatcatca gcaggtaatc tggaaccgcg aacgaatcag caactcacaa 9420
aacgggatcg tgaaagaaat caaaggcgcg gacacgttca tctttggtca tacgccagca 9480
gtgaaaccac tcaagtttgc caaccaaatg tatatcgata ccggcgcagt gttctgcgga 9540
aacctaacat tgattcaggt acagggagaa ggcgcatgag actcgaaagc gtagctaaat 9600
ttcattcgcc aaaaagcccg atgatgagcg actcaccacg ggccacggct tctgactctc 9660
tttccggtac tgatgtgatg gctgctatgg ggatggcgca atcacaagcc ggattcggta 9720

```
tggctgcatt ctgcggtaag cacgaactca gccagaacga caaacaaaag gctatcaact   9780
atctgatgca atttgcacac aaggtatcgg ggaaataccg tggtgtggca aagcttgaag   9840
gaaatactaa ggcaaaggta ctgcaagtgc tcgcaacatt cgcttatgcg gattattgcc   9900
gtagtgccgc gacgccgggg gcaagatgca gagattgcca tggtacaggc cgtgcggttg   9960
atattgccaa aacagagctg tgggggagag ttgtcgagaa agagtgcgga agatgcaaag  10020
gcgtcggcta ttcaaggatg ccagcaagcg cagcatatcg cgctgtgacg atgctaatcc  10080
caaaccttac ccaacccacc tggtcacgca ctgttaagcc gctgtatgac gctctggtgg  10140
tgcaatgcca caaagaagag tcaatcgcag acaacatttt gaatgcggtc acacgttagc  10200
agcatgattg ccacggatgg caacatatta acggcatgat attgacttat tgaataaaat  10260
tgggtaaatt tgactcaacg atgggttaat tcgctcgttg tggtagtgag atgaaaagag  10320
gcggcgctta ctaccgattc cgcctagttg gtcacttcga cgtatcgtct ggaactccaa  10380
ccatcgcagg cagagaggtc tgcaaaatgc aatcccgaaa cagttcgcag gtaatagtta  10440
gagcctgcat aacggtttcg ggattttta tatctgcaca acaggtaaga gcattgagtc  10500
gataatcgtg aagagtcggc gagcctggtt agccagtgct ctttccgttg tgctgaatta  10560
agcgaatacc ggaagcagaa ccggatcacc aaatgcgtac aggcgtcatc gccgcccagc  10620
aacagcacaa cccaaactga gccgtagcca ctgtctgtcc tgaattcatt agtaatagtt  10680
acgctgcggc cttttacaca tgaccttcgt gaaagcgggt ggcaggaggt cgcgctaaca  10740
acctcctgcc gttttgcccg tgcatatcgg tcacgaacaa atctgattac taaacacagt  10800
agcctggatt tgttctatca gtaatcgacc ttattcctaa ttaaatagag caaatcccct  10860
tattgggggt aagacatgaa gatgccagaa aaacatgacc tgttggccgc cattctcgcg  10920
gcaaaggaac aaggcatcgg ggcaatcctt gcgtttgcaa tggcgtacct tcgcggcaga  10980
tataatggcg gtgcgtttac aaaaacagta atcgacgcaa cgatgtgcgc cattatcgcc  11040
tggttcattc gtgaccttct cgacttcgcc ggactaagta gcaatctcgc ttatataacg  11100
agcgtgttta tcggctacat cggtactgac tcgattggtt cgcttatcaa acgcttcgct  11160
gctaaaaaag ccggagtaga agatggtaga aatcaataat caacgtaagg cgttcctcga  11220
tatgctggcg tggtcggagg gaactgataa cggacgtcag aaaaccagaa atcatggtta  11280
tgacgtcatt gtaggcggag agctatttac tgattactcc gatcaccctc gcaaacttgt  11340
cacgctaaac ccaaaactca aatcaacagg cgcttaagac tggccgtcgt tttacaacac  11400
agaaagagtt tgtagaaacg caaaaaggcc atccgtcagg ggccttctgc ttagtttgat  11460
gcctggcagt tccctactct cgccttccgc ttcctcgctc actgactcgc tgcgctcggt  11520
cgttcggctg cggcgagcgg tatcagctca ctcaaaggcg gtaatacggt tatccacaga  11580
atcaggggat aacgcaggaa agaacatgtg agcaaaaggc cagcaaaagg ccaggaaccg  11640
taaaaaggcc gcgttgctgg cgtttttcca taggctccgc ccccctgacg agcatcacaa  11700
aaatcgacgc tcaagtcaga ggtggcgaaa cccgacagga ctataaagat accaggcgtt  11760
tccccctgga agctccctcg tgcgctctcc tgttccgacc ctgccgctta ccggatacct  11820
gtccgccttt ctcccttcgg gaagcgtggc gctttctcat agctcacgct gtaggtatct  11880
cagttcggtg taggtcgttc gctccaagct gggctgtgtg cacgaacccc ccgttcagcc  11940
cgaccgctgc gccttatccg gtaactatcg tcttgagtcc aacccggtaa gacacgactt  12000
atcgccactg gcagcagcca ctggtaacag gattagcaga gcgaggtatg taggcggtgc  12060
```

```
tacagagttc ttgaagtggt gggctaacta cggctacact agaagaacag tatttggtat  12120

ctgcgctctg ctgaagccag ttaccttcgg aaaaagagtt ggtagctctt gatccggcaa  12180

acaaaccacc gctggtagcg gtggtttttt tgtttgcaag cagcagatta cgcgcagaaa  12240

aaaaggatct caagaagatc ctttgatctt ttctacgggg tctgacgctc agtggaacga  12300

cgcgcgcgta actcacgtta agggattttg gtcatgagct tgcgccgtcc cgtcaagtca  12360

gcgtaatgct ctgcttt                                                12377


<210> SEQ ID NO 14
<211> LENGTH: 12454
<212> TYPE: DNA
<213> ORGANISM: Artificial Sequence
<220> FEATURE:
<223> OTHER INFORMATION: constructed sequence

<400> SEQUENCE: 14

tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720

ttatcgcgag cccatttata cccatataaa tcagcatcca tgttggaatt taatcgcggc    780

ctcgacgttt cccgttgaat atggctcata ttcttccttt ttcaatatta ttgaagcatt    840

tatcagggtt attgtctcat gagcggatac atatttgaat gtatttagaa aaataaacaa    900

ataggggtca gtgttacaac caattaacca attctgaaca ttatcgcgag cccatttata    960

cctgaatatg gctcataaca ccccttgttt gcctggcggc agtagcgcgg tggtcccacc   1020

tgaccccatg ccgaactcag aagtgaaacg ccgtagcgcc gatggtagtg tggggactcc   1080

ccatgcgaga gtagggaact gccaggcatc aaataaaacg aaaggctcag tcgaaagact   1140

gggcctttcg cccgggctaa ttagggggtg tcgcccttat tcgactctat agtgaagttc   1200

ctattctcta gaaagtatag gaacttctga agtggggtcg acttaattaa ggctgcgcgc   1260

tcgctcgctc actgaggccg cccgggcaaa gcccgggcgt cgggcgacct ttggtcgccc   1320

ggcctcagtg agcgagcgag cgcgcagaga gggagtggcc aactccatca ctaggggttc   1380

cttgtagtta atgattaacc cgccatgcta cttatctacg tagcaagcta gctagttatt   1440

aatagtaatc aattacgggg tcattagttc atagcccata tatggagttc cgcgttacat   1500

aacttacggt aaatggcccg cctggctgac cgcccaacga cccccgccca ttgacgtcaa   1560

taatgacgta tgttcccata gtaacgccaa tagggacttt ccattgacgt caatgggtgg   1620

agtatttacg gtaaactgcc cacttggcag tacatcaagt gtatcatatg ccaagtacgc   1680

cccctattga cgtcaatgac ggtaaatggc ccgcctggca ttatgcccag tacatgacct   1740
```

```
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tattttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatgg   3120
cggacgaggc ggccctcgcc cttcagcccg gcggctcccc ctcggcggcg ggggccgaca   3180
gggaggccgc gtcgtccccc gccggggagc cgctccgcaa gaggccgcgg agagatggtc   3240
ccggcctcga gcggagcccg ggcgagcccg gtggggcggc cccagagcgt gaggtgccgg   3300
cggcggccag gggctgcccg ggtgcggcgg cggcggcgct gtggcgggag gcggaggcag   3360
aggcggcggc ggcaggcggg gagcaagagg cccaggcgac tgcggcggct ggggaaggag   3420
acaatgggcc gggcctgcag ggcccatctc gggagccacc gctggccgac aacttgtacg   3480
acgaagacga cgacgacgag ggcgaggagg aggaagaggc ggcggcggcg gcgattgggt   3540
accgagataa ccttctgttc ggtgatgaaa ttatcactaa tggttttcat tcctgtgaaa   3600
gtgatgagga ggatagagcc tcacatgcaa gctctagtga ctggactcca aggccacgga   3660
taggtccata tacttttgtt cagcaacatc ttatgattgg cacagatcct cgaacaattc   3720
ttaaagattt attgccggaa acaatacctc cacctgagtt ggatgatatg acactgtggc   3780
agattgttat taatatcctt tcagaaccac caaaaaggaa aaaaagaaaa gatattaata   3840
caattgaaga tgctgtgaaa ttactgcaag agtgcaaaaa aattatagtt ctaactggag   3900
ctggggtgtc tgtttcatgt ggaatacctg acttcaggtc aagggatggt atttatgctc   3960
gccttgctgt agacttccca gatcttccag atcctcaagc gatgtttgat attgaatatt   4020
tcagaaaaga tccaagacca ttcttcaagt ttgcaaagga aatatatcct ggacaattcc   4080
```

-continued agccatctct ctgtcacaaa ttcatagcct tgtcagataa ggaaggaaaa ctacttcgca 4140
actataccca gaacatagac acgctggaac aggttgcggg aatccaaagg ataattcagt 4200
gtcatggttc ctttgcaaca gcatcttgcc tgatttgtaa atacaaagtt gactgtgaag 4260
ctgtacgagg agatattttt aatcaggtag ttcctcgatg tcctaggtgc ccagctgatg 4320
aaccgcttgc tatcatgaaa ccagagattg tgtttttgg tgaaaattta ccagaacagt 4380
ttcatagagc catgaagtat gacaaagatg aagttgacct cctcattgtt attgggtctt 4440
ccctcaaagt aagaccagta gcactaattc caagttccat accccatgaa gtgcctcaga 4500
tattaattaa tagagaacct ttgcctcatc tgcattttga tgtagagctt cttggagact 4560
gtgatgtcat aattaatgaa ttgtgtcata ggttaggtgg tgaatatgcc aaactttgct 4620
gtaaccctgt aaagctttca gaaattactg aaaaacctcc acgaacacaa aaagaattgg 4680
cttatttgtc agagttgcca cccacacctc ttcatgtttc agaagactca agttcaccag 4740
aaagaacttc accaccagat tcttcagtga ttgtcacact tttagaccaa gcagctaaga 4800
gtaatgatga tttagatgtg tctgaatcaa aaggttgtat ggaagaaaaa ccacaggaag 4860
tacaaacttc taggaatgtt gaaagtattg ctgaacagat ggaaaatccg gatttgaaga 4920
atgttggttc tagtactggg gagaaaaatg aaagaacttc agtggctgga acagtgagaa 4980
aatgctggcc taatagagtg gcaaaggagc agattagtag gcggcttgat ggtaatcagt 5040
atctgttttt gccaccaaat cgttacattt tccatggcgc tgaggtatat tcagactctg 5100
aagatgacgt cttatcctct agttcttgtg gcagtaacag tgatagtggg acatgccaga 5160
gtccaagttt agaagaaccc atggaggatg aaagtgaaat tgaagaattc tacaatggct 5220
tagaagatga gcctgatgtt ccagagagag ctggaggagc tggatttggg actgatggag 5280
atgatcaaga ggcaattaat gaagctatat ctgtgaaaca ggaagtaaca gacatgaact 5340
atccatcaaa caaatcagac tacaaagacc atgacggtga ttataaagat catgacatcg 5400
attacaagga tgacgatgac aagtgatgag gccgcatagt actgcggatc ctgcagatct 5460
gcctcgactg tgccttctag ttgccagcca tctgttgttt gcccctcccc cgtgccttcc 5520
ttgaccctgg aaggtgccac tcccactgtc ctttcctaat aaaatgagga aattgcatcg 5580
cattgtctga gtaggtgtca ttctattctg gggggtgggg tggggcagga cagcaagggg 5640
gaggattggg aagacaatag caggcatgct ggggactcga gttctacgta gataagtagc 5700
atggcgggtt aatcattaac tacaaggaac ccctagtgat ggagttggcc actccctctc 5760
tgcgcgctcg ctcgctcact gaggccgggc gaccaaaggt cgcccgacgc ccgggctttg 5820
cccgggcggc ctcagtgagc gagcgagcgc gcagccttaa ttaacctaag gaaaatgaag 5880
tgaagttcct atactttcta gagaatagga acttctatag tgagtcgaat aagggcgaca 5940
caaaatttat tctaaatgca taataaatac tgataacatc ttatagtttg tattatattt 6000
tgtattatcg ttgacatgta taattttgat atcaaaaact gattttccct ttattatttt 6060
cgagatttat ttttcttaatt ctctttaaca aactagaaat attgtatata caaaaaatca 6120
taaataatag atgaatagtt taattatagg tgttcatcaa tcgaaaaagc aacgtatctt 6180
atttaaagtg cgttgctttt ttctcattta taaggttaaa taattctcat atatcaagca 6240
aagtgacagg cgcccttaaa tattctgaca aatgctcttt ccctaaactc cccccataaa 6300
aaaacccgcc gaagcgggtt tttacgttat ttgcggatta acgattactc gttatcagaa 6360
ccgcccaggg ggcccgagct taaccttttt atttggggga gagggaagtc atgaaaaaac 6420
taacctttga aattcgatct ccagcacatc agcaaaacgc tattcacgca gtacagcaaa 6480

-continued

```
tccttccaga cccaaccaaa ccaatcgtag taaccattca ggaacgcaac cgcagcttag   6540
accaaaacag gaagctatgg gcctgcttag gtgacgtctc tcgtcaggtt gaatggcatg   6600
gtcgctggct ggatgcagaa agctggaagt gtgtgtttac cgcagcatta aagcagcagg   6660
atgttgttcc taaccttgcc gggaatggct ttgtggtaat aggccagtca accagcagga   6720
tgcgtgtagg cgaatttgcg gagctattag agcttataca ggcattcggt acagagcgtg   6780
gcgttaagtg gtcagacgaa gcgagactgg ctctggagtg gaaagcgaga tggggagaca   6840
gggctgcatg ataaatgtcg ttagtttctc cggtggcagg acgtcagcat atttgctctg   6900
gctaatggag caaaagcgac gggcaggtaa agacgtgcat tacgttttca tggatacagg   6960
ttgtgaacat ccaatgacat atcggtttgt cagggaagtt gtgaagttct gggatatacc   7020
gctcaccgta ttgcaggttg atatcaaccc ggagcttgga cagccaaatg gttatacggt   7080
atgggaacca aaggatattc agacgcgaat gcctgttctg aagccattta tcgatatggt   7140
aaagaaatat ggcactccat acgtcggcgg cgcgttctgc actgacagat taaaactcgt   7200
tcccttcacc aaatactgtg atgaccattt cgggcgaggg aattacacca cgtggattgg   7260
catcagagct gatgaaccga agcggctaaa gccaaagcct ggaatcagat atcttgctga   7320
actgtcagac tttgagaagg aagatatcct cgcatggtgg aagcaacaac cattcgattt   7380
gcaaataccg gaacatctcg gtaactgcat attctgcatt aaaaaatcaa cgcaaaaaat   7440
cggacttgcc tgcaaagatg aggagggatt gcagcgtgtt tttaatgagg tcatcacggg   7500
atcccatgtg cgtgacggac atcgggaaac gccaaaggag attatgtacc gaggaagaat   7560
gtcgctggac ggtatcgcga aaatgtattc agaaaatgat tatcaagccc tgtatcagga   7620
catggtacga gctaaaagat tcgataccgg ctcttgttct gagtcatgcg aaatatttgg   7680
agggcagctt gatttcgact tcgggaggga agctgcatga tgcgatgtta tcggtgcggt   7740
gaatgcaaag aagataaccg cttccgacca aatcaacctt actggaatcg atggtgtctc   7800
cggtgtgaaa gaacaccaac aggggtgtta ccactaccgc aggaaaagga ggacgtgtgg   7860
cgagacagcg acgaagtatc accgacataa tctgcgaaaa ctgcaaatac cttccaacga   7920
aacgcaccag aaataaaccc aagccaatcc caaaagaatc tgacgtaaaa accttcaact   7980
acacggctca cctgtgggat atccggtggc taagacgtcg tgcgaggaaa acaaggtgat   8040
tgaccaaaat cgaagttacg aacaagaaag cgtcgagcga gctttaacgt gcgctaactg   8100
cggtcagaag ctgcatgtgc tggaagttca cgtgtgtgag cactgctgcg cagaactgat   8160
gagcgatccg aatagctcga tgcacgagga agaagatgat ggctaaacca gcgcgaagac   8220
gatgtaaaaa cgatgaatgc cgggaatggt ttcaccctgc attcgctaat cagtggtggt   8280
gctctccaga gtgtggaacc aagatagcac tcgaacgacg aagtaaagaa cgcgaaaaag   8340
cggaaaaagc agcagagaag aaacgacgac gagaggagca gaaacagaaa gataaactta   8400
agattcgaaa actcgcctta aagccccgca gttactggat taaacaagcc caacaagccg   8460
taaacgcctt catcagagaa agagaccgcg acttaccatg tatctcgtgc ggaacgctca   8520
cgtctgctca gtgggatgcc ggacattacc ggacaactgc tgcggcacct caactccgat   8580
ttaatgaacg caatattcac aagcaatgcg tggtgtgcaa ccagcacaaa agcggaaatc   8640
tcgttccgta tcgcgtcgaa ctgattagcc gcatcgggca ggaagcagta gacgaaatcg   8700
aatcaaacca taaccgccat cgctggacta tcgaagagtg caaggcgatc aaggcagagt   8760
accaacagaa actcaaagac ctgcgaaata gcagaagtga ggccgcatga cgttctcagt   8820
```

-continued aaaaaccatt ccagacatgc tcgttgaagc atacggaaat cagacagaag tagcacgcag 8880
actgaaatgt agtcgcggta cggtcagaaa atacgttgat gataaagacg ggaaaatgca 8940
cgccatcgtc aacgacgttc tcatggttca tcgcggatgg agtgaaagag atgcgctatt 9000
acgaaaaaat tgatggcagc aaataccgaa atatttgggt agttggcgat ctgcacggat 9060
gctacacgaa cctgatgaac aaactggata cgattggatt cgacaacaaa aaagacctgc 9120
ttatctcggt gggcgatttg gttgatcgtg gtgcagagaa cgttgaatgc ctggaattaa 9180
tcacattccc ctggttcaga gctgtacgtg gaaaccatga gcaaatgatg attgatggct 9240
tatcagagcg tggaaacgtt aatcactggc tgcttaatgg cggtggctgg ttctttaatc 9300
tcgattacga caaagaaatt ctggctaaag ctcttgccca taaagcagat gaacttccgt 9360
taatcatcga actggtgagc aaagataaaa aatatgttat ctgccacgcc gattatccct 9420
ttgacgaata cgagtttgga aagccagttg atcatcagca ggtaatctgg aaccgcgaac 9480
gaatcagcaa ctcacaaaac gggatcgtga aagaaatcaa aggcgcggac acgttcatct 9540
ttggtcatac gccagcagtg aaaccactca agtttgccaa ccaaatgtat atcgataccg 9600
gcgcagtgtt ctgcggaaac ctaacattga ttcaggtaca gggagaaggc gcatgagact 9660
cgaaagcgta gctaaatttc attcgccaaa aagcccgatg atgagcgact caccacgggc 9720
cacggcttct gactctcttt ccggtactga tgtgatggct gctatgggga tggcgcaatc 9780
acaagccgga ttcggtatgg ctgcattctg cggtaagcac gaactcagcc agaacgacaa 9840
acaaaaggct atcaactatc tgatgcaatt tgcacacaag gtatcgggga aataccgtgg 9900
tgtggcaaag cttgaaggaa atactaaggc aaaggtactg caagtgctcg caacattcgc 9960
ttatgcggat tattgccgta gtgccgcgac gccgggggca agatgcagag attgccatgg 10020
tacaggccgt gcggttgata ttgccaaaac agagctgtgg gggagagttg tcgagaaaga 10080
gtgcggaaga tgcaaaggcg tcggctattc aaggatgcca gcaagcgcag catatcgcgc 10140
tgtgacgatg ctaatcccaa accttaccca acccacctgg tcacgcactg ttaagccgct 10200
gtatgacgct ctggtggtgc aatgccacaa agaagagtca atcgcagaca acattttgaa 10260
tgcggtcaca cgttagcagc atgattgcca cggatggcaa catattaacg gcatgatatt 10320
gacttattga ataaaattgg gtaaatttga ctcaacgatg ggttaattcg ctcgttgtgg 10380
tagtgagatg aaaagaggcg gcgcttacta ccgattccgc ctagttggtc acttcgacgt 10440
atcgtctgga actccaacca tcgcaggcag agaggtctgc aaaatgcaat cccgaaacag 10500
ttcgcaggta atagttagag cctgcataac ggtttcggga tttttatat ctgcacaaca 10560 ggtaagagca ttgagtcgat aatcgtgaag agtcggcgag cctggttagc cagtgctctt 10620
tccgttgtgc tgaattaagc gaataccgga agcagaaccg gatcaccaaa tgcgtacagg 10680
cgtcatcgcc gcccagcaac agcacaaccc aaactgagcc gtagccactg tctgtcctga 10740
attcattagt aatagttacg ctgcggcctt ttacacatga ccttcgtgaa agcgggtggc 10800
aggaggtcgc gctaacaacc tcctgccgtt ttgcccgtgc atatcggtca cgaacaaatc 10860
tgattactaa acacagtagc ctggatttgt tctatcagta atcgacctta ttcctaatta 10920
aatagagcaa atccccttat tgggggtaag acatgaagat gccagaaaaa catgacctgt 10980
tggccgccat tctcgcggca aaggaacaag gcatcggggc aatccttgcg tttgcaatgg 11040
cgtaccttcg cggcagatat aatggcggtg cgtttacaaa aacagtaatc gacgcaacga 11100
tgtgcgccat tatcgcctgg ttcattcgtg accttctcga cttcgccgga ctaagtagca 11160
atctcgctta tataacgagc gtgtttatcg gctacatcgg tactgactcg attggttcgc 11220
ttatcaaacg cttcgctgct aaaaaagccg gagtagaaga tggtagaaat caataatcaa 11280
cgtaaggcgt tcctcgatat gctggcgtgg tcggagggaa ctgataacgg acgtcagaaa 11340
accagaaatc atggttatga cgtcattgta ggcggagagc tatttactga ttactccgat 11400
caccctcgca aacttgtcac gctaaaccca aaactcaaat caacaggcgc ttaagactgg 11460
ccgtcgtttt acaacacaga aagagtttgt agaaacgcaa aaaggccatc cgtcaggggc 11520
cttctgctta gtttgatgcc tggcagttcc ctactctcgc cttccgcttc ctcgctcact 11580
gactcgctgc gctcggtcgt tcggctgcgg cgagcggtat cagctcactc aaaggcggta 11640
atacggttat ccacagaatc aggggataac gcaggaaaga acatgtgagc aaaaggccag 11700
caaaaggcca ggaaccgtaa aaaggccgcg ttgctggcgt ttttccatag gctccgcccc 11760
cctgacgagc atcacaaaaa tcgacgctca agtcagaggt ggcgaaaccc gacaggacta 11820
taaagatacc aggcgtttcc ccctggaagc tccctcgtgc gctctcctgt tccgaccctg 11880
ccgcttaccg gatacctgtc cgcctttctc ccttcgggaa gcgtggcgct ttctcatagc 11940
tcacgctgta ggtatctcag ttcggtgtag gtcgttcgct ccaagctggg ctgtgtgcac 12000
gaaccccccg ttcagcccga ccgctgcgcc ttatccggta actatcgtct tgagtccaac 12060
ccggtaagac acgacttatc gccactggca gcagccactg gtaacaggat tagcagagcg 12120
aggtatgtag gcggtgctac agagttcttg aagtggtggg ctaactacgg ctacactaga 12180
agaacagtat ttggtatctg cgctctgctg aagccagtta ccttcggaaa aagagttggt 12240
agctcttgat ccggcaaaca aaccaccgct ggtagcggtg gtttttttgt ttgcaagcag 12300
cagattacgc gcagaaaaaa aggatctcaa gaagatcctt tgatcttttc tacggggtct 12360
gacgctcagt ggaacgacgc gcgcgtaact cacgttaagg gattttggtc atgagcttgc 12420
gccgtcccgt caagtcagcg taatgctctg cttt 12454

<210> SEQ ID NO 15
<211> LENGTH: 12392
<212> TYPE: DNA
<213> ORGANISM: Artificial Sequence
<220> FEATURE:
<223> OTHER INFORMATION: constructed sequence

<400> SEQUENCE: 15
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780

-continued

```
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tatttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cgggggtgg cggcaggtgg gggtgccggg cggggcgggg ccgcctcggg ccggggaggg    2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gcgccgccac   3120
catggccgac gaagccgcac tcgcgctgca accagggggt tccccgtctg cagcaggcgc   3180
```

```
cgatagagaa gcagccagct cgccagcagg agaaccgctc cggaagcgac ccaggagaga   3240
tggcccaggc ctggaacgct caccgggtga accaggaggt gccgctcctg aacgggaagt   3300
gcccgcagct gctaggggct gtccaggagc agccgcagca gcactctggc gcgaagccga   3360
agccgaggct gctgcagccg gaggagaaca agaagcccaa gcgaccgctg cagcaggaga   3420
gggcgacaac ggacccggcc tgcaaggacc gtcccgcgaa cctccgctgg ccgacaatct   3480
gtacgacgag gacgatgatg atgagggcga agaagaagag gaagccgccg ctgctgctat   3540
tggatacaga gacaaccttc tcttcggcga cgagatcatc accaatggat tccactcctg   3600
tgaatctgac gaagaagatc gggcctccca tgctagcagc tctgactgga cgccacggcc   3660
aaggatcggt ccgtacacct tcgtgcagca gcacctgatg atcggcacag atccccgcac   3720
cattctgaag gatctgctgc ccgagactat cccacccccct gagctggacg acatgactct   3780
gtggcagatt gtgatcaaca tcctttccga gcccccaaag cggaagaagc gcaaggatat   3840
taacaccatc gaggacgccg tgaagcttct gcaggagtgc aaaaagatca tcgtgctgac   3900
tggtgcaggg gtgtccgtgt cctgcggcat tccggatttc agaagccgcg acggaatcta   3960
cgccagactc gcggtcgact ttcccgatct gcctgaccct caggccatgt tcgatattga   4020
atacttccgc aaggacccga ggccgttctt taagttcgcc aaggagatct accctgggca   4080
gttccaaccc tccctctgcc ataagttcat tgcgctgagc gataaggaag gaaagctgct   4140
gcggaactac acccagaaca tcgacactct tgagcaagtg gcgggtatcc agagaatcat   4200
ccaatgccac ggctccttcg ccactgcctc ctgcctgatc tgcaagtaca aggtcgattg   4260
tgaagccgtc aggggcgata tcttcaacca agtggtcccg cgatgcccaa gatgcccggc   4320
ggatgaaccc ttggccatca tgaagcctga aatcgtgttc ttcggggaaa acctccccga   4380
acagtttcac cgcgccatga agtacgacaa ggacgaagtg gatctcctga ttgtgattgg   4440
ttccagcttg aaagtccggc cagtggcctt gatcccctcc tcgattccac acgaagtgcc   4500
tcaaatcctt attaaccggg aaccactgcc gcatcttcac ttcgatgtgg aactgctggg   4560
agactgcgac gtgattatta acgaactgtg tcaccgcttg ggtggcgaat acgccaagct   4620
gtgctgcaac cctgtgaaac tgtcggagat caccgaaaag ccgcccagaa ctcaaaaaga   4680
gctggcctac ctgtccgagc tccctccgac tccgctgcat gtgtccgagg attcgtcgtc   4740
cccggaaagg acttcgcctc cggactcctc cgtgatcgtg accctgctcg accaagccgc   4800
caagtcgaac gacgatctgg acgtgtcgga atccaagggc tgcatggaag aaaagcctca   4860
agaggtgcag acttcacgga acgtggagtc catcgccgaa cagatggaaa acccggacct   4920
gaagaacgtg ggaagcagca ctggcgaaaa gaacgagaga acctccgtgg ccggtactgt   4980
ccggaagtgc tggccgaaca gggtggccaa ggaacagata tcccggagac ttgacggcaa   5040
ccagtacctc ttcctccccc ctaaccgcta tatttttcac ggggccgagg tgtacagcga   5100
ctccgaggac gatgtgctgt catcctcatc atgcggttcc aattccgact ccggaacctg   5160
tcagagcccc tccctggagg aacctatgga ggacgaatcc gagatcgagg aattctacaa   5220
cggtctggag gacgagcctg atgtcccgga acgcgctgga ggagctggct tcggaaccga   5280
cggggacgac caggaagcca tcaacgaggc catctcggtg aagcaggaag tgaccgatat   5340
gaactacccg tccaacaagt cctgagcggc cgcatagtac tgcggatcct gcagatctgc   5400
ctcgactgtg ccttctagtt gccagccatc tgttgtttgc ccctcccccg tgccttcctt   5460
gaccctggaa ggtgccactc ccactgtcct ttcctaataa aatgaggaaa ttgcatcgca   5520
```

-continued

```
ttgtctgagt aggtgtcatt ctattctggg gggtggggtg gggcaggaca gcaaggggga   5580
ggattgggaa gacaatagca ggcatgctgg ggactcgagt tctacgtaga taagtagcat   5640
ggcgggttaa tcattaacta caaggaaccc ctagtgatgg agttggccac tccctctctg   5700
cgcgctcgct cgctcactga ggccgggcga ccaaaggtcg cccgacgccc gggctttgcc   5760
cgggcggcct cagtgagcga gcgagcgcgc agccttaatt aacctaagga aaatgaagtg   5820
aagttcctat actttctaga gaataggaac ttctatagtg agtcgaataa gggcgacaca   5880
aaatttattc taaatgcata ataaatactg ataacatctt atagtttgta ttatattttg   5940
tattatcgtt gacatgtata attttgatat caaaaactga ttttcccttt attattttcg   6000
agatttattt tcttaattct ctttaacaaa ctagaaatat tgtatataca aaaaatcata   6060
aataatagat gaatagttta attataggtg ttcatcaatc gaaaaagcaa cgtatcttat   6120
ttaaagtgcg ttgctttttt ctcatttata aggttaaata attctcatat atcaagcaaa   6180
gtgacaggcg cccttaaata ttctgacaaa tgctctttcc ctaaactccc cccataaaaa   6240
aacccgccga agcgggtttt tacgttattt gcggattaac gattactcgt tatcagaacc   6300
gcccaggggg cccgagctta acctttttat ttgggggaga gggaagtcat gaaaaaacta   6360
acctttgaaa ttcgatctcc agcacatcag caaaacgcta ttcacgcagt acagcaaatc   6420
cttccagacc caaccaaacc aatcgtagta accattcagg aacgcaaccg cagcttagac   6480
caaaacagga agctatgggc ctgcttaggt gacgtctctc gtcaggttga atggcatggt   6540
cgctggctgg atgcagaaag ctggaagtgt gtgtttaccg cagcattaaa gcagcaggat   6600
gttgttccta accttgccgg gaatggcttt gtggtaatag gccagtcaac cagcaggatg   6660
cgtgtaggcg aatttgcgga gctattagag cttatacagg cattcggtac agagcgtggc   6720
gttaagtggt cagacgaagc gagactggct ctggagtgga aagcgagatg gggagacagg   6780
gctgcatgat aaatgtcgtt agtttctccg gtggcaggac gtcagcatat ttgctctggc   6840
taatggagca aaagcgacgg gcaggtaaag acgtgcatta cgttttcatg gatacaggtt   6900
gtgaacatcc aatgacatat cggtttgtca gggaagttgt gaagttctgg gatataccgc   6960
tcaccgtatt gcaggttgat atcaacccgg agcttggaca gccaaatggt tatacggtat   7020
gggaaccaaa ggatattcag acgcgaatgc ctgttctgaa gccatttatc gatatggtaa   7080
agaaatatgg cactccatac gtcggcggcg cgttctgcac tgacagatta aaactcgttc   7140
ccttcaccaa atactgtgat gaccatttcg ggcgagggaa ttacaccacg tggattggca   7200
tcagagctga tgaaccgaag cggctaaagc caaagcctgg aatcagatat cttgctgaac   7260
tgtcagactt tgagaaggaa gatatcctcg catggtggaa gcaacaacca ttcgatttgc   7320
aaataccgga acatctcggt aactgcatat tctgcattaa aaaatcaacg caaaaaatcg   7380
gacttgcctg caaagatgag gagggattgc agcgtgtttt taatgaggtc atcacgggat   7440
cccatgtgcg tgacggacat cgggaaacgc caaaggagat tatgtaccga ggaagaatgt   7500
cgctggacgg tatcgcgaaa atgtattcag aaaatgatta tcaagccctg tatcaggaca   7560
tggtacgagc taaaagattc gataccggct cttgttctga gtcatgcgaa atatttggag   7620
ggcagcttga tttcgacttc gggagggaag ctgcatgatg cgatgttatc ggtgcggtga   7680
atgcaaagaa gataaccgct tccgaccaaa tcaaccttac tggaatcgat ggtgtctccg   7740
gtgtgaaaga acaccaacag ggtgttacc actaccgcag gaaaaggagg acgtgtggcg   7800
agacagcgac gaagtatcac cgacataatc tgcgaaaact gcaaatacct tccaacgaaa   7860
cgcaccagaa ataaacccaa gccaatccca aaagaatctg acgtaaaaac cttcaactac   7920
```

```
acggctcacc tgtgggatat ccggtggcta agacgtcgtg cgaggaaaac aaggtgattg   7980
accaaaatcg aagttacgaa caagaaagcg tcgagcgagc tttaacgtgc gctaactgcg   8040
gtcagaagct gcatgtgctg gaagttcacg tgtgtgagca ctgctgcgca gaactgatga   8100
gcgatccgaa tagctcgatg cacgaggaag aagatgatgg ctaaaccagc gcgaagacga   8160
tgtaaaaacg atgaatgccg ggaatggttt caccctgcat tcgctaatca gtggtggtgc   8220
tctccagagt gtggaaccaa gatagcactc gaacgacgaa gtaaagaacg cgaaaaagcg   8280
gaaaaagcag cagagaagaa acgacgacga gaggagcaga aacagaaaga taaacttaag   8340
attcgaaaac tcgccttaaa gccccgcagt tactggatta aacaagccca acaagccgta   8400
aacgccttca tcagagaaag agaccgcgac ttaccatgta tctcgtgcgg aacgctcacg   8460
tctgctcagt gggatgccgg acattaccgg acaactgctg cggcacctca actccgattt   8520
aatgaacgca atattcacaa gcaatgcgtg gtgtgcaacc agcacaaaag cggaaatctc   8580
gttccgtatc gcgtcgaact gattagccgc atcgggcagg aagcagtaga cgaaatcgaa   8640
tcaaaccata accgccatcg ctggactatc gaagagtgca aggcgatcaa ggcagagtac   8700
caacagaaac tcaaagacct gcgaaatagc agaagtgagg ccgcatgacg ttctcagtaa   8760
aaaccattcc agacatgctc gttgaagcat acggaaatca gacagaagta gcacgcagac   8820
tgaaatgtag tcgcggtacg gtcagaaaat acgttgatga taaagacggg aaaatgcacg   8880
ccatcgtcaa cgacgttctc atggttcatc gcggatggag tgaaagagat gcgctattac   8940
gaaaaaattg atggcagcaa ataccgaaat atttgggtag ttggcgatct gcacggatgc   9000
tacacgaacc tgatgaacaa actggatacg attggattcg acaacaaaaa agacctgctt   9060
atctcggtgg gcgatttggt tgatcgtggt gcagagaacg ttgaatgcct ggaattaatc   9120
acattcccct ggttcagagc tgtacgtgga aaccatgagc aaatgatgat tgatggctta   9180
tcagagcgtg gaaacgttaa tcactggctg cttaatggcg gtggctggtt ctttaatctc   9240
gattacgaca aagaaattct ggctaaagct cttgcccata aagcagatga acttccgtta   9300
atcatcgaac tggtgagcaa agataaaaaa tatgttatct gccacgccga ttatcccttt   9360
gacgaatacg agtttggaaa gccagttgat catcagcagg taatctggaa ccgcgaacga   9420
atcagcaact cacaaaacgg gatcgtgaaa gaaatcaaag gcgcggacac gttcatcttt   9480
ggtcatacgc cagcagtgaa accactcaag tttgccaacc aaatgtatat cgataccggc   9540
gcagtgttct gcggaaacct aacattgatt caggtacagg gagaaggcgc atgagactcg   9600
aaagcgtagc taaatttcat tcgccaaaaa gcccgatgat gagcgactca ccacgggcca   9660
cggcttctga ctctctttcc ggtactgatg tgatggctgc tatggggatg gcgcaatcac   9720
aagccggatt cggtatggct gcattctgcg gtaagcacga actcagccag aacgacaaac   9780
aaaaggctat caactatctg atgcaatttg cacacaaggt atcggggaaa taccgtggtg   9840
tggcaaagct tgaaggaaat actaaggcaa aggtactgca agtgctcgca acattcgctt   9900
atgcggatta ttgccgtagt gccgcgacgc cgggggcaag atgcagagat tgccatggta   9960
caggccgtgc ggttgatatt gccaaaacag agctgtgggg gagagttgtc gagaaagagt  10020
gcggaagatg caaaggcgtc ggctattcaa ggatgccagc aagcgcagca tatcgcgctg  10080
tgacgatgct aatcccaaac cttacccaac ccacctggtc acgcactgtt aagccgctgt  10140
atgacgctct ggtggtgcaa tgccacaaag aagagtcaat cgcagacaac attttgaatg  10200
cggtcacacg ttagcagcat gattgccacg gatggcaaca tattaacggc atgatattga  10260
```

cttattgaat aaaattgggt aaatttgact caacgatggg ttaattcgct cgttgtggta 10320
gtgagatgaa aagaggcggc gcttactacc gattccgcct agttggtcac ttcgacgtat 10380
cgtctggaac tccaaccatc gcaggcagag aggtctgcaa aatgcaatcc cgaaacagtt 10440
cgcaggtaat agttagagcc tgcataacgg tttcgggatt ttttatatct gcacaacagg 10500
taagagcatt gagtcgataa tcgtgaagag tcggcgagcc tggttagcca gtgctctttc 10560
cgttgtgctg aattaagcga ataccggaag cagaaccgga tcaccaaatg cgtacaggcg 10620
tcatcgccgc ccagcaacag cacaacccaa actgagccgt agccactgtc tgtcctgaat 10680
tcattagtaa tagttacgct gcggcctttt acacatgacc ttcgtgaaag cgggtggcag 10740
gaggtcgcgc taacaacctc ctgccgtttt gcccgtgcat atcggtcacg aacaaatctg 10800
attactaaac acagtagcct ggatttgttc tatcagtaat cgaccttatt cctaattaaa 10860
tagagcaaat ccccttattg ggggtaagac atgaagatgc cagaaaaaca tgacctgttg 10920
gccgccattc tcgcggcaaa ggaacaaggc atcggggcaa tccttgcgtt tgcaatggcg 10980
taccttcgcg gcagatataa tggcggtgcg tttacaaaaa cagtaatcga cgcaacgatg 11040
tgcgccatta tcgcctggtt cattcgtgac cttctcgact tcgccggact aagtagcaat 11100
ctcgcttata taacgagcgt gtttatcggc tacatcggta ctgactcgat tggttcgctt 11160
atcaaacgct tcgctgctaa aaaagccgga gtagaagatg gtagaaatca ataatcaacg 11220
taaggcgttc ctcgatatgc tggcgtggtc ggagggaact gataacggac gtcagaaaac 11280
cagaaatcat ggttatgacg tcattgtagg cggagagcta tttactgatt actccgatca 11340
ccctcgcaaa cttgtcacgc taaacccaaa actcaaatca acaggcgctt aagactggcc 11400
gtcgttttac aacacagaaa gagtttgtag aaacgcaaaa aggccatccg tcaggggcct 11460
tctgcttagt ttgatgcctg gcagttccct actctcgcct tccgcttcct cgctcactga 11520
ctcgctgcgc tcggtcgttc ggctgcggcg agcggtatca gctcactcaa aggcggtaat 11580
acggttatcc acagaatcag gggataacgc aggaaagaac atgtgagcaa aaggccagca 11640
aaaggccagg aaccgtaaaa aggccgcgtt gctggcgttt ttccataggc tccgcccccc 11700
tgacgagcat cacaaaaatc gacgctcaag tcagaggtgg cgaaacccga caggactata 11760
aagataccag gcgtttcccc ctggaagctc cctcgtgcgc tctcctgttc cgaccctgcc 11820
gcttaccgga tacctgtccg cctttctccc ttcgggaagc gtggcgcttt ctcatagctc 11880
acgctgtagg tatctcagtt cggtgtaggt cgttcgctcc aagctgggct gtgtgcacga 11940
accccccgtt cagcccgacc gctgcgcctt atccggtaac tatcgtcttg agtccaaccc 12000
ggtaagacac gacttatcgc cactggcagc agccactggt aacaggatta gcagagcgag 12060
gtatgtaggc ggtgctacag agttcttgaa gtggtgggct aactacggct acactagaag 12120
aacagtattt ggtatctgcg ctctgctgaa gccagttacc ttcggaaaaa gagttggtag 12180
ctcttgatcc ggcaaacaaa ccaccgctgg tagcggtggt ttttttgttt gcaagcagca 12240
gattacgcgc agaaaaaaag gatctcaaga agatcctttg atcttttcta cggggtctga 12300
cgctcagtgg aacgacgcgc gcgtaactca cgttaaggga ttttggtcat gagcttgcgc 12360
cgtcccgtca agtcagcgta atgctctgct tt 12392

<210> SEQ ID NO 16
<211> LENGTH: 12419
<212> TYPE: DNA
<213> ORGANISM: Artificial Sequence
<220> FEATURE:
<223> OTHER INFORMATION: constructed sequence

<400> SEQUENCE: 16
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320
ggcctcagtg agcgagcgag cgcgcagaga gggagtggcc aactccatca ctaggggttc 1380
cttgtagtta atgattaacc cgccatgcta cttatctacg tagcaagcta gctagttatt 1440
aatagtaatc aattacgggg tcattagttc atagcccata tatggagttc cgcgttacat 1500
aacttacggt aaatggcccg cctggctgac cgcccaacga cccccgccca ttgacgtcaa 1560
taatgacgta tgttcccata gtaacgccaa tagggacttt ccattgacgt caatgggtgg 1620
agtatttacg gtaaactgcc cacttggcag tacatcaagt gtatcatatg ccaagtacgc 1680
cccctattga cgtcaatgac ggtaaatggc ccgcctggca ttatgcccag tacatgacct 1740
tatgggactt tcctacttgg cagtacatct acgtattagt catcgctatt aacatggtcg 1800
aggtgagccc cacgttctgc ttcactctcc ccatctcccc cccctcccca cccccaattt 1860
tgtatttatt tatttttttaa ttattttgtg cagcgatggg ggcggggggg gggggggggc 1920
gcgcgccagg cggggcgggg cggggcgagg ggcggggcgg ggcgaggcgg agaggtgcgg 1980
cggcagccaa tcagagcggc gcgctccgaa agtttccttt tatggcgagg cggcggcggc 2040
ggcggcccta taaaaagcga agcgcgcggc gggcggggag tcgctgcgac gctgccttcg 2100
ccccgtgccc cgctccgccg ccgcctcgcg ccgcccgccc cggctctgac tgaccgcgtt 2160
actcccacag gtgagcgggc gggacggccc ttctcctccg ggctgtaatt agcgcttggt 2220
ttaatgacgg cttgtttctt ttctgtggct gcgtgaaagc cttgaggggc tccgggaggg 2280

```
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cgggggtgg cggcaggtgg gggtgccggg cggggcgggg ccgcctcggg ccggggaggg   2700
ctcgggggag ggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gcgccgccac   3120
catggccgac gaagccgcac tcgcgctgca accagggggt tccccgtctg cagcaggcgc   3180
cgatagagaa gcagccagct cgccagcagg agaaccgctc cggaagcgac ccaggagaga   3240
tggcccaggc ctggaacgct caccgggtga accaggaggt gccgctcctg aacgggaagt   3300
gcccgcagct gctaggggct gtccaggagc agccgcagca gcactctggc gcgaagccga   3360
agccgaggct gctgcagccg gaggagaaca agaagcccaa gcgaccgctg cagcaggaga   3420
gggcgacaac ggacccggcc tgcaaggacc gtcccgcgaa cctccgctgg ccgacaatct   3480
gtacgacgag gacgatgatg atgagggcga agaagaagag gaagccgccg ctgctgctat   3540
tggatacaga gacaaccttc tcttcggcga cgagatcatc accaatggat tccactcctg   3600
tgaatctgac gaagaagatc gggcctccca tgctagcagc tctgactgga cgccacggcc   3660
aaggatcggt ccgtacacct tcgtgcagca gcacctgatg atcggcacag atccccgcac   3720
cattctgaag gatctgctgc ccgagactat cccacccccct gagctggacg acatgactct   3780
gtggcagatt gtgatcaaca tcctttccga gcccccaaag cggaagaagc gcaaggatat   3840
taacaccatc gaggacgccg tgaagcttct gcaggagtgc aaaaagatca tcgtgctgac   3900
tggtgcaggg gtgtccgtgt cctgcggcat tccggatttc agaagccgcg acggaatcta   3960
cgccagactc gcggtcgact ttcccgatct gcctgaccct caggccatgt tcgatattga   4020
atacttccgc aaggacccga ggccgttctt taagttcgcc aaggagatct accctgggca   4080
gttccaaccc tccctctgcc ataagttcat tgcgctgagc gataaggaag gaaagctgct   4140
gcggaactac acccagaaca tcgacactct tgagcaagtg gcgggtatcc agagaatcat   4200
ccaatgccac ggctccttcg ccactgcctc ctgcctgatc tgcaagtaca aggtcgattg   4260
tgaagccgtc aggggcgata tcttcaacca agtggtcccg cgatgcccaa gatgcccggc   4320
ggatgaaccc ttggccatca tgaagcctga aatcgtgttc ttcggggaaa acctccccga   4380
acagtttcac cgcgccatga agtacgacaa ggacgaagtg gatctcctga ttgtgattgg   4440
ttccagcttg aaagtccggc cagtggcctt gatcccctcc tcgattccac acgaagtgcc   4500
tcaaatcctt attaaccggg aaccactgcc gcatcttcac ttcgatgtgg aactgctggg   4560
agactgcgac gtgattatta acgaactgtg tcaccgcttg ggtggcgaat acgccaagct   4620
gtgctgcaac cctgtgaaac tgtcggagat caccgaaaag ccgcccagaa ctcaaaaaga   4680
```

gctggcctac ctgtccgagc tccctccgac tccgctgcat gtgtccgagg attcgtcgtc 4740
cccggaaagg acttcgcctc cggactcctc cgtgatcgtg accctgctcg accaagccgc 4800
caagtcgaac gacgatctgg acgtgtcgga atccaagggc tgcatggaag aaaagcctca 4860
agaggtgcag acttcacgga acgtggagtc catcgccgaa cagatggaaa acccggacct 4920
gaagaacgtg ggaagcagca ctggcgaaaa gaacgagaga acctccgtgg ccggtactgt 4980
ccggaagtgc tggccgaaca gggtggccaa ggaacagata tcccggagac ttgacggcaa 5040
ccagtacctc ttcctccccc ctaaccgcta tatttttcac ggggccgagg tgtacagcga 5100
ctccgaggac gatgtgctgt catcctcatc atgcggttcc aattccgact ccggaacctg 5160
tcagagcccc tccctggagg aacctatgga ggacgaatcc gagatcgagg aattctacaa 5220
cggtctggag gacgagcctg atgtcccgga acgcgctgga ggagctggct tcggaaccga 5280
cggggacgac caggaagcca tcaacgaggc catctcggtg aagcaggaag tgaccgatat 5340
gaactacccg tccaacaagt cctacccata cgatgttcca gattacgctt gagcggccgc 5400
atagtactgc ggatcctgca gatctgcctc gactgtgcct tctagttgcc agccatctgt 5460
tgtttgcccc tcccccgtgc cttccttgac cctggaaggt gccactccca ctgtcctttc 5520
ctaataaaat gaggaaattg catcgcattg tctgagtagg tgtcattcta ttctgggggg 5580
tggggtgggg caggacagca agggggagga ttgggaagac aatagcaggc atgctgggga 5640
ctcgagttct acgtagataa gtagcatggc gggttaatca ttaactacaa ggaaccccta 5700
gtgatggagt tggccactcc ctctctgcgc gctcgctcgc tcactgaggc cgggcgacca 5760
aaggtcgccc gacgcccggg ctttgcccgg gcggcctcag tgagcgagcg agcgcgcagc 5820
cttaattaac ctaaggaaaa tgaagtgaag ttcctatact ttctagagaa taggaacttc 5880
tatagtgagt cgaataaggg cgacacaaaa tttattctaa atgcataata aatactgata 5940
acatcttata gtttgtatta tattttgtat tatcgttgac atgtataatt ttgatatcaa 6000
aaactgattt tccctttatt attttcgaga tttattttct taattctctt taacaaacta 6060
gaaatattgt atatacaaaa aatcataaat aatagatgaa tagtttaatt ataggtgttc 6120
atcaatcgaa aaagcaacgt atcttattta aagtgcgttg ctttttttctc atttataagg 6180
ttaaataatt ctcatatatc aagcaaagtg acaggcgccc ttaaatattc tgacaaatgc 6240
tctttcccta aactcccccc ataaaaaaac ccgccgaagc gggtttttac gttatttgcg 6300
gattaacgat tactcgttat cagaaccgcc caggggggccc gagcttaacc tttttatttg 6360
ggggagaggg aagtcatgaa aaaactaacc tttgaaattc gatctccagc acatcagcaa 6420
aacgctattc acgcagtaca gcaaatcctt ccagacccaa ccaaaccaat cgtagtaacc 6480
attcaggaac gcaaccgcag cttagaccaa aacaggaagc tatgggcctg cttaggtgac 6540
gtctctcgtc aggttgaatg gcatggtcgc tggctggatg cagaaagctg gaagtgtgtg 6600
tttaccgcag cattaaagca gcaggatgtt gttcctaacc ttgccgggaa tggctttgtg 6660
gtaataggcc agtcaaccag caggatgcgt gtaggcgaat ttgcggagct attagagctt 6720
atacaggcat tcggtacaga gcgtggcgtt aagtggtcag acgaagcgag actggctctg 6780
gagtggaaag cgagatgggg agacagggct gcatgataaa tgtcgttagt ttctccggtg 6840
gcaggacgtc agcatatttg ctctggctaa tggagcaaaa gcgacgggca ggtaaagacg 6900
tgcattacgt tttcatggat acaggttgtg aacatccaat gacatatcgg tttgtcaggg 6960
aagttgtgaa gttctgggat ataccgctca ccgtattgca ggttgatatc aacccggagc 7020

-continued ttggacagcc aaatggttat acggtatggg aaccaaagga tattcagacg cgaatgcctg 7080
ttctgaagcc atttatcgat atggtaaaga aatatggcac tccatacgtc ggcggcgcgt 7140
tctgcactga cagattaaaa ctcgttccct tcaccaaata ctgtgatgac catttcgggc 7200
gagggaatta caccacgtgg attggcatca gagctgatga accgaagcgg ctaaagccaa 7260
agcctggaat cagatatctt gctgaactgt cagactttga gaaggaagat atcctcgcat 7320
ggtggaagca acaaccattc gatttgcaaa taccggaaca tctcggtaac tgcatattct 7380
gcattaaaaa atcaacgcaa aaaatcggac ttgcctgcaa agatgaggag ggattgcagc 7440
gtgtttttaa tgaggtcatc acgggatccc atgtgcgtga cggacatcgg gaaacgccaa 7500
aggagattat gtaccgagga agaatgtcgc tggacggtat cgcgaaaatg tattcagaaa 7560
atgattatca agccctgtat caggacatgg tacgagctaa aagattcgat accggctctt 7620
gttctgagtc atgcgaaata tttggagggc agcttgattt cgacttcggg agggaagctg 7680
catgatgcga tgttatcggt gcggtgaatg caaagaagat aaccgcttcc gaccaaatca 7740
accttactgg aatcgatggt gtctccggtg tgaaagaaca ccaacagggg tgttaccact 7800
accgcaggaa aaggaggacg tgtggcgaga cagcgacgaa gtatcaccga cataatctgc 7860
gaaaactgca aataccttcc aacgaaacgc accagaaata aacccaagcc aatcccaaaa 7920
gaatctgacg taaaaacctt caactacacg gctcacctgt gggatatccg gtggctaaga 7980
cgtcgtgcga ggaaaacaag gtgattgacc aaaatcgaag ttacgaacaa gaaagcgtcg 8040
agcgagcttt aacgtgcgct aactgcggtc agaagctgca tgtgctggaa gttcacgtgt 8100
gtgagcactg ctgcgcagaa ctgatgagcg atccgaatag ctcgatgcac gaggaagaag 8160
atgatggcta aaccagcgcg aagacgatgt aaaaacgatg aatgccggga atggtttcac 8220
cctgcattcg ctaatcagtg gtggtgctct ccagagtgtg gaaccaagat agcactcgaa 8280
cgacgaagta aagaacgcga aaaagcggaa aaagcagcag agaagaaacg acgacgagag 8340
gagcagaaac agaaagataa acttaagatt cgaaaactcg ccttaaagcc ccgcagttac 8400
tggattaaac aagcccaaca agccgtaaac gccttcatca gagaaagaga ccgcgactta 8460
ccatgtatct cgtgcggaac gctcacgtct gctcagtggg atgccggaca ttaccggaca 8520
actgctgcgg cacctcaact ccgatttaat gaacgcaata ttcacaagca atgcgtggtg 8580
tgcaaccagc acaaaagcgg aaatctcgtt ccgtatcgcg tcgaactgat tagccgcatc 8640
gggcaggaag cagtagacga aatcgaatca aaccataacc gccatcgctg gactatcgaa 8700
gagtgcaagg cgatcaaggc agagtaccaa cagaaactca aagacctgcg aaatagcaga 8760
agtgaggccg catgacgttc tcagtaaaaa ccattccaga catgctcgtt gaagcatacg 8820
gaaatcagac agaagtagca cgcagactga aatgtagtcg cggtacggtc agaaaatacg 8880
ttgatgataa agacgggaaa atgcacgcca tcgtcaacga cgttctcatg gttcatcgcg 8940
gatggagtga aagagatgcg ctattacgaa aaaattgatg gcagcaaata ccgaaatatt 9000
tgggtagttg gcgatctgca cggatgctac acgaacctga tgaacaaact ggatacgatt 9060
ggattcgaca acaaaaaaga cctgcttatc tcggtgggcg atttggttga tcgtggtgca 9120
gagaacgttg aatgcctgga attaatcaca ttcccctggt tcagagctgt acgtggaaac 9180
catgagcaaa tgatgattga tggcttatca gagcgtggaa acgttaatca ctggctgctt 9240
aatggcggtg gctggttctt taatctcgat tacgacaaag aaattctggc taaagctctt 9300
gcccataaag cagatgaact tccgttaatc atcgaactgg tgagcaaaga taaaaaatat 9360
gttatctgcc acgccgatta tccctttgac gaatacgagt ttggaaagcc agttgatcat 9420

-continued

```
cagcaggtaa tctggaaccg cgaacgaatc agcaactcac aaaacgggat cgtgaaagaa   9480
atcaaaggcg cggacacgtt catctttggt catacgccag cagtgaaacc actcaagttt   9540
gccaaccaaa tgtatatcga taccggcgca gtgttctgcg gaaacctaac attgattcag   9600
gtacagggag aaggcgcatg agactcgaaa gcgtagctaa atttcattcg ccaaaaagcc   9660
cgatgatgag cgactcacca cgggccacgg cttctgactc tctttccggt actgatgtga   9720
tggctgctat ggggatggcg caatcacaag ccggattcgg tatggctgca ttctgcggta   9780
agcacgaact cagccagaac gacaaacaaa aggctatcaa ctatctgatg caatttgcac   9840
acaaggtatc ggggaaatac cgtggtgtgg caaagcttga aggaaatact aaggcaaagg   9900
tactgcaagt gctcgcaaca ttcgcttatg cggattattg ccgtagtgcc gcgacgccgg   9960
gggcaagatg cagagattgc catggtacag gccgtgcggt tgatattgcc aaaacagagc  10020
tgtgggggag agttgtcgag aaagagtgcg gaagatgcaa aggcgtcggc tattcaagga  10080
tgccagcaag cgcagcatat cgcgctgtga cgatgctaat cccaaacctt acccaaccca  10140
cctggtcacg cactgttaag ccgctgtatg acgctctggt ggtgcaatgc cacaaagaag  10200
agtcaatcgc agacaacatt ttgaatgcgg tcacacgtta gcagcatgat tgccacggat  10260
ggcaacatat taacggcatg atattgactt attgaataaa attgggtaaa tttgactcaa  10320
cgatgggtta attcgctcgt tgtggtagtg agatgaaaag aggcggcgct tactaccgat  10380
tccgcctagt tggtcacttc gacgtatcgt ctggaactcc aaccatcgca ggcagagagg  10440
tctgcaaaat gcaatcccga aacagttcgc aggtaatagt tagagcctgc ataacggttt  10500
cgggattttt tatatctgca caacaggtaa gagcattgag tcgataatcg tgaagagtcg  10560
gcgagcctgg ttagccagtg ctctttccgt tgtgctgaat taagcgaata ccggaagcag  10620
aaccggatca ccaaatgcgt acaggcgtca tcgccgccca gcaacagcac aacccaaact  10680
gagccgtagc cactgtctgt cctgaattca ttagtaatag ttacgctgcg gccttttaca  10740
catgaccttc gtgaaagcgg gtggcaggag gtcgcgctaa caacctcctg ccgttttgcc  10800
cgtgcatatc ggtcacgaac aaatctgatt actaaacaca gtagcctgga tttgttctat  10860
cagtaatcga ccttattcct aattaaatag agcaaatccc cttattgggg gtaagacatg  10920
aagatgccag aaaaacatga cctgttggcc gccattctcg cggcaaagga acaaggcatc  10980
ggggcaatcc ttgcgtttgc aatggcgtac cttcgcggca gatataatgg cggtgcgttt  11040
acaaaaacag taatcgacgc aacgatgtgc gccattatcg cctggttcat tcgtgacctt  11100
ctcgacttcg ccggactaag tagcaatctc gcttatataa cgagcgtgtt tatcggctac  11160
atcggtactg actcgattgg ttcgcttatc aaacgcttcg ctgctaaaaa agccggagta  11220
gaagatggta gaaatcaata atcaacgtaa ggcgttcctc gatatgctgg cgtggtcgga  11280
gggaactgat aacggacgtc agaaaaccag aaatcatggt tatgacgtca ttgtaggcgg  11340
agagctattt actgattact ccgatcaccc tcgcaaactt gtcacgctaa acccaaaact  11400
caaatcaaca ggcgcttaag actggccgtc gttttacaac acagaaagag tttgtagaaa  11460
cgcaaaaagg ccatccgtca ggggccttct gcttagtttg atgcctggca gttccctact  11520
ctcgccttcc gcttcctcgc tcactgactc gctgcgctcg gtcgttcggc tgcggcgagc  11580
ggtatcagct cactcaaagg cggtaatacg gttatccaca gaatcagggg ataacgcagg  11640
aaagaacatg tgagcaaaag gccagcaaaa ggccaggaac cgtaaaaagg ccgcgttgct  11700
ggcgtttttc cataggctcc gcccccctga cgagcatcac aaaaatcgac gctcaagtca  11760
```

gaggtggcga aacccgacag gactataaag ataccaggcg tttccccctg gaagctccct 11820
cgtgcgctct cctgttccga ccctgccgct taccggatac ctgtccgcct ttctcccttc 11880
gggaagcgtg gcgctttctc atagctcacg ctgtaggtat ctcagttcgg tgtaggtcgt 11940
tcgctccaag ctgggctgtg tgcacgaacc ccccgttcag cccgaccgct gcgccttatc 12000
cggtaactat cgtcttgagt ccaacccggt aagacacgac ttatcgccac tggcagcagc 12060
cactggtaac aggattagca gagcgaggta tgtaggcggt gctacagagt tcttgaagtg 12120
gtgggctaac tacggctaca ctagaagaac agtatttggt atctgcgctc tgctgaagcc 12180
agttaccttc ggaaaaagag ttggtagctc ttgatccggc aaacaaacca ccgctggtag 12240
cggtggtttt tttgtttgca agcagcagat tacgcgcaga aaaaaaggat ctcaagaaga 12300
tcctttgatc ttttctacgg ggtctgacgc tcagtggaac gacgcgcgcg taactcacgt 12360
taagggattt tggtcatgag cttgcgccgt cccgtcaagt cagcgtaatg ctctgcttt 12419

<210> SEQ ID NO 17
<211> LENGTH: 12377
<212> TYPE: DNA
<213> ORGANISM: Artificial Sequence
<220> FEATURE:
<223> OTHER INFORMATION: constructed sequence

<400> SEQUENCE: 17
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320
ggcctcagtg agcgagcgag cgcgcagaga gggagtggcc aactccatca ctaggggttc 1380
cttgtagtta atgattaacc cgccatgcta cttatctacg tagcaagcta gctagttatt 1440

-continued

```
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tattttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cgggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatgg   3120
cggacgaggc ggccctcgcc cttcagcccg gcggctcccc ctcggcggcg gggccgaca   3180
gggaggccgc gtcgtccccc gccggggagc cgctccgcaa gaggccgcgg agagatggtc   3240
ccggcctcga gcggagcccg ggcgagcccg gtggggcggc cccagagcgt gaggtgccgg   3300
cggcggccag ggctgcccg ggtgcggcgg cggcggcgct gtggcgggag gcggaggcag   3360
aggcggcggc ggcaggcggg gagcaagagg cccaggcgac tgcggcggct ggggaaggag   3420
acaatgggcc gggcctgcag ggcccatctc gggagccacc gctggccgac aacttgtacg   3480
acgaagacga cgacgacgag ggcgaggagg aggaagaggc ggcggcggcg gcgattgggt   3540
accgagataa ccttctgttc ggtgatgaaa ttatcactaa tggttttcat tcctgtgaaa   3600
gtgatgagga ggatagagcc tcacatgcaa gctctagtga ctggactcca aggccacgga   3660
taggtccata tacttttgtt cagcaacatc ttatgattgg cacagatcct cgaacaattc   3720
ttaaagattt attgccggaa acaatacctc cacctgagtt ggatgatatg acactgtggc   3780
```

-continued

```
agattgttat taatatcctt tcagaaccac caaaaaggaa aaaaagaaaa gatattaata   3840
caattgaaga tgctgtgaaa ttactgcaag agtgcaaaaa aattatagtt ctaactggag   3900
ctggggtgtc tgtttcatgt ggaatacctg acttcaggtc aagggatggt atttatgctc   3960
gccttgctgt agacttccca gatcttccag atcctcaagc gatgtttgat attgaatatt   4020
tcagaaaaga tccaagacca ttcttcaagt ttgcaaagga aatatatcct ggacaattcc   4080
agccatctct ctgtcacaaa ttcatagcct tgtcagataa ggaaggaaaa ctacttcgca   4140
actataccca gaacatagac acgctggaac aggttgcggg aatccaaagg ataattcagt   4200
gtcatggttc ctttgcaaca gcatcttgcc tgatttgtaa atacaaagtt gactgtgaag   4260
ctgtacgagg agatattttt aatcaggtag ttcctcgatg tcctaggtgc ccagctgatg   4320
aaccgcttgc tatcatgaaa ccagagattg tgttttttgg tgaaaattta ccagaacagt   4380
ttcatagagc catgaagtat gacaaagatg aagttgacct cctcattgtt attgggtctt   4440
ccctcaaagt aagaccagta gcactaattc caagttccat accccatgaa gtgcctcaga   4500
tattaattaa tagagaacct ttgcctcatc tgcattttga tgtagagctt cttggagact   4560
gtgatgtcat aattaatgaa ttgtgtcata ggttaggtgg tgaatatgcc aaactttgct   4620
gtaaccctgt aaagctttca gaaattactg aaaaacctcc acgaacacaa aaagaattgg   4680
cttatttgtc agagttgcca cccacacctc ttcatgtttc agaagactca agttcaccag   4740
aaagaacttc accaccagat tcttcagtga ttgtcacact tttagaccaa gcagctaaga   4800
gtaatgatga tttagatgtg tctgaatcaa aaggttgtat ggaagaaaaa ccacaggaag   4860
tacaaacttc taggaatgtt gaaagtattg ctgaacagat ggaaaatccg gatttgaaga   4920
atgttggttc tagtactggg gagaaaaatg aaagaacttc agtggctgga acagtgagaa   4980
aatgctggcc taatagagtg gcaaaggagc agattagtag gcggcttgat ggtaatcagt   5040
atctgttttt gccaccaaat cgttacattt tccatggcgc tgaggtatat tcagactctg   5100
aagatgacgt cttatcctct agttcttgtg gcagtaacag tgatagtggg acatgccaga   5160
gtccaagttt agaagaaccc atggaggatg aaagtgaaat tgaagaattc tacaatggct   5220
tagaagatga gcctgatgtt ccagagagag ctggaggagc tggatttggg actgatggag   5280
atgatcaaga ggcaattaat gaagctatat ctgtgaaaca ggaagtaaca gacatgaact   5340
atccatcaaa caaatcatga agtactgcgg atcctgcaga tctgcctcga ctgtgccttc   5400
tagttgccag ccatctgttg tttgcccctc ccccgtgcct tccttgaccc tggaaggtgc   5460
cactcccact gtcctttcct aataaaatga ggaaattgca tcgcattgtc tgagtaggtg   5520
tcattctatt ctggggggtg gggtggggca ggacagcaag ggggaggatt gggaagacaa   5580
tagcaggcat gctggggact cgagttctac gtagataagt agcatggcgg gttaatcatt   5640
aactacaagg aacccctagt gatggagttg gccactccct ctctgcgcgc tcgctcgctc   5700
actgaggccg ggcgaccaaa ggtcgcccga cgcccgggct ttgcccgggc ggcctcagtg   5760
agcgagcgag cgcgcagcct taattaacct aaggaaaatg aagtgaagtt cctatacttt   5820
ctagagaata ggaacttcta tagtgagtcg aataagggcg acacaaaatt tattctaaat   5880
gcataataaa tactgataac atcttatagt ttgtattata ttttgtatta tcgttgacat   5940
gtataatttt gatatcaaaa actgattttc cctttattat tttcgagatt tatttttctta   6000
attctcttta acaaactaga aatattgtat atacaaaaaa tcataaataa tagatgaata   6060
gtttaattat aggtgttcat caatcgaaaa agcaacgtat cttatttaaa gtgcgttgct   6120
tttttctcat ttataaggtt aaataattct catatatcaa gcaaagtgac aggcgccctt   6180
```

-continued

```
aaatattctg acaaatgctc tttccctaaa ctccccccat aaaaaaaccc gccgaagcgg   6240
gtttttacgt tatttgcgga ttaacgatta ctcgttatca gaaccgccca gggggcccga   6300
gcttaacctt tttatttggg ggagagggaa gtcatgaaaa aactaacctt tgaaattcga   6360
tctccagcac atcagcaaaa cgctattcac gcagtacagc aaatccttcc agacccaacc   6420
aaaccaatcg tagtaaccat tcaggaacgc aaccgcagct tagaccaaaa caggaagcta   6480
tgggcctgct taggtgacgt ctctcgtcag gttgaatggc atggtcgctg gctggatgca   6540
gaaagctgga agtgtgtgtt taccgcagca ttaaagcagc aggatgttgt tcctaacctt   6600
gccgggaatg gctttgtggt aataggccag tcaaccagca ggatgcgtgt aggcgaattt   6660
gcggagctat tagagcttat acaggcattc ggtacagagc gtggcgttaa gtggtcagac   6720
gaagcgagac tggctctgga gtggaaagcg agatggggag acagggctgc atgataaatg   6780
tcgttagttt ctccggtggc aggacgtcag catatttgct ctggctaatg gagcaaaagc   6840
gacgggcagg taaagacgtg cattacgttt tcatggatac aggttgtgaa catccaatga   6900
catatcggtt tgtcagggaa gttgtgaagt tctgggatat accgctcacc gtattgcagg   6960
ttgatatcaa cccggagctt ggacagccaa atggttatac ggtatgggaa ccaaaggata   7020
ttcagacgcg aatgcctgtt ctgaagccat ttatcgatat ggtaaagaaa tatggcactc   7080
catacgtcgg cggcgcgttc tgcactgaca gattaaaact cgttcccttc accaaatact   7140
gtgatgacca tttcgggcga gggaattaca ccacgtggat tggcatcaga gctgatgaac   7200
cgaagcggct aaagccaaag cctggaatca gatatcttgc tgaactgtca gactttgaga   7260
aggaagatat cctcgcatgg tggaagcaac aaccattcga tttgcaaata ccggaacatc   7320
tcggtaactg catattctgc attaaaaaat caacgcaaaa aatcggactt gcctgcaaag   7380
atgaggaggg attgcagcgt gtttttaatg aggtcatcac gggatcccat gtgcgtgacg   7440
gacatcggga aacgccaaag gagattatgt accgaggaag aatgtcgctg gacggtatcg   7500
cgaaaatgta ttcagaaaat gattatcaag ccctgtatca ggacatggta cgagctaaaa   7560
gattcgatac cggctcttgt tctgagtcat gcgaaatatt tggagggcag cttgatttcg   7620
acttcgggag ggaagctgca tgatgcgatg ttatcggtgc ggtgaatgca aagaagataa   7680
ccgcttccga ccaaatcaac cttactggaa tcgatggtgt ctccggtgtg aaagaacacc   7740
aacaggggtg ttaccactac cgcaggaaaa ggaggacgtg tggcgagaca gcgacgaagt   7800
atcaccgaca taatctgcga aaactgcaaa taccttccaa cgaaacgcac cagaaataaa   7860
cccaagccaa tcccaaaaga atctgacgta aaaaccttca actacacggc tcacctgtgg   7920
gatatccggt ggctaagacg tcgtgcgagg aaaacaaggt gattgaccaa aatcgaagtt   7980
acgaacaaga aagcgtcgag cgagctttaa cgtgcgctaa ctgcggtcag aagctgcatg   8040
tgctggaagt tcacgtgtgt gagcactgct gcgcagaact gatgagcgat ccgaatagct   8100
cgatgcacga ggaagaagat gatggctaaa ccagcgcgaa gacgatgtaa aaacgatgaa   8160
tgccgggaat ggtttcaccc tgcattcgct aatcagtggt ggtgctctcc agagtgtgga   8220
accaagatag cactcgaacg acgaagtaaa gaacgcgaaa aagcggaaaa agcagcagag   8280
aagaaacgac gacgagagga gcagaaacag aaagataaac ttaagattcg aaaactcgcc   8340
ttaaagcccc gcagttactg gattaaacaa gcccaacaag ccgtaaacgc cttcatcaga   8400
gaaagagacc gcgacttacc atgtatctcg tgcggaacgc tcacgtctgc tcagtgggat   8460
gccggacatt accggacaac tgctgcggca cctcaactcc gatttaatga acgcaatatt   8520
```

-continued

```
cacaagcaat gcgtggtgtg caaccagcac aaaagcggaa atctcgttcc gtatcgcgtc   8580
gaactgatta gccgcatcgg gcaggaagca gtagacgaaa tcgaatcaaa ccataaccgc   8640
catcgctgga ctatcgaaga gtgcaaggcg atcaaggcag agtaccaaca gaaactcaaa   8700
gacctgcgaa atagcagaag tgaggccgca tgacgttctc agtaaaaacc attccagaca   8760
tgctcgttga agcatacgga aatcagacag aagtagcacg cagactgaaa tgtagtcgcg   8820
gtacggtcag aaaatacgtt gatgataaag acgggaaaat gcacgccatc gtcaacgacg   8880
ttctcatggt tcatcgcgga tggagtgaaa gagatgcgct attacgaaaa aattgatggc   8940
agcaaatacc gaaatatttg ggtagttggc gatctgcacg gatgctacac gaacctgatg   9000
aacaaactgg atacgattgg attcgacaac aaaaaagacc tgcttatctc ggtgggcgat   9060
ttggttgatc gtggtgcaga gaacgttgaa tgcctggaat taatcacatt cccctggttc   9120
agagctgtac gtggaaacca tgagcaaatg atgattgatg gcttatcaga gcgtggaaac   9180
gttaatcact ggctgcttaa tggcggtggc tggttcttta atctcgatta cgacaaagaa   9240
attctggcta aagctcttgc ccataaagca gatgaacttc cgttaatcat cgaactggtg   9300
agcaaagata aaaaatatgt tatctgccac gccgattatc cctttgacga atacgagttt   9360
ggaaagccag ttgatcatca gcaggtaatc tggaaccgcg aacgaatcag caactcacaa   9420
aacgggatcg tgaaagaaat caaaggcgcg gacacgttca tctttggtca tacgccagca   9480
gtgaaaccac tcaagtttgc caaccaaatg tatatcgata ccggcgcagt gttctgcgga   9540
aacctaacat tgattcaggt acagggagaa ggcgcatgag actcgaaagc gtagctaaat   9600
ttcattcgcc aaaaagcccg atgatgagcg actcaccacg ggccacggct tctgactctc   9660
tttccggtac tgatgtgatg gctgctatgg ggatggcgca atcacaagcc ggattcggta   9720
tggctgcatt ctgcggtaag cacgaactca gccagaacga caaacaaaag gctatcaact   9780
atctgatgca atttgcacac aaggtatcgg ggaaataccg tggtgtggca aagcttgaag   9840
gaaatactaa ggcaaaggta ctgcaagtgc tcgcaacatt cgcttatgcg gattattgcc   9900
gtagtgccgc gacgccgggg gcaagatgca gagattgcca tggtacaggc cgtgcggttg   9960
atattgccaa aacagagctg tgggggagag ttgtcgagaa agagtgcgga agatgcaaag  10020
gcgtcggcta ttcaaggatg ccagcaagcg cagcatatcg cgctgtgacg atgctaatcc  10080
caaaccttac ccaacccacc tggtcacgca ctgttaagcc gctgtatgac gctctggtgg  10140
tgcaatgcca caaagaagag tcaatcgcag acaacatttt gaatgcggtc acacgttagc  10200
agcatgattg ccacggatgg caacatatta acggcatgat attgacttat tgaataaaat  10260
tgggtaaatt tgactcaacg atgggttaat tcgctcgttg tggtagtgag atgaaaagag  10320
gcggcgctta ctaccgattc cgcctagttg gtcacttcga cgtatcgtct ggaactccaa  10380
ccatcgcagg cagagaggtc tgcaaaatgc aatcccgaaa cagttcgcag gtaatagtta  10440
gagcctgcat aacggtttcg ggattttttta tatctgcaca acaggtaaga gcattgagtc  10500
gataatcgtg aagagtcggc gagcctggtt agccagtgct ctttccgttg tgctgaatta  10560
agcgaatacc ggaagcagaa ccggatcacc aaatgcgtac aggcgtcatc gccgcccagc  10620
aacagcacaa cccaaactga gccgtagcca ctgtctgtcc tgaattcatt agtaatagtt  10680
acgctgcggc cttttacaca tgaccttcgt gaaagcgggt ggcaggaggt cgcgctaaca  10740
acctcctgcc gttttgcccg tgcatatcgg tcacgaacaa atctgattac taaacacagt  10800
agcctggatt tgttctatca gtaatcgacc ttattcctaa ttaaatagag caaatcccct  10860
tattgggggt aagacatgaa gatgccagaa aaacatgacc tgttggccgc cattctcgcg  10920
```

```
gcaaaggaac aaggcatcgg ggcaatcctt gcgtttgcaa tggcgtacct tcgcggcaga  10980
tataatggcg gtgcgtttac aaaaacagta atcgacgcaa cgatgtgcgc cattatcgcc  11040
tggttcattc gtgaccttct cgacttcgcc ggactaagta gcaatctcgc ttatataacg  11100
agcgtgttta tcggctacat cggtactgac tcgattggtt cgcttatcaa acgcttcgct  11160
gctaaaaaag ccggagtaga agatggtaga aatcaataat caacgtaagg cgttcctcga  11220
tatgctggcg tggtcggagg gaactgataa cggacgtcag aaaaccagaa atcatggtta  11280
tgacgtcatt gtaggcggag agctatttac tgattactcc gatcaccctc gcaaacttgt  11340
cacgctaaac ccaaaactca aatcaacagg cgcttaagac tggccgtcgt tttacaacac  11400
agaaagagtt tgtagaaacg caaaaaggcc atccgtcagg ggccttctgc ttagtttgat  11460
gcctggcagt tccctactct cgccttccgc ttcctcgctc actgactcgc tgcgctcggt  11520
cgttcggctg cggcgagcgg tatcagctca ctcaaaggcg gtaatacggt tatccacaga  11580
atcaggggat aacgcaggaa agaacatgtg agcaaaaggc cagcaaaagg ccaggaaccg  11640
taaaaaggcc gcgttgctgg cgtttttcca taggctccgc ccccctgacg agcatcacaa  11700
aaatcgacgc tcaagtcaga ggtggcgaaa cccgacagga ctataaagat accaggcgtt  11760
tccccctgga agctccctcg tgcgctctcc tgttccgacc ctgccgctta ccggatacct  11820
gtccgccttt ctcccttcgg gaagcgtggc gctttctcat agctcacgct gtaggtatct  11880
cagttcggtg taggtcgttc gctccaagct gggctgtgtg cacgaacccc ccgttcagcc  11940
cgaccgctgc gccttatccg gtaactatcg tcttgagtcc aacccggtaa gacacgactt  12000
atcgccactg gcagcagcca ctggtaacag gattagcaga gcgaggtatg taggcggtgc  12060
tacagagttc ttgaagtggt gggctaacta cggctacact agaagaacag tatttggtat  12120
ctgcgctctg ctgaagccag ttaccttcgg aaaaagagtt ggtagctctt gatccggcaa  12180
acaaaccacc gctggtagcg gtggtttttt tgtttgcaag cagcagatta cgcgcagaaa  12240
aaaaggatct caagaagatc ctttgatctt ttctacgggg tctgacgctc agtggaacga  12300
cgcgcgcgta actcacgtta agggattttg gtcatgagct tgcgccgtcc cgtcaagtca  12360
gcgtaatgct ctgcttt                                                 12377

<210> SEQ ID NO 18
<211> LENGTH: 12306
<212> TYPE: DNA
<213> ORGANISM: Artificial Sequence
<220> FEATURE:
<223> OTHER INFORMATION: constructed sequence

<400> SEQUENCE: 18

tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
```

```
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gccacccaca   1440
agccagttcc tgtccctgag gacttggctc agggactctg ggaatgtggt agacatgggg   1500
tggccccacc aaatgcatcc ttatgggaac ctgctccctg ggagccatga aaagagcgtg   1560
gacttcgagg tggggccaca ggaagtggtc aggtccatct caggggacct gctgcccatc   1620
cacactgctg gccaggaaat gggggcaat tcatgcctcc tcagcacctt cagcactggg   1680
cggctcaaag aaggcaaggg actattctgg ggtcacacag catgcagcca gaggccaagg   1740
catgaggaag tccttcattt ccccaccccc acccacctca gatcctccaa ccggtttcat   1800
ggcagcccag ggtccagcgg catccaggat gctggtgggt agctgcacag cccaggccgc   1860
gggaggttgg ctgctctcac ctaacaggcc tatgtggccc tgacccctac ctaggaagct   1920
ggggacaatg gccaaggcgc ctcccctctc tgtgcctgtc tgtccaggtg cagcatagac   1980
acagcacccc tggggccaag agcacccagc cagggctgcc cccatgggtg ggcagggcag   2040
taaatgaatg agggacaggt tgggaggtgg ccagcccccct ccagcccatg gagggcacgg   2100
ggcaggagag ctgggctgag ccagcaggag cccagggagc ctggtctctg ccttcctatc   2160
ctggaggaag gtgaggctga acctccttcc ctccctccct ccctccccgc ccccactgca   2220
cgcagggctg gctgggctcc agctggcctc cgcatcaata tttcatcggc gtcaatagga   2280
ggcatcgggg acagccgctg cggcagcact cgagccagct caagcccgca gctcgcaggg   2340
agatccagct ccgtcctgcc tgcagcagca caaccctgca caccctgtac actagcggcc   2400
gccaccatgg cggacgaggc ggccctcgcc cttcagcccg gcggctcccc ctcggcggcg   2460
ggggccgaca gggaggccgc gtcgtccccc gccggggagc cgctccgcaa gaggccgcgg   2520
agagatggtc ccggcctcga gcggagcccg ggcgagcccg gtggggcggc cccagagcgt   2580
gaggtgccgg cggcggccag gggctgcccg ggtgcggcgg cggcggcgct gtggcgggag   2640
gcggaggcag aggcggcggc ggcaggcggg gagcaagagg cccaggcgac tgcggcggct   2700
ggggaaggag acaatgggcc gggcctgcag ggcccatctc gggagccacc gctggccgac   2760
aacttgtacg acgaagacga cgacgacgag ggcgaggagg aggaagaggc ggcggcggcg   2820
gcgattgggt accgagataa ccttctgttc ggtgatgaaa ttatcactaa tggttttcat   2880
tcctgtgaaa gtgatgagga ggatagagcc tcacatgcaa gctctagtga ctggactcca   2940
```

```
aggccacgga taggtccata tacttttgtt cagcaacatc ttatgattgg cacagatcct   3000
cgaacaattc ttaaagattt attgccggaa acaatacctc cacctgagtt ggatgatatg   3060
acactgtggc agattgttat taatatcctt tcagaaccac caaaaaggaa aaaaagaaaa   3120
gatattaata caattgaaga tgctgtgaaa ttactgcaag agtgcaaaaa aattatagtt   3180
ctaactggag ctggggtgtc tgtttcatgt ggaatacctg acttcaggtc aagggatggt   3240
atttatgctc gccttgctgt agacttccca gatcttccag atcctcaagc gatgtttgat   3300
attgaatatt tcagaaaaga tccaagacca ttcttcaagt ttgcaaagga aatatatcct   3360
ggacaattcc agccatctct ctgtcacaaa ttcatagcct tgtcagataa ggaaggaaaa   3420
ctacttcgca actataccca gaacatagac acgctggaac aggttgcggg aatccaaagg   3480
ataattcagt gtcatggttc ctttgcaaca gcatcttgcc tgatttgtaa atacaaagtt   3540
gactgtgaag ctgtacgagg agatattttt aatcaggtag ttcctcgatg tcctaggtgc   3600
ccagctgatg aaccgcttgc tatcatgaaa ccagagattg tgttttttgg tgaaaattta   3660
ccagaacagt ttcatagagc catgaagtat gacaaagatg aagttgacct cctcattgtt   3720
attgggtctt ccctcaaagt aagaccagta gcactaattc caagttccat accccatgaa   3780
gtgcctcaga tattaattaa tagagaacct ttgcctcatc tgcattttga tgtagagctt   3840
cttggagact gtgatgtcat aattaatgaa ttgtgtcata ggttaggtgg tgaatatgcc   3900
aaactttgct gtaaccctgt aaagctttca gaaattactg aaaaacctcc acgaacacaa   3960
aaagaattgg cttatttgtc agagttgcca cccacacctc ttcatgtttc agaagactca   4020
agttcaccag aaagaacttc accaccagat tcttcagtga ttgtcacact tttagaccaa   4080
gcagctaaga gtaatgatga tttagatgtg tctgaatcaa aaggttgtat ggaagaaaaa   4140
ccacaggaag tacaaacttc taggaatgtt gaaagtattg ctgaacagat ggaaaatccg   4200
gatttgaaga atgttggttc tagtactggg gagaaaaatg aaagaacttc agtggctgga   4260
acagtgagaa aatgctggcc taatagagtg gcaaaggagc agattagtag gcggcttgat   4320
ggtaatcagt atctgttttt gccaccaaat cgttacattt tccatggcgc tgaggtatat   4380
tcagactctg aagatgacgt cttatcctct agttcttgtg gcagtaacag tgatagtggg   4440
acatgccaga gtccaagttt agaagaaccc atggaggatg aaagtgaaat tgaagaattc   4500
tacaatggct tagaagatga gcctgatgtt ccagagagag ctggaggagc tggatttggg   4560
actgatggag atgatcaaga ggcaattaat gaagctatat ctgtgaaaca ggaagtaaca   4620
gacatgaact atccatcaaa caaatcatac ccatacgatg ttccagatta cgcttgaagt   4680
actgcggatc ctgcaggcgt cgacaatcaa cctctggatt acaaaatttg tgaaagattg   4740
actggtattc ttaactatgt tgctcctttt acgctatgtg gatacgctgc tttaatgcct   4800
ttgtatcatg ctattgcttc ccgtatggct ttcattttct cctccttgta taaatcctgg   4860
ttgctgtctc tttatgagga gttgtggccc gttgtcaggc aacgtggcgt ggtgtgcact   4920
gtgtttgctg acgcaacccc cactggttgg ggcattgcca ccacctgtca gctcctttcc   4980
gggactttcg ctttccccct ccctattgcc acggcggaac tcatcgccgc ctgccttgcc   5040
cgctgctgga caggggctcg gctgttgggc actgacaatt ccgtggtgtt gtcggggaag   5100
ctgacgtcct ttccatggct gctcgcctgt gttgccacct ggattctgcg cgggacgtcc   5160
ttctgctacg tcccttcggc cctcaatcca gcggaccttc cttcccgcgg cctgctgccg   5220
gctctgcggc ctcttccgcg tcttcgcctt cgccctcaga cgagtcggat ctccctttgg   5280
```

gccgcctccc cgcctggaat tcctgcagat ctgcctcgac tgtgccttct agttgccagc 5340
catctgttgt ttgcccctcc cccgtgcctt ccttgaccct ggaaggtgcc actcccactg 5400
tcctttccta ataaaatgag gaaattgcat cgcattgtct gagtaggtgt cattctattc 5460
tggggggtgg ggtggggcag gacagcaagg gggaggattg ggaagacaat agcaggcatg 5520
ctggggactc gagttctacg tagataagta gcatggcggg ttaatcatta actacaagga 5580
acccctagtg atggagttgg ccactccctc tctgcgcgct cgctcgctca ctgaggccgg 5640
gcgaccaaag gtcgcccgac gcccgggctt tgcccgggcg gcctcagtga gcgagcgagc 5700
gcgcagcctt aattaaccta aggaaaatga agtgaagttc ctatactttc tagagaatag 5760
gaacttctat agtgagtcga ataagggcga cacaaaattt attctaaatg cataataaat 5820
actgataaca tcttatagtt tgtattatat tttgtattat cgttgacatg tataattttg 5880
atatcaaaaa ctgattttcc ctttattatt ttcgagattt attttcttaa ttctctttaa 5940
caaactagaa atattgtata tacaaaaaat cataaataat agatgaatag tttaattata 6000
ggtgttcatc aatcgaaaaa gcaacgtatc ttatttaaag tgcgttgctt ttttctcatt 6060
tataaggtta aataattctc atatatcaag caaagtgaca ggcgccctta aatattctga 6120
caaatgctct ttccctaaac tccccccata aaaaaacccg ccgaagcggg tttttacgtt 6180
atttgcggat taacgattac tcgttatcag aaccgcccag ggggcccgag cttaaccttt 6240
ttatttgggg gagagggaag tcatgaaaaa actaaccttt gaaattcgat ctccagcaca 6300
tcagcaaaac gctattcacg cagtacagca aatccttcca gacccaacca aaccaatcgt 6360
agtaaccatt caggaacgca accgcagctt agaccaaaac aggaagctat gggcctgctt 6420
aggtgacgtc tctcgtcagg ttgaatggca tggtcgctgg ctggatgcag aaagctggaa 6480
gtgtgtgttt accgcagcat taaagcagca ggatgttgtt cctaaccttg ccgggaatgg 6540
ctttgtggta ataggccagt caaccagcag gatgcgtgta ggcgaatttg cggagctatt 6600
agagcttata caggcattcg gtacagagcg tggcgttaag tggtcagacg aagcgagact 6660
ggctctggag tggaaagcga gatggggaga cagggctgca tgataaatgt cgttagtttc 6720
tccggtggca ggacgtcagc atatttgctc tggctaatgg agcaaaagcg acgggcaggt 6780
aaagacgtgc attacgtttt catggataca ggttgtgaac atccaatgac atatcggttt 6840
gtcagggaag ttgtgaagtt ctgggatata ccgctcaccg tattgcaggt tgatatcaac 6900
ccggagcttg gacagccaaa tggttatacg gtatgggaac caaaggatat tcagacgcga 6960
atgcctgttc tgaagccatt tatcgatatg gtaaagaaat atggcactcc atacgtcggc 7020
ggcgcgttct gcactgacag attaaaactc gttcccttca ccaaatactg tgatgaccat 7080
ttcgggcgag ggaattacac cacgtggatt ggcatcagag ctgatgaacc gaagcggcta 7140
aagccaaagc ctggaatcag atatcttgct gaactgtcag actttgagaa ggaagatatc 7200
ctcgcatggt ggaagcaaca accattcgat ttgcaaatac cggaacatct cggtaactgc 7260
atattctgca ttaaaaaatc aacgcaaaaa atcggacttg cctgcaaaga tgaggaggga 7320
ttgcagcgtg tttttaatga ggtcatcacg ggatcccatg tgcgtgacgg acatcgggaa 7380
acgccaaagg agattatgta ccgaggaaga atgtcgctgg acggtatcgc gaaaatgtat 7440
tcagaaaatg attatcaagc cctgtatcag gacatggtac gagctaaaag attcgatacc 7500
ggctcttgtt ctgagtcatg cgaaatattt ggagggcagc ttgatttcga cttcgggagg 7560
gaagctgcat gatgcgatgt tatcggtgcg gtgaatgcaa agaagataac cgcttccgac 7620
caaatcaacc ttactggaat cgatggtgtc tccggtgtga aagaacacca acaggggtgt 7680
taccactacc gcaggaaaag gaggacgtgt ggcgagacag cgacgaagta tcaccgacat 7740
aatctgcgaa aactgcaaat accttccaac gaaacgcacc agaaataaac ccaagccaat 7800
cccaaaagaa tctgacgtaa aaaccttcaa ctacacggct cacctgtggg atatccggtg 7860
gctaagacgt cgtgcgagga aaacaaggtg attgaccaaa atcgaagtta cgaacaagaa 7920
agcgtcgagc gagctttaac gtgcgctaac tgcggtcaga agctgcatgt gctggaagtt 7980
cacgtgtgtg agcactgctg cgcagaactg atgagcgatc cgaatagctc gatgcacgag 8040
gaagaagatg atggctaaac cagcgcgaag acgatgtaaa aacgatgaat gccgggaatg 8100
gtttcaccct gcattcgcta atcagtggtg gtgctctcca gagtgtggaa ccaagatagc 8160
actcgaacga cgaagtaaag aacgcgaaaa agcggaaaaa gcagcagaga agaaacgacg 8220
acgagaggag cagaaacaga aagataaact taagattcga aaactcgcct taaagccccg 8280
cagttactgg attaaacaag cccaacaagc cgtaaacgcc ttcatcagag aaagagaccg 8340
cgacttacca tgtatctcgt gcggaacgct cacgtctgct cagtgggatg ccggacatta 8400
ccggacaact gctgcggcac ctcaactccg atttaatgaa cgcaatattc acaagcaatg 8460
cgtggtgtgc aaccagcaca aaagcggaaa tctcgttccg tatcgcgtcg aactgattag 8520
ccgcatcggg caggaagcag tagacgaaat cgaatcaaac cataaccgcc atcgctggac 8580
tatcgaagag tgcaaggcga tcaaggcaga gtaccaacag aaactcaaag acctgcgaaa 8640
tagcagaagt gaggccgcat gacgttctca gtaaaaacca ttccagacat gctcgttgaa 8700
gcatacggaa atcagacaga agtagcacgc agactgaaat gtagtcgcgg tacggtcaga 8760
aaatacgttg atgataaaga cgggaaaatg cacgccatcg tcaacgacgt tctcatggtt 8820
catcgcggat ggagtgaaag agatgcgcta ttacgaaaaa attgatggca gcaaataccg 8880
aaatatttgg gtagttggcg atctgcacgg atgctacacg aacctgatga acaaactgga 8940
tacgattgga ttcgacaaca aaaaagacct gcttatctcg gtgggcgatt tggttgatcg 9000
tggtgcagag aacgttgaat gcctggaatt aatcacattc ccctggttca gagctgtacg 9060
tggaaaccat gagcaaatga tgattgatgg cttatcagag cgtggaaacg ttaatcactg 9120
gctgcttaat ggcggtggct ggttctttaa tctcgattac gacaaagaaa ttctggctaa 9180
agctcttgcc cataaagcag atgaacttcc gttaatcatc gaactggtga gcaaagataa 9240
aaaatatgtt atctgccacg ccgattatcc ctttgacgaa tacgagtttg gaaagccagt 9300
tgatcatcag caggtaatct ggaaccgcga acgaatcagc aactcacaaa acgggatcgt 9360
gaaagaaatc aaaggcgcgg acacgttcat ctttggtcat acgccagcag tgaaaccact 9420
caagtttgcc aaccaaatgt atatcgatac cggcgcagtg ttctgcggaa acctaacatt 9480
gattcaggta cagggagaag gcgcatgaga ctcgaaagcg tagctaaatt tcattcgcca 9540
aaaagcccga tgatgagcga ctcaccacgg gccacggctt ctgactctct ttccggtact 9600
gatgtgatgg ctgctatggg gatggcgcaa tcacaagccg gattcggtat ggctgcattc 9660
tgcggtaagc acgaactcag ccagaacgac aaacaaaagg ctatcaacta tctgatgcaa 9720
tttgcacaca aggtatcggg gaaataccgt ggtgtggcaa agcttgaagg aaatactaag 9780
gcaaaggtac tgcaagtgct cgcaacattc gcttatgcgg attattgccg tagtgccgcg 9840
acgccggggg caagatgcag agattgccat ggtacaggcc gtgcggttga tattgccaaa 9900
acagagctgt gggggagagt tgtcgagaaa gagtgcggaa gatgcaaagg cgtcggctat 9960
tcaaggatgc cagcaagcgc agcatatcgc gctgtgacga tgctaatccc aaaccttacc 10020

-continued caacccacct ggtcacgcac tgttaagccg ctgtatgacg ctctggtggt gcaatgccac 10080
aaagaagagt caatcgcaga caacattttg aatgcggtca cacgttagca gcatgattgc 10140
cacggatggc aacatattaa cggcatgata ttgacttatt gaataaaatt gggtaaattt 10200
gactcaacga tgggttaatt cgctcgttgt ggtagtgaga tgaaaagagg cggcgcttac 10260
taccgattcc gcctagttgg tcacttcgac gtatcgtctg gaactccaac catcgcaggc 10320
agagaggtct gcaaaatgca atcccgaaac agttcgcagg taatagttag agcctgcata 10380
acggtttcgg gatttttat atctgcacaa caggtaagag cattgagtcg ataatcgtga 10440
agagtcggcg agcctggtta gccagtgctc tttccgttgt gctgaattaa gcgaataccg 10500
gaagcagaac cggatcacca aatgcgtaca ggcgtcatcg ccgcccagca acagcacaac 10560
ccaaactgag ccgtagccac tgtctgtcct gaattcatta gtaatagtta cgctgcggcc 10620
ttttacacat gaccttcgtg aaagcgggtg gcaggaggtc gcgctaacaa cctcctgccg 10680
ttttgcccgt gcatatcggt cacgaacaaa tctgattact aaacacagta gcctggattt 10740
gttctatcag taatcgacct tattcctaat taaatagagc aaatcccctt attgggggta 10800
agacatgaag atgccagaaa aacatgacct gttggccgcc attctcgcgg caaaggaaca 10860
aggcatcggg gcaatccttg cgtttgcaat ggcgtacctt cgcggcagat ataatggcgg 10920
tgcgtttaca aaaacagtaa tcgacgcaac gatgtgcgcc attatcgcct ggttcattcg 10980
tgaccttctc gacttcgccg gactaagtag caatctcgct tatataacga gcgtgtttat 11040
cggctacatc ggtactgact cgattggttc gcttatcaaa cgcttcgctg ctaaaaaagc 11100
cggagtagaa gatggtagaa atcaataatc aacgtaaggc gttcctcgat atgctggcgt 11160
ggtcggaggg aactgataac ggacgtcaga aaaccagaaa tcatggttat gacgtcattg 11220
taggcggaga gctatttact gattactccg atcaccctcg caaacttgtc acgctaaacc 11280
caaaactcaa atcaacaggc gcttaagact ggccgtcgtt ttacaacaca gaaagagttt 11340
gtagaaacgc aaaaaggcca tccgtcaggg gccttctgct tagtttgatg cctggcagtt 11400
ccctactctc gccttccgct tcctcgctca ctgactcgct gcgctcggtc gttcggctgc 11460
ggcgagcggt atcagctcac tcaaaggcgg taatacggtt atccacagaa tcaggggata 11520
acgcaggaaa gaacatgtga gcaaaaggcc agcaaaaggc caggaaccgt aaaaaggccg 11580
cgttgctggc gtttttccat aggctccgcc cccctgacga gcatcacaaa aatcgacgct 11640
caagtcagag gtggcgaaac ccgacaggac tataaagata ccaggcgttt ccccctggaa 11700
gctccctcgt gcgctctcct gttccgaccc tgccgcttac cggatacctg tccgcctttc 11760
tcccttcggg aagcgtggcg ctttctcata gctcacgctg taggtatctc agttcggtgt 11820
aggtcgttcg ctccaagctg ggctgtgtgc acgaaccccc cgttcagccc gaccgctgcg 11880
ccttatccgg taactatcgt cttgagtcca acccggtaag acacgactta tcgccactgg 11940
cagcagccac tggtaacagg attagcagag cgaggtatgt aggcggtgct acagagttct 12000
tgaagtggtg gcctaactac ggctacacta gaagaacagt atttggtatc tgcgctctgc 12060
tgaagccagt taccttcgga aaaagagttg gtagctcttg atccggcaaa caaaccaccg 12120
ctggtagcgg tggttttttt gtttgcaagc agcagattac gcgcagaaaa aaaggatctc 12180
aagaagatcc tttgatcttt tctacggggt ctgacgctca gtggaacgac gcgcgcgtaa 12240
ctcacgttaa gggattttgg tcatgagctt gcgccgtccc gtcaagtcag cgtaatgctc 12300
tgcttt 12306

<210> SEQ ID NO 19
<211> LENGTH: 12294
<212> TYPE: DNA
<213> ORGANISM: Artificial Sequence
<220> FEATURE:
<223> OTHER INFORMATION: constructed sequence

<400> SEQUENCE: 19
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320
ggcctcagtg agcgagcgag cgcgcagaga gggagtggcc aactccatca ctaggggttc 1380
cttgtagtta atgattaacc cgccatgcta cttatctacg tagcaagcta gccacccaca 1440
agccagttcc tgtccctgag gacttggctc agggactctg ggaatgtggt agacatgggg 1500
tggccccacc aaatgcatcc ttatgggaac ctgctccctg ggagccatga aaagagcgtg 1560
gacttcgagg tggggccaca ggaagtggtc aggtccatct caggggacct gctgcccatc 1620
cacactgctg gccaggaaat gggggcaat tcatgcctcc tcagcacctt cagcactggg 1680
cggctcaaag aaggcaaggg actattctgg ggtcacacag catgcagcca gaggccaagg 1740
catgaggaag tccttcattt ccccaccccc acccacctca gatcctccaa ccggtttcat 1800
ggcagcccag ggtccagcgg catccaggat gctggtgggt agctgcacag cccaggccgc 1860
gggaggttgg ctgctctcac ctaacaggcc tatgtggccc tgacccctac ctaggaagct 1920
ggggacaatg gccaaggcgc ctcccctctc tgtgcctgtc tgtccaggtg cagcatagac 1980
acagcacccc tggggccaag agcacccagc cagggctgcc cccatgggtg ggcagggcag 2040
taaatgaatg agggacaggt tgggaggtgg ccagccccct ccagcccatg gagggcacgg 2100

-continued

```
ggcaggagag ctgggctgag ccagcaggag cccagggagc ctggtctctg ccttcctatc   2160
ctggaggaag gtgaggctga acctccttcc ctccctccct ccctccccgc ccccactgca   2220
cgcagggctg gctgggctcc agctggcctc cgcatcaata tttcatcggc gtcaatagga   2280
ggcatcgggg acagccgctg cggcagcact cgagccagct caagcccgca gctcgcaggg   2340
agatccagct ccgtcctgcc tgcagcagca caaccctgca caccctgtac actagcggcc   2400
gcgccgccac catggccgac gaagccgcac tcgcgctgca accagggggt tccccgtctg   2460
cagcaggcgc cgatagagaa gcagccagct cgccagcagg agaaccgctc cggaagcgac   2520
ccaggagaga tggcccaggc ctggaacgct caccgggtga accaggaggt gccgctcctg   2580
aacgggaagt gcccgcagct gctaggggct gtccaggagc agccgcagca gcactctggc   2640
gcgaagccga agccgaggct gctgcagccg gaggagaaca agaagcccaa gcgaccgctg   2700
cagcaggaga gggcgacaac ggacccggcc tgcaaggacc gtcccgcgaa cctccgctgg   2760
ccgacaatct gtacgacgag gacgatgatg atgagggcga agaagaagag gaagccgccg   2820
ctgctgctat tggatacaga gacaaccttc tcttcggcga cgagatcatc accaatggat   2880
tccactcctg tgaatctgac gaagaagatc gggcctccca tgctagcagc tctgactgga   2940
cgccacggcc aaggatcggt ccgtacacct tcgtgcagca gcacctgatg atcggcacag   3000
atccccgcac cattctgaag gatctgctgc ccgagactat cccacccccct gagctggacg   3060
acatgactct gtggcagatt gtgatcaaca tcctttccga gcccccaaag cggaagaagc   3120
gcaaggatat taacaccatc gaggacgccg tgaagcttct gcaggagtgc aaaaagatca   3180
tcgtgctgac tggtgcaggg gtgtccgtgt cctgcggcat tccggatttc agaagccgcg   3240
acggaatcta cgccagactc gcggtcgact ttcccgatct gcctgaccct caggccatgt   3300
tcgatattga atacttccgc aaggacccga ggccgttctt taagttcgcc aaggagatct   3360
accctgggca gttccaaccc tccctctgcc ataagttcat tgcgctgagc gataaggaag   3420
gaaagctgct gcggaactac acccagaaca tcgacactct tgagcaagtg gcgggtatcc   3480
agagaatcat ccaatgccac ggctccttcg ccactgcctc ctgcctgatc tgcaagtaca   3540
aggtcgattg tgaagccgtc aggggcgata tcttcaacca agtggtcccg cgatgcccaa   3600
gatgcccggc ggatgaaccc ttggccatca tgaagcctga aatcgtgttc ttcgggggaaa  3660
acctccccga acagtttcac cgcgccatga agtacgacaa ggacgaagtg gatctcctga   3720
ttgtgattgg ttccagcttg aaagtccggc cagtggcctt gatcccctcc tcgattccac   3780
acgaagtgcc tcaaatcctt attaaccggg aaccactgcc gcatcttcac ttcgatgtgg   3840
aactgctggg agactgcgac gtgattatta acgaactgtg tcaccgcttg ggtggcgaat   3900
acgccaagct gtgctgcaac cctgtgaaac tgtcggagat caccgaaaag ccgcccagaa   3960
ctcaaaaaga gctggcctac ctgtccgagc tccctccgac tccgctgcat gtgtccgagg   4020
attcgtcgtc cccggaaagg acttcgcctc cggactcctc cgtgatcgtg accctgctcg   4080
accaagccgc caagtcgaac gacgatctgg acgtgtcgga atccaagggc tgcatggaag   4140
aaaagcctca agaggtgcag acttcacgga acgtggagtc catcgccgaa cagatggaaa   4200
acccggacct gaagaacgtg ggaagcagca ctggcgaaaa gaacgagaga acctccgtgg   4260
ccggtactgt ccggaagtgc tggccgaaca gggtggccaa ggaacagata tcccggagac   4320
ttgacggcaa ccagtacctc ttcctccccc ctaaccgcta tatttttcac ggggccgagg   4380
tgtacagcga ctccgaggac gatgtgctgt catcctcatc atgcggttcc aattccgact   4440
ccggaacctg tcagagcccc tccctggagg aacctatgga ggacgaatcc gagatcgagg   4500
```

aattctacaa cggtctggag gacgagcctg atgtcccgga acgcgctgga ggagctggct 4560
tcggaaccga cggggacgac caggaagcca tcaacgaggc catctcggtg aagcaggaag 4620
tgaccgatat gaactacccg tccaacaagt cctgagcggc cgcatagtac tgcggatcct 4680
gcaggcgtcg acaatcaacc tctggattac aaaatttgtg aaagattgac tggtattctt 4740
aactatgttg ctccttttac gctatgtgga tacgctgctt taatgccttt gtatcatgct 4800
attgcttccc gtatggcttt cattttctcc tccttgtata aatcctggtt gctgtctctt 4860
tatgaggagt tgtggcccgt tgtcaggcaa cgtggcgtgg tgtgcactgt gtttgctgac 4920
gcaaccccca ctggttgggg cattgccacc acctgtcagc tcctttccgg gactttcgct 4980
ttccccctcc ctattgccac ggcggaactc atcgccgcct gccttgcccg ctgctggaca 5040
ggggctcggc tgttgggcac tgacaattcc gtggtgttgt cggggaagct gacgtccttt 5100
ccatggctgc tcgcctgtgt tgccacctgg attctgcgcg ggacgtcctt ctgctacgtc 5160
ccttcggccc tcaatccagc ggaccttcct tcccgcggcc tgctgccggc tctgcggcct 5220
cttccgcgtc ttcgccttcg ccctcagacg agtcggatct ccctttgggc cgcctccccg 5280
cctggaattc ctgcagatct gcctcgactg tgccttctag ttgccagcca tctgttgttt 5340
gcccctcccc cgtgccttcc ttgaccctgg aaggtgccac tcccactgtc ctttcctaat 5400
aaaatgagga aattgcatcg cattgtctga gtaggtgtca ttctattctg gggggtgggg 5460
tggggcagga cagcaagggg gaggattggg aagacaatag caggcatgct ggggactcga 5520
gttctacgta gataagtagc atggcgggtt aatcattaac tacaaggaac ccctagtgat 5580
ggagttggcc actccctctc tgcgcgctcg ctcgctcact gaggccgggc gaccaaaggt 5640
cgcccgacgc ccgggctttg cccgggcggc ctcagtgagc gagcgagcgc gcagccttaa 5700
ttaacctaag gaaaatgaag tgaagttcct atactttcta gagaatagga acttctatag 5760
tgagtcgaat aagggcgaca caaaatttat tctaaatgca taataaatac tgataacatc 5820
ttatagtttg tattatattt tgtattatcg ttgacatgta taattttgat atcaaaaact 5880
gattttccct ttattatttt cgagatttat ttttcttaatt ctctttaaca aactagaaat 5940
attgtatata caaaaaatca taaataatag atgaatagtt taattatagg tgttcatcaa 6000
tcgaaaaagc aacgtatctt atttaaagtg cgttgctttt ttctcattta taaggttaaa 6060
taattctcat atatcaagca aagtgacagg cgcccttaaa tattctgaca aatgctcttt 6120
ccctaaactc cccccataaa aaaacccgcc gaagcgggtt tttacgttat ttgcggatta 6180
acgattactc gttatcagaa ccgcccaggg ggcccgagct taaccttttt atttgggggga 6240 gagggaagtc atgaaaaaac taacctttga aattcgatct ccagcacatc agcaaaacgc 6300
tattcacgca gtacagcaaa tccttccaga cccaaccaaa ccaatcgtag taaccattca 6360
ggaacgcaac cgcagcttag accaaaacag gaagctatgg gcctgcttag gtgacgtctc 6420
tcgtcaggtt gaatggcatg gtcgctggct ggatgcagaa agctggaagt gtgtgtttac 6480
cgcagcatta aagcagcagg atgttgttcc taaccttgcc gggaatggct ttgtggtaat 6540
aggccagtca accagcagga tgcgtgtagg cgaatttgcg gagctattag agcttataca 6600
ggcattcggt acagagcgtg gcgttaagtg gtcagacgaa gcgagactgg ctctggagtg 6660
gaaagcgaga tggggagaca gggctgcatg ataaatgtcg ttagtttctc cggtggcagg 6720
acgtcagcat atttgctctg gctaatggag caaaagcgac gggcaggtaa agacgtgcat 6780
tacgttttca tggatacagg ttgtgaacat ccaatgacat atcggtttgt cagggaagtt 6840

-continued

```
gtgaagttct gggatatacc gctcaccgta ttgcaggttg atatcaaccc ggagcttgga   6900
cagccaaatg gttatacggt atgggaacca aaggatattc agacgcgaat gcctgttctg   6960
aagccattta tcgatatggt aaagaaatat ggcactccat acgtcggcgg cgcgttctgc   7020
actgacagat taaaactcgt tcccttcacc aaatactgtg atgaccattt cgggcgaggg   7080
aattacacca cgtggattgg catcagagct gatgaaccga agcggctaaa gccaaagcct   7140
ggaatcagat atcttgctga actgtcagac tttgagaagg aagatatcct cgcatggtgg   7200
aagcaacaac cattcgattt gcaaataccg gaacatctcg gtaactgcat attctgcatt   7260
aaaaaatcaa cgcaaaaaat cggacttgcc tgcaaagatg aggagggatt gcagcgtgtt   7320
tttaatgagg tcatcacggg atcccatgtg cgtgacggac atcgggaaac gccaaaggag   7380
attatgtacc gaggaagaat gtcgctggac ggtatcgcga aaatgtattc agaaaatgat   7440
tatcaagccc tgtatcagga catggtacga gctaaaagat tcgataccgg ctcttgttct   7500
gagtcatgcg aaatatttgg agggcagctt gatttcgact tcgggaggga agctgcatga   7560
tgcgatgtta tcggtgcggt gaatgcaaag aagataaccg cttccgacca aatcaacctt   7620
actggaatcg atggtgtctc cggtgtgaaa gaacaccaac aggggtgtta ccactaccgc   7680
aggaaaagga ggacgtgtgg cgagacagcg acgaagtatc accgacataa tctgcgaaaa   7740
ctgcaaatac cttccaacga aacgcaccag aaataaaccc aagccaatcc caaaagaatc   7800
tgacgtaaaa accttcaact acacggctca cctgtgggat atccggtggc taagacgtcg   7860
tgcgaggaaa acaaggtgat tgaccaaaat cgaagttacg aacaagaaag cgtcgagcga   7920
gctttaacgt gcgctaactg cggtcagaag ctgcatgtgc tggaagttca cgtgtgtgag   7980
cactgctgcg cagaactgat gagcgatccg aatagctcga tgcacgagga agaagatgat   8040
ggctaaacca gcgcgaagac gatgtaaaaa cgatgaatgc cgggaatggt ttcaccctgc   8100
attcgctaat cagtggtggt gctctccaga gtgtggaacc aagatagcac tcgaacgacg   8160
aagtaaagaa cgcgaaaaag cggaaaaagc agcagagaag aaacgacgac gagaggagca   8220
gaaacagaaa gataaactta agattcgaaa actcgcctta aagccccgca gttactggat   8280
taaacaagcc caacaagccg taaacgcctt catcagagaa agagaccgcg acttaccatg   8340
tatctcgtgc ggaacgctca cgtctgctca gtgggatgcc ggacattacc ggacaactgc   8400
tgcggcacct caactccgat ttaatgaacg caatattcac aagcaatgcg tggtgtgcaa   8460
ccagcacaaa agcggaaatc tcgttccgta tcgcgtcgaa ctgattagcc gcatcgggca   8520
ggaagcagta gacgaaatcg aatcaaacca taaccgccat cgctggacta tcgaagagtg   8580
caaggcgatc aaggcagagt accaacagaa actcaaagac ctgcgaaata gcagaagtga   8640
ggccgcatga cgttctcagt aaaaaccatt ccagacatgc tcgttgaagc atacggaaat   8700
cagacagaag tagcacgcag actgaaatgt agtcgcggta cggtcagaaa atacgttgat   8760
gataaagacg ggaaaatgca cgccatcgtc aacgacgttc tcatggttca tcgcggatgg   8820
agtgaaagag atgcgctatt acgaaaaaat tgatggcagc aaataccgaa atatttgggt   8880
agttggcgat ctgcacggat gctacacgaa cctgatgaac aaactggata cgattggatt   8940
cgacaacaaa aaagacctgc ttatctcggt gggcgatttg gttgatcgtg gtgcagagaa   9000
cgttgaatgc ctggaattaa tcacattccc ctggttcaga gctgtacgtg gaaaccatga   9060
gcaaatgatg attgatggct tatcagagcg tggaaacgtt aatcactggc tgcttaatgg   9120
cggtggctgg ttctttaatc tcgattacga caaagaaatt ctggctaaag ctcttgccca   9180
taaagcagat gaacttccgt taatcatcga actggtgagc aaagataaaa aatatgttat   9240
```

```
ctgccacgcc gattatccct ttgacgaata cgagtttgga aagccagttg atcatcagca   9300
ggtaatctgg aaccgcgaac gaatcagcaa ctcacaaaac gggatcgtga aagaaatcaa   9360
aggcgcggac acgttcatct ttggtcatac gccagcagtg aaaccactca agtttgccaa   9420
ccaaatgtat atcgataccg gcgcagtgtt ctgcggaaac ctaacattga ttcaggtaca   9480
gggagaaggc gcatgagact cgaaagcgta gctaaatttc attcgccaaa aagcccgatg   9540
atgagcgact caccacgggc cacggcttct gactctcttt ccggtactga tgtgatggct   9600
gctatgggga tggcgcaatc acaagccgga ttcggtatgg ctgcattctg cggtaagcac   9660
gaactcagcc agaacgacaa acaaaaggct atcaactatc tgatgcaatt tgcacacaag   9720
gtatcgggga aataccgtgg tgtggcaaag cttgaaggaa atactaaggc aaaggtactg   9780
caagtgctcg caacattcgc ttatgcggat tattgccgta gtgccgcgac gccgggggca   9840
agatgcagag attgccatgg tacaggccgt gcggttgata ttgccaaaac agagctgtgg   9900
gggagagttg tcgagaaaga gtgcggaaga tgcaaaggcg tcggctattc aaggatgcca   9960
gcaagcgcag catatcgcgc tgtgacgatg ctaatcccaa accttaccca acccacctgg  10020
tcacgcactg ttaagccgct gtatgacgct ctggtggtgc aatgccacaa agaagagtca  10080
atcgcagaca acattttgaa tgcggtcaca cgttagcagc atgattgcca cggatggcaa  10140
catattaacg gcatgatatt gacttattga ataaaattgg gtaaatttga ctcaacgatg  10200
ggttaattcg ctcgttgtgg tagtgagatg aaaagaggcg gcgcttacta ccgattccgc  10260
ctagttggtc acttcgacgt atcgtctgga actccaacca tcgcaggcag agaggtctgc  10320
aaaatgcaat cccgaaacag ttcgcaggta atagttagag cctgcataac ggtttcggga  10380
tttttatat ctgcacaaca ggtaagagca ttgagtcgat aatcgtgaag agtcggcgag  10440
cctggttagc cagtgctctt tccgttgtgc tgaattaagc gaataccgga agcagaaccg  10500
gatcaccaaa tgcgtacagg cgtcatcgcc gcccagcaac agcacaaccc aaactgagcc  10560
gtagccactg tctgtcctga attcattagt aatagttacg ctgcggcctt ttacacatga  10620
ccttcgtgaa agcgggtggc aggaggtcgc gctaacaacc tcctgccgtt ttgcccgtgc  10680
atatcggtca cgaacaaatc tgattactaa acacagtagc ctggatttgt tctatcagta  10740
atcgacctta ttcctaatta aatagagcaa atccccttat tgggggtaag acatgaagat  10800
gccagaaaaa catgacctgt tggccgccat tctcgcggca aaggaacaag gcatcggggc  10860
aatccttgcg tttgcaatgg cgtaccttcg cggcagatat aatggcggtg cgtttacaaa  10920
aacagtaatc gacgcaacga tgtgcgccat tatcgcctgg ttcattcgtg accttctcga  10980
cttcgccgga ctaagtagca atctcgctta tataacgagc gtgtttatcg gctacatcgg  11040
tactgactcg attggttcgc ttatcaaacg cttcgctgct aaaaaagccg gagtagaaga  11100
tggtagaaat caataatcaa cgtaaggcgt tcctcgatat gctggcgtgg tcggagggaa  11160
ctgataacgg acgtcagaaa accagaaatc atggttatga cgtcattgta ggcggagagc  11220
tatttactga ttactccgat caccctcgca aacttgtcac gctaaaccca aaactcaaat  11280
caacaggcgc ttaagactgg ccgtcgtttt acaacacaga aagagtttgt agaaacgcaa  11340
aaaggccatc cgtcaggggc cttctgctta gtttgatgcc tggcagttcc ctactctcgc  11400
cttccgcttc ctcgctcact gactcgctgc gctcggtcgt tcggctgcgg cgagcggtat  11460
cagctcactc aaaggcggta atacggttat ccacagaatc aggggataac gcaggaaaga  11520
acatgtgagc aaaaggccag caaaaggcca ggaaccgtaa aaaggccgcg ttgctggcgt  11580
```

ttttccatag gctccgcccc cctgacgagc atcacaaaaa tcgacgctca agtcagaggt 11640
ggcgaaaccc gacaggacta taaagatacc aggcgtttcc ccctggaagc tccctcgtgc 11700
gctctcctgt tccgaccctg ccgcttaccg gatacctgtc cgcctttctc ccttcgggaa 11760
gcgtggcgct ttctcatagc tcacgctgta ggtatctcag ttcggtgtag gtcgttcgct 11820
ccaagctggg ctgtgtgcac gaaccccccg ttcagcccga ccgctgcgcc ttatccggta 11880
actatcgtct tgagtccaac ccggtaagac acgacttatc gccactggca gcagccactg 11940
gtaacaggat tagcagagcg aggtatgtag gcggtgctac agagttcttg aagtggtggg 12000
ctaactacgg ctacactaga agaacagtat ttggtatctg cgctctgctg aagccagtta 12060
ccttcggaaa aagagttggt agctcttgat ccggcaaaca aaccaccgct ggtagcggtg 12120
gtttttttgt ttgcaagcag cagattacgc gcagaaaaaa aggatctcaa gaagatcctt 12180
tgatcttttc tacggggtct gacgctcagt ggaacgacgc gcgcgtaact cacgttaagg 12240
gattttggtc atgagcttgc gccgtcccgt caagtcagcg taatgctctg cttt 12294

<210> SEQ ID NO 20
<211> LENGTH: 12321
<212> TYPE: DNA
<213> ORGANISM: Artificial Sequence
<220> FEATURE:
<223> OTHER INFORMATION: constructed sequence

<400> SEQUENCE: 20
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320
ggcctcagtg agcgagcgag cgcgcagaga gggagtggcc aactccatca ctaggggttc 1380
cttgtagtta atgattaacc cgccatgcta cttatctacg tagcaagcta gccacccaca 1440
agccagttcc tgtccctgag gacttggctc agggactctg ggaatgtggt agacatgggg 1500
tggccccacc aaatgcatcc ttatgggaac ctgctccctg ggagccatga aaagagcgtg 1560
gacttcgagg tggggccaca ggaagtggtc aggtccatct caggggacct gctgcccatc 1620
cacactgctg gccaggaaat ggggggcaat tcatgcctcc tcagcacctt cagcactggg 1680
cggctcaaag aaggcaaggg actattctgg ggtcacacag catgcagcca gaggccaagg 1740
catgaggaag tccttcattt ccccaccccc acccacctca gatcctccaa ccggtttcat 1800
ggcagcccag ggtccagcgg catccaggat gctggtgggt agctgcacag cccaggccgc 1860
gggaggttgg ctgctctcac ctaacaggcc tatgtggccc tgacccctac ctaggaagct 1920
ggggacaatg gccaaggcgc ctcccctctc tgtgcctgtc tgtccaggtg cagcatagac 1980
acagcacccc tggggccaag agcacccagc cagggctgcc cccatgggtg ggcagggcag 2040
taaatgaatg agggacaggt tgggaggtgg ccagccccct ccagcccatg gagggcacgg 2100
ggcaggagag ctgggctgag ccagcaggag cccagggagc ctggtctctg ccttcctatc 2160
ctggaggaag gtgaggctga acctccttcc ctccctccct ccctccccgc ccccactgca 2220
cgcagggctg gctgggctcc agctggcctc cgcatcaata tttcatcggc gtcaatagga 2280
ggcatcgggg acagccgctg cggcagcact cgagccagct caagcccgca gctcgcaggg 2340
agatccagct ccgtcctgcc tgcagcagca caaccctgca caccctgtac actagcggcc 2400
gcgccgccac catggccgac gaagccgcac tcgcgctgca accagggggt tccccgtctg 2460
cagcaggcgc cgatagagaa gcagccagct cgccagcagg agaaccgctc cggaagcgac 2520
ccaggagaga tggcccaggc ctggaacgct caccgggtga accaggaggt gccgctcctg 2580
aacgggaagt gcccgcagct gctaggggct gtccaggagc agccgcagca gcactctggc 2640
gcgaagccga agccgaggct gctgcagccg gaggagaaca agaagcccaa gcgaccgctg 2700
cagcaggaga gggcgacaac ggacccggcc tgcaaggacc gtcccgcgaa cctccgctgg 2760
ccgacaatct gtacgacgag gacgatgatg atgagggcga agaagaagag gaagccgccg 2820
ctgctgctat tggatacaga gacaaccttc tcttcggcga cgagatcatc accaatggat 2880
tccactcctg tgaatctgac gaagaagatc gggcctccca tgctagcagc tctgactgga 2940
cgccacggcc aaggatcggt ccgtacacct tcgtgcagca gcacctgatg atcggcacag 3000
atccccgcac cattctgaag gatctgctgc ccgagactat cccaccccct gagctggacg 3060
acatgactct gtggcagatt gtgatcaaca tcctttccga gcccccaaag cggaagaagc 3120
gcaaggatat taacaccatc gaggacgccg tgaagcttct gcaggagtgc aaaaagatca 3180
tcgtgctgac tggtgcaggg gtgtccgtgt cctgcggcat tccggatttc agaagccgcg 3240
acggaatcta cgccagactc gcggtcgact ttcccgatct gcctgaccct caggccatgt 3300
tcgatattga atacttccgc aaggacccga ggccgttctt taagttcgcc aaggagatct 3360
accctgggca gttccaaccc tccctctgcc ataagttcat tgcgctgagc gataaggaag 3420
gaaagctgct gcggaactac acccagaaca tcgacactct tgagcaagtg gcgggtatcc 3480
agagaatcat ccaatgccac ggctccttcg ccactgcctc ctgcctgatc tgcaagtaca 3540
aggtcgattg tgaagccgtc aggggcgata tcttcaacca agtggtcccg cgatgcccaa 3600
gatgcccggc ggatgaaccc ttggccatca tgaagcctga aatcgtgttc ttcggggaaa 3660
acctccccga acagtttcac cgcgccatga agtacgacaa ggacgaagtg gatctcctga 3720

-continued

```
ttgtgattgg ttccagcttg aaagtccggc cagtggcctt gatcccctcc tcgattccac   3780
acgaagtgcc tcaaatcctt attaaccggg aaccactgcc gcatcttcac ttcgatgtgg   3840
aactgctggg agactgcgac gtgattatta acgaactgtg tcaccgcttg ggtggcgaat   3900
acgccaagct gtgctgcaac cctgtgaaac tgtcggagat caccgaaaag ccgcccagaa   3960
ctcaaaaaga gctggcctac ctgtccgagc tccctccgac tccgctgcat gtgtccgagg   4020
attcgtcgtc cccggaaagg acttcgcctc cggactcctc cgtgatcgtg accctgctcg   4080
accaagccgc caagtcgaac gacgatctgg acgtgtcgga atccaagggc tgcatggaag   4140
aaaagcctca agaggtgcag acttcacgga acgtggagtc catcgccgaa cagatggaaa   4200
acccggacct gaagaacgtg ggaagcagca ctggcgaaaa gaacgagaga acctccgtgg   4260
ccggtactgt ccggaagtgc tggccgaaca gggtggccaa ggaacagata tcccggagac   4320
ttgacggcaa ccagtacctc ttcctccccc ctaaccgcta tatttttcac ggggccgagg   4380
tgtacagcga ctccgaggac gatgtgctgt catcctcatc atgcggttcc aattccgact   4440
ccggaacctg tcagagcccc tccctggagg aacctatgga ggacgaatcc gagatcgagg   4500
aattctacaa cggtctggag gacgagcctg atgtcccgga acgcgctgga ggagctggct   4560
tcggaaccga cggggacgac caggaagcca tcaacgaggc catctcggtg aagcaggaag   4620
tgaccgatat gaactacccg tccaacaagt cctacccata cgatgttcca gattacgctt   4680
gagcggccgc atagtactgc ggatcctgca ggcgtcgaca atcaacctct ggattacaaa   4740
atttgtgaaa gattgactgg tattcttaac tatgttgctc cttttacgct atgtggatac   4800
gctgctttaa tgcctttgta tcatgctatt gcttcccgta tggctttcat tttctcctcc   4860
ttgtataaat cctggttgct gtctctttat gaggagttgt ggcccgttgt caggcaacgt   4920
ggcgtggtgt gcactgtgtt tgctgacgca acccccactg gttggggcat tgccaccacc   4980
tgtcagctcc tttccgggac tttcgctttc cccctcccta ttgccacggc ggaactcatc   5040
gccgcctgcc ttgcccgctg ctggacaggg gctcggctgt tgggcactga caattccgtg   5100
gtgttgtcgg ggaagctgac gtcctttcca tggctgctcg cctgtgttgc cacctggatt   5160
ctgcgcggga cgtccttctg ctacgtccct tcggccctca atccagcgga ccttccttcc   5220
cgcggcctgc tgccggctct gcggcctctt ccgcgtcttc gccttcgccc tcagacgagt   5280
cggatctccc tttgggccgc ctccccgcct ggaattcctg cagatctgcc tcgactgtgc   5340
cttctagttg ccagccatct gttgtttgcc cctcccccgt gccttccttg accctggaag   5400
gtgccactcc cactgtcctt tcctaataaa atgaggaaat tgcatcgcat tgtctgagta   5460
ggtgtcattc tattctgggg ggtggggtgg ggcaggacag caagggggag gattgggaag   5520
acaatagcag gcatgctggg gactcgagtt ctacgtagat aagtagcatg gcgggttaat   5580
cattaactac aaggaacccc tagtgatgga gttggccact ccctctctgc gcgctcgctc   5640
gctcactgag gccgggcgac caaaggtcgc ccgacgcccg ggctttgccc gggcggcctc   5700
agtgagcgag cgagcgcgca gccttaatta acctaaggaa aatgaagtga agttcctata   5760
ctttctagag aataggaact tctatagtga gtcgaataag ggcgacacaa aatttattct   5820
aaatgcataa taaatactga taacatctta tagtttgtat tatattttgt attatcgttg   5880
acatgtataa ttttgatatc aaaaactgat ttccctttta ttattttcga gatttatttt   5940
cttaattctc tttaacaaac tagaaatatt gtatatacaa aaaatcataa ataatagatg   6000
aatagtttaa ttataggtgt tcatcaatcg aaaaagcaac gtatcttatt taaagtgcgt   6060
tgcttttttc tcatttataa ggttaaataa ttctcatata tcaagcaaag tgacaggcgc   6120
```

```
ccttaaatat tctgacaaat gctctttccc taaactcccc ccataaaaaa acccgccgaa   6180
gcgggttttt acgttatttg cggattaacg attactcgtt atcagaaccg cccagggggc   6240
ccgagcttaa cctttttatt tgggggagag ggaagtcatg aaaaaactaa cctttgaaat   6300
tcgatctcca gcacatcagc aaaacgctat tcacgcagta cagcaaatcc ttccagaccc   6360
aaccaaacca atcgtagtaa ccattcagga acgcaaccgc agcttagacc aaaacaggaa   6420
gctatgggcc tgcttaggtg acgtctctcg tcaggttgaa tggcatggtc gctggctgga   6480
tgcagaaagc tggaagtgtg tgtttaccgc agcattaaag cagcaggatg ttgttcctaa   6540
ccttgccggg aatggctttg tggtaatagg ccagtcaacc agcaggatgc gtgtaggcga   6600
atttgcggag ctattagagc ttatacaggc attcggtaca gagcgtggcg ttaagtggtc   6660
agacgaagcg agactggctc tggagtggaa agcgagatgg ggagacaggg ctgcatgata   6720
aatgtcgtta gtttctccgg tggcaggacg tcagcatatt tgctctggct aatggagcaa   6780
aagcgacggg caggtaaaga cgtgcattac gttttcatgg atacaggttg tgaacatcca   6840
atgacatatc ggtttgtcag ggaagttgtg aagttctggg atataccgct caccgtattg   6900
caggttgata tcaacccgga gcttggacag ccaaatggtt atacggtatg ggaaccaaag   6960
gatattcaga cgcgaatgcc tgttctgaag ccatttatcg atatggtaaa gaaatatggc   7020
actccatacg tcggcggcgc gttctgcact gacagattaa aactcgttcc cttcaccaaa   7080
tactgtgatg accatttcgg gcgagggaat tacaccacgt ggattggcat cagagctgat   7140
gaaccgaagc ggctaaagcc aaagcctgga atcagatatc ttgctgaact gtcagacttt   7200
gagaaggaag atatcctcgc atggtggaag caacaaccat tcgatttgca aataccggaa   7260
catctcggta actgcatatt ctgcattaaa aaatcaacgc aaaaaatcgg acttgcctgc   7320
aaagatgagg agggattgca gcgtgttttt aatgaggtca tcacgggatc ccatgtgcgt   7380
gacggacatc gggaaacgcc aaaggagatt atgtaccgag gaagaatgtc gctggacggt   7440
atcgcgaaaa tgtattcaga aaatgattat caagccctgt atcaggacat ggtacgagct   7500
aaaagattcg ataccggctc ttgttctgag tcatgcgaaa tatttggagg gcagcttgat   7560
ttcgacttcg ggagggaagc tgcatgatgc gatgttatcg gtgcggtgaa tgcaaagaag   7620
ataaccgctt ccgaccaaat caaccttact ggaatcgatg gtgtctccgg tgtgaaagaa   7680
caccaacagg ggtgttacca ctaccgcagg aaaaggagga cgtgtggcga gacagcgacg   7740
aagtatcacc gacataatct gcgaaaactg caaatacctt ccaacgaaac gcaccagaaa   7800
taaacccaag ccaatcccaa aagaatctga cgtaaaaacc ttcaactaca cggctcacct   7860
gtgggatatc cggtggctaa gacgtcgtgc gaggaaaaca aggtgattga ccaaaatcga   7920
agttacgaac aagaaagcgt cgagcgagct ttaacgtgcg ctaactgcgg tcagaagctg   7980
catgtgctgg aagttcacgt gtgtgagcac tgctgcgcag aactgatgag cgatccgaat   8040
agctcgatgc acgaggaaga agatgatggc taaaccagcg cgaagacgat gtaaaaacga   8100
tgaatgccgg gaatggtttc accctgcatt cgctaatcag tggtggtgct ctccagagtg   8160
tggaaccaag atagcactcg aacgacgaag taaagaacgc gaaaaagcgg aaaaagcagc   8220
agagaagaaa cgacgacgag aggagcagaa acagaaagat aaacttaaga ttcgaaaact   8280
cgccttaaag ccccgcagtt actggattaa acaagcccaa caagccgtaa acgccttcat   8340
cagagaaaga gaccgcgact taccatgtat ctcgtgcgga acgctcacgt ctgctcagtg   8400
ggatgccgga cattaccgga caactgctgc ggcacctcaa ctccgattta atgaacgcaa   8460
```

-continued tattcacaag caatgcgtgg tgtgcaacca gcacaaaagc ggaaatctcg ttccgtatcg 8520
cgtcgaactg attagccgca tcgggcagga agcagtagac gaaatcgaat caaaccataa 8580
ccgccatcgc tggactatcg aagagtgcaa ggcgatcaag gcagagtacc aacagaaact 8640
caaagacctg cgaaatagca gaagtgaggc cgcatgacgt tctcagtaaa aaccattcca 8700
gacatgctcg ttgaagcata cggaaatcag acagaagtag cacgcagact gaaatgtagt 8760
cgcggtacgg tcagaaaata cgttgatgat aaagacggga aaatgcacgc catcgtcaac 8820
gacgttctca tggttcatcg cggatggagt gaaagagatg cgctattacg aaaaaattga 8880
tggcagcaaa taccgaaata tttgggtagt tggcgatctg cacggatgct acacgaacct 8940
gatgaacaaa ctggatacga ttggattcga caacaaaaaa gacctgctta tctcggtggg 9000
cgatttggtt gatcgtggtg cagagaacgt tgaatgcctg gaattaatca cattcccctg 9060
gttcagagct gtacgtggaa accatgagca aatgatgatt gatggcttat cagagcgtgg 9120
aaacgttaat cactggctgc ttaatggcgg tggctggttc tttaatctcg attacgacaa 9180
agaaattctg gctaaagctc ttgcccataa agcagatgaa cttccgttaa tcatcgaact 9240
ggtgagcaaa gataaaaaat atgttatctg ccacgccgat tatccctttg acgaatacga 9300
gtttggaaag ccagttgatc atcagcaggt aatctggaac cgcgaacgaa tcagcaactc 9360
acaaaacggg atcgtgaaag aaatcaaagg cgcggacacg ttcatctttg gtcatacgcc 9420
agcagtgaaa ccactcaagt ttgccaacca aatgtatatc gataccggcg cagtgttctg 9480
cggaaaccta acattgattc aggtacaggg agaaggcgca tgagactcga aagcgtagct 9540
aaatttcatt cgccaaaaag cccgatgatg agcgactcac cacgggccac ggcttctgac 9600
tctctttccg gtactgatgt gatggctgct atggggatgg cgcaatcaca agccggattc 9660
ggtatggctg cattctgcgg taagcacgaa ctcagccaga acgacaaaca aaaggctatc 9720
aactatctga tgcaatttgc acacaaggta tcggggaaat accgtggtgt ggcaaagctt 9780
gaaggaaata ctaaggcaaa ggtactgcaa gtgctcgcaa cattcgctta tgcggattat 9840
tgccgtagtg ccgcgacgcc gggggcaaga tgcagagatt gccatggtac aggccgtgcg 9900
gttgatattg ccaaaacaga gctgtggggg agagttgtcg agaaagagtg cggaagatgc 9960
aaaggcgtcg gctattcaag gatgccagca agcgcagcat atcgcgctgt gacgatgcta 10020
atcccaaacc ttacccaacc cacctggtca cgcactgtta agccgctgta tgacgctctg 10080
gtggtgcaat gccacaaaga agagtcaatc gcagacaaca ttttgaatgc ggtcacacgt 10140
tagcagcatg attgccacgg atggcaacat attaacggca tgatattgac ttattgaata 10200
aaattgggta aatttgactc aacgatgggt taattcgctc gttgtggtag tgagatgaaa 10260
agaggcggcg cttactaccg attccgccta gttggtcact tcgacgtatc gtctggaact 10320
ccaaccatcg caggcagaga ggtctgcaaa atgcaatccc gaaacagttc gcaggtaata 10380
gttagagcct gcataacggt ttcgggattt tttatatctg cacaacaggt aagagcattg 10440
agtcgataat cgtgaagagt cggcgagcct ggttagccag tgctctttcc gttgtgctga 10500
attaagcgaa taccggaagc agaaccggat caccaaatgc gtacaggcgt catcgccgcc 10560
cagcaacagc acaacccaaa ctgagccgta gccactgtct gtcctgaatt cattagtaat 10620
agttacgctg cggcctttta cacatgacct tcgtgaaagc gggtggcagg aggtcgcgct 10680
aacaacctcc tgccgttttg cccgtgcata tcggtcacga acaaatctga ttactaaaca 10740
cagtagcctg gatttgttct atcagtaatc gaccttattc ctaattaaat agagcaaatc 10800
cccttattgg gggtaagaca tgaagatgcc agaaaaacat gacctgttgg ccgccattct 10860

```
cgcggcaaag gaacaaggca tcggggcaat ccttgcgttt gcaatggcgt accttcgcgg  10920
cagatataat ggcggtgcgt ttacaaaaac agtaatcgac gcaacgatgt gcgccattat  10980
cgcctggttc attcgtgacc ttctcgactt cgccggacta agtagcaatc tcgcttatat  11040
aacgagcgtg tttatcggct acatcggtac tgactcgatt ggttcgctta tcaaacgctt  11100
cgctgctaaa aaagccggag tagaagatgg tagaaatcaa taatcaacgt aaggcgttcc  11160
tcgatatgct ggcgtggtcg gagggaactg ataacggacg tcagaaaacc agaaatcatg  11220
gttatgacgt cattgtaggc ggagagctat ttactgatta ctccgatcac cctcgcaaac  11280
ttgtcacgct aaacccaaaa ctcaaatcaa caggcgctta agactggccg tcgttttaca  11340
acacagaaag agtttgtaga aacgcaaaaa ggccatccgt caggggcctt ctgcttagtt  11400
tgatgcctgg cagttcccta ctctcgcctt ccgcttcctc gctcactgac tcgctgcgct  11460
cggtcgttcg gctgcggcga gcggtatcag ctcactcaaa ggcggtaata cggttatcca  11520
cagaatcagg ggataacgca ggaaagaaca tgtgagcaaa aggccagcaa aaggccagga  11580
accgtaaaaa ggccgcgttg ctggcgtttt tccataggct ccgcccccct gacgagcatc  11640
acaaaaatcg acgctcaagt cagaggtggc gaaacccgac aggactataa agataccagg  11700
cgtttccccc tggaagctcc ctcgtgcgct ctcctgttcc gaccctgccg cttaccggat  11760
acctgtccgc ctttctccct tcgggaagcg tggcgctttc tcatagctca cgctgtaggt  11820
atctcagttc ggtgtaggtc gttcgctcca agctgggctg tgtgcacgaa ccccccgttc  11880
agcccgaccg ctgcgcctta tccggtaact atcgtcttga gtccaacccg gtaagacacg  11940
acttatcgcc actggcagca gccactggta acaggattag cagagcgagg tatgtaggcg  12000
gtgctacaga gttcttgaag tggtgggcta actacggcta cactagaaga acagtatttg  12060
gtatctgcgc tctgctgaag ccagttacct tcggaaaaag agttggtagc tcttgatccg  12120
gcaaacaaac caccgctggt agcggtggtt tttttgtttg caagcagcag attacgcgca  12180
gaaaaaaagg atctcaagaa gatcctttga tcttttctac ggggtctgac gctcagtgga  12240
acgacgcgcg cgtaactcac gttaagggat tttggtcatg agcttgcgcc gtcccgtcaa  12300
gtcagcgtaa tgctctgctt t                                            12321
```

<210> SEQ ID NO 21
<211> LENGTH: 11959
<212> TYPE: DNA
<213> ORGANISM: Artificial Sequence
<220> FEATURE:
<223> OTHER INFORMATION: constructed sequence

<400> SEQUENCE: 21

```
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
```

-continued

```
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tattttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc gggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cgggggtgg cggcaggtgg gggtgccggg cggggcgggg ccgcctcggg ccggggaggg    2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
```

ccgtcccctt ctccctctcc agcctcgggg ctgtccgcgg ggggacggct gccttcgggg 3000
gggacggggc agggcggggt tcggcttctg gcgtgtgacc ggcggctcta gacaattgta 3060
ctaaccttct tctctttcct ctcctgacag gttggtgtac actagcggcc gccaccatga 3120
tggacttgga gctgccgccg ccgggactcc cgtcccagca ggacatggat ttgattgaca 3180
tactttggag gcaagatata gatcttggag taagtcgaga agtatttgac ttcagtcagc 3240
gacggaaaga gtatgagctg gaaaaacaga aaaaacttga aaaggaaaga caagaacaac 3300
tccaaaagga gcaagagaaa gcctttttcg ctcagttaca actagatgaa gagacaggtg 3360
aatttctccc aattcagcca gcccagcaca tccagtcaga aaccagtgga tctgccaact 3420
actcccaggt tgcccacatt cccaaatcag atgctttgta ctttgatgac tgcatgcagc 3480
ttttggcgca gacattcccg tttgtagatg acaatgaggt ttcttcggct acgtttcagt 3540
cacttgttcc tgatattccc ggtcacatcg agagcccagt cttcattgct actaatcagg 3600
ctcagtcacc tgaaacttct gttgctcagg tagcccctgt tgatttagac ggtatgcaac 3660
aggacattga gcaagtttgg gaggagctat tatccattcc tgagttacag tgtcttaata 3720
ttgaaaatga caagctggtt gagactacca tggttccaag tccagaagcc aaactgacag 3780
aagttgacaa ttatcatttt tactcatcta taccctcaat ggaaaaagaa gtaggtaact 3840
gtagtccaca ttttcttaat gcttttgagg attccttcag cagcatcctc tccacagaag 3900
accccaacca gttgacagtg aactcattaa attcagatgc cacagtcaac acagattttg 3960
gtgatgaatt ttattctgct ttcatagctg agcccagtat cagcaacagc atgccctcac 4020
ctgctacttt aagccattca ctctctgaac ttctaaatgg gcccattgat gtttctgatc 4080
tatcactttg caaagctttc aaccaaaacc accctgaaag cacagcagaa ttcaatgatt 4140
ctgactccgg catttcacta aacacaagtc ccagtgtggc atcaccagaa cactcagtgg 4200
aatcttccag ctatggagac acactacttg gcctcagtga ttctgaagtg gaagagctag 4260
atagtgcccc tggaagtgtc aaacagaatg gtcctaaaac accagtacat tcttctgggg 4320
atatggtaca accccttgtca ccatctcagg ggcagagcac tcacgtgcat gatgcccaat 4380
gtgagaacac accagagaaa gaattgcctg taagtcctgg tcatcggaaa accccattca 4440
caaaagacaa acattcaagc cgcttggagg ctcatctcac aagagatgaa cttagggcaa 4500
aagctctcca tatcccattc cctgtagaaa aaatcattaa cctccctgtt gttgacttca 4560
acgaaatgat gtccaaagag cagttcaatg aagctcaact tgcattaatt cgggatatac 4620
gtaggagggg taagaataaa gtggctgctc agaattgcag aaaaagaaaa ctggaaaata 4680
tagtagaact agagcaagat ttagatcatt tgaaagatga aaaagaaaaa ttgctcaaag 4740
aaaaaggaga aaatgacaaa agccttcacc tactgaaaaa acaactcagc accttatatc 4800
tcgaagtttt cagcatgcta cgtgatgaag atggaaaacc ttattctcct agtgaatact 4860
ccctgcagca aacaagagat ggcaatgttt tccttgttcc caaaagtaag aagccagatg 4920
ttaagaaaaa ctgaggccgc atagtactgc ggatcctgca gatctgcctc gactgtgcct 4980
tctagttgcc agccatctgt tgtttgcccc tcccccgtgc cttccttgac cctggaaggt 5040
gccactccca ctgtcctttc ctaataaaat gaggaaattg catcgcattg tctgagtagg 5100
tgtcattcta ttctgggggg tggggtgggg caggacagca agggggagga ttgggaagac 5160
aatagcaggc atgctgggga ctcgagttct acgtagataa gtagcatggc gggttaatca 5220
ttaactacaa ggaaccccta gtgatggagt tggccactcc ctctctgcgc gctcgctcgc 5280

-continued

```
tcactgaggc cgggcgacca aaggtcgccc gacgcccggg ctttgcccgg gcggcctcag   5340
tgagcgagcg agcgcgcagc cttaattaac ctaaggaaaa tgaagtgaag ttcctatact   5400
ttctagagaa taggaacttc tatagtgagt cgaataaggg cgacacaaaa tttattctaa   5460
atgcataata aatactgata acatcttata gtttgtatta tattttgtat tatcgttgac   5520
atgtataatt ttgatatcaa aaactgattt tccctttatt attttcgaga tttattttct   5580
taattctctt taacaaacta gaaatattgt atatacaaaa aatcataaat aatagatgaa   5640
tagtttaatt ataggtgttc atcaatcgaa aaagcaacgt atcttattta aagtgcgttg   5700
ctttttttctc atttataagg ttaaataatt ctcatatatc aagcaaagtg acaggcgccc   5760
ttaaatattc tgacaaatgc tctttcccta aactccccccc ataaaaaaac ccgccgaagc   5820
gggtttttac gttatttgcg gattaacgat tactcgttat cagaaccgcc caggggggccc   5880
gagcttaacc tttttatttg ggggagaggg aagtcatgaa aaaactaacc tttgaaattc   5940
gatctccagc acatcagcaa aacgctattc acgcagtaca gcaaatcctt ccagacccaa   6000
ccaaaccaat cgtagtaacc attcaggaac gcaaccgcag cttagaccaa aacaggaagc   6060
tatgggcctg cttaggtgac gtctctcgtc aggttgaatg gcatggtcgc tggctggatg   6120
cagaaagctg gaagtgtgtg tttaccgcag cattaaagca gcaggatgtt gttcctaacc   6180
ttgccgggaa tggctttgtg gtaataggcc agtcaaccag caggatgcgt gtaggcgaat   6240
ttgcggagct attagagctt atacaggcat tcggtacaga gcgtggcgtt aagtggtcag   6300
acgaagcgag actggctctg gagtggaaag cgagatgggg agacagggct gcatgataaa   6360
tgtcgttagt ttctccggtg gcaggacgtc agcatatttg ctctggctaa tggagcaaaa   6420
gcgacgggca ggtaaagacg tgcattacgt tttcatggat acaggttgtg aacatccaat   6480
gacatatcgg tttgtcaggg aagttgtgaa gttctgggat ataccgctca ccgtattgca   6540
ggttgatatc aacccggagc ttggacagcc aaatggttat acggtatggg aaccaaagga   6600
tattcagacg cgaatgcctg ttctgaagcc atttatcgat atggtaaaga aatatggcac   6660
tccatacgtc ggcggcgcgt tctgcactga cagattaaaa ctcgttccct tcaccaaata   6720
ctgtgatgac catttcgggc gagggaatta caccacgtgg attggcatca gagctgatga   6780
accgaagcgg ctaaagccaa agcctggaat cagatatctt gctgaactgt cagactttga   6840
gaaggaagat atcctcgcat ggtggaagca acaaccattc gatttgcaaa taccggaaca   6900
tctcggtaac tgcatattct gcattaaaaa atcaacgcaa aaaatcggac ttgcctgcaa   6960
agatgaggag ggattgcagc gtgtttttaa tgaggtcatc acgggatccc atgtgcgtga   7020
cggacatcgg gaaacgccaa aggagattat gtaccgagga agaatgtcgc tggacggtat   7080
cgcgaaaatg tattcagaaa atgattatca agccctgtat caggacatgg tacgagctaa   7140
aagattcgat accggctctt gttctgagtc atgcgaaata tttggagggc agcttgattt   7200
cgacttcggg agggaagctg catgatgcga tgttatcggt gcggtgaatg caaagaagat   7260
aaccgcttcc gaccaaatca accttactgg aatcgatggt gtctccggtg tgaaagaaca   7320
ccaacagggg tgttaccact accgcaggaa aaggaggacg tgtggcgaga cagcgacgaa   7380
gtatcaccga cataatctgc gaaaactgca aataccttcc aacgaaacgc accagaaata   7440
aacccaagcc aatcccaaaa gaatctgacg taaaaacctt caactacacg gctcacctgt   7500
gggatatccg gtggctaaga cgtcgtgcga ggaaaacaag gtgattgacc aaaatcgaag   7560
ttacgaacaa gaaagcgtcg agcgagcttt aacgtgcgct aactgcggtc agaagctgca   7620
tgtgctggaa gttcacgtgt gtgagcactg ctgcgcagaa ctgatgagcg atccgaatag   7680
```

-continued

```
ctcgatgcac gaggaagaag atgatggcta aaccagcgcg aagacgatgt aaaaacgatg   7740
aatgccggga atggtttcac cctgcattcg ctaatcagtg gtggtgctct ccagagtgtg   7800
gaaccaagat agcactcgaa cgacgaagta aagaacgcga aaaagcggaa aaagcagcag   7860
agaagaaacg acgacgagag gagcagaaac agaaagataa acttaagatt cgaaaactcg   7920
ccttaaagcc ccgcagttac tggattaaac aagcccaaca agccgtaaac gccttcatca   7980
gagaaagaga ccgcgactta ccatgtatct cgtgcggaac gctcacgtct gctcagtggg   8040
atgccggaca ttaccggaca actgctgcgg cacctcaact ccgatttaat gaacgcaata   8100
ttcacaagca atgcgtggtg tgcaaccagc acaaaagcgg aaatctcgtt ccgtatcgcg   8160
tcgaactgat tagccgcatc gggcaggaag cagtagacga aatcgaatca aaccataacc   8220
gccatcgctg gactatcgaa gagtgcaagg cgatcaaggc agagtaccaa cagaaactca   8280
aagacctgcg aaatagcaga agtgaggccg catgacgttc tcagtaaaaa ccattccaga   8340
catgctcgtt gaagcatacg gaaatcagac agaagtagca cgcagactga aatgtagtcg   8400
cggtacggtc agaaaatacg ttgatgataa agacgggaaa atgcacgcca tcgtcaacga   8460
cgttctcatg gttcatcgcg gatggagtga aagagatgcg ctattacgaa aaaattgatg   8520
gcagcaaata ccgaaatatt tgggtagttg gcgatctgca cggatgctac acgaacctga   8580
tgaacaaact ggatacgatt ggattcgaca acaaaaaaga cctgcttatc tcggtgggcg   8640
atttggttga tcgtggtgca gagaacgttg aatgcctgga attaatcaca ttcccctggt   8700
tcagagctgt acgtggaaac catgagcaaa tgatgattga tggcttatca gagcgtggaa   8760
acgttaatca ctggctgctt aatggcggtg gctggttctt taatctcgat tacgacaaag   8820
aaattctggc taaagctctt gcccataaag cagatgaact tccgttaatc atcgaactgg   8880
tgagcaaaga taaaaaatat gttatctgcc acgccgatta tccctttgac gaatacgagt   8940
ttggaaagcc agttgatcat cagcaggtaa tctggaaccg cgaacgaatc agcaactcac   9000
aaaacgggat cgtgaaagaa atcaaaggcg cggacacgtt catctttggt catacgccag   9060
cagtgaaacc actcaagttt gccaaccaaa tgtatatcga taccggcgca gtgttctgcg   9120
gaaacctaac attgattcag gtacagggag aaggcgcatg agactcgaaa gcgtagctaa   9180
atttcattcg ccaaaaagcc cgatgatgag cgactcacca cgggccacgg cttctgactc   9240
tctttccggt actgatgtga tggctgctat ggggatggcg caatcacaag ccggattcgg   9300
tatggctgca ttctgcggta agcacgaact cagccagaac gacaaacaaa aggctatcaa   9360
ctatctgatg caatttgcac acaaggtatc ggggaaatac cgtggtgtgg caaagcttga   9420
aggaaatact aaggcaaagg tactgcaagt gctcgcaaca ttcgcttatg cggattattg   9480
ccgtagtgcc gcgacgccgg gggcaagatg cagagattgc catggtacag gccgtgcggt   9540
tgatattgcc aaaacagagc tgtgggggag agttgtcgag aaagagtgcg gaagatgcaa   9600
aggcgtcggc tattcaagga tgccagcaag cgcagcatat cgcgctgtga cgatgctaat   9660
cccaaacctt acccaaccca cctggtcacg cactgttaag ccgctgtatg acgctctggt   9720
ggtgcaatgc cacaaagaag agtcaatcgc agacaacatt ttgaatgcgg tcacacgtta   9780
gcagcatgat tgccacggat ggcaacatat taacggcatg atattgactt attgaataaa   9840
attgggtaaa tttgactcaa cgatgggtta attcgctcgt tgtggtagtg agatgaaaag   9900
aggcggcgct tactaccgat tccgcctagt tggtcacttc gacgtatcgt ctggaactcc   9960
aaccatcgca ggcagagagg tctgcaaaat gcaatcccga aacagttcgc aggtaatagt  10020
```

-continued

```
tagagcctgc ataacggttt cgggattttt tatatctgca caacaggtaa gagcattgag  10080

tcgataatcg tgaagagtcg gcgagcctgg ttagccagtg ctctttccgt tgtgctgaat  10140

taagcgaata ccggaagcag aaccggatca ccaaatgcgt acaggcgtca tcgccgccca  10200

gcaacagcac aacccaaact gagccgtagc cactgtctgt cctgaattca ttagtaatag  10260

ttacgctgcg gccttttaca catgaccttc gtgaaagcgg gtggcaggag gtcgcgctaa  10320

caacctcctg ccgttttgcc cgtgcatatc ggtcacgaac aaatctgatt actaaacaca  10380

gtagcctgga tttgttctat cagtaatcga ccttattcct aattaaatag agcaaatccc  10440

cttattgggg gtaagacatg aagatgccag aaaaacatga cctgttggcc gccattctcg  10500

cggcaaagga acaaggcatc ggggcaatcc ttgcgtttgc aatggcgtac cttcgcggca  10560

gatataatgg cggtgcgttt acaaaaacag taatcgacgc aacgatgtgc gccattatcg  10620

cctggttcat tcgtgacctt ctcgacttcg ccggactaag tagcaatctc gcttatataa  10680

cgagcgtgtt tatcggctac atcggtactg actcgattgg ttcgcttatc aaacgcttcg  10740

ctgctaaaaa agccggagta gaagatggta gaaatcaata atcaacgtaa ggcgttcctc  10800

gatatgctgg cgtggtcgga gggaactgat aacggacgtc agaaaaccag aaatcatggt  10860

tatgacgtca ttgtaggcgg agagctattt actgattact ccgatcaccc tcgcaaactt  10920

gtcacgctaa acccaaaact caaatcaaca ggcgcttaag actggccgtc gttttacaac  10980

acagaaagag tttgtagaaa cgcaaaaagg ccatccgtca ggggccttct gcttagtttg  11040

atgcctggca gttccctact ctcgccttcc gcttcctcgc tcactgactc gctgcgctcg  11100

gtcgttcggc tgcggcgagc ggtatcagct cactcaaagg cggtaatacg gttatccaca  11160

gaatcagggg ataacgcagg aaagaacatg tgagcaaaag gccagcaaaa ggccaggaac  11220

cgtaaaaagg ccgcgttgct ggcgtttttc cataggctcc gcccccctga cgagcatcac  11280

aaaaatcgac gctcaagtca gaggtggcga aacccgacag gactataaag ataccaggcg  11340

tttccccctg gaagctccct cgtgcgctct cctgttccga ccctgccgct taccggatac  11400

ctgtccgcct ttctcccttc gggaagcgtg gcgctttctc atagctcacg ctgtaggtat  11460

ctcagttcgg tgtaggtcgt tcgctccaag ctgggctgtg tgcacgaacc ccccgttcag  11520

cccgaccgct gcgccttatc cggtaactat cgtcttgagt ccaacccggt aagacacgac  11580

ttatcgccac tggcagcagc cactggtaac aggattagca gagcgaggta tgtaggcggt  11640

gctacagagt tcttgaagtg gtgggctaac tacggctaca ctagaagaac agtatttggt  11700

atctgcgctc tgctgaagcc agttaccttc ggaaaaagag ttggtagctc ttgatccggc  11760

aaacaaacca ccgctggtag cggtggtttt tttgtttgca agcagcagat tacgcgcaga  11820

aaaaaaggat ctcaagaaga tcctttgatc ttttctacgg ggtctgacgc tcagtggaac  11880

gacgcgcgcg taactcacgt taagggattt tggtcatgag cttgcgccgt cccgtcaagt  11940

cagcgtaatg ctctgcttt                                                11959
```

<210> SEQ ID NO 22
<211> LENGTH: 12025
<212> TYPE: DNA
<213> ORGANISM: Artificial Sequence
<220> FEATURE:
<223> OTHER INFORMATION: constructed sequence

<400> SEQUENCE: 22

```
tagaaaaact catcgagcat caaatgaaac tgcaatttat tcatatcagg attatcaata     60

ccatattttt gaaaaagccg tttctgtaat gaaggagaaa actcaccgag gcagttccat    120
```

-continued

```
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc cccctcccca cccccaattt   1860
tgtatttatt tatttttaa ttattttgtg cagcgatggg ggcggggggg gggggggggc   1920
gcgcgccagg cggggcgggg cggggcgagg ggcggggcgg ggcgaggcgg agaggtgcgg   1980
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
```

-continued

```
gggctgcgag gggaacaaag gctgcgtgcg gggtgtgtgc gtggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag ggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatga   3120
tggacttgga gctgccgccg ccgggactcc cgtcccagca ggacatggat ttgattgaca   3180
tactttggag gcaagatata gatcttggag taagtcgaga agtatttgac ttcagtcagc   3240
gacggaaaga gtatgagctg gaaaaacaga aaaaacttga aaaggaaaga caagaacaac   3300
tccaaaagga gcaagagaaa gcctttttcg ctcagttaca actagatgaa gagacaggtg   3360
aatttctccc aattcagcca gcccagcaca tccagtcaga aaccagtgga tctgccaact   3420
actcccaggt tgcccacatt cccaaatcag atgctttgta ctttgatgac tgcatgcagc   3480
ttttggcgca gacattcccg tttgtagatg acaatgaggt ttcttcggct acgtttcagt   3540
cacttgttcc tgatattccc ggtcacatcg agagcccagt cttcattgct actaatcagg   3600
ctcagtcacc tgaaacttct gttgctcagg tagcccctgt tgatttagac ggtatgcaac   3660
aggacattga gcaagtttgg gaggagctat tatccattcc tgagttacag tgtcttaata   3720
ttgaaaatga caagctggtt gagactacca tggttccaag tccagaagcc aaactgacag   3780
aagttgacaa ttatcatttt tactcatcta taccctcaat ggaaaaagaa gtaggtaact   3840
gtagtccaca ttttcttaat gcttttgagg attccttcag cagcatcctc tccacagaag   3900
accccaacca gttgacagtg aactcattaa attcagatgc cacagtcaac acagattttg   3960
gtgatgaatt ttattctgct ttcatagctg agcccagtat cagcaacagc atgccctcac   4020
ctgctacttt aagccattca ctctctgaac ttctaaatgg gcccattgat gtttctgatc   4080
tatcactttg caaagctttc aaccaaaacc accctgaaag cacagcagaa ttcaatgatt   4140
ctgactccgg catttcacta aacacaagtc ccagtgtggc atcaccagaa cactcagtgg   4200
aatcttccag ctatggagac acactacttg gcctcagtga ttctgaagtg gaagagctag   4260
atagtgcccc tggaagtgtc aaacagaatg gtcctaaaac accagtacat tcttctgggg   4320
atatggtaca acccttgtca ccatctcagg ggcagagcac tcacgtgcat gatgcccaat   4380
gtgagaacac accagagaaa gaattgcctg taagtcctgg tcatcggaaa accccattca   4440
caaaagacaa acattcaagc cgcttggagg ctcatctcac aagagatgaa cttagggcaa   4500
aagctctcca tatcccattc cctgtagaaa aaatcattaa cctccctgtt gttgacttca   4560
acgaaatgat gtccaaagag cagttcaatg aagctcaact tgcattaatt cgggatatac   4620
gtaggagggg taagaataaa gtggctgctc agaattgcag aaaaagaaaa ctggaaaata   4680
tagtagaact agagcaagat ttagatcatt tgaaagatga aaaagaaaaa ttgctcaaag   4740
aaaaaggaga aaatgacaaa agccttcacc tactgaaaaa acaactcagc accttatatc   4800
tcgaagtttt cagcatgcta cgtgatgaag atggaaaacc ttattctcct agtgaatact   4860
```

-continued

```
ccctgcagca aacaagagat ggcaatgttt tccttgttcc caaaagtaag aagccagatg   4920
ttaagaaaaa cgactacaaa gaccatgacg gtgattataa agatcatgac atcgattaca   4980
aggatgacga tgacaagtga ggccgcatag tactgcggat cctgcagatc tgcctcgact   5040
gtgccttcta gttgccagcc atctgttgtt tgcccctccc ccgtgccttc cttgaccctg   5100
gaaggtgcca ctcccactgt cctttcctaa taaaatgagg aaattgcatc gcattgtctg   5160
agtaggtgtc attctattct ggggggtggg gtggggcagg acagcaaggg ggaggattgg   5220
gaagacaata gcaggcatgc tggggactcg agttctacgt agataagtag catggcgggt   5280
taatcattaa ctacaaggaa cccctagtga tggagttggc cactccctct ctgcgcgctc   5340
gctcgctcac tgaggccggg cgaccaaagg tcgcccgacg cccgggcttt gcccgggcgg   5400
cctcagtgag cgagcgagcg cgcagcctta attaacctaa ggaaaatgaa gtgaagttcc   5460
tatactttct agagaatagg aacttctata gtgagtcgaa taagggcgac acaaaattta   5520
ttctaaatgc ataataaata ctgataacat cttatagttt gtattatatt ttgtattatc   5580
gttgacatgt ataattttga tatcaaaaac tgattttccc tttattattt tcgagattta   5640
ttttcttaat tctctttaac aaactagaaa tattgtatat acaaaaaatc ataaataata   5700
gatgaatagt ttaattatag gtgttcatca atcgaaaaag caacgtatct tatttaaagt   5760
gcgttgcttt tttctcattt ataaggttaa ataattctca tatatcaagc aaagtgacag   5820
gcgcccttaa atattctgac aaatgctctt tccctaaact ccccccataa aaaaacccgc   5880
cgaagcgggt ttttacgtta tttgcggatt aacgattact cgttatcaga accgcccagg   5940
gggcccgagc ttaacctttt tatttggggg agagggaagt catgaaaaaa ctaacctttg   6000
aaattcgatc tccagcacat cagcaaaacg ctattcacgc agtacagcaa atccttccag   6060
acccaaccaa accaatcgta gtaaccattc aggaacgcaa ccgcagctta gaccaaaaca   6120
ggaagctatg ggcctgctta ggtgacgtct ctcgtcaggt tgaatggcat ggtcgctggc   6180
tggatgcaga aagctggaag tgtgtgttta ccgcagcatt aaagcagcag gatgttgttc   6240
ctaaccttgc cgggaatggc tttgtggtaa taggccagtc aaccagcagg atgcgtgtag   6300
gcgaatttgc ggagctatta gagcttatac aggcattcgg tacagagcgt ggcgttaagt   6360
ggtcagacga agcgagactg gctctggagt ggaaagcgag atggggagac agggctgcat   6420
gataaatgtc gttagtttct ccggtggcag gacgtcagca tatttgctct ggctaatgga   6480
gcaaaagcga cgggcaggta aagacgtgca ttacgttttc atggatacag gttgtgaaca   6540
tccaatgaca tatcggtttg tcagggaagt tgtgaagttc tgggatatac cgctcaccgt   6600
attgcaggtt gatatcaacc cggagcttgg acagccaaat ggttatacgg tatgggaacc   6660
aaaggatatt cagacgcgaa tgcctgttct gaagccattt atcgatatgg taaagaaata   6720
tggcactcca tacgtcggcg gcgcgttctg cactgacaga ttaaaactcg ttcccttcac   6780
caaatactgt gatgaccatt tcgggcgagg gaattacacc acgtggattg gcatcagagc   6840
tgatgaaccg aagcggctaa agccaaagcc tggaatcaga tatcttgctg aactgtcaga   6900
ctttgagaag gaagatatcc tcgcatggtg gaagcaacaa ccattcgatt tgcaaatacc   6960
ggaacatctc ggtaactgca tattctgcat taaaaaatca acgcaaaaaa tcggacttgc   7020
ctgcaaagat gaggagggat tgcagcgtgt ttttaatgag gtcatcacgg gatcccatgt   7080
gcgtgacgga catcgggaaa cgccaaagga gattatgtac cgaggaagaa tgtcgctgga   7140
cggtatcgcg aaaatgtatt cagaaaatga ttatcaagcc ctgtatcagg acatggtacg   7200
```

-continued

```
agctaaaaga ttcgataccg gctcttgttc tgagtcatgc gaaatatttg gagggcagct   7260
tgatttcgac ttcgggaggg aagctgcatg atgcgatgtt atcggtgcgg tgaatgcaaa   7320
gaagataacc gcttccgacc aaatcaacct tactggaatc gatggtgtct ccggtgtgaa   7380
agaacaccaa caggggtgtt accactaccg caggaaaagg aggacgtgtg gcgagacagc   7440
gacgaagtat caccgacata atctgcgaaa actgcaaata ccttccaacg aaacgcacca   7500
gaaataaacc caagccaatc ccaaaagaat ctgacgtaaa aaccttcaac tacacggctc   7560
acctgtggga tatccggtgg ctaagacgtc gtgcgaggaa aacaaggtga ttgaccaaaa   7620
tcgaagttac gaacaagaaa gcgtcgagcg agctttaacg tgcgctaact gcggtcagaa   7680
gctgcatgtg ctggaagttc acgtgtgtga gcactgctgc gcagaactga tgagcgatcc   7740
gaatagctcg atgcacgagg aagaagatga tggctaaacc agcgcgaaga cgatgtaaaa   7800
acgatgaatg ccgggaatgg tttcaccctg cattcgctaa tcagtggtgg tgctctccag   7860
agtgtggaac caagatagca ctcgaacgac gaagtaaaga acgcgaaaaa gcggaaaaag   7920
cagcagagaa gaaacgacga cgagaggagc agaaacagaa agataaactt aagattcgaa   7980
aactcgcctt aaagccccgc agttactgga ttaaacaagc ccaacaagcc gtaaacgcct   8040
tcatcagaga aagagaccgc gacttaccat gtatctcgtg cggaacgctc acgtctgctc   8100
agtgggatgc cggacattac cggacaactg ctgcggcacc tcaactccga tttaatgaac   8160
gcaatattca caagcaatgc gtggtgtgca accagcacaa aagcggaaat ctcgttccgt   8220
atcgcgtcga actgattagc cgcatcgggc aggaagcagt agacgaaatc gaatcaaacc   8280
ataaccgcca tcgctggact atcgaagagt gcaaggcgat caaggcagag taccaacaga   8340
aactcaaaga cctgcgaaat agcagaagtg aggccgcatg acgttctcag taaaaaccat   8400
tccagacatg ctcgttgaag catacggaaa tcagacagaa gtagcacgca gactgaaatg   8460
tagtcgcggt acggtcagaa aatacgttga tgataaagac gggaaaatgc acgccatcgt   8520
caacgacgtt ctcatggttc atcgcggatg gagtgaaaga gatgcgctat tacgaaaaaa   8580
ttgatggcag caaataccga aatatttggg tagttggcga tctgcacgga tgctacacga   8640
acctgatgaa caaactggat acgattggat tcgacaacaa aaaagacctg cttatctcgg   8700
tgggcgattt ggttgatcgt ggtgcagaga acgttgaatg cctggaatta atcacattcc   8760
cctggttcag agctgtacgt ggaaaccatg agcaaatgat gattgatggc ttatcagagc   8820
gtggaaacgt taatcactgg ctgcttaatg gcggtggctg gttctttaat ctcgattacg   8880
acaaagaaat tctggctaaa gctcttgccc ataaagcaga tgaacttccg ttaatcatcg   8940
aactggtgag caaagataaa aaatatgtta tctgccacgc cgattatccc tttgacgaat   9000
acgagtttgg aaagccagtt gatcatcagc aggtaatctg gaaccgcgaa cgaatcagca   9060
actcacaaaa cgggatcgtg aaagaaatca aaggcgcgga cacgttcatc tttggtcata   9120
cgccagcagt gaaaccactc aagtttgcca accaaatgta tatcgatacc ggcgcagtgt   9180
tctgcggaaa cctaacattg attcaggtac agggagaagg cgcatgagac tcgaaagcgt   9240
agctaaattt cattcgccaa aaagcccgat gatgagcgac tcaccacggg ccacggcttc   9300
tgactctctt tccggtactg atgtgatggc tgctatgggg atggcgcaat cacaagccgg   9360
attcggtatg gctgcattct gcggtaagca cgaactcagc cagaacgaca aacaaaaggc   9420
tatcaactat ctgatgcaat ttgcacacaa ggtatcgggg aaataccgtg gtgtggcaaa   9480
gcttgaagga aatactaagg caaaggtact gcaagtgctc gcaacattcg cttatgcgga   9540
ttattgccgt agtgccgcga cgccgggggc aagatgcaga gattgccatg gtacaggccg   9600
```

```
tgcggttgat attgccaaaa cagagctgtg ggggagagtt gtcgagaaag agtgcggaag   9660
atgcaaaggc gtcggctatt caaggatgcc agcaagcgca gcatatcgcg ctgtgacgat   9720
gctaatccca aaccttaccc aacccacctg gtcacgcact gttaagccgc tgtatgacgc   9780
tctggtggtg caatgccaca aagaagagtc aatcgcagac aacattttga atgcggtcac   9840
acgttagcag catgattgcc acggatggca acatattaac ggcatgatat tgacttattg   9900
aataaaattg ggtaaatttg actcaacgat gggttaattc gctcgttgtg gtagtgagat   9960
gaaaagaggc ggcgcttact accgattccg cctagttggt cacttcgacg tatcgtctgg  10020
aactccaacc atcgcaggca gagaggtctg caaaatgcaa tcccgaaaca gttcgcaggt  10080
aatagttaga gcctgcataa cggtttcggg atttttata tctgcacaac aggtaagagc  10140
attgagtcga taatcgtgaa gagtcggcga gcctggttag ccagtgctct ttccgttgtg  10200
ctgaattaag cgaataccgg aagcagaacc ggatcaccaa atgcgtacag gcgtcatcgc  10260
cgcccagcaa cagcacaacc caaactgagc cgtagccact gtctgtcctg aattcattag  10320
taatagttac gctgcggcct tttacacatg accttcgtga aagcgggtgg caggaggtcg  10380
cgctaacaac ctcctgccgt tttgcccgtg catatcggtc acgaacaaat ctgattacta  10440
aacacagtag cctggatttg ttctatcagt aatcgacctt attcctaatt aaatagagca  10500
aatcccctta ttgggggtaa gacatgaaga tgccagaaaa acatgacctg ttggccgcca  10560
ttctcgcggc aaaggaacaa ggcatcgggg caatccttgc gtttgcaatg gcgtaccttc  10620
gcggcagata taatggcggt gcgtttacaa aaacagtaat cgacgcaacg atgtgcgcca  10680
ttatcgcctg gttcattcgt gaccttctcg acttcgccgg actaagtagc aatctcgctt  10740
atataacgag cgtgtttatc ggctacatcg gtactgactc gattggttcg cttatcaaac  10800
gcttcgctgc taaaaaagcc ggagtagaag atggtagaaa tcaataatca acgtaaggcg  10860
ttcctcgata tgctggcgtg gtcggaggga actgataacg gacgtcagaa aaccagaaat  10920
catggttatg acgtcattgt aggcggagag ctatttactg attactccga tcaccctcgc  10980
aaacttgtca cgctaaaccc aaaactcaaa tcaacaggcg cttaagactg gccgtcgttt  11040
tacaacacag aaagagtttg tagaaacgca aaaaggccat ccgtcagggg ccttctgctt  11100
agtttgatgc ctggcagttc cctactctcg ccttccgctt cctcgctcac tgactcgctg  11160
cgctcggtcg ttcggctgcg gcgagcggta tcagctcact caaaggcggt aatacggtta  11220
tccacagaat caggggataa cgcaggaaag aacatgtgag caaaaggcca gcaaaaggcc  11280
aggaaccgta aaaaggccgc gttgctggcg tttttccata ggctccgccc ccctgacgag  11340
catcacaaaa atcgacgctc aagtcagagg tggcgaaacc cgacaggact ataaagatac  11400
caggcgtttc cccctggaag ctccctcgtg cgctctcctg ttccgaccct gccgcttacc  11460
ggatacctgt ccgcctttct cccttcggga agcgtggcgc tttctcatag ctcacgctgt  11520
aggtatctca gttcggtgta ggtcgttcgc tccaagctgg gctgtgtgca cgaacccccc  11580
gttcagcccg accgctgcgc cttatccggt aactatcgtc ttgagtccaa cccggtaaga  11640
cacgacttat cgccactggc agcagccact ggtaacagga ttagcagagc gaggtatgta  11700
ggcggtgcta cagagttctt gaagtggtgg gctaactacg gctacactag aagaacagta  11760
tttggtatct gcgctctgct gaagccagtt accttcggaa aaagagttgg tagctcttga  11820
tccggcaaac aaaccaccgc tggtagcggt ggtttttttg tttgcaagca gcagattacg  11880
cgcagaaaaa aaggatctca agaagatcct ttgatctttt ctacggggtc tgacgctcag  11940
```

tggaacgacg cgcgcgtaac tcacgttaag ggattttggt catgagcttg cgccgtcccg 12000
tcaagtcagc gtaatgctct gcttt 12025

<210> SEQ ID NO 23
<211> LENGTH: 11951
<212> TYPE: DNA
<213> ORGANISM: Artificial Sequence
<220> FEATURE:
<223> OTHER INFORMATION: constructed sequence

<400> SEQUENCE: 23
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420
tgcaaccggc gcaggaacac tgccagcgca tcaacaatat tttcacctga atcaggatat 480
tcttctaata cctggaacgc tgtttttccg gggatcgcag tggtgagtaa ccatgcatca 540
tcaggagtac ggataaaatg cttgatggtc ggaagtggca taaattccgt cagccagttt 600
agtctgacca tctcatctgt aacatcattg gcaacgctac ctttgccatg tttcagaaac 660
aactctggcg catcgggctt cccatacaag cgatagattg tcgcacctga ttgcccgaca 720
ttatcgcgag cccatttata cccatataaa tcagcatcca tgttggaatt taatcgcggc 780
ctcgacgttt cccgttgaat atggctcata ttcttccttt ttcaatatta ttgaagcatt 840
tatcagggtt attgtctcat gagcggatac atatttgaat gtatttagaa aaataaacaa 900
ataggggtca gtgttacaac caattaacca attctgaaca ttatcgcgag cccatttata 960
cctgaatatg gctcataaca ccccttgttt gcctggcggc agtagcgcgg tggtcccacc 1020
tgaccccatg ccgaactcag aagtgaaacg ccgtagcgcc gatggtagtg tggggactcc 1080
ccatgcgaga gtagggaact gccaggcatc aaataaaacg aaaggctcag tcgaaagact 1140
gggcctttcg cccgggctaa ttagggggtg tcgcccttat tcgactctat agtgaagttc 1200
ctattctcta gaaagtatag gaacttctga agtggggtcg acttaattaa ggctgcgcgc 1260
tcgctcgctc actgaggccg cccgggcaaa gcccgggcgt cgggcgacct ttggtcgccc 1320
ggcctcagtg agcgagcgag cgcgcagaga gggagtggcc aactccatca ctaggggttc 1380
cttgtagtta atgattaacc cgccatgcta cttatctacg tagcaagcta gctagttatt 1440
aatagtaatc aattacgggg tcattagttc atagcccata tatggagttc cgcgttacat 1500
aacttacggt aaatggcccg cctggctgac cgcccaacga cccccgccca ttgacgtcaa 1560
taatgacgta tgttcccata gtaacgccaa tagggacttt ccattgacgt caatgggtgg 1620
agtatttacg gtaaactgcc cacttggcag tacatcaagt gtatcatatg ccaagtacgc 1680
cccctattga cgtcaatgac ggtaaatggc ccgcctggca ttatgcccag tacatgacct 1740
tatgggactt tcctacttgg cagtacatct acgtattagt catcgctatt aacatggtcg 1800
aggtgagccc cacgttctgc ttcactctcc ccatctcccc cccctcccca cccccaattt 1860
tgtatttatt tatttttaa ttattttgtg cagcgatggg ggcgggggg gggggggggc 1920 gcgcgccagg cggggcgggg cggggcgagg ggcggggcgg ggcgaggcgg agaggtgcgg 1980

```
cggcagccaa tcagagcggc gcgctccgaa agtttccttt tatggcgagg cggcggcggc   2040
ggcggcccta taaaaagcga agcgcgcggc gggcggggag tcgctgcgac gctgccttcg   2100
ccccgtgccc cgctccgccg ccgcctcgcg ccgcccgccc cggctctgac tgaccgcgtt   2160
actcccacag gtgagcgggc gggacggccc ttctcctccg ggctgtaatt agcgcttggt   2220
ttaatgacgg cttgtttctt ttctgtggct gcgtgaaagc cttgaggggc tccgggaggg   2280
ccctttgtgc ggggggagcg gctcgggggg tgcgtgcgtg tgtgtgtgcg tggggagcgc   2340
cgcgtgcggc tccgcgctgc ccggcggctg tgagcgctgc gggcgcggcg cggggctttg   2400
tgcgctccgc agtgtgcgcg aggggagcgc ggccgggggc ggtgccccgc ggtgcggggg   2460
gggctgcgag gggaacaaag gctgcgtgcg gggtgtgtgc gtgggggggt gagcaggggg   2520
tgtgggcgcg tcggtcgggc tgcaaccccc cctgcacccc cctccccgag ttgctgagca   2580
cggcccggct tcgggtgcgg ggctccgtac ggggcgtggc gcggggctcg ccgtgccggg   2640
cggggggtgg cggcaggtgg gggtgccggg cggggcgggg ccgcctcggg ccggggaggg   2700
ctcgggggag gggcgcggcg gcccccggag cgccggcggc tgtcgaggcg cggcgagccg   2760
cagccattgc cttttatggt aatcgtgcga gagggcgcag ggacttcctt tgtcccaaat   2820
ctgtgcggag ccgaaatctg ggaggcgccg ccgcaccccc tctagcgggc gcggggcgaa   2880
gcggtgcggc gccggcagga aggaaatggg cggggagggc cttcgtgcgt cgccgcgccg   2940
ccgtcccctt ctccctctcc agcctcgggg ctgtccgcgg ggggacggct gccttcgggg   3000
gggacggggc agggcggggt tcggcttctg gcgtgtgacc ggcggctcta gacaattgta   3060
ctaaccttct tctctttcct ctcctgacag gttggtgtac actagcggcc gccaccatga   3120
tggacctcga actgccgccg cctggcctcc caagccaaca ggatatggac ctgattgaca   3180
tcctgtggcg gcaggacatt gatctgggtg tcagccgcga ggtgttcgat ttctcgcaac   3240
gccggaagga atacgaactc gagaagcaga agaagctcga gaaagagcgg caggaacagc   3300
tccagaagga acaggaaaag gccttcttcg cacaacttca gctggacgag gaaaccggcg   3360
aattcctgcc tattcaacca gcccagcaca tccagagcga aacctccggc agcgccaact   3420
attcccaagt ggctcacatc ccgaagtccg acgccctgta ctttgacgat tgtatgcagc   3480
tgctggcaca gaccttcccc ttcgtcgatg ataacgaggt gtcctccgcg acgtttcagt   3540
cgctggtccc cgacatcccc ggtcatatcg agagccctgt gttcatcgcc accaaccagg   3600
ctcagtcccc cgaaacctca gtggcacaag tggcgccggt ggacttggac ggcatgcagc   3660
aagacatcga acaagtctgg gaggagcttc tgtccatccc cgagctgcaa tgcctcaaca   3720
tcgagaatga caagctcgtg gagactacta tggtcccgtc cccggaagct aagctgaccg   3780
aggtcgacaa ctaccatttc tactcctcaa tcccctccat ggaaaaggaa gtcggaaact   3840
gctcgcctca tttcctcaac gccttcgagg actccttctc gtcaattctg tccactgagg   3900
accccaacca gctgaccgtc aattccttga actcggatgc cactgtgaac accgacttcg   3960
gcgacgaatt ctacagcgcg ttcatcgccg aaccgagcat ctcgaactcc atgccctcgc   4020
ccgccacctt gtcacattcc ctgtctgagc tgctgaacgg gccgattgac gtgtcagacc   4080
tgagcctgtg taaagccttc aaccagaatc acccggagtc gactgccgaa ttcaacgact   4140
cggactccgg gatctcactg aacactagcc ctagcgtggc ctcgcccgaa cactccgtgg   4200
agtccagctc ctatggcgat actcttctgg gtctgtccga ctccgaagtg gaagaactgg   4260
actctgcccc cggaagcgtg aaacagaacg gacctaagac cccagtgcac tcctccgggg   4320
```

-continued

```
atatggtgca gccgttgtca ccgagccagg ggcaatccac ccacgtgcat gacgctcagt   4380
gcgagaacac ccccgagaaa gaactcccag tgtcccccgg acaccgaaag accccgttta   4440
ccaaggacaa gcactcctca cggctggaag cacaccttac tcgggatgaa ctcagagcca   4500
aggccctcca cattcctttc cccgtggaga agattatcaa tctccctgtg gtggatttca   4560
acgagatgat gagcaaggaa cagttcaacg aagcgcagct ggcgctgatc agggacatca   4620
ggcgcagagg aaagaacaaa gtggccgccc aaaactgccg gaagagaaag ctcgaaaaca   4680
tcgtggagct cgaacaggac ttggaccacc tgaaggatga aaaagaaaag ctgctgaagg   4740
agaagggaga gaacgacaag tccctccatc tgctgaagaa gcagctgagc acactgtacc   4800
tcgaagtgtt ttccatgctg cgcgatgagg atggaaagcc gtactccccg tccgaatact   4860
cgctgcaaca gacgcgcgac ggaaacgtgt tcctcgtgcc aaagtccaag aagcctgacg   4920
tgaagaagaa ctgaagtact gcggatcctg cagatctgcc tcgactgtgc cttctagttg   4980
ccagccatct gttgtttgcc cctcccccgt gccttccttg accctggaag gtgccactcc   5040
cactgtcctt tcctaataaa atgaggaaat tgcatcgcat tgtctgagta ggtgtcattc   5100
tattctgggg ggtggggtgg ggcaggacag caagggggag gattgggaag acaatagcag   5160
gcatgctggg gactcgagtt ctacgtagat aagtagcatg gcgggttaat cattaactac   5220
aaggaacccc tagtgatgga gttggccact ccctctctgc gcgctcgctc gctcactgag   5280
gccgggcgac caaaggtcgc ccgacgcccg ggctttgccc gggcggcctc agtgagcgag   5340
cgagcgcgca gccttaatta acctaaggaa aatgaagtga agttcctata ctttctagag   5400
aataggaact tctatagtga gtcgaataag ggcgacacaa aatttattct aaatgcataa   5460
taaatactga taacatctta tagtttgtat tatattttgt attatcgttg acatgtataa   5520
ttttgatatc aaaaactgat tttcccttta ttattttcga gatttatttt cttaattctc   5580
tttaacaaac tagaaatatt gtatatacaa aaaatcataa ataatagatg aatagtttaa   5640
ttataggtgt tcatcaatcg aaaaagcaac gtatcttatt taaagtgcgt tgcttttttc   5700
tcatttataa ggttaaataa ttctcatata tcaagcaaag tgacaggcgc ccttaaatat   5760
tctgacaaat gctctttccc taaactcccc ccataaaaaa acccgccgaa gcgggttttt   5820
acgttatttg cggattaacg attactcgtt atcagaaccg cccagggggc ccgagcttaa   5880
ccttttatt tgggggagag ggaagtcatg aaaaaactaa cctttgaaat tcgatctcca   5940
gcacatcagc aaaacgctat tcacgcagta cagcaaatcc ttccagaccc aaccaaacca   6000
atcgtagtaa ccattcagga acgcaaccgc agcttagacc aaaacaggaa gctatgggcc   6060
tgcttaggtg acgtctctcg tcaggttgaa tggcatggtc gctggctgga tgcagaaagc   6120
tggaagtgtg tgtttaccgc agcattaaag cagcaggatg ttgttcctaa ccttgccggg   6180
aatggctttg tggtaatagg ccagtcaacc agcaggatgc gtgtaggcga atttgcggag   6240
ctattagagc ttatacaggc attcggtaca gagcgtggcg ttaagtggtc agacgaagcg   6300
agactggctc tggagtggaa agcgagatgg ggagacaggg ctgcatgata aatgtcgtta   6360
gtttctccgg tggcaggacg tcagcatatt tgctctggct aatggagcaa aagcgacggg   6420
caggtaaaga cgtgcattac gttttcatgg atacaggttg tgaacatcca atgacatatc   6480
ggtttgtcag ggaagttgtg aagttctggg atataccgct caccgtattg caggttgata   6540
tcaacccgga gcttggacag ccaaatggtt atacggtatg ggaaccaaag gatattcaga   6600
cgcgaatgcc tgttctgaag ccatttatcg atatggtaaa gaaatatggc actccatacg   6660
tcggcggcgc gttctgcact gacagattaa aactcgttcc cttcaccaaa tactgtgatg   6720
```

-continued

```
accatttcgg gcgagggaat tacaccacgt ggattggcat cagagctgat gaaccgaagc   6780
ggctaaagcc aaagcctgga atcagatatc ttgctgaact gtcagacttt gagaaggaag   6840
atatcctcgc atggtggaag caacaaccat tcgatttgca aataccggaa catctcggta   6900
actgcatatt ctgcattaaa aaatcaacgc aaaaaatcgg acttgcctgc aaagatgagg   6960
agggattgca gcgtgttttt aatgaggtca tcacgggatc ccatgtgcgt gacggacatc   7020
gggaaacgcc aaaggagatt atgtaccgag gaagaatgtc gctggacggt atcgcgaaaa   7080
tgtattcaga aaatgattat caagccctgt atcaggacat ggtacgagct aaaagattcg   7140
ataccggctc ttgttctgag tcatgcgaaa tatttggagg gcagcttgat ttcgacttcg   7200
ggagggaagc tgcatgatgc gatgttatcg gtgcggtgaa tgcaaagaag ataaccgctt   7260
ccgaccaaat caaccttact ggaatcgatg gtgtctccgg tgtgaaagaa caccaacagg   7320
ggtgttacca ctaccgcagg aaaaggagga cgtgtggcga gacagcgacg aagtatcacc   7380
gacataatct gcgaaaactg caaatacctt ccaacgaaac gcaccagaaa taaacccaag   7440
ccaatcccaa aagaatctga cgtaaaaacc ttcaactaca cggctcacct gtgggatatc   7500
cggtggctaa gacgtcgtgc gaggaaaaca aggtgattga ccaaaatcga agttacgaac   7560
aagaaagcgt cgagcgagct ttaacgtgcg ctaactgcgg tcagaagctg catgtgctgg   7620
aagttcacgt gtgtgagcac tgctgcgcag aactgatgag cgatccgaat agctcgatgc   7680
acgaggaaga agatgatggc taaaccagcg cgaagacgat gtaaaaacga tgaatgccgg   7740
gaatggtttc accctgcatt cgctaatcag tggtggtgct ctccagagtg tggaaccaag   7800
atagcactcg aacgacgaag taaagaacgc gaaaaagcgg aaaaagcagc agagaagaaa   7860
cgacgacgag aggagcagaa acagaaagat aaacttaaga ttcgaaaact cgccttaaag   7920
ccccgcagtt actggattaa acaagcccaa caagccgtaa acgccttcat cagagaaaga   7980
gaccgcgact taccatgtat ctcgtgcgga acgctcacgt ctgctcagtg ggatgccgga   8040
cattaccgga caactgctgc ggcacctcaa ctccgattta atgaacgcaa tattcacaag   8100
caatgcgtgg tgtgcaacca gcacaaaagc ggaaatctcg ttccgtatcg cgtcgaactg   8160
attagccgca tcgggcagga agcagtagac gaaatcgaat caaaccataa ccgccatcgc   8220
tggactatcg aagagtgcaa ggcgatcaag gcagagtacc aacagaaact caaagacctg   8280
cgaaatagca gaagtgaggc cgcatgacgt tctcagtaaa aaccattcca gacatgctcg   8340
ttgaagcata cggaaatcag acagaagtag cacgcagact gaaatgtagt cgcggtacgg   8400
tcagaaaata cgttgatgat aaagacggga aaatgcacgc catcgtcaac gacgttctca   8460
tggttcatcg cggatggagt gaaagagatg cgctattacg aaaaaattga tggcagcaaa   8520
taccgaaata tttgggtagt tggcgatctg cacggatgct acacgaacct gatgaacaaa   8580
ctggatacga ttggattcga caacaaaaaa gacctgctta tctcggtggg cgatttggtt   8640
gatcgtggtg cagagaacgt tgaatgcctg gaattaatca cattcccctg gttcagagct   8700
gtacgtggaa accatgagca aatgatgatt gatggcttat cagagcgtgg aaacgttaat   8760
cactggctgc ttaatggcgg tggctggttc tttaatctcg attacgacaa agaaattctg   8820
gctaaagctc ttgcccataa agcagatgaa cttccgttaa tcatcgaact ggtgagcaaa   8880
gataaaaaat atgttatctg ccacgccgat tatccctttg acgaatacga gtttggaaag   8940
ccagttgatc atcagcaggt aatctggaac cgcgaacgaa tcagcaactc acaaaacggg   9000
atcgtgaaag aaatcaaagg cgcggacacg ttcatctttg gtcatacgcc agcagtgaaa   9060
```

```
ccactcaagt ttgccaacca aatgtatatc gataccggcg cagtgttctg cggaaaccta   9120
acattgattc aggtacaggg agaaggcgca tgagactcga aagcgtagct aaatttcatt   9180
cgccaaaaag cccgatgatg agcgactcac cacgggccac ggcttctgac tctctttccg   9240
gtactgatgt gatggctgct atggggatgg cgcaatcaca agccggattc ggtatggctg   9300
cattctgcgg taagcacgaa ctcagccaga acgacaaaca aaaggctatc aactatctga   9360
tgcaatttgc acacaaggta tcggggaaat accgtggtgt ggcaaagctt gaaggaaata   9420
ctaaggcaaa ggtactgcaa gtgctcgcaa cattcgctta tgcggattat tgccgtagtg   9480
ccgcgacgcc gggggcaaga tgcagagatt gccatggtac aggccgtgcg gttgatattg   9540
ccaaaacaga gctgtggggg agagttgtcg agaaagagtg cggaagatgc aaaggcgtcg   9600
gctattcaag gatgccagca agcgcagcat atcgcgctgt gacgatgcta atcccaaacc   9660
ttacccaacc cacctggtca cgcactgtta agccgctgta tgacgctctg gtggtgcaat   9720
gccacaaaga agagtcaatc gcagacaaca ttttgaatgc ggtcacacgt tagcagcatg   9780
attgccacgg atggcaacat attaacggca tgatattgac ttattgaata aaattgggta   9840
aatttgactc aacgatgggt taattcgctc gttgtggtag tgagatgaaa agaggcggcg   9900
cttactaccg attccgccta gttggtcact tcgacgtatc gtctggaact ccaaccatcg   9960
caggcagaga ggtctgcaaa atgcaatccc gaaacagttc gcaggtaata gttagagcct  10020
gcataacggt ttcgggattt tttatatctg cacaacaggt aagagcattg agtcgataat  10080
cgtgaagagt cggcgagcct ggttagccag tgctctttcc gttgtgctga attaagcgaa  10140
taccggaagc agaaccggat caccaaatgc gtacaggcgt catcgccgcc cagcaacagc  10200
acaacccaaa ctgagccgta gccactgtct gtcctgaatt cattagtaat agttacgctg  10260
cggcctttta cacatgacct tcgtgaaagc gggtggcagg aggtcgcgct aacaacctcc  10320
tgccgttttg cccgtgcata tcggtcacga acaaatctga ttactaaaca cagtagcctg  10380
gatttgttct atcagtaatc gaccttattc ctaattaaat agagcaaatc cccttattgg  10440
gggtaagaca tgaagatgcc agaaaaacat gacctgttgg ccgccattct cgcggcaaag  10500
gaacaaggca tcggggcaat ccttgcgttt gcaatggcgt accttcgcgg cagatataat  10560
ggcggtgcgt ttacaaaaac agtaatcgac gcaacgatgt gcgccattat cgcctggttc  10620
attcgtgacc ttctcgactt cgccggacta agtagcaatc tcgcttatat aacgagcgtg  10680
tttatcggct acatcggtac tgactcgatt ggttcgctta tcaaacgctt cgctgctaaa  10740
aaagccggag tagaagatgg tagaaatcaa taatcaacgt aaggcgttcc tcgatatgct  10800
ggcgtggtcg gagggaactg ataacggacg tcagaaaacc agaaatcatg gttatgacgt  10860
cattgtaggc ggagagctat ttactgatta ctccgatcac cctcgcaaac ttgtcacgct  10920
aaacccaaaa ctcaaatcaa caggcgctta agactggccg tcgttttaca acacagaaag  10980
agtttgtaga aacgcaaaaa ggccatccgt caggggcctt ctgcttagtt tgatgcctgg  11040
cagttcccta ctctcgcctt ccgcttcctc gctcactgac tcgctgcgct cggtcgttcg  11100
gctgcggcga gcggtatcag ctcactcaaa ggcggtaata cggttatcca cagaatcagg  11160
ggataacgca ggaaagaaca tgtgagcaaa aggccagcaa aaggccagga accgtaaaaa  11220
ggccgcgttg ctggcgtttt tccataggct ccgcccccct gacgagcatc acaaaaatcg  11280
acgctcaagt cagaggtggc gaaacccgac aggactataa agataccagg cgtttccccc  11340
tggaagctcc ctcgtgcgct ctcctgttcc gaccctgccg cttaccggat acctgtccgc  11400
ctttctccct tcgggaagcg tggcgctttc tcatagctca cgctgtaggt atctcagttc  11460
```

```
ggtgtaggtc gttcgctcca agctgggctg tgtgcacgaa ccccccgttc agcccgaccg  11520
ctgcgcctta tccggtaact atcgtcttga gtccaacccg gtaagacacg acttatcgcc  11580
actggcagca gccactggta acaggattag cagagcgagg tatgtaggcg gtgctacaga  11640
gttcttgaag tggtggccta actacggcta cactagaaga acagtatttg gtatctgcgc  11700
tctgctgaag ccagttacct tcggaaaaag agttggtagc tcttgatccg gcaaacaaac  11760
caccgctggt agcggtggtt tttttgtttg caagcagcag attacgcgca gaaaaaaagg  11820
atctcaagaa gatcctttga tcttttctac ggggtctgac gctcagtgga acgacgcgcg  11880
cgtaactcac gttaagggat tttggtcatg agcttgcgcc gtcccgtcaa gtcagcgtaa  11940
tgctctgctt t                                                      11951
```

<210> SEQ ID NO 24
<211> LENGTH: 11978
<212> TYPE: DNA
<213> ORGANISM: Artificial Sequence
<220> FEATURE:
<223> OTHER INFORMATION: constructed sequence

<400> SEQUENCE: 24

```
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
```

-continued aacttacggt aaatggcccg cctggctgac cgcccaacga cccccgccca ttgacgtcaa 1560
taatgacgta tgttcccata gtaacgccaa tagggacttt ccattgacgt caatgggtgg 1620
agtatttacg gtaaactgcc cacttggcag tacatcaagt gtatcatatg ccaagtacgc 1680
cccctattga cgtcaatgac ggtaaatggc ccgcctggca ttatgcccag tacatgacct 1740
tatgggactt tcctacttgg cagtacatct acgtattagt catcgctatt aacatggtcg 1800
aggtgagccc cacgttctgc ttcactctcc ccatctcccc cccctcccca cccccaattt 1860
tgtatttatt tatttttaa ttattttgtg cagcgatggg ggcggggggg ggggggggc 1920 gcgcgccagg cggggcgggg cggggcgagg ggcggggcgg ggcgaggcgg agaggtgcgg 1980
cggcagccaa tcagagcggc gcgctccgaa agtttccttt tatggcgagg cggcggcggc 2040
ggcggcccta taaaaagcga agcgcgcggc gggcggggag tcgctgcgac gctgccttcg 2100
ccccgtgccc cgctccgccg ccgcctcgcg ccgcccgccc cggctctgac tgaccgcgtt 2160
actcccacag gtgagcgggc gggacggccc ttctcctccg ggctgtaatt agcgcttggt 2220
ttaatgacgg cttgtttctt ttctgtggct gcgtgaaagc cttgaggggc tccgggaggg 2280
ccctttgtgc ggggggagcg gctcgggggg tgcgtgcgtg tgtgtgtgcg tggggagcgc 2340
cgcgtgcggc tccgcgctgc ccggcggctg tgagcgctgc gggcgcggcg cggggctttg 2400
tgcgctccgc agtgtgcgcg aggggagcgc ggccgggggc ggtgccccgc ggtgcggggg 2460
gggctgcgag gggaacaaag gctgcgtgcg gggtgtgtgc gtgggggggt gagcaggggg 2520
tgtgggcgcg tcggtcgggc tgcaaccccc cctgcacccc cctccccgag ttgctgagca 2580
cggcccggct tcgggtgcgg ggctccgtac ggggcgtggc gcggggctcg ccgtgccggg 2640 cgggggggtgg cggcaggtgg gggtgccggg cggggcgggg ccgcctcggg ccggggaggg 2700
ctcgggggag gggcgcggcg gcccccggag cgccggcggc tgtcgaggcg cggcgagccg 2760
cagccattgc cttttatggt aatcgtgcga gagggcgcag ggacttcctt tgtcccaaat 2820
ctgtgcggag ccgaaatctg ggaggcgccg ccgcaccccc tctagcgggc gcgggggcgaa 2880 gcggtgcggc gccggcagga aggaaatggg cggggagggc cttcgtgcgt cgccgcgccg 2940
ccgtcccctt ctccctctcc agcctcgggg ctgtccgcgg ggggacggct gccttcgggg 3000
gggacggggc agggcggggt tcggcttctg gcgtgtgacc ggcggctcta gacaattgta 3060
ctaaccttct tctctttcct ctcctgacag gttggtgtac actagcggcc gccaccatga 3120
tggacctcga actgccgccg cctggcctcc caagccaaca ggatatggac ctgattgaca 3180
tcctgtggcg gcaggacatt gatctgggtg tcagccgcga ggtgttcgat ttctcgcaac 3240
gccggaagga atacgaactc gagaagcaga agaagctcga gaaagagcgg caggaacagc 3300
tccagaagga acaggaaaag gccttcttcg cacaacttca gctggacgag gaaaccggcg 3360
aattcctgcc tattcaacca gcccagcaca tccagagcga aacctccggc agcgccaact 3420
attcccaagt ggctcacatc ccgaagtccg acgccctgta ctttgacgat tgtatgcagc 3480
tgctggcaca gaccttcccc ttcgtcgatg ataacgaggt gtcctccgcg acgtttcagt 3540
cgctggtccc cgacatcccc ggtcatatcg agagccctgt gttcatcgcc accaaccagg 3600
ctcagtcccc cgaaacctca gtggcacaag tggcgccggt ggacttggac ggcatgcagc 3660
aagacatcga acaagtctgg gaggagcttc tgtccatccc cgagctgcaa tgcctcaaca 3720
tcgagaatga caagctcgtg gagactacta tggtcccgtc cccggaagct aagctgaccg 3780
aggtcgacaa ctaccatttc tactcctcaa tcccctccat ggaaaaggaa gtcggaaact 3840
gctcgcctca tttcctcaac gccttcgagg actccttctc gtcaattctg tccactgagg 3900

-continued

```
accccaacca gctgaccgtc aattccttga actcggatgc cactgtgaac accgacttcg   3960
gcgacgaatt ctacagcgcg ttcatcgccg aaccgagcat ctcgaactcc atgccctcgc   4020
ccgccacctt gtcacattcc ctgtctgagc tgctgaacgg gccgattgac gtgtcagacc   4080
tgagcctgtg taaagccttc aaccagaatc acccggagtc gactgccgaa ttcaacgact   4140
cggactccgg gatctcactg aacactagcc ctagcgtggc ctcgcccgaa cactccgtgg   4200
agtccagctc ctatggcgat actcttctgg gtctgtccga ctccgaagtg gaagaactgg   4260
actctgcccc cggaagcgtg aaacagaacg gacctaagac cccagtgcac tcctccgggg   4320
atatggtgca gccgttgtca ccgagccagg ggcaatccac ccacgtgcat gacgctcagt   4380
gcgagaacac ccccgagaaa gaactcccag tgtcccccgg acaccgaaag accccgttta   4440
ccaaggacaa gcactcctca cggctggaag cacaccttac tcgggatgaa ctcagagcca   4500
aggccctcca cattcctttc cccgtggaga agattatcaa tctccctgtg gtggatttca   4560
acgagatgat gagcaaggaa cagttcaacg aagcgcagct ggcgctgatc agggacatca   4620
ggcgcagagg aaagaacaaa gtggccgccc aaaactgccg gaagagaaag ctcgaaaaca   4680
tcgtggagct cgaacaggac ttggaccacc tgaaggatga aaaagaaaag ctgctgaagg   4740
agaagggaga gaacgacaag tccctccatc tgctgaagaa gcagctgagc acactgtacc   4800
tcgaagtgtt ttccatgctg cgcgatgagg atggaaagcc gtactccccg tccgaatact   4860
cgctgcaaca gacgcgcgac ggaaacgtgt tcctcgtgcc aaagtccaag aagcctgacg   4920
tgaagaagaa ctacccatac gatgttccag attacgcttg aagtactgcg gatcctgcag   4980
atctgcctcg actgtgcctt ctagttgcca gccatctgtt gtttgcccct cccccgtgcc   5040
ttccttgacc ctggaaggtg ccactcccac tgtcctttcc taataaaatg aggaaattgc   5100
atcgcattgt ctgagtaggt gtcattctat tctggggggt ggggtggggc aggacagcaa   5160
gggggaggat tgggaagaca atagcaggca tgctggggac tcgagttcta cgtagataag   5220
tagcatggcg ggttaatcat taactacaag gaacccctag tgatggagtt ggccactccc   5280
tctctgcgcg ctcgctcgct cactgaggcc gggcgaccaa aggtcgcccg acgcccgggc   5340
tttgcccggg cggcctcagt gagcgagcga gcgcgcagcc ttaattaacc taaggaaaat   5400
gaagtgaagt tcctatactt tctagagaat aggaacttct atagtgagtc gaataagggc   5460
gacacaaaat ttattctaaa tgcataataa atactgataa catcttatag tttgtattat   5520
attttgtatt atcgttgaca tgtataattt tgatatcaaa aactgatttt ccctttatta   5580
ttttcgagat ttattttctt aattctcttt aacaaactag aaatattgta tatacaaaaa   5640
atcataaata atagatgaat agtttaatta taggtgttca tcaatcgaaa aagcaacgta   5700
tcttatttaa agtgcgttgc tttttctca tttataaggt taaataattc tcatatatca    5760
agcaaagtga caggcgccct taaatattct gacaaatgct ctttccctaa actcccccca   5820
taaaaaaacc cgccgaagcg ggtttttacg ttatttgcgg attaacgatt actcgttatc   5880
agaaccgccc agggggcccg agcttaacct ttttatttgg gggagaggga agtcatgaaa   5940
aaactaacct ttgaaattcg atctccagca catcagcaaa acgctattca cgcagtacag   6000
caaatccttc cagacccaac caaaccaatc gtagtaacca ttcaggaacg caaccgcagc   6060
ttagaccaaa acaggaagct atgggcctgc ttaggtgacg tctctcgtca ggttgaatgg   6120
catggtcgct ggctggatgc agaaagctgg aagtgtgtgt ttaccgcagc attaaagcag   6180
caggatgttg ttcctaacct tgccgggaat ggctttgtgg taataggcca gtcaaccagc   6240
```

-continued

```
aggatgcgtg taggcgaatt tgcggagcta ttagagctta tacaggcatt cggtacagag   6300
cgtggcgtta agtggtcaga cgaagcgaga ctggctctgg agtggaaagc gagatgggga   6360
gacagggctg catgataaat gtcgttagtt tctccggtgg caggacgtca gcatatttgc   6420
tctggctaat ggagcaaaag cgacgggcag gtaaagacgt gcattacgtt ttcatggata   6480
caggttgtga acatccaatg acatatcggt ttgtcaggga agttgtgaag ttctgggata   6540
taccgctcac cgtattgcag gttgatatca acccggagct tggacagcca aatggttata   6600
cggtatggga accaaaggat attcagacgc gaatgcctgt tctgaagcca tttatcgata   6660
tggtaaagaa atatggcact ccatacgtcg gcggcgcgtt ctgcactgac agattaaaac   6720
tcgttccctt caccaaatac tgtgatgacc atttcgggcg agggaattac accacgtgga   6780
ttggcatcag agctgatgaa ccgaagcggc taaagccaaa gcctggaatc agatatcttg   6840
ctgaactgtc agactttgag aaggaagata tcctcgcatg gtggaagcaa caaccattcg   6900
atttgcaaat accggaacat ctcggtaact gcatattctg cattaaaaaa tcaacgcaaa   6960
aaatcggact tgcctgcaaa gatgaggagg gattgcagcg tgtttttaat gaggtcatca   7020
cgggatccca tgtgcgtgac ggacatcggg aaacgccaaa ggagattatg taccgaggaa   7080
gaatgtcgct ggacggtatc gcgaaaatgt attcagaaaa tgattatcaa gccctgtatc   7140
aggacatggt acgagctaaa agattcgata ccggctcttg ttctgagtca tgcgaaatat   7200
ttggagggca gcttgatttc gacttcggga gggaagctgc atgatgcgat gttatcggtg   7260
cggtgaatgc aaagaagata accgcttccg accaaatcaa ccttactgga atcgatggtg   7320
tctccggtgt gaaagaacac caacaggggt gttaccacta ccgcaggaaa aggaggacgt   7380
gtggcgagac agcgacgaag tatcaccgac ataatctgcg aaaactgcaa ataccttcca   7440
acgaaacgca ccagaaataa acccaagcca atcccaaaag aatctgacgt aaaaaccttc   7500
aactacacgg ctcacctgtg ggatatccgg tggctaagac gtcgtgcgag gaaaacaagg   7560
tgattgacca aaatcgaagt tacgaacaag aaagcgtcga gcgagcttta acgtgcgcta   7620
actgcggtca gaagctgcat gtgctggaag ttcacgtgtg tgagcactgc tgcgcagaac   7680
tgatgagcga tccgaatagc tcgatgcacg aggaagaaga tgatggctaa accagcgcga   7740
agacgatgta aaaacgatga atgccgggaa tggtttcacc ctgcattcgc taatcagtgg   7800
tggtgctctc cagagtgtgg aaccaagata gcactcgaac gacgaagtaa agaacgcgaa   7860
aaagcggaaa aagcagcaga gaagaaacga cgacgagagg agcagaaaca gaaagataaa   7920
cttaagattc gaaaactcgc cttaaagccc cgcagttact ggattaaaca agcccaacaa   7980
gccgtaaacg ccttcatcag agaaagagac cgcgacttac catgtatctc gtgcggaacg   8040
ctcacgtctg ctcagtggga tgccggacat taccggacaa ctgctgcggc acctcaactc   8100
cgatttaatg aacgcaatat tcacaagcaa tgcgtggtgt gcaaccagca caaaagcgga   8160
aatctcgttc cgtatcgcgt cgaactgatt agccgcatcg ggcaggaagc agtagacgaa   8220
atcgaatcaa accataaccg ccatcgctgg actatcgaag agtgcaaggc gatcaaggca   8280
gagtaccaac agaaactcaa agacctgcga aatagcagaa gtgaggccgc atgacgttct   8340
cagtaaaaac cattccagac atgctcgttg aagcatacgg aaatcagaca gaagtagcac   8400
gcagactgaa atgtagtcgc ggtacggtca gaaaatacgt tgatgataaa gacgggaaaa   8460
tgcacgccat cgtcaacgac gttctcatgg ttcatcgcgg atggagtgaa agagatgcgc   8520
tattacgaaa aaattgatgg cagcaaatac cgaaatattt gggtagttgg cgatctgcac   8580
ggatgctaca cgaacctgat gaacaaactg gatacgattg gattcgacaa caaaaaagac   8640
```

ctgcttatct cggtgggcga tttggttgat cgtggtgcag agaacgttga atgcctggaa 8700
ttaatcacat tcccctggtt cagagctgta cgtggaaacc atgagcaaat gatgattgat 8760
ggcttatcag agcgtggaaa cgttaatcac tggctgctta atggcggtgg ctggttcttt 8820
aatctcgatt acgacaaaga aattctggct aaagctcttg cccataaagc agatgaactt 8880
ccgttaatca tcgaactggt gagcaaagat aaaaaatatg ttatctgcca cgccgattat 8940
ccctttgacg aatacgagtt tggaaagcca gttgatcatc agcaggtaat ctggaaccgc 9000
gaacgaatca gcaactcaca aaacgggatc gtgaaagaaa tcaaaggcgc ggacacgttc 9060
atctttggtc atacgccagc agtgaaacca ctcaagtttg ccaaccaaat gtatatcgat 9120
accggcgcag tgttctgcgg aaacctaaca ttgattcagg tacagggaga aggcgcatga 9180
gactcgaaag cgtagctaaa tttcattcgc caaaaagccc gatgatgagc gactcaccac 9240
gggccacggc ttctgactct ctttccggta ctgatgtgat ggctgctatg gggatggcgc 9300
aatcacaagc cggattcggt atggctgcat tctgcggtaa gcacgaactc agccagaacg 9360
acaaacaaaa ggctatcaac tatctgatgc aatttgcaca caaggtatcg ggaaatacc 9420
gtggtgtggc aaagcttgaa ggaaatacta aggcaaaggt actgcaagtg ctcgcaacat 9480
tcgcttatgc ggattattgc cgtagtgccg cgacgccggg ggcaagatgc agagattgcc 9540
atggtacagg ccgtgcggtt gatattgcca aaacagagct gtgggggaga gttgtcgaga 9600
aagagtgcgg aagatgcaaa ggcgtcggct attcaaggat gccagcaagc gcagcatatc 9660
gcgctgtgac gatgctaatc ccaaacctta cccaacccac ctggtcacgc actgttaagc 9720
cgctgtatga cgctctggtg gtgcaatgcc acaaagaaga gtcaatcgca gacaacattt 9780
tgaatgcggt cacacgttag cagcatgatt gccacggatg gcaacatatt aacggcatga 9840
tattgactta ttgaataaaa ttgggtaaat ttgactcaac gatgggttaa ttcgctcgtt 9900
gtggtagtga gatgaaaaga ggcggcgctt actaccgatt ccgcctagtt ggtcacttcg 9960
acgtatcgtc tggaactcca accatcgcag gcagagaggt ctgcaaaatg caatcccgaa 10020
acagttcgca ggtaatagtt agagcctgca taacggtttc gggatttttt atatctgcac 10080
aacaggtaag agcattgagt cgataatcgt gaagagtcgg cgagcctggt tagccagtgc 10140
tctttccgtt gtgctgaatt aagcgaatac cggaagcaga accggatcac caaatgcgta 10200
caggcgtcat cgccgcccag caacagcaca acccaaactg agccgtagcc actgtctgtc 10260
ctgaattcat tagtaatagt tacgctgcgg ccttttacac atgaccttcg tgaaagcggg 10320
tggcaggagg tcgcgctaac aacctcctgc cgttttgccc gtgcatatcg gtcacgaaca 10380
aatctgatta ctaaacacag tagcctggat ttgttctatc agtaatcgac cttattccta 10440
attaaataga gcaaatcccc ttattggggg taagacatga agatgccaga aaaacatgac 10500
ctgttggccg ccattctcgc ggcaaaggaa caaggcatcg gggcaatcct tgcgtttgca 10560
atggcgtacc ttcgcggcag atataatggc ggtgcgttta caaaaaacagt aatcgacgca 10620
acgatgtgcg ccattatcgc ctggttcatt cgtgaccttc tcgacttcgc cggactaagt 10680
agcaatctcg cttatataac gagcgtgttt atcggctaca tcggtactga ctcgattggt 10740
tcgcttatca aacgcttcgc tgctaaaaaa gccggagtag aagatggtag aaatcaataa 10800
tcaacgtaag gcgttcctcg atatgctggc gtggtcggag ggaactgata acggacgtca 10860
gaaaaccaga aatcatggtt atgacgtcat tgtaggcgga gagctattta ctgattactc 10920
cgatcaccct cgcaaacttg tcacgctaaa cccaaaactc aaatcaacag gcgcttaaga 10980

```
ctggccgtcg ttttacaaca cagaaagagt ttgtagaaac gcaaaaaggc catccgtcag  11040
gggccttctg cttagtttga tgcctggcag ttccctactc tcgccttccg cttcctcgct  11100
cactgactcg ctgcgctcgg tcgttcggct gcggcgagcg gtatcagctc actcaaaggc  11160
ggtaatacgg ttatccacag aatcagggga taacgcagga aagaacatgt gagcaaaagg  11220
ccagcaaaag gccaggaacc gtaaaaaggc cgcgttgctg gcgtttttcc ataggctccg  11280
cccccctgac gagcatcaca aaaatcgacg ctcaagtcag aggtggcgaa acccgacagg  11340
actataaaga taccaggcgt ttccccctgg aagctccctc gtgcgctctc ctgttccgac  11400
cctgccgctt accggatacc tgtccgcctt tctcccttcg ggaagcgtgg cgctttctca  11460
tagctcacgc tgtaggtatc tcagttcggt gtaggtcgtt cgctccaagc tgggctgtgt  11520
gcacgaaccc cccgttcagc ccgaccgctg cgccttatcc ggtaactatc gtcttgagtc  11580
caacccggta agacacgact tatcgccact ggcagcagcc actggtaaca ggattagcag  11640
agcgaggtat gtaggcggtg ctacagagtt cttgaagtgg tggcctaact acggctacac  11700
tagaagaaca gtatttggta tctgcgctct gctgaagcca gttaccttcg gaaaaagagt  11760
tggtagctct tgatccggca aacaaaccac cgctggtagc ggtggttttt ttgtttgcaa  11820
gcagcagatt acgcgcagaa aaaaaggatc tcaagaagat cctttgatct tttctacggg  11880
gtctgacgct cagtggaacg acgcgcgcgt aactcacgtt aagggatttt ggtcatgagc  11940
ttgcgccgtc ccgtcaagtc agcgtaatgc tctgcttt                          11978
```

<210> SEQ ID NO 25
<211> LENGTH: 11853
<212> TYPE: DNA
<213> ORGANISM: Artificial Sequence
<220> FEATURE:
<223> OTHER INFORMATION: constructed sequence

<400> SEQUENCE: 25

```
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
```

-continued

```
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gccacccaca   1440
agccagttcc tgtccctgag gacttggctc agggactctg ggaatgtggt agacatgggg   1500
tggccccacc aaatgcatcc ttatgggaac ctgctccctg ggagccatga aaagagcgtg   1560
gacttcgagg tggggccaca ggaagtggtc aggtccatct caggggacct gctgcccatc   1620
cacactgctg gccaggaaat ggggggcaat tcatgcctcc tcagcacctt cagcactggg   1680
cggctcaaag aaggcaaggg actattctgg ggtcacacag catgcagcca gaggccaagg   1740
catgaggaag tccttcattt ccccaccccc acccacctca gatcctccaa ccggtttcat   1800
ggcagcccag ggtccagcgg catccaggat gctggtgggt agctgcacag cccaggccgc   1860
gggaggttgg ctgctctcac ctaacaggcc tatgtggccc tgacccctac ctaggaagct   1920
ggggacaatg gccaaggcgc ctcccctctc tgtgcctgtc tgtccaggtg cagcatagac   1980
acagcacccc tggggccaag agcacccagc cagggctgcc cccatgggtg ggcagggcag   2040
taaatgaatg agggacaggt tgggaggtgg ccagccccct ccagcccatg gagggcacgg   2100
ggcaggagag ctgggctgag ccagcaggag cccagggagc ctggtctctg ccttcctatc   2160
ctggaggaag gtgaggctga acctccttcc ctccctccct ccctccccgc cccccactgca   2220
cgcagggctg gctgggctcc agctggcctc cgcatcaata tttcatcggc gtcaatagga   2280
ggcatcgggg acagccgctg cggcagcact cgagccagct caagcccgca gctcgcaggg   2340
agatccagct ccgtcctgcc tgcagcagca caaccctgca caccctgtac actagcggcc   2400
gccaccatga tggacttgga gctgccgccg ccgggactcc cgtcccagca ggacatggat   2460
ttgattgaca tactttggag gcaagatata gatcttggag taagtcgaga agtatttgac   2520
ttcagtcagc gacggaaaga gtatgagctg gaaaaacaga aaaaacttga aaaggaaaga   2580
caagaacaac tccaaaagga gcaagagaaa gcctttttcg ctcagttaca actagatgaa   2640
gagacaggtg aatttctccc aattcagcca gcccagcaca tccagtcaga aaccagtgga   2700
tctgccaact actcccaggt tgcccacatt cccaaatcag atgctttgta ctttgatgac   2760
tgcatgcagc ttttggcgca gacattcccg tttgtagatg acaatgaggt ttcttcggct   2820
acgtttcagt cacttgttcc tgatattccc ggtcacatcg agagcccagt cttcattgct   2880
actaatcagg ctcagtcacc tgaaacttct gttgctcagg tagcccctgt tgatttagac   2940
ggtatgcaac aggacattga gcaagtttgg gaggagctat tatccattcc tgagttacag   3000
tgtcttaata ttgaaaatga caagctggtt gagactacca tggttccaag tccagaagcc   3060
aaactgacag aagttgacaa ttatcatttt tactcatcta taccctcaat ggaaaaagaa   3120
gtaggtaact gtagtccaca ttttcttaat gcttttgagg attccttcag cagcatcctc   3180
tccacagaag accccaacca gttgacagtg aactcattaa attcagatgc cacagtcaac   3240
acagattttg gtgatgaatt ttattctgct ttcatagctg agcccagtat cagcaacagc   3300
atgccctcac ctgctacttt aagccattca ctctctgaac ttctaaatgg gcccattgat   3360
gtttctgatc tatcactttg caaagctttc aaccaaaacc accctgaaag cacagcagaa   3420
```

ttcaatgatt ctgactccgg catttcacta aacacaagtc ccagtgtggc atcaccagaa 3480
cactcagtgg aatcttccag ctatggagac acactacttg gcctcagtga ttctgaagtg 3540
gaagagctag atagtgcccc tggaagtgtc aaacagaatg gtcctaaaac accagtacat 3600
tcttctgggg atatggtaca acccttgtca ccatctcagg ggcagagcac tcacgtgcat 3660
gatgcccaat gtgagaacac accagagaaa gaattgcctg taagtcctgg tcatcggaaa 3720
accccattca caaaagacaa acattcaagc cgcttggagg ctcatctcac aagagatgaa 3780
cttagggcaa aagctctcca tatcccattc cctgtagaaa aaatcattaa cctccctgtt 3840
gttgacttca acgaaatgat gtccaaagag cagttcaatg aagctcaact tgcattaatt 3900
cgggatatac gtaggagggg taagaataaa gtggctgctc agaattgcag aaaaagaaaa 3960
ctggaaaata tagtagaact agagcaagat ttagatcatt tgaaagatga aaaagaaaaa 4020
ttgctcaaag aaaaaggaga aaatgacaaa agccttcacc tactgaaaaa acaactcagc 4080
accttatatc tcgaagtttt cagcatgcta cgtgatgaag atggaaaacc ttattctcct 4140
agtgaatact ccctgcagca aacaagagat ggcaatgttt tccttgttcc caaaagtaag 4200
aagccagatg ttaagaaaaa ctgaagtact gcggatcctg caggcgtcga caatcaacct 4260
ctggattaca aaatttgtga aagattgact ggtattctta actatgttgc tccttttacg 4320
ctatgtggat acgctgcttt aatgcctttg tatcatgcta ttgcttcccg tatggctttc 4380
attttctcct ccttgtataa atcctggttg ctgtctcttt atgaggagtt gtggcccgtt 4440
gtcaggcaac gtggcgtggt gtgcactgtg tttgctgacg caacccccac tggttggggc 4500
attgccacca cctgtcagct cctttccggg actttcgctt tccccctccc tattgccacg 4560
gcggaactca tcgccgcctg ccttgcccgc tgctggacag gggctcggct gttgggcact 4620
gacaattccg tggtgttgtc ggggaagctg acgtcctttc catggctgct cgcctgtgtt 4680
gccacctgga ttctgcgcgg gacgtccttc tgctacgtcc cttcggccct caatccagcg 4740
gaccttcctt cccgcggcct gctgccggct ctgcggcctc ttccgcgtct tcgccttcgc 4800
cctcagacga gtcggatctc cctttgggcc gcctccccgc ctggaattcc tgcagatctg 4860
cctcgactgt gccttctagt tgccagccat ctgttgtttg cccctccccc gtgccttcct 4920
tgaccctgga aggtgccact cccactgtcc tttcctaata aaatgaggaa attgcatcgc 4980
attgtctgag taggtgtcat tctattctgg ggggtggggt ggggcaggac agcaaggggg 5040
aggattggga agacaatagc aggcatgctg gggactcgag ttctacgtag ataagtagca 5100
tggcgggtta atcattaact acaaggaacc cctagtgatg gagttggcca ctccctctct 5160
gcgcgctcgc tcgctcactg aggccgggcg accaaaggtc gcccgacgcc cgggctttgc 5220
ccgggcggcc tcagtgagcg agcgagcgcg cagccttaat taacctaagg aaaatgaagt 5280
gaagttccta tactttctag agaataggaa cttctatagt gagtcgaata agggcgacac 5340
aaaatttatt ctaaatgcat aataaatact gataacatct tatagtttgt attatatttt 5400
gtattatcgt tgacatgtat aattttgata tcaaaaactg attttccctt tattattttc 5460
gagatttatt ttcttaattc tctttaacaa actagaaata ttgtatatac aaaaaatcat 5520
aaataataga tgaatagttt aattataggt gttcatcaat cgaaaaagca acgtatctta 5580
tttaaagtgc gttgcttttt tctcatttat aaggttaaat aattctcata tatcaagcaa 5640
agtgacaggc gcccttaaat attctgacaa atgctctttc cctaaactcc ccccataaaa 5700
aaacccgccg aagcgggttt ttacgttatt tgcggattaa cgattactcg ttatcagaac 5760
cgcccagggg gcccgagctt aaccttttta tttgggggag agggaagtca tgaaaaaact 5820

```
aacctttgaa attcgatctc cagcacatca gcaaaacgct attcacgcag tacagcaaat   5880
ccttccagac ccaaccaaac caatcgtagt aaccattcag gaacgcaacc gcagcttaga   5940
ccaaaacagg aagctatggg cctgcttagg tgacgtctct cgtcaggttg aatggcatgg   6000
tcgctggctg gatgcagaaa gctggaagtg tgtgtttacc gcagcattaa agcagcagga   6060
tgttgttcct aaccttgccg ggaatggctt tgtggtaata ggccagtcaa ccagcaggat   6120
gcgtgtaggc gaatttgcgg agctattaga gcttatacag gcattcggta cagagcgtgg   6180
cgttaagtgg tcagacgaag cgagactggc tctggagtgg aaagcgagat ggggagacag   6240
ggctgcatga taaatgtcgt tagtttctcc ggtggcagga cgtcagcata tttgctctgg   6300
ctaatggagc aaaagcgacg ggcaggtaaa gacgtgcatt acgttttcat ggatacaggt   6360
tgtgaacatc caatgacata tcggtttgtc agggaagttg tgaagttctg ggatataccg   6420
ctcaccgtat tgcaggttga tatcaacccg gagcttggac agccaaatgg ttatacggta   6480
tgggaaccaa aggatattca gacgcgaatg cctgttctga agccatttat cgatatggta   6540
aagaaatatg gcactccata cgtcggcggc gcgttctgca ctgacagatt aaaactcgtt   6600
cccttcacca aatactgtga tgaccatttc gggcgaggga attacaccac gtggattggc   6660
atcagagctg atgaaccgaa gcggctaaag ccaaagcctg gaatcagata tcttgctgaa   6720
ctgtcagact ttgagaagga agatatcctc gcatggtgga agcaacaacc attcgatttg   6780
caaataccgg aacatctcgg taactgcata ttctgcatta aaaaatcaac gcaaaaaatc   6840
ggacttgcct gcaaagatga ggagggattg cagcgtgttt ttaatgaggt catcacggga   6900
tcccatgtgc gtgacggaca tcgggaaacg ccaaaggaga ttatgtaccg aggaagaatg   6960
tcgctggacg gtatcgcgaa aatgtattca gaaaatgatt atcaagccct gtatcaggac   7020
atggtacgag ctaaaagatt cgataccggc tcttgttctg agtcatgcga aatatttgga   7080
gggcagcttg atttcgactt cgggagggaa gctgcatgat gcgatgttat cggtgcggtg   7140
aatgcaaaga agataaccgc ttccgaccaa atcaacctta ctggaatcga tggtgtctcc   7200
ggtgtgaaag aacaccaaca ggggtgttac cactaccgca ggaaaaggag gacgtgtggc   7260
gagacagcga cgaagtatca ccgacataat ctgcgaaaac tgcaaatacc ttccaacgaa   7320
acgcaccaga aataaaccca agccaatccc aaaagaatct gacgtaaaaa ccttcaacta   7380
cacggctcac ctgtgggata tccggtggct aagacgtcgt gcgaggaaaa caaggtgatt   7440
gaccaaaatc gaagttacga acaagaaagc gtcgagcgag ctttaacgtg cgctaactgc   7500
ggtcagaagc tgcatgtgct ggaagttcac gtgtgtgagc actgctgcgc agaactgatg   7560
agcgatccga atagctcgat gcacgaggaa gaagatgatg gctaaaccag cgcgaagacg   7620
atgtaaaaac gatgaatgcc gggaatggtt tcaccctgca ttcgctaatc agtggtggtg   7680
ctctccagag tgtggaacca agatagcact cgaacgacga agtaaagaac gcgaaaaagc   7740
ggaaaaagca gcagagaaga aacgacgacg agaggagcag aaacagaaag ataaacttaa   7800
gattcgaaaa ctcgccttaa agccccgcag ttactggatt aaacaagccc aacaagccgt   7860
aaacgccttc atcagagaaa gagaccgcga cttaccatgt atctcgtgcg gaacgctcac   7920
gtctgctcag tgggatgccg gacattaccg gacaactgct gcggcacctc aactccgatt   7980
taatgaacgc aatattcaca agcaatgcgt ggtgtgcaac cagcacaaaa gcggaaatct   8040
cgttccgtat cgcgtcgaac tgattagccg catcgggcag gaagcagtag acgaaatcga   8100
atcaaaccat aaccgccatc gctggactat cgaagagtgc aaggcgatca aggcagagta   8160
```

```
ccaacagaaa ctcaaagacc tgcgaaatag cagaagtgag gccgcatgac gttctcagta   8220
aaaaccattc cagacatgct cgttgaagca tacggaaatc agacagaagt agcacgcaga   8280
ctgaaatgta gtcgcggtac ggtcagaaaa tacgttgatg ataaagacgg gaaaatgcac   8340
gccatcgtca acgacgttct catggttcat cgcggatgga gtgaaagaga tgcgctatta   8400
cgaaaaaatt gatggcagca aataccgaaa tatttgggta gttggcgatc tgcacggatg   8460
ctacacgaac ctgatgaaca aactggatac gattggattc gacaacaaaa aagacctgct   8520
tatctcggtg ggcgatttgg ttgatcgtgg tgcagagaac gttgaatgcc tggaattaat   8580
cacattcccc tggttcagag ctgtacgtgg aaaccatgag caaatgatga ttgatggctt   8640
atcagagcgt ggaaacgtta atcactggct gcttaatggc ggtggctggt tctttaatct   8700
cgattacgac aaagaaattc tggctaaagc tcttgcccat aaagcagatg aacttccgtt   8760
aatcatcgaa ctggtgagca aagataaaaa atatgttatc tgccacgccg attatccctt   8820
tgacgaatac gagtttggaa agccagttga tcatcagcag gtaatctgga accgcgaacg   8880
aatcagcaac tcacaaaacg ggatcgtgaa agaaatcaaa ggcgcggaca cgttcatctt   8940
tggtcatacg ccagcagtga aaccactcaa gtttgccaac caaatgtata tcgataccgg   9000
cgcagtgttc tgcggaaacc taacattgat tcaggtacag ggagaaggcg catgagactc   9060
gaaagcgtag ctaaatttca ttcgccaaaa agcccgatga tgagcgactc accacgggcc   9120
acggcttctg actctctttc cggtactgat gtgatggctg ctatggggat ggcgcaatca   9180
caagccggat tcggtatggc tgcattctgc ggtaagcacg aactcagcca gaacgacaaa   9240
caaaaggcta tcaactatct gatgcaattt gcacacaagg tatcggggaa ataccgtggt   9300
gtggcaaagc ttgaaggaaa tactaaggca aaggtactgc aagtgctcgc aacattcgct   9360
tatgcggatt attgccgtag tgccgcgacg ccgggggcaa gatgcagaga ttgccatggt   9420
acaggccgtg cggttgatat tgccaaaaca gagctgtggg ggagagttgt cgagaaagag   9480
tgcggaagat gcaaaggcgt cggctattca aggatgccag caagcgcagc atatcgcgct   9540
gtgacgatgc taatcccaaa ccttacccaa cccacctggt cacgcactgt taagccgctg   9600
tatgacgctc tggtggtgca atgccacaaa gaagagtcaa tcgcagacaa cattttgaat   9660
gcggtcacac gttagcagca tgattgccac ggatggcaac atattaacgg catgatattg   9720
acttattgaa taaaattggg taaatttgac tcaacgatgg gttaattcgc tcgttgtggt   9780
agtgagatga aaagaggcgg cgcttactac cgattccgcc tagttggtca cttcgacgta   9840
tcgtctggaa ctccaaccat cgcaggcaga gaggtctgca aatgcaatc ccgaaacagt   9900
tcgcaggtaa tagttagagc ctgcataacg gtttcgggat tttttatatc tgcacaacag   9960
gtaagagcat tgagtcgata atcgtgaaga gtcggcgagc ctggttagcc agtgctcttt  10020
ccgttgtgct gaattaagcg aataccggaa gcagaaccgg atcaccaaat gcgtacaggc  10080
gtcatcgccg cccagcaaca gcacaaccca aactgagccg tagccactgt ctgtcctgaa  10140
ttcattagta atagttacgc tgcggccttt tacacatgac cttcgtgaaa gcgggtggca  10200
ggaggtcgcg ctaacaacct cctgccgttt tgcccgtgca tatcggtcac gaacaaatct  10260
gattactaaa cacagtagcc tggatttgtt ctatcagtaa tcgaccttat tcctaattaa  10320
atagagcaaa tccccttatt gggggtaaga catgaagatg ccagaaaaac atgacctgtt  10380
ggccgccatt ctcgcggcaa aggaacaagg catcggggca atccttgcgt ttgcaatggc  10440
gtaccttcgc ggcagatata atggcggtgc gtttacaaaa acagtaatcg acgcaacgat  10500
gtgcgccatt atcgcctggt tcattcgtga ccttctcgac ttcgccggac taagtagcaa  10560
```

```
tctcgcttat ataacgagcg tgtttatcgg ctacatcggt actgactcga ttggttcgct  10620

tatcaaacgc ttcgctgcta aaaaagccgg agtagaagat ggtagaaatc aataatcaac  10680

gtaaggcgtt cctcgatatg ctggcgtggt cggagggaac tgataacgga cgtcagaaaa  10740

ccagaaatca tggttatgac gtcattgtag gcggagagct atttactgat tactccgatc  10800

accctcgcaa acttgtcacg ctaaacccaa aactcaaatc aacaggcgct taagactggc  10860

cgtcgtttta caacacagaa agagtttgta gaaacgcaaa aaggccatcc gtcaggggcc  10920

ttctgcttag tttgatgcct ggcagttccc tactctcgcc ttccgcttcc tcgctcactg  10980

actcgctgcg ctcggtcgtt cggctgcggc gagcggtatc agctcactca aaggcggtaa  11040

tacggttatc cacagaatca ggggataacg caggaaagaa catgtgagca aaaggccagc  11100

aaaaggccag gaaccgtaaa aaggccgcgt tgctggcgtt tttccatagg ctccgccccc  11160

ctgacgagca tcacaaaaat cgacgctcaa gtcagaggtg gcgaaacccg acaggactat  11220

aaagatacca ggcgtttccc cctggaagct ccctcgtgcg ctctcctgtt ccgaccctgc  11280

cgcttaccgg atacctgtcc gcctttctcc cttcgggaag cgtggcgctt tctcatagct  11340

cacgctgtag gtatctcagt tcggtgtagg tcgttcgctc caagctgggc tgtgtgcacg  11400

aaccccccgt tcagcccgac cgctgcgcct tatccggtaa ctatcgtctt gagtccaacc  11460

cggtaagaca cgacttatcg ccactggcag cagccactgg taacaggatt agcagagcga  11520

ggtatgtagg cggtgctaca gagttcttga agtggtggcc taactacggc tacactagaa  11580

gaacagtatt tggtatctgc gctctgctga agccagttac cttcggaaaa agagttggta  11640

gctcttgatc cggcaaacaa accaccgctg gtagcggtgg tttttttgtt tgcaagcagc  11700

agattacgcg cagaaaaaaa ggatctcaag aagatccttt gatcttttct acggggtctg  11760

acgctcagtg gaacgacgcg cgcgtaactc acgttaaggg attttggtca tgagcttgcg  11820

ccgtcccgtc aagtcagcgt aatgctctgc ttt                               11853


<210> SEQ ID NO 26
<211> LENGTH: 11880
<212> TYPE: DNA
<213> ORGANISM: Artificial Sequence
<220> FEATURE:
<223> OTHER INFORMATION: constructed sequence

<400> SEQUENCE: 26

tagaaaaact catcgagcat caaatgaaac tgcaatttat tcatatcagg attatcaata     60

ccatattttt gaaaaagccg tttctgtaat gaaggagaaa actcaccgag gcagttccat    120

aggatggcaa gatcctggta tcggtctgcg attccgactc gtccaacatc aatacaacct    180

attaatttcc cctcgtcaaa aataaggtta tcaagtgaga aatcaccatg agtgacgact    240

gaatccggtg agaatggcaa aagtttatgc atttctttcc agacttgttc aacaggccag    300

ccattacgct cgtcatcaaa atcactcgca tcaaccaaac cgttattcat tcgtgattgc    360

gcctgagcga ggcgaaatac gcgatcgctg ttaaaaggac aattacaaac aggaatcgag    420

tgcaaccggc gcaggaacac tgccagcgca tcaacaatat tttcacctga atcaggatat    480

tcttctaata cctggaacgc tgtttttccg gggatcgcag tggtgagtaa ccatgcatca    540

tcaggagtac ggataaaatg cttgatggtc ggaagtggca taaattccgt cagccagttt    600

agtctgacca tctcatctgt aacatcattg gcaacgctac ctttgccatg tttcagaaac    660

aactctggcg catcgggctt cccatacaag cgatagattg tcgcacctga ttgcccgaca    720
```

-continued

```
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gccacccaca   1440
agccagttcc tgtccctgag gacttggctc agggactctg ggaatgtggt agacatgggg   1500
tggccccacc aaatgcatcc ttatgggaac ctgctccctg ggagccatga aaagagcgtg   1560
gacttcgagg tggggccaca ggaagtggtc aggtccatct caggggacct gctgcccatc   1620
cacactgctg gccaggaaat ggggggcaat tcatgcctcc tcagcacctt cagcactggg   1680
cggctcaaag aaggcaaggg actattctgg ggtcacacag catgcagcca gaggccaagg   1740
catgaggaag tccttcattt ccccaccccc acccacctca gatcctccaa ccggtttcat   1800
ggcagcccag ggtccagcgg catccaggat gctggtgggt agctgcacag cccaggccgc   1860
gggaggttgg ctgctctcac ctaacaggcc tatgtggccc tgacccctac ctaggaagct   1920
ggggacaatg gccaaggcgc ctcccctctc tgtgcctgtc tgtccaggtg cagcatagac   1980
acagcacccc tggggccaag agcacccagc cagggctgcc cccatgggtg ggcagggcag   2040
taaatgaatg agggacaggt tgggaggtgg ccagcccccct ccagcccatg gagggcacgg   2100
ggcaggagag ctgggctgag ccagcaggag cccagggagc ctggtctctg ccttcctatc   2160
ctggaggaag gtgaggctga acctccttcc ctccctccct ccctccccgc ccccactgca   2220
cgcagggctg gctgggctcc agctggcctc cgcatcaata tttcatcggc gtcaatagga   2280
ggcatcgggg acagccgctg cggcagcact cgagccagct caagcccgca gctcgcaggg   2340
agatccagct ccgtcctgcc tgcagcagca caaccctgca caccctgtac actagcggcc   2400
gccaccatga tggacttgga gctgccgccg ccgggactcc cgtcccagca ggacatggat   2460
ttgattgaca tactttggag gcaagatata gatcttggag taagtcgaga agtatttgac   2520
ttcagtcagc gacggaaaga gtatgagctg gaaaaacaga aaaaacttga aaaggaaaga   2580
caagaacaac tccaaaagga gcaagagaaa gcctttttcg ctcagttaca actagatgaa   2640
gagacaggtg aatttctccc aattcagcca gcccagcaca tccagtcaga aaccagtgga   2700
tctgccaact actcccaggt tgcccacatt cccaaatcag atgctttgta ctttgatgac   2760
tgcatgcagc ttttggcgca gacattcccg tttgtagatg acaatgaggt ttcttcggct   2820
acgtttcagt cacttgttcc tgatattccc ggtcacatcg agagcccagt cttcattgct   2880
actaatcagg ctcagtcacc tgaaacttct gttgctcagg tagcccctgt tgatttagac   2940
ggtatgcaac aggacattga gcaagtttgg gaggagctat tatccattcc tgagttacag   3000
tgtcttaata ttgaaaatga caagctggtt gagactacca tggttccaag tccagaagcc   3060
aaactgacag aagttgacaa ttatcatttt tactcatcta taccctcaat ggaaaaagaa   3120
```

gtaggtaact gtagtccaca ttttcttaat gcttttgagg attccttcag cagcatcctc 3180
tccacagaag accccaacca gttgacagtg aactcattaa attcagatgc cacagtcaac 3240
acagattttg gtgatgaatt ttattctgct ttcatagctg agcccagtat cagcaacagc 3300
atgccctcac ctgctacttt aagccattca ctctctgaac ttctaaatgg gcccattgat 3360
gtttctgatc tatcactttg caaagctttc aaccaaaacc accctgaaag cacagcagaa 3420
ttcaatgatt ctgactccgg catttcacta aacacaagtc ccagtgtggc atcaccagaa 3480
cactcagtgg aatcttccag ctatggagac acactacttg gcctcagtga ttctgaagtg 3540
gaagagctag atagtgcccc tggaagtgtc aaacagaatg gtcctaaaac accagtacat 3600
tcttctgggg atatggtaca acccttgtca ccatctcagg ggcagagcac tcacgtgcat 3660
gatgcccaat gtgagaacac accagagaaa gaattgcctg taagtcctgg tcatcggaaa 3720
accccattca caaaagacaa acattcaagc cgcttggagg ctcatctcac aagagatgaa 3780
cttagggcaa aagctctcca tatcccattc cctgtagaaa aaatcattaa cctccctgtt 3840
gttgacttca acgaaatgat gtccaaagag cagttcaatg aagctcaact tgcattaatt 3900
cgggatatac gtaggagggg taagaataaa gtggctgctc agaattgcag aaaaagaaaa 3960
ctggaaaata tagtagaact agagcaagat ttagatcatt tgaaagatga aaaagaaaaa 4020
ttgctcaaag aaaaaggaga aaatgacaaa agccttcacc tactgaaaaa acaactcagc 4080
accttatatc tcgaagtttt cagcatgcta cgtgatgaag atggaaaacc ttattctcct 4140
agtgaatact ccctgcagca aacaagagat ggcaatgttt tccttgttcc caaaagtaag 4200
aagccagatg ttaagaaaaa ctacccatac gatgttccag attacgcttg aagtactgcg 4260
gatcctgcag gcgtcgacaa tcaacctctg gattacaaaa tttgtgaaag attgactggt 4320
attcttaact atgttgctcc ttttacgcta tgtggatacg ctgctttaat gcctttgtat 4380
catgctattg cttcccgtat ggctttcatt ttctcctcct tgtataaatc ctggttgctg 4440
tctctttatg aggagttgtg gcccgttgtc aggcaacgtg gcgtggtgtg cactgtgttt 4500
gctgacgcaa cccccactgg ttggggcatt gccaccacct gtcagctcct ttccgggact 4560
ttcgctttcc ccctccctat tgccacggcg gaactcatcg ccgcctgcct tgcccgctgc 4620
tggacagggg ctcggctgtt gggcactgac aattccgtgg tgttgtcggg gaagctgacg 4680
tcctttccat ggctgctcgc ctgtgttgcc acctggattc tgcgcgggac gtccttctgc 4740
tacgtccctt cggccctcaa tccagcggac cttccttccc gcggcctgct gccggctctg 4800
cggcctcttc cgcgtcttcg ccttcgccct cagacgagtc ggatctccct ttgggccgcc 4860
tccccgcctg gaattcctgc agatctgcct cgactgtgcc ttctagttgc cagccatctg 4920
ttgtttgccc ctcccccgtg ccttccttga ccctggaagg tgccactccc actgtccttt 4980
cctaataaaa tgaggaaatt gcatcgcatt gtctgagtag gtgtcattct attctggggg 5040
gtggggtggg gcaggacagc aagggggagg attgggaaga caatagcagg catgctgggg 5100
actcgagttc tacgtagata agtagcatgg cgggttaatc attaactaca aggaacccct 5160
agtgatggag ttggccactc cctctctgcg cgctcgctcg ctcactgagg ccgggcgacc 5220
aaaggtcgcc cgacgcccgg gctttgcccg ggcggcctca gtgagcgagc gagcgcgcag 5280
ccttaattaa cctaaggaaa atgaagtgaa gttcctatac tttctagaga ataggaactt 5340
ctatagtgag tcgaataagg gcgacacaaa atttattcta aatgcataat aaatactgat 5400
aacatcttat agtttgtatt atattttgta ttatcgttga catgtataat tttgatatca 5460

-continued

```
aaaactgatt ttccctttat tattttcgag atttattttc ttaattctct ttaacaaact   5520
agaaatattg tatatacaaa aaatcataaa taatagatga atagtttaat tataggtgtt   5580
catcaatcga aaaagcaacg tatcttattt aaagtgcgtt gctttttttct catttataag   5640
gttaaataat tctcatatat caagcaaagt gacaggcgcc cttaaatatt ctgacaaatg   5700
ctctttccct aaactccccc cataaaaaaa cccgccgaag cgggtttttta cgttatttgc   5760
ggattaacga ttactcgtta tcagaaccgc ccagggggcc cgagcttaac ctttttattt   5820
gggggagagg gaagtcatga aaaaactaac ctttgaaatt cgatctccag cacatcagca   5880
aaacgctatt cacgcagtac agcaaatcct tccagaccca accaaaccaa tcgtagtaac   5940
cattcaggaa cgcaaccgca gcttagacca aaacaggaag ctatgggcct gcttaggtga   6000
cgtctctcgt caggttgaat ggcatggtcg ctggctggat gcagaaagct ggaagtgtgt   6060
gtttaccgca gcattaaagc agcaggatgt tgttcctaac cttgccggga atggctttgt   6120
ggtaataggc cagtcaacca gcaggatgcg tgtaggcgaa tttgcggagc tattagagct   6180
tatacaggca ttcggtacag agcgtggcgt taagtggtca gacgaagcga gactggctct   6240
ggagtggaaa gcgagatggg gagacagggc tgcatgataa atgtcgttag tttctccggt   6300
ggcaggacgt cagcatattt gctctggcta atggagcaaa agcgacgggc aggtaaagac   6360
gtgcattacg ttttcatgga tacaggttgt gaacatccaa tgacatatcg gtttgtcagg   6420
gaagttgtga agttctggga tataccgctc accgtattgc aggttgatat caacccggag   6480
cttggacagc caaatggtta tacggtatgg gaaccaaagg atattcagac gcgaatgcct   6540
gttctgaagc catttatcga tatggtaaag aaatatggca ctccatacgt cggcggcgcg   6600
ttctgcactg acagattaaa actcgttccc ttcaccaaat actgtgatga ccatttcggg   6660
cgagggaatt acaccacgtg gattggcatc agagctgatg aaccgaagcg gctaaagcca   6720
aagcctggaa tcagatatct tgctgaactg tcagactttg agaaggaaga tatcctcgca   6780
tggtggaagc aacaaccatt cgatttgcaa ataccggaac atctcggtaa ctgcatattc   6840
tgcattaaaa aatcaacgca aaaaatcgga cttgcctgca aagatgagga gggattgcag   6900
cgtgttttta atgaggtcat cacgggatcc catgtgcgtg acggacatcg ggaaacgcca   6960
aaggagatta tgtaccgagg aagaatgtcg ctggacggta tcgcgaaaat gtattcagaa   7020
aatgattatc aagccctgta tcaggacatg gtacgagcta aaagattcga taccggctct   7080
tgttctgagt catgcgaaat atttggaggg cagcttgatt tcgacttcgg gagggaagct   7140
gcatgatgcg atgttatcgg tgcggtgaat gcaaagaaga taaccgcttc cgaccaaatc   7200
aaccttactg gaatcgatgg tgtctccggt gtgaaagaac accaacaggg gtgttaccac   7260
taccgcagga aaaggaggac gtgtggcgag acagcgacga agtatcaccg acataatctg   7320
cgaaaactgc aaatacettc caacgaaacg caccagaaat aaacccaagc caatcccaaa   7380
agaatctgac gtaaaaacct tcaactacac ggctcacctg tgggatatcc ggtggctaag   7440
acgtcgtgcg aggaaaacaa ggtgattgac caaaatcgaa gttacgaaca agaaagcgtc   7500
gagcgagctt taacgtgcgc taactgcggt cagaagctgc atgtgctgga agttcacgtg   7560
tgtgagcact gctgcgcaga actgatgagc gatccgaata gctcgatgca cgaggaagaa   7620
gatgatggct aaaccagcgc gaagacgatg taaaaacgat gaatgccggg aatggtttca   7680
ccctgcattc gctaatcagt ggtggtgctc tccagagtgt ggaaccaaga tagcactcga   7740
acgacgaagt aaagaacgcg aaaaagcgga aaaagcagca gagaagaaac gacgacgaga   7800
ggagcagaaa cagaaagata aacttaagat tcgaaaactc gccttaaagc cccgcagtta   7860
```

```
ctggattaaa caagcccaac aagccgtaaa cgccttcatc agagaaagag accgcgactt   7920
accatgtatc tcgtgcggaa cgctcacgtc tgctcagtgg gatgccggac attaccggac   7980
aactgctgcg gcacctcaac tccgatttaa tgaacgcaat attcacaagc aatgcgtggt   8040
gtgcaaccag cacaaaagcg gaaatctcgt tccgtatcgc gtcgaactga ttagccgcat   8100
cgggcaggaa gcagtagacg aaatcgaatc aaaccataac cgccatcgct ggactatcga   8160
agagtgcaag gcgatcaagg cagagtacca acagaaactc aaagacctgc gaaatagcag   8220
aagtgaggcc gcatgacgtt ctcagtaaaa accattccag acatgctcgt tgaagcatac   8280
ggaaatcaga cagaagtagc acgcagactg aaatgtagtc gcggtacggt cagaaaatac   8340
gttgatgata aagacgggaa aatgcacgcc atcgtcaacg acgttctcat ggttcatcgc   8400
ggatggagtg aaagagatgc gctattacga aaaaattgat ggcagcaaat accgaaatat   8460
ttgggtagtt ggcgatctgc acggatgcta cacgaacctg atgaacaaac tggatacgat   8520
tggattcgac aacaaaaaag acctgcttat ctcggtgggc gatttggttg atcgtggtgc   8580
agagaacgtt gaatgcctgg aattaatcac attcccctgg ttcagagctg tacgtggaaa   8640
ccatgagcaa atgatgattg atggcttatc agagcgtgga aacgttaatc actggctgct   8700
taatggcggt ggctggttct ttaatctcga ttacgacaaa gaaattctgg ctaaagctct   8760
tgcccataaa gcagatgaac ttccgttaat catcgaactg gtgagcaaag ataaaaaata   8820
tgttatctgc cacgccgatt atccctttga cgaatacgag tttggaaagc cagttgatca   8880
tcagcaggta atctggaacc gcgaacgaat cagcaactca caaaacggga tcgtgaaaga   8940
aatcaaaggc gcggacacgt tcatctttgg tcatacgcca gcagtgaaac cactcaagtt   9000
tgccaaccaa atgtatatcg ataccggcgc agtgttctgc ggaaacctaa cattgattca   9060
ggtacaggga gaaggcgcat gagactcgaa agcgtagcta aatttcattc gccaaaaagc   9120
ccgatgatga gcgactcacc acgggccacg gcttctgact ctctttccgg tactgatgtg   9180
atggctgcta tggggatggc gcaatcacaa gccggattcg gtatggctgc attctgcggt   9240
aagcacgaac tcagccagaa cgacaaacaa aaggctatca actatctgat gcaatttgca   9300
cacaaggtat cggggaaata ccgtggtgtg gcaaagcttg aaggaaatac taaggcaaag   9360
gtactgcaag tgctcgcaac attcgcttat gcggattatt gccgtagtgc cgcgacgccg   9420
ggggcaagat gcagagattg ccatggtaca ggccgtgcgg ttgatattgc caaaacagag   9480
ctgtggggga gagttgtcga gaaagagtgc ggaagatgca aaggcgtcgg ctattcaagg   9540
atgccagcaa gcgcagcata tcgcgctgtg acgatgctaa tcccaaacct tacccaaccc   9600
acctggtcac gcactgttaa gccgctgtat gacgctctgg tggtgcaatg ccacaaagaa   9660
gagtcaatcg cagacaacat tttgaatgcg gtcacacgtt agcagcatga ttgccacgga   9720
tggcaacata ttaacggcat gatattgact tattgaataa aattgggtaa atttgactca   9780
acgatgggtt aattcgctcg ttgtggtagt gagatgaaaa gaggcggcgc ttactaccga   9840
ttccgcctag ttggtcactt cgacgtatcg tctggaactc caaccatcgc aggcagagag   9900
gtctgcaaaa tgcaatcccg aaacagttcg caggtaatag ttagagcctg cataacggtt   9960
tcgggatttt ttatatctgc acaacaggta agagcattga gtcgataatc gtgaagagtc  10020
ggcgagcctg gttagccagt gctctttccg ttgtgctgaa ttaagcgaat accggaagca  10080
gaaccggatc accaaatgcg tacaggcgtc atcgccgccc agcaacagca caacccaaac  10140
tgagccgtag ccactgtctg tcctgaattc attagtaata gttacgctgc ggccttttac  10200
```

acatgacctt cgtgaaagcg ggtggcagga ggtcgcgcta acaacctcct gccgttttgc 10260
ccgtgcatat cggtcacgaa caaatctgat tactaaacac agtagcctgg atttgttcta 10320
tcagtaatcg accttattcc taattaaata gagcaaatcc ccttattggg ggtaagacat 10380
gaagatgcca gaaaaacatg acctgttggc cgccattctc gcggcaaagg aacaaggcat 10440
cggggcaatc cttgcgtttg caatggcgta ccttcgcggc agatataatg gcggtgcgtt 10500
tacaaaaaca gtaatcgacg caacgatgtg cgccattatc gcctggttca ttcgtgacct 10560
tctcgacttc gccggactaa gtagcaatct cgcttatata acgagcgtgt ttatcggcta 10620
catcggtact gactcgattg gttcgcttat caaacgcttc gctgctaaaa aagccggagt 10680
agaagatggt agaaatcaat aatcaacgta aggcgttcct cgatatgctg gcgtggtcgg 10740
agggaactga taacggacgt cagaaaacca gaaatcatgg ttatgacgtc attgtaggcg 10800
gagagctatt tactgattac tccgatcacc ctcgcaaact tgtcacgcta aacccaaaac 10860
tcaaatcaac aggcgcttaa gactggccgt cgttttacaa cacagaaaga gtttgtagaa 10920
acgcaaaaag gccatccgtc aggggccttc tgcttagttt gatgcctggc agttccctac 10980
tctcgccttc cgcttcctcg ctcactgact cgctgcgctc ggtcgttcgg ctgcggcgag 11040
cggtatcagc tcactcaaag gcggtaatac ggttatccac agaatcaggg gataacgcag 11100
gaaagaacat gtgagcaaaa ggccagcaaa aggccaggaa ccgtaaaaag gccgcgttgc 11160
tggcgttttt ccataggctc cgcccccctg acgagcatca caaaaatcga cgctcaagtc 11220
agaggtggcg aaacccgaca ggactataaa gataccaggc gtttccccct ggaagctccc 11280
tcgtgcgctc tcctgttccg accctgccgc ttaccggata cctgtccgcc tttctccctt 11340
cgggaagcgt ggcgctttct catagctcac gctgtaggta tctcagttcg gtgtaggtcg 11400
ttcgctccaa gctgggctgt gtgcacgaac cccccgttca gcccgaccgc tgcgccttat 11460
ccggtaacta tcgtcttgag tccaacccgg taagacacga cttatcgcca ctggcagcag 11520
ccactggtaa caggattagc agagcgaggt atgtaggcgg tgctacagag ttcttgaagt 11580
ggtgggctaa ctacggctac actagaagaa cagtatttgg tatctgcgct ctgctgaagc 11640
cagttacctt cggaaaaaga gttggtagct cttgatccgg caaacaaacc accgctggta 11700
gcggtggttt ttttgtttgc aagcagcaga ttacgcgcag aaaaaaagga tctcaagaag 11760
atcctttgat cttttctacg gggtctgacg ctcagtggaa cgacgcgcgc gtaactcacg 11820
ttaagggatt ttggtcatga gcttgcgccg tcccgtcaag tcagcgtaat gctctgcttt 11880

<210> SEQ ID NO 27
<211> LENGTH: 11853
<212> TYPE: DNA
<213> ORGANISM: Artificial Sequence
<220> FEATURE:
<223> OTHER INFORMATION: constructed sequence

<400> SEQUENCE: 27
tagaaaaact catcgagcat caaatgaaac tgcaatttat tcatatcagg attatcaata 60
ccatattttt gaaaaagccg tttctgtaat gaaggagaaa actcaccgag gcagttccat 120
aggatggcaa gatcctggta tcggtctgcg attccgactc gtccaacatc aatacaacct 180
attaatttcc cctcgtcaaa aataaggtta tcaagtgaga aatcaccatg agtgacgact 240
gaatccggtg agaatggcaa aagtttatgc atttctttcc agacttgttc aacaggccag 300
ccattacgct cgtcatcaaa atcactcgca tcaaccaaac cgttattcat tcgtgattgc 360
gcctgagcga ggcgaaatac gcgatcgctg ttaaaaggac aattacaaac aggaatcgag 420

-continued

```
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gccacccaca   1440
agccagttcc tgtccctgag gacttggctc agggactctg ggaatgtggt agacatgggg   1500
tggccccacc aaatgcatcc ttatgggaac ctgctccctg ggagccatga aaagagcgtg   1560
gacttcgagg tggggccaca ggaagtggtc aggtccatct caggggacct gctgcccatc   1620
cacactgctg gccaggaaat ggggggcaat tcatgcctcc tcagcacctt cagcactggg   1680
cggctcaaag aaggcaaggg actattctgg ggtcacacag catgcagcca gaggccaagg   1740
catgaggaag tccttcattt ccccaccccc acccacctca gatcctccaa ccggtttcat   1800
ggcagcccag ggtccagcgg catccaggat gctggtgggt agctgcacag cccaggccgc   1860
gggaggttgg ctgctctcac ctaacaggcc tatgtggccc tgacccctac ctaggaagct   1920
ggggacaatg gccaaggcgc ctcccctctc tgtgcctgtc tgtccaggtg cagcatagac   1980
acagcacccc tggggccaag agcacccagc cagggctgcc cccatgggtg ggcagggcag   2040
taaatgaatg agggacaggt tgggaggtgg ccagcccccct ccagcccatg gagggcacgg   2100
ggcaggagag ctgggctgag ccagcaggag cccagggagc ctggtctctg ccttcctatc   2160
ctggaggaag gtgaggctga acctccttcc ctccctccct ccctccccgc ccccactgca   2220
cgcagggctg gctgggctcc agctggcctc cgcatcaata tttcatcggc gtcaatagga   2280
ggcatcgggg acagccgctg cggcagcact cgagccagct caagcccgca gctcgcaggg   2340
agatccagct ccgtcctgcc tgcagcagca caaccctgca caccctgtac actagcggcc   2400
gccaccatga tggacctcga actgccgccg cctggcctcc caagccaaca ggatatggac   2460
ctgattgaca tcctgtggcg gcaggacatt gatctgggtg tcagccgcga ggtgttcgat   2520
ttctcgcaac gccggaagga atacgaactc gagaagcaga agaagctcga gaaagagcgg   2580
caggaacagc tccagaagga acaggaaaag gccttcttcg cacaacttca gctggacgag   2640
gaaaccggcg aattcctgcc tattcaacca gcccagcaca tccagagcga aacctccggc   2700
agcgccaact attcccaagt ggctcacatc ccgaagtccg acgccctgta ctttgacgat   2760
```

-continued

```
tgtatgcagc tgctggcaca gaccttcccc ttcgtcgatg ataacgaggt gtcctccgcg   2820
acgtttcagt cgctggtccc cgacatcccc ggtcatatcg agagccctgt gttcatcgcc   2880
accaaccagg ctcagtcccc cgaaacctca gtggcacaag tggcgccggt ggacttggac   2940
ggcatgcagc aagacatcga acaagtctgg gaggagcttc tgtccatccc cgagctgcaa   3000
tgcctcaaca tcgagaatga caagctcgtg gagactacta tggtcccgtc cccggaagct   3060
aagctgaccg aggtcgacaa ctaccatttc tactcctcaa tcccctccat ggaaaaggaa   3120
gtcggaaact gctcgcctca tttcctcaac gccttcgagg actccttctc gtcaattctg   3180
tccactgagg accccaacca gctgaccgtc aattccttga actcggatgc cactgtgaac   3240
accgacttcg gcgacgaatt ctacagcgcg ttcatcgccg aaccgagcat ctcgaactcc   3300
atgccctcgc ccgccacctt gtcacattcc ctgtctgagc tgctgaacgg gccgattgac   3360
gtgtcagacc tgagcctgtg taaagccttc aaccagaatc acccggagtc gactgccgaa   3420
ttcaacgact cggactccgg gatctcactg aacactagcc ctagcgtggc ctcgcccgaa   3480
cactccgtgg agtccagctc ctatggcgat actcttctgg gtctgtccga ctccgaagtg   3540
gaagaactgg actctgcccc cggaagcgtg aaacagaacg gacctaagac cccagtgcac   3600
tcctccgggg atatggtgca gccgttgtca ccgagccagg ggcaatccac ccacgtgcat   3660
gacgctcagt gcgagaacac ccccgagaaa gaactcccag tgtcccccgg acaccgaaag   3720
accccgttta ccaaggacaa gcactcctca cggctggaag cacaccttac tcgggatgaa   3780
ctcagagcca aggccctcca cattcctttc cccgtggaga agattatcaa tctccctgtg   3840
gtggatttca acgagatgat gagcaaggaa cagttcaacg aagcgcagct ggcgctgatc   3900
agggacatca ggcgcagagg aaagaacaaa gtggccgccc aaaactgccg gaagagaaag   3960
ctcgaaaaca tcgtggagct cgaacaggac ttggaccacc tgaaggatga aaaagaaaag   4020
ctgctgaagg agaagggaga gaacgacaag tccctccatc tgctgaagaa gcagctgagc   4080
acactgtacc tcgaagtgtt ttccatgctg cgcgatgagg atggaaagcc gtactccccg   4140
tccgaatact cgctgcaaca gacgcgcgac ggaaacgtgt tcctcgtgcc aaagtccaag   4200
aagcctgacg tgaagaagaa ctgaagtact gcggatcctg caggcgtcga caatcaacct   4260
ctggattaca aaatttgtga aagattgact ggtattctta actatgttgc tccttttacg   4320
ctatgtggat acgctgcttt aatgcctttg tatcatgcta ttgcttcccg tatggctttc   4380
attttctcct ccttgtataa atcctggttg ctgtctcttt atgaggagtt gtggcccgtt   4440
gtcaggcaac gtggcgtggt gtgcactgtg tttgctgacg caacccccac tggttggggc   4500
attgccacca cctgtcagct cctttccggg actttcgctt tccccctccc tattgccacg   4560
gcggaactca tcgccgcctg ccttgcccgc tgctggacag gggctcggct gttgggcact   4620
gacaattccg tggtgttgtc ggggaagctg acgtcctttc catggctgct cgcctgtgtt   4680
gccacctgga ttctgcgcgg gacgtccttc tgctacgtcc cttcggccct caatccagcg   4740
gaccttcctt cccgcggcct gctgccggct ctgcggcctc ttccgcgtct tcgccttcgc   4800
cctcagacga gtcggatctc cctttgggcc gcctccccgc ctggaattcc tgcagatctg   4860
cctcgactgt gccttctagt tgccagccat ctgttgtttg cccctccccc gtgccttcct   4920
tgaccctgga aggtgccact cccactgtcc tttcctaata aaatgaggaa attgcatcgc   4980
attgtctgag taggtgtcat tctattctgg ggggtggggt ggggcaggac agcaaggggg   5040
aggattggga agacaatagc aggcatgctg gggactcgag ttctacgtag ataagtagca   5100
tggcgggtta atcattaact acaaggaacc cctagtgatg gagttggcca ctccctctct   5160
```

gcgcgctcgc tcgctcactg aggccgggcg accaaaggtc gcccgacgcc cgggctttgc 5220
ccgggcggcc tcagtgagcg agcgagcgcg cagccttaat taacctaagg aaaatgaagt 5280
gaagttccta tactttctag agaataggaa cttctatagt gagtcgaata agggcgacac 5340
aaaatttatt ctaaatgcat aataaatact gataacatct tatagtttgt attatatttt 5400
gtattatcgt tgacatgtat aattttgata tcaaaaactg attttccctt tattattttc 5460
gagatttatt ttcttaattc tctttaacaa actagaaata ttgtatatac aaaaaatcat 5520
aaataataga tgaatagttt aattataggt gttcatcaat cgaaaaagca acgtatctta 5580
tttaaagtgc gttgcttttt tctcatttat aaggttaaat aattctcata tatcaagcaa 5640
agtgacaggc gcccttaaat attctgacaa atgctctttc cctaaactcc ccccataaaa 5700
aaacccgccg aagcgggttt ttacgttatt tgcggattaa cgattactcg ttatcagaac 5760
cgcccagggg gcccgagctt aacctttttta tttgggggag agggaagtca tgaaaaaact 5820
aacctttgaa attcgatctc cagcacatca gcaaaacgct attcacgcag tacagcaaat 5880
ccttccagac ccaaccaaac caatcgtagt aaccattcag gaacgcaacc gcagcttaga 5940
ccaaaacagg aagctatggg cctgcttagg tgacgtctct cgtcaggttg aatggcatgg 6000
tcgctggctg gatgcagaaa gctggaagtg tgtgtttacc gcagcattaa agcagcagga 6060
tgttgttcct aaccttgccg ggaatggctt tgtggtaata ggccagtcaa ccagcaggat 6120
gcgtgtaggc gaatttgcgg agctattaga gcttatacag gcattcggta cagagcgtgg 6180
cgttaagtgg tcagacgaag cgagactggc tctggagtgg aaagcgagat ggggagacag 6240
ggctgcatga taaatgtcgt tagtttctcc ggtggcagga cgtcagcata tttgctctgg 6300
ctaatggagc aaaagcgacg ggcaggtaaa gacgtgcatt acgttttcat ggatacaggt 6360
tgtgaacatc caatgacata tcggtttgtc agggaagttg tgaagttctg ggatataccg 6420
ctcaccgtat tgcaggttga tatcaacccg gagcttggac agccaaatgg ttatacggta 6480
tgggaaccaa aggatattca gacgcgaatg cctgttctga agccatttat cgatatggta 6540
aagaaatatg gcactccata cgtcggcggc gcgttctgca ctgacagatt aaaactcgtt 6600
cccttcacca aatactgtga tgaccatttc gggcgaggga attacaccac gtggattggc 6660
atcagagctg atgaaccgaa gcggctaaag ccaaagcctg gaatcagata tcttgctgaa 6720
ctgtcagact ttgagaagga agatatcctc gcatggtgga agcaacaacc attcgatttg 6780
caaataccgg aacatctcgg taactgcata ttctgcatta aaaaatcaac gcaaaaaatc 6840
ggacttgcct gcaaagatga ggagggattg cagcgtgttt ttaatgaggt catcacggga 6900
tcccatgtgc gtgacggaca tcgggaaacg ccaaaggaga ttatgtaccg aggaagaatg 6960
tcgctggacg gtatcgcgaa aatgtattca gaaaatgatt atcaagccct gtatcaggac 7020
atggtacgag ctaaaagatt cgataccggc tcttgttctg agtcatgcga aatatttgga 7080
gggcagcttg atttcgactt cgggagggaa gctgcatgat gcgatgttat cggtgcggtg 7140
aatgcaaaga agataaccgc ttccgaccaa atcaacctta ctggaatcga tggtgtctcc 7200
ggtgtgaaag aacaccaaca ggggtgttac cactaccgca ggaaaaggag gacgtgtggc 7260
gagacagcga cgaagtatca ccgacataat ctgcgaaaac tgcaaatacc ttccaacgaa 7320
acgcaccaga aataaaccca agccaatccc aaaagaatct gacgtaaaaa ccttcaacta 7380
cacggctcac ctgtgggata tccggtggct aagacgtcgt gcgaggaaaa caaggtgatt 7440
gaccaaaatc gaagttacga acaagaaagc gtcgagcgag ctttaacgtg cgctaactgc 7500

-continued

```
ggtcagaagc tgcatgtgct ggaagttcac gtgtgtgagc actgctgcgc agaactgatg   7560
agcgatccga atagctcgat gcacgaggaa gaagatgatg gctaaaccag cgcgaagacg   7620
atgtaaaaac gatgaatgcc gggaatggtt tcaccctgca ttcgctaatc agtggtggtg   7680
ctctccagag tgtggaacca agatagcact cgaacgacga agtaaagaac gcgaaaaagc   7740
ggaaaaagca gcagagaaga aacgacgacg agaggagcag aaacagaaag ataaacttaa   7800
gattcgaaaa ctcgccttaa agccccgcag ttactggatt aaacaagccc aacaagccgt   7860
aaacgccttc atcagagaaa gagaccgcga cttaccatgt atctcgtgcg gaacgctcac   7920
gtctgctcag tgggatgccg gacattaccg gacaactgct gcggcacctc aactccgatt   7980
taatgaacgc aatattcaca agcaatgcgt ggtgtgcaac cagcacaaaa gcggaaatct   8040
cgttccgtat cgcgtcgaac tgattagccg catcgggcag gaagcagtag acgaaatcga   8100
atcaaaccat aaccgccatc gctggactat cgaagagtgc aaggcgatca aggcagagta   8160
ccaacagaaa ctcaaagacc tgcgaaatag cagaagtgag gccgcatgac gttctcagta   8220
aaaaccattc cagacatgct cgttgaagca tacggaaatc agacagaagt agcacgcaga   8280
ctgaaatgta gtcgcggtac ggtcagaaaa tacgttgatg ataaagacgg gaaaatgcac   8340
gccatcgtca acgacgttct catggttcat cgcggatgga gtgaaagaga tgcgctatta   8400
cgaaaaaatt gatggcagca aataccgaaa tatttgggta gttggcgatc tgcacggatg   8460
ctacacgaac ctgatgaaca aactggatac gattggattc gacaacaaaa aagacctgct   8520
tatctcggtg ggcgatttgg ttgatcgtgg tgcagagaac gttgaatgcc tggaattaat   8580
cacattcccc tggttcagag ctgtacgtgg aaaccatgag caaatgatga ttgatggctt   8640
atcagagcgt ggaaacgtta atcactggct gcttaatggc ggtggctggt tctttaatct   8700
cgattacgac aaagaaattc tggctaaagc tcttgcccat aaagcagatg aacttccgtt   8760
aatcatcgaa ctggtgagca aagataaaaa atatgttatc tgccacgccg attatccctt   8820
tgacgaatac gagtttggaa agccagttga tcatcagcag gtaatctgga accgcgaacg   8880
aatcagcaac tcacaaaacg ggatcgtgaa agaaatcaaa ggcgcggaca cgttcatctt   8940
tggtcatacg ccagcagtga aaccactcaa gtttgccaac caaatgtata tcgataccgg   9000
cgcagtgttc tgcggaaacc taacattgat tcaggtacag ggagaaggcg catgagactc   9060
gaaagcgtag ctaaatttca ttcgccaaaa agcccgatga tgagcgactc accacgggcc   9120
acggcttctg actctctttc cggtactgat gtgatggctg ctatggggat ggcgcaatca   9180
caagccggat tcggtatggc tgcattctgc ggtaagcacg aactcagcca gaacgacaaa   9240
caaaaggcta tcaactatct gatgcaattt gcacacaagg tatcggggaa ataccgtggt   9300
gtggcaaagc ttgaaggaaa tactaaggca aaggtactgc aagtgctcgc aacattcgct   9360
tatgcggatt attgccgtag tgccgcgacg ccgggggcaa gatgcagaga ttgccatggt   9420
acaggccgtg cggttgatat tgccaaaaca gagctgtggg ggagagttgt cgagaaagag   9480
tgcggaagat gcaaaggcgt cggctattca aggatgccag caagcgcagc atatcgcgct   9540
gtgacgatgc taatcccaaa ccttacccaa cccacctggt cacgcactgt taagccgctg   9600
tatgacgctc tggtggtgca atgccacaaa gaagagtcaa tcgcagacaa cattttgaat   9660
gcggtcacac gttagcagca tgattgccac ggatggcaac atattaacgg catgatattg   9720
acttattgaa taaaattggg taaatttgac tcaacgatgg gttaattcgc tcgttgtggt   9780
agtgagatga aaagaggcgg cgcttactac cgattccgcc tagttggtca cttcgacgta   9840
tcgtctggaa ctccaaccat cgcaggcaga gaggtctgca aaatgcaatc ccgaaacagt   9900
```

tcgcaggtaa tagttagagc ctgcataacg gtttcgggat tttttatatc tgcacaacag 9960
gtaagagcat tgagtcgata atcgtgaaga gtcggcgagc ctggttagcc agtgctcttt 10020
ccgttgtgct gaattaagcg aataccggaa gcagaaccgg atcaccaaat gcgtacaggc 10080
gtcatcgccg cccagcaaca gcacaaccca aactgagccg tagccactgt ctgtcctgaa 10140
ttcattagta atagttacgc tgcggccttt tacacatgac cttcgtgaaa gcgggtggca 10200
ggaggtcgcg ctaacaacct cctgccgttt tgcccgtgca tatcggtcac gaacaaatct 10260
gattactaaa cacagtagcc tggatttgtt ctatcagtaa tcgaccttat tcctaattaa 10320
atagagcaaa tccccttatt gggggtaaga catgaagatg ccagaaaaac atgacctgtt 10380
ggccgccatt ctcgcggcaa aggaacaagg catcggggca atccttgcgt ttgcaatggc 10440
gtaccttcgc ggcagatata atggcggtgc gtttacaaaa acagtaatcg acgcaacgat 10500
gtgcgccatt atcgcctggt tcattcgtga ccttctcgac ttcgccggac taagtagcaa 10560
tctcgcttat ataacgagcg tgtttatcgg ctacatcggt actgactcga ttggttcgct 10620
tatcaaacgc ttcgctgcta aaaaagccgg agtagaagat ggtagaaatc aataatcaac 10680
gtaaggcgtt cctcgatatg ctggcgtggt cggagggaac tgataacgga cgtcagaaaa 10740
ccagaaatca tggttatgac gtcattgtag gcggagagct atttactgat tactccgatc 10800
accctcgcaa acttgtcacg ctaaacccaa aactcaaatc aacaggcgct taagactggc 10860
cgtcgtttta caacacagaa agagtttgta gaaacgcaaa aaggccatcc gtcaggggcc 10920
ttctgcttag tttgatgcct ggcagttccc tactctcgcc ttccgcttcc tcgctcactg 10980
actcgctgcg ctcggtcgtt cggctgcggc gagcggtatc agctcactca aaggcggtaa 11040
tacggttatc cacagaatca ggggataacg caggaaagaa catgtgagca aaaggccagc 11100
aaaaggccag gaaccgtaaa aaggccgcgt tgctggcgtt tttccatagg ctccgccccc 11160
ctgacgagca tcacaaaaat cgacgctcaa gtcagaggtg gcgaaacccg acaggactat 11220
aaagatacca ggcgtttccc cctggaagct ccctcgtgcg ctctcctgtt ccgaccctgc 11280
cgcttaccgg atacctgtcc gcctttctcc cttcgggaag cgtggcgctt tctcatagct 11340
cacgctgtag gtatctcagt tcggtgtagg tcgttcgctc caagctgggc tgtgtgcacg 11400
aaccccccgt tcagcccgac cgctgcgcct tatccggtaa ctatcgtctt gagtccaacc 11460
cggtaagaca cgacttatcg ccactggcag cagccactgg taacaggatt agcagagcga 11520
ggtatgtagg cggtgctaca gagttcttga agtggtgggc taactacggc tacactagaa 11580
gaacagtatt tggtatctgc gctctgctga agccagttac cttcggaaaa agagttggta 11640
gctcttgatc cggcaaacaa accaccgctg gtagcggtgg tttttttgtt tgcaagcagc 11700
agattacgcg cagaaaaaaa ggatctcaag aagatccttt gatcttttct acggggtctg 11760
acgctcagtg gaacgacgcg cgcgtaactc acgttaaggg attttggtca tgagcttgcg 11820
ccgtcccgtc aagtcagcgt aatgctctgc ttt 11853

<210> SEQ ID NO 28
<211> LENGTH: 11880
<212> TYPE: DNA
<213> ORGANISM: Artificial Sequence
<220> FEATURE:
<223> OTHER INFORMATION: constructed sequence

<400> SEQUENCE: 28
tagaaaaact catcgagcat caaatgaaac tgcaatttat tcatatcagg attatcaata 60

-continued

```
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gccacccaca   1440
agccagttcc tgtccctgag gacttggctc agggactctg ggaatgtggt agacatgggg   1500
tggccccacc aaatgcatcc ttatgggaac ctgctccctg ggagccatga aaagagcgtg   1560
gacttcgagg tggggccaca ggaagtggtc aggtccatct caggggacct gctgcccatc   1620
cacactgctg gccaggaaat ggggggcaat tcatgcctcc tcagcacctt cagcactggg   1680
cggctcaaag aaggcaaggg actattctgg ggtcacacag catgcagcca gaggccaagg   1740
catgaggaag tccttcattt ccccaccccc acccacctca gatcctccaa ccggtttcat   1800
ggcagcccag ggtccagcgg catccaggat gctggtgggt agctgcacag cccaggccgc   1860
gggaggttgg ctgctctcac ctaacaggcc tatgtggccc tgacccctac ctaggaagct   1920
ggggacaatg gccaaggcgc ctcccctctc tgtgcctgtc tgtccaggtg cagcatagac   1980
acagcacccc tggggccaag agcacccagc cagggctgcc cccatgggtg ggcagggcag   2040
taaatgaatg agggacaggt tgggaggtgg ccagcccccct ccagcccatg gagggcacgg   2100
ggcaggagag ctgggctgag ccagcaggag cccagggagc ctggtctctg ccttcctatc   2160
ctggaggaag gtgaggctga acctccttcc ctccctccct ccctccccgc ccccactgca   2220
cgcagggctg gctgggctcc agctggcctc cgcatcaata tttcatcggc gtcaatagga   2280
ggcatcgggg acagccgctg cggcagcact cgagccagct caagcccgca gctcgcaggg   2340
agatccagct ccgtcctgcc tgcagcagca caaccctgca caccctgtac actagcggcc   2400
gccaccatga tggacctcga actgccgccg cctggcctcc caagccaaca ggatatggac   2460
```

```
ctgattgaca tcctgtggcg gcaggacatt gatctgggtg tcagccgcga ggtgttcgat   2520
ttctcgcaac gccggaagga atacgaactc gagaagcaga agaagctcga gaaagagcgg   2580
caggaacagc tccagaagga acaggaaaag gccttcttcg cacaacttca gctggacgag   2640
gaaaccggcg aattcctgcc tattcaacca gcccagcaca tccagagcga aacctccggc   2700
agcgccaact attcccaagt ggctcacatc ccgaagtccg acgccctgta ctttgacgat   2760
tgtatgcagc tgctggcaca gaccttcccc ttcgtcgatg ataacgaggt gtcctccgcg   2820
acgtttcagt cgctggtccc cgacatcccc ggtcatatcg agagccctgt gttcatcgcc   2880
accaaccagg ctcagtcccc cgaaacctca gtggcacaag tggcgccggt ggacttggac   2940
ggcatgcagc aagacatcga acaagtctgg gaggagcttc tgtccatccc cgagctgcaa   3000
tgcctcaaca tcgagaatga caagctcgtg gagactacta tggtcccgtc cccggaagct   3060
aagctgaccg aggtcgacaa ctaccatttc tactcctcaa tcccctccat ggaaaaggaa   3120
gtcggaaact gctcgcctca tttcctcaac gccttcgagg actccttctc gtcaattctg   3180
tccactgagg accccaacca gctgaccgtc aattccttga actcggatgc cactgtgaac   3240
accgacttcg gcgacgaatt ctacagcgcg ttcatcgccg aaccgagcat ctcgaactcc   3300
atgccctcgc ccgccacctt gtcacattcc ctgtctgagc tgctgaacgg gccgattgac   3360
gtgtcagacc tgagcctgtg taaagccttc aaccagaatc acccggagtc gactgccgaa   3420
ttcaacgact cggactccgg gatctcactg aacactagcc ctagcgtggc ctcgcccgaa   3480
cactccgtgg agtccagctc ctatggcgat actcttctgg gtctgtccga ctccgaagtg   3540
gaagaactgg actctgcccc cggaagcgtg aaacagaacg gacctaagac cccagtgcac   3600
tcctccgggg atatggtgca gccgttgtca ccgagccagg ggcaatccac ccacgtgcat   3660
gacgctcagt gcgagaacac ccccgagaaa gaactcccag tgtcccccgg acaccgaaag   3720
accccgttta ccaaggacaa gcactcctca cggctggaag cacaccttac tcgggatgaa   3780
ctcagagcca aggccctcca cattcctttc cccgtggaga agattatcaa tctccctgtg   3840
gtggatttca acgagatgat gagcaaggaa cagttcaacg aagcgcagct ggcgctgatc   3900
agggacatca ggcgcagagg aaagaacaaa gtggccgccc aaaactgccg gaagagaaag   3960
ctcgaaaaca tcgtggagct cgaacaggac ttggaccacc tgaaggatga aaaagaaaag   4020
ctgctgaagg agaagggaga gaacgacaag tccctccatc tgctgaagaa gcagctgagc   4080
acactgtacc tcgaagtgtt ttccatgctg cgcgatgagg atggaaagcc gtactccccg   4140
tccgaatact cgctgcaaca gacgcgcgac ggaaacgtgt tcctcgtgcc aaagtccaag   4200
aagcctgacg tgaagaagaa ctacccatac gatgttccag attacgcttg aagtactgcg   4260
gatcctgcag gcgtcgacaa tcaacctctg gattacaaaa tttgtgaaag attgactggt   4320
attcttaact atgttgctcc ttttacgcta tgtggatacg ctgctttaat gcctttgtat   4380
catgctattg cttcccgtat ggctttcatt ttctcctcct tgtataaatc ctggttgctg   4440
tctctttatg aggagttgtg gcccgttgtc aggcaacgtg gcgtggtgtg cactgtgttt   4500
gctgacgcaa cccccactgg ttggggcatt gccaccacct gtcagctcct ttccgggact   4560
ttcgctttcc ccctccctat tgccacggcg gaactcatcg ccgcctgcct tgcccgctgc   4620
tggacagggg ctcggctgtt gggcactgac aattccgtgg tgttgtcggg gaagctgacg   4680
tcctttccat ggctgctcgc ctgtgttgcc acctggattc tgcgcgggac gtccttctgc   4740
tacgtccctt cggccctcaa tccagcggac cttccttccc gcggcctgct gccggctctg   4800
```

cggcctcttc cgcgtcttcg ccttcgccct cagacgagtc ggatctccct ttgggccgcc 4860
tccccgcctg gaattcctgc agatctgcct cgactgtgcc ttctagttgc cagccatctg 4920
ttgtttgccc ctcccccgtg ccttccttga ccctggaagg tgccactccc actgtccttt 4980
cctaataaaa tgaggaaatt gcatcgcatt gtctgagtag gtgtcattct attctggggg 5040
gtggggtggg gcaggacagc aagggggagg attgggaaga caatagcagg catgctgggg 5100
actcgagttc tacgtagata agtagcatgg cgggttaatc attaactaca aggaacccct 5160
agtgatggag ttggccactc cctctctgcg cgctcgctcg ctcactgagg ccgggcgacc 5220
aaaggtcgcc cgacgcccgg gctttgcccg ggcggcctca gtgagcgagc gagcgcgcag 5280
ccttaattaa cctaaggaaa atgaagtgaa gttcctatac tttctagaga ataggaactt 5340
ctatagtgag tcgaataagg gcgacacaaa atttattcta aatgcataat aaatactgat 5400
aacatcttat agtttgtatt atattttgta ttatcgttga catgtataat tttgatatca 5460
aaaactgatt ttccctttat tattttcgag atttattttc ttaattctct ttaacaaact 5520
agaaatattg tatatacaaa aaatcataaa taatagatga atagtttaat tataggtgtt 5580
catcaatcga aaaagcaacg tatcttattt aaagtgcgtt gctttttct catttataag 5640 gttaaataat tctcatatat caagcaaagt gacaggcgcc cttaaatatt ctgacaaatg 5700
ctctttccct aaactccccc cataaaaaaa cccgccgaag cgggttttta cgttatttgc 5760
ggattaacga ttactcgtta tcagaaccgc ccagggggcc cgagcttaac ctttttattt 5820
gggggagagg gaagtcatga aaaaactaac ctttgaaatt cgatctccag cacatcagca 5880
aaacgctatt cacgcagtac agcaaatcct tccagaccca accaaaccaa tcgtagtaac 5940
cattcaggaa cgcaaccgca gcttagacca aaacaggaag ctatgggcct gcttaggtga 6000
cgtctctcgt caggttgaat ggcatggtcg ctggctggat gcagaaagct ggaagtgtgt 6060
gtttaccgca gcattaaagc agcaggatgt tgttcctaac cttgccggga atggctttgt 6120
ggtaataggc cagtcaacca gcaggatgcg tgtaggcgaa tttgcggagc tattagagct 6180
tatacaggca ttcggtacag agcgtggcgt taagtggtca gacgaagcga gactggctct 6240
ggagtggaaa gcgagatggg gagacagggc tgcatgataa atgtcgttag tttctccggt 6300
ggcaggacgt cagcatattt gctctggcta atggagcaaa agcgacgggc aggtaaagac 6360
gtgcattacg ttttcatgga tacaggttgt gaacatccaa tgacatatcg gtttgtcagg 6420
gaagttgtga agttctggga tataccgctc accgtattgc aggttgatat caacccggag 6480
cttggacagc caaatggtta tacggtatgg gaaccaaagg atattcagac gcgaatgcct 6540
gttctgaagc catttatcga tatggtaaag aaatatggca ctccatacgt cggcggcgcg 6600
ttctgcactg acagattaaa actcgttccc ttcaccaaat actgtgatga ccatttcggg 6660
cgagggaatt acaccacgtg gattggcatc agagctgatg aaccgaagcg gctaaagcca 6720
aagcctggaa tcagatatct tgctgaactg tcagactttg agaaggaaga tatcctcgca 6780
tggtggaagc aacaaccatt cgatttgcaa ataccggaac atctcggtaa ctgcatattc 6840
tgcattaaaa aatcaacgca aaaaatcgga cttgcctgca aagatgagga gggattgcag 6900
cgtgttttta atgaggtcat cacgggatcc catgtgcgtg acggacatcg ggaaacgcca 6960
aaggagatta tgtaccgagg aagaatgtcg ctggacggta tcgcgaaaat gtattcagaa 7020
aatgattatc aagccctgta tcaggacatg gtacgagcta aaagattcga taccggctct 7080
tgttctgagt catgcgaaat atttggaggg cagcttgatt tcgacttcgg gagggaagct 7140
gcatgatgcg atgttatcgg tgcggtgaat gcaaagaaga taaccgcttc cgaccaaatc 7200

-continued

```
aaccttactg gaatcgatgg tgtctccggt gtgaaagaac accaacaggg gtgttaccac   7260
taccgcagga aaaggaggac gtgtggcgag acagcgacga agtatcaccg acataatctg   7320
cgaaaactgc aaataccttc caacgaaacg caccagaaat aaacccaagc caatcccaaa   7380
agaatctgac gtaaaaacct tcaactacac ggctcacctg tgggatatcc ggtggctaag   7440
acgtcgtgcg aggaaaacaa ggtgattgac caaaatcgaa gttacgaaca agaaagcgtc   7500
gagcgagctt taacgtgcgc taactgcggt cagaagctgc atgtgctgga agttcacgtg   7560
tgtgagcact gctgcgcaga actgatgagc gatccgaata gctcgatgca cgaggaagaa   7620
gatgatggct aaaccagcgc gaagacgatg taaaaacgat gaatgccggg aatggtttca   7680
ccctgcattc gctaatcagt ggtggtgctc tccagagtgt ggaaccaaga tagcactcga   7740
acgacgaagt aaagaacgcg aaaaagcgga aaaagcagca gagaagaaac gacgacgaga   7800
ggagcagaaa cagaaagata aacttaagat tcgaaaactc gccttaaagc cccgcagtta   7860
ctggattaaa caagcccaac aagccgtaaa cgccttcatc agagaaagag accgcgactt   7920
accatgtatc tcgtgcggaa cgctcacgtc tgctcagtgg gatgccggac attaccggac   7980
aactgctgcg gcacctcaac tccgatttaa tgaacgcaat attcacaagc aatgcgtggt   8040
gtgcaaccag cacaaaagcg gaaatctcgt tccgtatcgc gtcgaactga ttagccgcat   8100
cgggcaggaa gcagtagacg aaatcgaatc aaaccataac cgccatcgct ggactatcga   8160
agagtgcaag gcgatcaagg cagagtacca acagaaactc aaagacctgc gaaatagcag   8220
aagtgaggcc gcatgacgtt ctcagtaaaa accattccag acatgctcgt tgaagcatac   8280
ggaaatcaga cagaagtagc acgcagactg aaatgtagtc gcggtacggt cagaaaatac   8340
gttgatgata aagacgggaa aatgcacgcc atcgtcaacg acgttctcat ggttcatcgc   8400
ggatggagtg aaagagatgc gctattacga aaaaattgat ggcagcaaat accgaaatat   8460
ttgggtagtt ggcgatctgc acggatgcta cacgaacctg atgaacaaac tggatacgat   8520
tggattcgac aacaaaaaag acctgcttat ctcggtgggc gatttggttg atcgtggtgc   8580
agagaacgtt gaatgcctgg aattaatcac attcccctgg ttcagagctg tacgtggaaa   8640
ccatgagcaa atgatgattg atggcttatc agagcgtgga aacgttaatc actggctgct   8700
taatggcggt ggctggttct ttaatctcga ttacgacaaa gaaattctgg ctaaagctct   8760
tgcccataaa gcagatgaac ttccgttaat catcgaactg gtgagcaaag ataaaaaata   8820
tgttatctgc cacgccgatt atccctttga cgaatacgag tttggaaagc cagttgatca   8880
tcagcaggta atctggaacc gcgaacgaat cagcaactca caaaacggga tcgtgaaaga   8940
aatcaaaggc gcggacacgt tcatctttgg tcatacgcca gcagtgaaac cactcaagtt   9000
tgccaaccaa atgtatatcg ataccggcgc agtgttctgc ggaaacctaa cattgattca   9060
ggtacaggga gaaggcgcat gagactcgaa agcgtagcta aatttcattc gccaaaaagc   9120
ccgatgatga gcgactcacc acgggccacg gcttctgact ctctttccgg tactgatgtg   9180
atggctgcta tggggatggc gcaatcacaa gccggattcg gtatggctgc attctgcggt   9240
aagcacgaac tcagccagaa cgacaaacaa aaggctatca actatctgat gcaatttgca   9300
cacaaggtat cggggaaata ccgtggtgtg gcaaagcttg aaggaaatac taaggcaaag   9360
gtactgcaag tgctcgcaac attcgcttat gcggattatt gccgtagtgc cgcgacgccg   9420
gggcaagat gcagagattg ccatggtaca ggccgtgcgg ttgatattgc caaaacagag   9480
ctgtggggga gagttgtcga gaaagagtgc ggaagatgca aaggcgtcgg ctattcaagg   9540
```

-continued

```
atgccagcaa gcgcagcata tcgcgctgtg acgatgctaa tcccaaacct tacccaaccc   9600
acctggtcac gcactgttaa gccgctgtat gacgctctgg tggtgcaatg ccacaaagaa   9660
gagtcaatcg cagacaacat tttgaatgcg gtcacacgtt agcagcatga ttgccacgga   9720
tggcaacata ttaacggcat gatattgact tattgaataa aattgggtaa atttgactca   9780
acgatgggtt aattcgctcg ttgtggtagt gagatgaaaa gaggcggcgc ttactaccga   9840
ttccgcctag ttggtcactt cgacgtatcg tctggaactc caaccatcgc aggcagagag   9900
gtctgcaaaa tgcaatcccg aaacagttcg caggtaatag ttagagcctg cataacggtt   9960
tcgggatttt ttatatctgc acaacaggta agagcattga gtcgataatc gtgaagagtc  10020
ggcgagcctg gttagccagt gctctttccg ttgtgctgaa ttaagcgaat accggaagca  10080
gaaccggatc accaaatgcg tacaggcgtc atcgccgccc agcaacagca caacccaaac  10140
tgagccgtag ccactgtctg tcctgaattc attagtaata gttacgctgc ggccttttac  10200
acatgacctt cgtgaaagcg ggtggcagga ggtcgcgcta acaacctcct gccgttttgc  10260
ccgtgcatat cggtcacgaa caaatctgat tactaaacac agtagcctgg atttgttcta  10320
tcagtaatcg accttattcc taattaaata gagcaaatcc ccttattggg ggtaagacat  10380
gaagatgcca gaaaaacatg acctgttggc cgccattctc gcggcaaagg aacaaggcat  10440
cggggcaatc cttgcgtttg caatggcgta ccttcgcggc agatataatg gcggtgcgtt  10500
tacaaaaaca gtaatcgacg caacgatgtg cgccattatc gcctggttca ttcgtgacct  10560
tctcgacttc gccggactaa gtagcaatct cgcttatata acgagcgtgt ttatcggcta  10620
catcggtact gactcgattg gttcgcttat caaacgcttc gctgctaaaa aagccggagt  10680
agaagatggt agaaatcaat aatcaacgta aggcgttcct cgatatgctg gcgtggtcgg  10740
agggaactga taacggacgt cagaaaacca gaaatcatgg ttatgacgtc attgtaggcg  10800
gagagctatt tactgattac tccgatcacc ctcgcaaact tgtcacgcta aacccaaaac  10860
tcaaatcaac aggcgcttaa gactggccgt cgttttacaa cacagaaaga gtttgtagaa  10920
acgcaaaaag gccatccgtc aggggccttc tgcttagttt gatgcctggc agttccctac  10980
tctcgccttc cgcttcctcg ctcactgact cgctgcgctc ggtcgttcgg ctgcggcgag  11040
cggtatcagc tcactcaaag gcggtaatac ggttatccac agaatcaggg gataacgcag  11100
gaaagaacat gtgagcaaaa ggccagcaaa aggccaggaa ccgtaaaaag gccgcgttgc  11160
tggcgttttt ccataggctc cgcccccctg acgagcatca caaaaatcga cgctcaagtc  11220
agaggtggcg aaacccgaca ggactataaa gataccaggc gtttccccct ggaagctccc  11280
tcgtgcgctc tcctgttccg accctgccgc ttaccggata cctgtccgcc tttctccctt  11340
cgggaagcgt ggcgctttct catagctcac gctgtaggta tctcagttcg gtgtaggtcg  11400
ttcgctccaa gctgggctgt gtgcacgaac cccccgttca gcccgaccgc tgcgccttat  11460
ccggtaacta tcgtcttgag tccaacccgg taagacacga cttatcgcca ctggcagcag  11520
ccactggtaa caggattagc agagcgaggt atgtaggcgg tgctacagag ttcttgaagt  11580
ggtgggctaa ctacggctac actagaagaa cagtatttgg tatctgcgct ctgctgaagc  11640
cagttacctt cggaaaaaga gttggtagct cttgatccgg caaacaaacc accgctggta  11700
gcggtggttt ttttgtttgc aagcagcaga ttacgcgcag aaaaaaagga tctcaagaag  11760
atcctttgat cttttctacg gggtctgacg ctcagtggaa cgacgcgcgc gtaactcacg  11820
ttaagggatt ttggtcatga gcttgcgccg tcccgtcaag tcagcgtaat gctctgcttt  11880
```

GENE THERAPY FOR OCULAR DISORDERS

CROSS-REFERENCE TO RELATED APPLICATIONS

This is a National Stage Entry under 35 U.S.C. 371 of International Patent Application No. PCT/US2018/029167, filed Apr. 24, 2018, which claims priority to U.S. Provisional Patent Application No. 62/488,989, filed Apr. 24, 2017. These applications are incorporated by reference herein.

STATEMENT REGARDING FEDERALLY SPONSORED RESEARCH OR DEVELOPMENT

This invention was made with government support under Grant No. EY019014 awarded by the National Institutes of Health (NIH). The government has certain rights in this invention.

BACKGROUND OF THE INVENTION

There are a number of disorders that cause visual impairment and blindness due to disease of the optic nerve. Damage and death of ganglion cell axons which comprise the optic nerve or loss of the myelin nerve sheath surrounding the optic nerve leads to loss of vision. The onset of disease can be rapid (1-2 weeks) and there can be pain on eye movements. Rapid onset is typical of demyelinating, inflammatory, ischemic and traumatic causes of optic nerve damage. This sort of rapid onset is typical of multiple sclerosis, which affects 2.5 million people globally. A more gradual loss of optic nerve function is associated with compression of the nerve or toxic, nutritional or hereditary conditions. For compressive or nutritional disorders, the primary insult is addressed. However, there are limited treatments for optic neuritis and other optic neuropathies consisting primarily of steroid administration and related treatments aimed at modulating inflammation (beta-interferons, glatiramer acetate, fingolamid, teriflunomide, alemtuzamab, dimethyl fumerate). Although some vision can return 6 months after an episode of optic neuritis, there is permanent vision loss from death of ganglion cells that is not addressed by immunosuppressants. Further, a significant number of people suffer recurrences in the initially affected or contralateral eye. It is thus desirable to protect the ganglion cells in order to prevent retinal ganglion cell death and resulting permanent vision loss.

Others have described the use of NRF2 to promote neuronal survival in neurodegeneration and acute nerve damage (Xiong et al, J Clin Invest. 2015 Apr. 1; 125(4): 1433-1445).

SUMMARY OF THE INVENTION

In one aspect, a recombinant adeno-associated virus (rAAV) is provided. In one embodiment, the rAAV includes an AAV capsid, and a vector genome packaged therein. In one embodiment, the vector genome includes (a) an AAV 5' inverted terminal repeat (ITR) sequence; (b) a promoter; (c) a coding sequence encoding a human NRF2; (d) an AAV 3' ITR. In one embodiment, the coding sequence of (c) is SEQ ID NO: 4. In another embodiment, the coding sequence of (c) is SEQ ID NO: 7. In one embodiment, the vector genome includes an AAV2 5' ITR, a CMV/CBA promoter, a Kozak sequence, the coding sequence of SEQ ID NO: 4 or SEQ ID NO: 7, a bGH polyA and an AAV2 3' ITR. In another embodiment, the vector genome includes an AAV2 5' ITR, a human Synuclein Gamma (human SNCG, hSNCG) promoter, a Kozak sequence, the coding sequence of SEQ ID NO: 4 or SEQ ID NO: 7, a Woodchuck Hepatitis Virus (WHP) Posttranscriptional Regulatory Element (WPRE), a bGH polyA and an AAV2 3' ITR.

In another embodiment, the vector genome includes (a) an AAV 5' inverted terminal repeat (ITR) sequence; (b) a promoter; (c) a coding sequence encoding a human SIRT1; (d) an AAV 3' ITR. In one embodiment, the coding sequence of (c) is SEQ ID NO: 2. In another embodiment, the coding sequence of (c) is SEQ ID NO: 12. In one embodiment, the vector genome includes an AAV2 5' ITR, a CMV/CBA promoter, a Kozak sequence, the coding sequence of SEQ ID NO: 2 or SEQ ID NO: 12, a bGH polyA and an AAV2 3' ITR. In another embodiment, the vector genome includes an AAV2 5' ITR, a hSNCG promoter, a Kozak sequence, the coding sequence of SEQ ID NO: 2 or SEQ ID NO: 12, a WPRE, a bGH polyA and an AAV2 3' ITR In another aspect, a composition is provided which includes an rAAV as described herein and a pharmaceutical acceptable carrier or excipient.

In another aspect, an aqueous suspension suitable for administration to a subject is provided. In one embodiment, the suspension includes an aqueous suspending liquid and about $1\times10^9$ viral particles to about $1\times10^{13}$ GC or viral particles per eye of a recombinant adeno-associated virus (rAAV) as described herein useful as a therapeutic for the treatment or prevention of optic neuropathy. In one embodiment, the suspension is suitable for subretinal or intravitreal injection.

In yet another aspect, a method of treating or preventing an optic disorder in a subject in need thereof with a rAAV as described herein, is provided. In one embodiment, the disorder is an MS related disorder. In another embodiment, the disorder is glaucoma.

In yet another aspect, a method of preserving retinal ganglion cell (RGC) function in a subject in need thereof with a rAAV as described herein, is provided.

Other aspects and advantages of the invention will be readily apparent from the following detailed description of the invention.

BRIEF DESCRIPTION OF THE DRAWINGS

FIG. 9 is an alignment of the coding sequence for native (SEQ ID NO: 4) and codon optimized hNRF2 (SEQ ID NO: 7). These sequences show 73.55% identity over the full length.

DETAILED DESCRIPTION OF THE INVENTION

Figure 1:
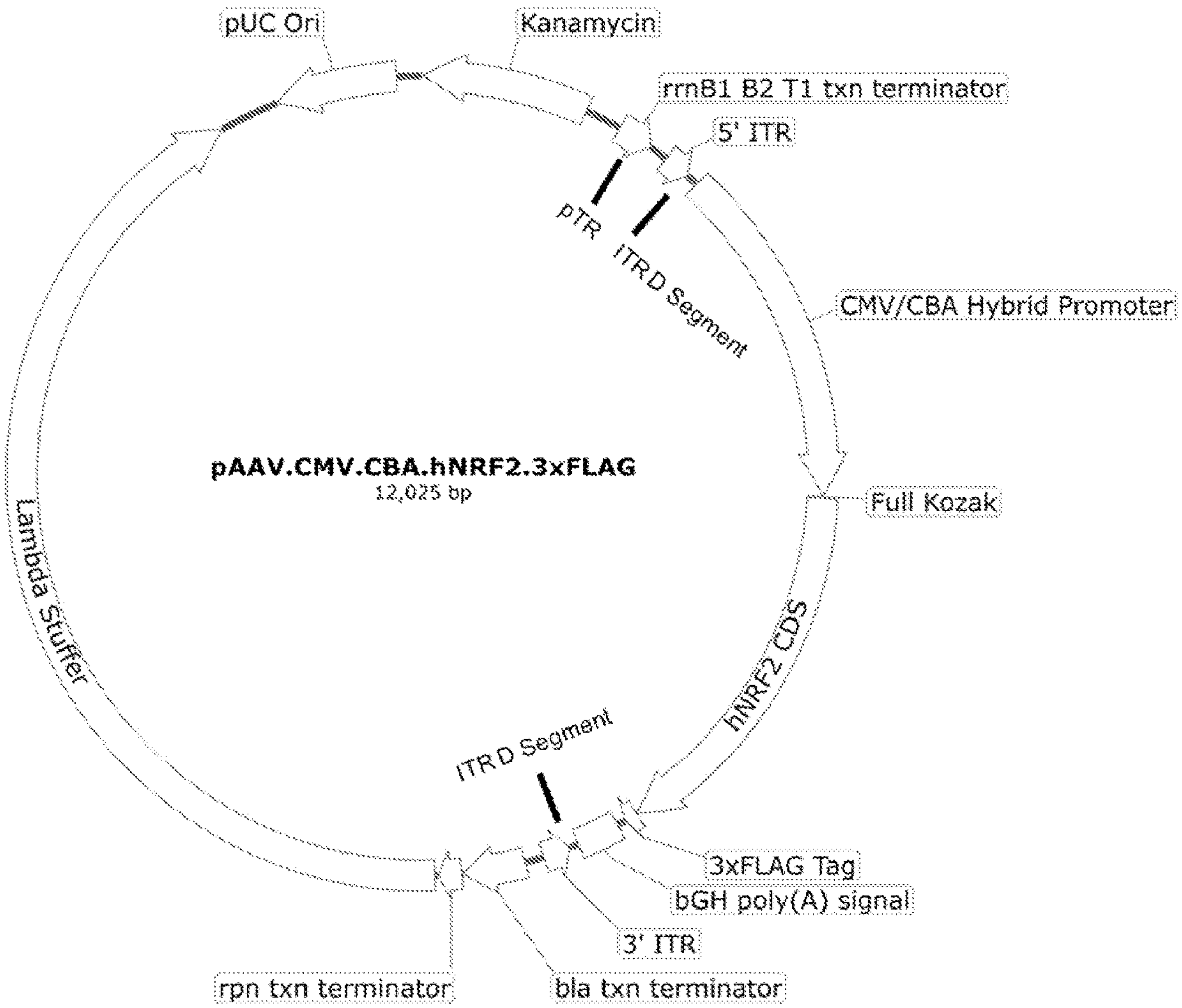
FIG. 1 provides a plasmid map of the pAAV-CMV/CBA-hNRF2-3xFLAG vector.

Described herein are several agents which can be delivered to retinal ganglion cells or other neurons to prevent or ameliorate permanent vision loss. The agents, NRF2 and Sirtuins (SIRT1, 2, 3, 4, 5, 6, 7) act by decreasing oxidative or metabolic stress and thus by providing neurotrophic support.

Sirtuins are NAD-dependent protein deacetylases. Intravitreal delivery of sirtuin activators such as resveratrol have been shown to reduce deficits from optic neuritis and optic crush injury in mouse models. (Shindler et al. Invest Ophthalmol Vis Sci 48(8):3602 (2007); Zuo et al Invest Ophthalmol Vis Sci 54(7):5097-102 (2013)). Sirtuin-1, encoded by SIRT1 (herein used interchangeably for the coding sequence and expression product), links transcriptional regulation directly to intracellular energetics and participates in the coordination of several separated cellular functions such as cell cycle, response to DNA damage, metobolism, apoptosis and autophagy. Two isoforms are known. Transcript variant 1, which includes the entire 747 amino acid protein (SEQ ID NO: 1), and transcript variant 2, which lacks amino acids 454-639 (using the numbering from transcript variant 1). Exemplified herein is the use of transcript variant 1. However, similar constructs utilizing transcript variant 2 are also contemplated herein. The native SIRT1 sequence encoding sirtuin-1 is shown in SEQ ID NO: 2. A codon-optimized SIRT1 sequence encoding sirtuin-1 is shown in SEQ ID NO: 12. It has been shown that activators of SIRT1 significantly attenuated retinal ganglion cells (RGCs) in a dose-dependent manner. Shindler, K S et al, Invest Ophthalmol Vis Sci. 2007 August;48(8):3602-9, which is incorporated herein by reference.

Nuclear factor-like 2 also called Nuclear factor erythroid 2-related factor 2, encoded by NFE2L2, also called NRF2, is a transcription factor that regulates a pathway of genes that decrease oxidative and other forms of stress. As used herein, the term "NRF2" is used interchangeably to refer to the nuclear factor-like 2 protein and its coding sequence. It has been shown that following optic nerve injury, RGC death is significantly increased in Nrf2 KO mice, and administration of AAV-NRF2 with Nrf2 reduces RGC death in retinitis pigmentosa mouse models. See, Kimura et al, Oxidative Medicine and Cellular Longevity, Volume 2017 (February 2017); and Xiong et al, J Clin Invest. 2015;125 (4):1433-1445, which are incorporated herein by reference.

Figure 2:
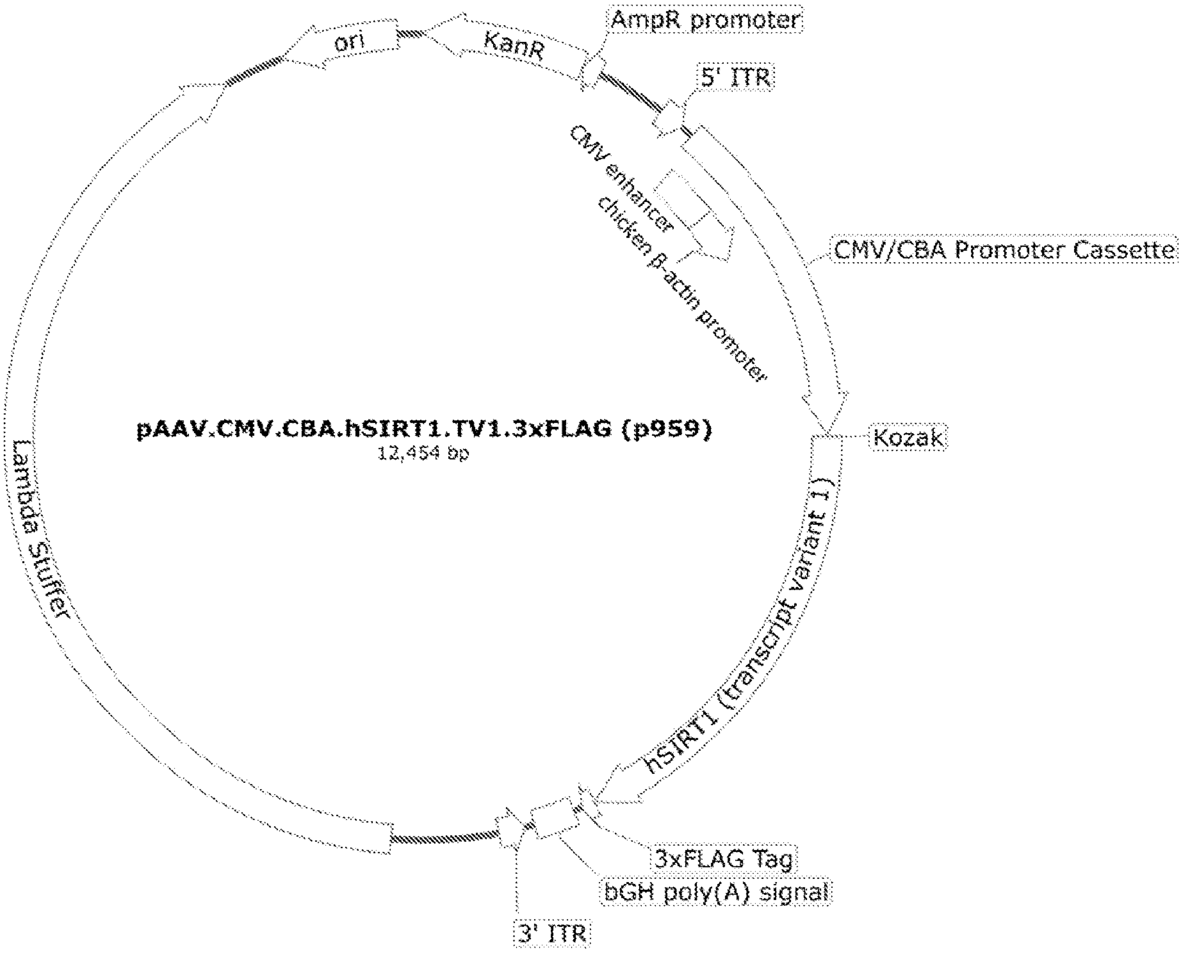
FIG. 2 provides a plasmid map of the pAAV-CMV/CBA-hSIRT1-3xFLAG vector.

Described herein are rAAV vectors capable of delivering NRF2 (FIG. 1) and sirtuins (SIRT1, 2; FIG. 2) to diseased tissue, including retinal cells in the eye. The vectors described herein are useful in the treatment of a wide variety of genetic and acquired optic nerve disorders that affect the structure or function of the optic nerve. In one embodiment, any of such optic disorders or conditions is referred to as optic neuropathy. Such optic disorders include glaucoma, optic neuritis, optic neuropathy, retinitis pigmentosa, amongst others. Other optic disorders include ischemic optic neuropathy, compressive optic neuropathy, infiltrative optic neuropathy, tramautic optic neuropathy, mitochondrial optic neuropathy, nutritional optic neuropathy, and toxic optic neuropathy. Still other optic disorders include hereditary optic neuropathy including leber's hereditary optic neuropathy, dominant optic atrophy, Behr's syndrome, and Berk-Tabatznki syndrome. In one embodiment, the ocular disorder negatively affects the retinal ganglion cells. In another embodiment, the disorder negatively affects any of the neuronal cells.

Glaucoma is a neurodegenerative disease of the eye and it is one of the major causes of irreversible blindness. It is estimated that, by 2020, more than 80 million people will be affected worldwide, with at least 6 to 8 million of them becoming bilaterally blind. Glaucoma is characterized by damage to the optic nerve and progressive degeneration of retinal ganglion cells (RGCs), which are critical elements for vision loss. The factors associated with pathogenesis of glaucoma include high intraocular pressure (IOP), increased oxidative stress, aging, glutamate neurotoxicity, and susceptibility genes such as optineurin and myocilin. In one embodiment, the ocular condition treated using the rAAV vectors described herein, is glaucoma.

MS is a central nervous system disease characterized by chronic inflammation and demyelination. Approximately 2.5 million people are affected globally, with an average age of onset of 30 years. About 50% of patients diagnosed after 25 years require a mobility aid. The disease is largely believed to be an autoimmune condition, with infiltration of CNS by autoreactive immune effector cells. The central "trigger" for disease onset is mostly undefined, with complex genetic modifiers and environmental factors believed to play a part. See, Dendrou et al. (Nat Rev Imm, 2009), which is incorporated herein by reference. See, McDougald et al, Investigative Ophthalmology & Visual Science March 2018, Vol.59, 1212-1220, which is incorporated herein by reference in its entirety.

Optic neuritis is a demyelinating inflammation of the optic nerve and it typically affects young adults ranging from 18 to 45 years of age. Patients usually present with an acute reduction of visual acuity, orbital pain exacerbated by eye movements, dyschromatopsia, and an afferent papillary defect, with or without swelling of the optic nerve head. There is a strong association between optic neuritis and multiple sclerosis (MS), an acute inflammatory demyelinating disease of the central nervous system (CNS), in which optic neuritis is the initial presentation of MS for approximately 20% of MS patients and a risk of developing MS by 15 years after the onset of optic neuritis is 50%. In one embodiment, the ocular condition treated using the rAAV vectors described herein, is optic neuritis. See, Kimura et al, cited above. In another embodiment, the ocular condition is autoimmune encephalomyelitis (EAE). In another embodiment, the condition is MS.

The results shown herein indicate that delivery of the proviral plasmid or of a recombinant adeno-associated virus (AAV) containing the NRF2 cDNA to eyes of mice leads to expression of NRF2 and in animals with optic neuritis, can ameliorate the disorder. Exemplified herein are AAV2 based vectors, but in other embodiments, AAV serotypes that transduce retinal ganglion cells efficiently after intravitreal injection (such as AAV7m8 and AAV8bp, both described herein) are also useful herein.

This invention describes reagents that are useful, in one embodiment, to prevent loss of axons/myelin in the optic nerve when it faces inflammatory, autoimmune, inherited or acquired disease. The reagents are delivered directly to retinal ganglion cells, whose axons comprise the optic nerve. The delivery (intravitreal injection) can be administered as an in office treatment. The effect of the reagents to be delivered (NRF2 and SIRT) is amplified because these reagents control the function of multiple survival pathways. Both proteins are normally produced in the human retina and so will not be viewed as foreign proteins (and engender an immune response). These reagents, delivered by rAAV, can both prevent acute loss of retinal ganglion cells and also prevent their loss going forward as the disease waxes and wanes.

In one aspect, the methods and compositions described herein involve compositions and methods for delivering a nucleic acid sequence encoding nuclear factor erythroid-derived 2, like 2 (NRF2, also known as NFE2L2) protein to subjects in need thereof for the treatment of optic neuropathy. In one embodiment, such compositions involve codon optimization of the NRF2 coding sequence. Such compositions include, in one embodiment, the hNRF2 coding sequence shown in SEQ ID NO: 7. It is desirable to increase the efficacy of the product, and thus, increase safety, since a lower dose of reagent may be used. Also encompassed herein are compositions which include the native NRF2 coding sequences, as shown in SEQ ID NO: 4.

In another aspect, the methods and compositions described herein involve compositions and methods for delivering a nucleic acid sequence encoding SIRT1 protein to subjects in need thereof for the treatment of optic neuropathy. In one embodiment, such compositions involve codon optimization of the SIRT1 coding sequence. It is desirable to increase the efficacy of the product, and thus, increase safety, since a lower dose of reagent may be used. In one embodiment, the coding sequence is that shown in SEQ ID NO: 12. Also encompassed herein are compositions which include the native SIRT1 coding sequences, as shown in SEQ ID NO: 2.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

The term "percent (%) identity" , "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Identity may be determined by preparing an alignment of the sequences and through the use of a variety of algorithms and/or computer programs known in the art or commercially available [e.g., BLAST, ExPASy; ClustalO; FASTA; using, e.g., Needleman-Wunsch algorithm, Smith-Waterman algorithm]. Alignments are performed using any of a variety of publicly or commercially available Multiple Sequence Alignment Programs. Sequence alignment programs are available for amino acid sequences, e.g., the "Clustal Omega" "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Multiple sequence alignment programs are also available for nucleic acid sequences. Examples of such programs include, "Clustal Omega" "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

In one aspect, a codon optimized, engineered nucleic acid sequence encoding human NRF2 is provided. Preferably, the codon optimized NRF2 coding sequence has less than about 80% identity, preferably about 75% identity or less to the full-length native NRF2 coding sequence (SEQ ID NO: 4). In one embodiment, the codon optimized NRF2 coding sequence has about 74% identity with the native NRF2 coding sequence of SEQ ID NO: 4. In one embodiment, the codon optimized NRF2 coding sequence is characterized by improved translation rate as compared to native NRF2 following AAV-mediated delivery (e.g., rAAV). In one embodiment, the codon optimized NRF2 coding sequence shares less than about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 69%, 68%, 67%, 66%, 65%, 64%, 63%, 62%, 61% or less identity to the full length native NRF2 coding sequence of SEQ ID NO: 4. In one embodiment, the codon optimized nucleic acid sequence is a variant of SEQ ID NO: 7. In another embodiment, the codon optimized nucleic acid sequence a sequence sharing about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or greater identity with SEQ ID NO: 7. In one embodiment, the codon optimized nucleic acid sequence is SEQ ID NO: 7. In another embodiment, the nucleic acid sequence is codon optimized for expression in humans. In other embodiments, a different NRF2 coding sequence is selected.

In one aspect, a codon optimized, engineered nucleic acid sequence encoding human SIRT1 is provided. Preferably, the codon optimized SIRT1 coding sequence has less than about 80% identity, preferably about 75% identity or less to the full-length native SIRT1 coding sequence (SEQ ID NO: 2). In one embodiment, the codon optimized SIRT1 coding sequence has about 73% identity with the native SIRT1 coding sequence of SEQ ID NO: 2. In one embodiment, the codon optimized SIRT1 coding sequence is characterized by improved translation rate as compared to native SIRT1 following AAV-mediated delivery (e.g., rAAV). In one embodiment, the codon optimized SIRT1 coding sequence shares less than about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or less identity to the full length native SIRT1 coding sequence of SEQ ID NO: 2. In another embodiment, the nucleic acid sequence is codon optimized for expression in humans. In one embodiment, the nucleic acid sequence is the sequence of SEQ ID NO: 12. In other embodiments, a different SIRT1 coding sequence is selected. Codon-optimized coding regions can be designed by various different methods. This optimization may be performed using methods which are available on-line (e.g., GeneArt), published methods, or a company which provides codon optimizing services, e.g., DNA2.0 (Menlo Park, CA.). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

By "engineered" is meant that the nucleic acid sequences encoding the SIRT1 or NRF2 protein described herein are assembled and placed into any suitable genetic element, e.g., naked DNA, phage, transposon, cosmid, episome, etc., which transfers the NRF2 or SIRT1 sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

As used herein, the term "host cell" may refer to the packaging cell line in which a recombinant AAV is produced from a production plasmid. In the alternative, the term "host cell" may refer to any target cell in which expression of the coding sequence is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. In certain embodiments herein, the term "host cell" refers to the cells employed to generate and package the viral vector or recombinant virus. In other embodiments herein, the term "host cell" refers to cultures of ocular cells or other neuronal cells of various mammalian species for in vitro assessment of the compositions described herein.

Still in other embodiments, the term "host cell" is intended to reference the target cells of the subject being treated in vivo for optic neuropathy. In one embodiment, the host cell or target cell is an ocular cell. As used herein, the term "ocular cells" refers to any cell in, or associated with the function of, the eye. The term may refer to any one of photoreceptor cells, including rod photoreceptors, cone photoreceptors and photosensitive ganglion cells, retinal pigment epithelium (RPE) cells, Mueller cells, choroidal cells, bipolar cells, horizontal cells, and amacrine cells. In one embodiment, the ocular cells are ganglion cells. In another embodiment, the host cell or target cell is a neuronal cell.

In one embodiment, the nucleic acid sequence encoding SIRT1 for NRF2 further comprises a nucleic acid encoding a tag polypeptide covalently linked thereto. The tag polypeptide may be selected from known "epitope tags" including, without limitation, a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide. Exemplified herein is the use of a FLAG tag polypeptide. Another example is an HA tag. In one embodiment, the HA tag has a coding sequence reproduced as nt 4222 to nt 4248 of SEQ ID NO: 28.

In another aspect, an expression cassette comprising a nucleic acid sequence that encodes SIRT1 or NRF2 is provided. In one embodiment, the sequence is a codon optimized sequence. In another embodiment, the codon optimized nucleic acid sequence is SEQ ID NO: 7 encoding human NRF2. In another embodiment, the nucleic acid sequence is SEQ ID NO: 4 encoding human NRF2. In another embodiment, the nucleic acid sequence is SEQ ID NO: 2 encoding human SIRT. In another embodiment, the nucleic acid sequence is SEQ ID NO: 12 encoding human SIRT.

As used herein, an "expression cassette" refers to a nucleic acid molecule which comprises the coding sequences for SIRT1 or NRF2 protein, promoter, and may include other regulatory sequences therefor, which cassette may be packaged into the capsid of a viral vector (e.g., a viral particle). Typically, such an expression cassette for generating a viral vector contains the SIRT1 or NRF2 sequences described herein flanked by packaging signals of the viral genome and other expression control sequences such as those described herein. For example, for an AAV viral vector, the packaging signals are the 5' inverted terminal repeat (ITR) and the 3' ITR. When packaged into the AAV capsid, the ITRs in conjunction with the expression cassette may be referred to herein as the "recombinant AAV (rAAV) genome" or "vector genome". In one embodiment, an expression cassette comprises a codon optimized nucleic acid sequence that encodes SIRT1 for NRF2 protein. In one embodiment, the cassette provides the codon optimized SIRT1 or NRF2 operatively associated with expression control sequences that direct expression of the codon optimized nucleic acid sequence that encodes SIRT1 or NRF2 in a host cell.

In another embodiment, an expression cassette for use in an AAV vector is provided. In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the nucleic acid sequence that encodes SIRT, optionally with additional sequences which direct expression of the nucleic acid sequence that encodes SIRT1 in a host cell. In one embodiment, the 5' and 3' ITRs flank the nucleic acid sequence that encodes NRF2, optionally with additional sequences which direct expression of the nucleic acid sequence that encodes NRF2 in a host cell. Thus, as described herein, a AAV expression cassette is meant to describe an expression cassette as described above flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, the AAV vector genome comprises an AAV 5' ITR, the NRF2 or SIRT1 coding sequences and any regulatory sequences, and an AAV 3' ITR. However, other configurations of these elements may be suitable. A shortened version of the 5' ITR, termed AITR, has been described in which the D-sequence and terminal resolution site (trs) are deleted. In other embodiments, the full-length AAV 5' and 3' ITRs are used. Each rAAV genome can be then introduced into a production plasmid.

As used herein, the term "regulatory sequences", "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the NRF2 or SIRT1 and/or expression control sequences that act in trans or at a distance to control the transcription and expression thereof.

In one aspect, a vector comprising any of the expression cassettes described herein is provided. As described herein, such vectors can be plasmids of variety of origins and are useful in certain embodiments for the generation of recombinant replication defective viruses as described further herein.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and (primarily in yeast and bacteria) "artificial chromosomes." Certain plasmids are described herein.

In one embodiment, the vector is a non-viral plasmid that comprises an expression cassette described thereof, e.g., "naked DNA", "naked plasmid DNA", RNA, and mRNA; coupled with various compositions and nano particles, including, e.g., micelles, liposomes, cationic lipid - nucleic acid compositions, poly-glycan compositions and other polymers, lipid and/or cholesterol-based—nucleic acid conjugates, and other constructs such as are described herein. See, e.g., X. Su et al, Mol. Pharmaceutics, 2011, 8 (3), pp 774-787; web publication: Mar. 21, 2011; W02013/182683, WO 2010/053572 and WO 2012/170930, all of which are incorporated herein by reference. Such non-viral NRF2 or SIRT1 vector may be administered by the routes described herein. The viral vectors, or non-viral vectors, can be formulated with a physiologically acceptable carrier for use in gene transfer and gene therapy applications.

In another embodiment, the vector is a viral vector that comprises an expression cassette described therein. "Virus vectors" are defined as replication defective viruses containing the exogenous or heterologous SIRT1 or NRF2 nucleic acid transgene. In one embodiment, an expression cassette as described herein may be engineered onto a plasmid which is used for drug delivery or for production of a viral vector. Suitable viral vectors are preferably replication defective and selected from amongst those which target ocular cells. Viral vectors may include any virus suitable for gene therapy, including but not limited to adenovirus; herpes virus; lentivirus; retrovirus; parvovirus, etc. However, for ease of understanding, the adeno-associated virus is referenced herein as an exemplary virus vector.

A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In another embodiment, a recombinant adeno-associated virus (rAAV) vector is provided. The rAAV compromises an AAV capsid, and a vector genome packaged therein. The vector genome comprises, in one embodiment: (a) an AAV 5' inverted terminal repeat (ITR) sequence; (b) a promoter; (c) a coding sequence encoding a human SIRT; and (d) an AAV 3' ITR. In another embodiment, the vector genome is the expression cassette described herein. In one embodiment, the SIRT1 sequence encodes a full length protein. In one embodiment, the SIRT1 sequence is the protein sequence of SEQ ID NO: 1. In another embodiment, the coding sequence is SEQ ID NO: 2 or a variant thereof. In another embodiment, the coding sequence is SEQ ID NO: 12 or a variant thereof.

The vector genome comprises, in another embodiment: (a) an AAV 5' inverted terminal repeat (ITR) sequence; (b) a promoter; (c) a coding sequence encoding a human NRF2; and (d) an AAV 3' ITR. In another embodiment, the vector genome is the expression cassette described herein. In one embodiment, the NRF2 sequence encodes a full length protein. In one embodiment, the NRF2 sequence is the protein sequence of SEQ ID NO: 3. In another embodiment, the coding sequence is SEQ ID NO: 4 or a variant thereof. In another embodiment, the coding sequence is SEQ ID NO: 7 or a variant thereof.

Adeno-associated virus (AAV), a member of the Parvovirus family, is a small nonenveloped, icosahedral virus with single-stranded linear DNA genomes of 4.7 kilobases (kb) to 6 kb. Among known AAV serotypes are AAV1, AAV2, AAV3, AAV4, AAVS, AAV6, AAV7, AAV8, AAV9 and others. The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, VA). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

Fragments of AAV may be readily utilized in a variety of vector systems and host cells. Among desirable AAV fragments are the cap proteins, including the vp1, vp2, vp3 and hypervariable regions, the rep proteins, including rep 78, rep 68, rep 52, and rep 40, and the sequences encoding these proteins. Such fragments may be used alone, in combination with other AAV seroptype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

The term "AAV" or "AAV serotype" as used herein refers to the dozens of naturally occurring and available adeno-associated viruses, as well as artificial AAVs. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, AAV1, AAV2, AAV3, AAV4, AAV5, AAV6, AAV7, AAV8, AAV9, AAV8bp, AAV7M8 and AAVAnc80, variants of any of the known or mentioned AAVs or AAVs yet to be discovered or variants or mixtures thereof See, e.g., WO 2005/033321, which is incorporated herein by reference. In one embodiment, the AAV capsid is an AAV2 capsid. In another embodiment, the AAV capsid is an AAV8bp capsid. See, WO 2014/024282, which is incorporated herein by reference. In another embodiment, the AAV capsid is an AAV7m8 capsid, which has shown preferential delivery to the outer retina. See, Dalkara et al, In Vivo-Directed Evolution of a New Adeno-Associated Virus for Therapeutic Outer Retinal Gene Delivery from the Vitreous, Sci Transl Med 5, 189ra76 (2013), which is incorporated herein by reference. In another embodiment, the rAAV capsid is selected from an AAV8 capsid or variant thereof, an AAV6 capsid or variant thereof, an AAV9 capsid or variant thereof, an AAV7 capsid or variant thereof, an AAV5 capsid or variant thereof, an AAV2 capsid or variant thereof, an AAV1 capsid or variant thereof, an AAV3 capsid or variant thereof, and an AAV4 capsid or variant thereof.

In one embodiment, a recombinant adeno-associated virus (rAAV) vector is provided which comprises an AAV7m8 capsid and an expression cassette described herein, wherein said expression cassette comprises nucleic acid sequences encoding SIRT1, inverted terminal repeat sequences and expression control sequences that direct expression of SIRT1 in a host cell.

In one embodiment, a recombinant adeno-associated virus (rAAV) vector is provided which comprises an AAV7m8 capsid and an expression cassette described herein, wherein said expression cassette comprises nucleic acid sequences encoding NRF2, inverted terminal repeat sequences and expression control sequences that direct expression of NRF2 in a host cell.

In one embodiment, a recombinant adeno-associated virus (rAAV) vector is provided which comprises an AAV2 capsid and an expression cassette described herein, wherein said expression cassette comprises nucleic acid sequences encoding SIRT1, inverted terminal repeat sequences and expression control sequences that direct expression of SIRT1 in a host cell.

In one embodiment, a recombinant adeno-associated virus (rAAV) vector is provided which comprises an AAV2 capsid and an expression cassette described herein, wherein said expression cassette comprises nucleic acid sequences encoding NRF2, inverted terminal repeat sequences and expression control sequences that direct expression of NRF2 in a host cell.

In still a further embodiment, a recombinant adeno-associated virus (AAV) vector is provided for delivery of the SIRT1 or NRF2 constructs and optimized sequences described herein. An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10) and (Dalkara D, Byrne L C, Klimczak R R, Visel M, Yin L, Merigan W H, et al. In vivo-directed evolution of a new adeno-associated virus for therapeutic outer retinal gene delivery from the vitreous. Sci Transl Med (2013) 5(189): 189ra76. doi: 10.1126/scitranslmed.3005708.) (AAV7m8). Each of these documents is incorporated herein by reference. These documents also describe other AAV capsids which may be selected for generating AAV and are incorporated by reference. In some embodiments, an AAV cap for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

As used herein, relating to AAV, the term variant means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV7m8 over the vp1, vp2 or vp3. In one embodiment, the AAV capsid shares at least 95% identity with the AAV2 over the vp1, vp2 or vp3. In another embodiment, the capsid is an AAV8 capsid with Y447F, Y733F and T494V mutations (also called "AAV8(C&G+T494V)" and "rep2-cap8 (Y447F+733F+T494V)"), as described by Kay et al, Targeting Photoreceptors via Intravitreal Delivery Using Novel, Capsid-Mutated AAV Vectors, PLoS One. 2013; 8(4): e62097. Published online 2013 Apr. 26, which is incorporated herein by reference.

In one embodiment, it is desirable to utilize an AAV capsid, which shows tropism for the desired target cell, e.g., ganglion or other ocular cells. In one embodiment, the AAV capsid is a tyrosine capsid-mutant in which certain surface exposed tyrosine residues are substituted with phenylalanine (F). Such AAV variants are described, e.g., in Mowat et al, Tyrosine capsid-mutant AAV vectors for gene delivery to the canine retina from a subretinal or intravitreal approach, Gene Therapy 21, 96-105 (January 2014), which is incorporated herein by reference.

In one embodiment, the AAV capsid is chosen from those that effectively transduce neuronal cells. In one embodiment, the AAV capsid is selected from AAV1, AAV2, AAV7, AAV8, AAV9, AAVrh.10, AAVS, AAVhu.11, AAV8DJ, AAVhu.32, AAVhu.37, AAVpi.2, AAVrh.8, AAVhu.48R3 and variants thereof See, Royo, et al, Brain Res, 2008 January, 1190:15-22; Petrosyan et al, Gene Therapy, 2014 December, 21(12):991-1000; Holehonnur et al, BMC Neuroscience, 2014, 15:28; and Cearley et al, Mol Ther. 2008 October; 16(10): 1710-1718, each of which is incorporated herein by reference.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/7m8 and AAV2/8bp are exemplary pseudotyped vectors.

In another embodiment, a self-complementary AAV is used. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

In still another embodiment, the expression cassette, including any of those described herein is employed to generate a recombinant AAV genome.

In one embodiment, the expression cassette described herein is engineered into a suitable genetic element (vector) useful for generating viral vectors and/or for delivery to a host cell, e.g., naked DNA, phage, transposon, cosmid, episome, etc., which transfers the SIRT1 or NRF2 sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY.

For packaging an expression cassette or rAAV genome or production plasmid into virions, the ITRs are the only AAV components required in cis in the same construct as the expression cassette. In one embodiment, the coding sequences for the replication (rep) and/or capsid (cap) are removed from the AAV genome and supplied in trans or by a packaging cell line in order to generate the AAV vector.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

In yet another system, the expression cassette flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

"Plasmids" generally are designated herein by a lower case p preceded and/or followed by capital letters and/or numbers, in accordance with standard naming conventions that are familiar to those of skill in the art. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

In one aspect, a production plasmid comprising an expression cassette comprising hNRF2 described above is provided. In one embodiment, the production plasmid is that shown in SEQ ID NO: 5, and FIG. 1. In another embodiment, the production plasmid is that shown in SEQ ID NO: 8. In another embodiment, the production plasmid is that shown in SEQ ID NO: 10. In another embodiment, the production plasmid is that shown in SEQ ID NO: 21. In another embodiment, the production plasmid is that shown in SEQ ID NO: 22. In another embodiment, the production plasmid is that shown in SEQ ID NO: 23. In another embodiment, the production plasmid is that shown in SEQ ID NO: 24. In another embodiment, the production plasmid is that shown in SEQ ID NO: 25. In another embodiment, the production plasmid is that shown in SEQ ID NO: 26. In another embodiment, the production plasmid is that shown in SEQ ID NO: 27. In another embodiment, the production plasmid is that shown in SEQ ID NO: 28. These plasmids are used in the examples for generation of the rAAV-human NRF2 vectors. In another aspect, a production plasmid comprising an expression cassette comprising hSIRT1 described above is provided. In one embodiment, the production plasmid is that shown in SEQ ID NO: 6, and FIG. 2. In another embodiment, the production plasmid is that shown in SEQ ID NO: 9. In another embodiment, the production plasmid is that shown in SEQ ID NO: 13. In another embodiment, the production plasmid is that shown in SEQ ID NO: 14. In another embodiment, the production plasmid is that shown in SEQ ID NO: 15. In another embodiment, the production plasmid is that shown in SEQ ID NO: 16. In another embodiment, the production plasmid is that shown in SEQ ID NO: 17. In another embodiment, the production plasmid is that shown in SEQ ID NO: 18. In another embodiment, the production plasmid is that shown in SEQ ID NO: 19. In another embodiment, the production plasmid is that shown in SEQ ID NO: 20. This plasmid is used in the examples for generation of the rAAV-human SIRT1 vector. Such a plasmid is one that contains a 5' AAV ITR sequence; a selected promoter; a polyA sequence; and a 3' ITR; additionally, it also contains a stuffer sequence, such as lambda.

In one embodiment, a non-coding lambda stuffer region is included in the vector backbone. An example of p643 which includes the hNRF2 coding sequence can be found in SEQ ID NO: 5. An example of p643 which includes the hSIRT1 coding sequence can be found in SEQ ID NO: 6. In another embodiment, the production plasmid is modified to optimized vector plasmid production efficiency. Such modifications include addition of other neutral sequences, or deletion of portion(s) of or the entire lambda stuffer sequence to modulate the level of supercoil of the vector plasmid. Such modifications are contemplated herein. In other embodiments, terminator and other sequences are included in the plasmid.

In one embodiment, the rAAV vector genome is of a size between about 3 kilobases (kb) to about 6 kb, about 4.7 kb to about 6 kb, about 3 kb to about 5.5 kb, or about 4.7 kb to 5.5 kb.

In certain embodiments, the rAAV expression cassette, the vector (such as rAAV vector), the virus (such as rAAV), or the production plasmid comprises AAV inverted terminal repeat sequences, a nucleic acid sequence that encodes NRF2, and expression control sequences that direct expression of the encoded protein in a host cell. In other embodiments, the rAAV expression cassette, the virus, the vector (such as rAAV vector), or the production plasmid further comprise one or more of an intron, a Kozak sequence, a polyA, post-transcriptional regulatory elements and others. In one embodiment, the post-transcriptional regulatory element is Woodchuck Hepatitis Virus (WHP) Posttranscriptional Regulatory Element (WPRE).

In certain embodiments, the rAAV expression cassette, the vector (such as rAAV vector), the virus (such as rAAV), or the production plasmid comprises AAV inverted terminal repeat sequences, a nucleic acid sequence that encodes SIRT1, and expression control sequences that direct expression of the encoded protein in a host cell. In other embodiments, the rAAV expression cassette, the virus, the vector (such as rAAV vector), or the production plasmid further comprise one or more of an intron, a Kozak sequence, a polyA, post-transcriptional regulatory elements and others. In one embodiment, the post-transcriptional regulatory element is Woodchuck Hepatitis Virus (WHP) Posttranscriptional Regulatory Element (WPRE).

The expression cassettes, vectors and plasmids include other components that can be optimized for a specific species using techniques known in the art including, e.g, codon optimization, as described herein. The components of the cassettes, vectors, plasmids and viruses or other compositions described herein include a promoter sequence as part of the expression control sequences. In another embodiment, the promoter is cell-specific. The term "cell-specific" means that the particular promoter selected for the recombinant vector can direct expression of the NRF2 or SIRT1 coding sequence in a particular cell type. In one embodiment, the promoter is specific for expression of the transgene in ocular cells. In one embodiment, the promoter is specific for expression of the transgene in ganglion cells. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In one embodiment, the photoreceptor-specific promoter is a human rhodopsin kinase promoter. The rhodopsin kinase promoter has been shown to be active in both rods and cones. See, e.g., Sun et al, Gene Therapy with a Promoter Targeting Both Rods and Cones Rescues Retinal Degeneration Caused by AIPL1 Mutations, Gene Ther. 2010 January; 17(1): 117-131, which is incorporated herein by reference in its entirety. In one embodiment, the promoter is modified to add one or more restriction sites to facilitate cloning.

In another embodiment, a neuron-specific promoter is used [see, e.g., the Lockery Lab neuron-specific promoters database, accessed at html]. Such neuron-specific promoters include, without limitation, e.g., synapsin I (SYN), calcium/calmodulin-dependent protein kinase II, tubulin alpha I, neuron-specific enolase and platelet-derived growth factor beta chain promoters. See, Hioki et al, Gene Therapy, June 2007, 14(11):872-82, which is incorporated herein by reference. Other neuron-specific promoters include the 67 kDa glutamic acid decarboxylase (GAD67), homeobox Dlx5/6, glutamate receptor 1 (GluR1), preprotachykinin 1 (Tac1) promoter, neuron-specific enolase (NSE) and dopaminergic receptor 1 (Drd1a) promoters. See, e.g., Delzor et al, Human Gene Therapy Methods. August 2012, 23(4): 242-254. In another embodiment, the promoter is a GUSb promoter (available on the world wide web at jci.org/articles/view/41615#B30).

In another embodiment, the promoter is a human rhodopsin promoter. In one embodiment, the promoter is modified to include restriction on the ends for cloning. See, e.g, Nathans and Hogness, Isolation and nucleotide sequence of the gene encoding human rhodopsin, PNAS, 81:4851-5 (August 1984), which is incorporated herein by reference in its entirety. In another embodiment, the promoter is a portion or fragment of the human rhodopsin promoter. In another embodiment, the promoter is a variant of the human rhodopsin promoter.

Other exemplary promoters include the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference in its entirety). In another preferred embodiment, the promoter is the human interphotoreceptor retinoid-binding protein proximal (IRBP) promoter. In one embodiment, the promoter is a 235 nt fragment of the hIRBP promoter. In one embodiment, the promoter is the RPGR proximal promoter (Shu et al, IOVS, May 2102, which is incorporated by reference in its entirety). Other promoters useful in the invention include, without limitation, the rod opsin promoter, the red-green opsin promoter, the blue opsin promoter, the cGMP-β-phosphodiesterase promoter (Qgueta et al, IOVS, Invest Ophthalmol Vis Sci. 2000 December;41 (13):4059-63), the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10): e13025), the RPE65 promoter; the retinal degeneration slow/peripherin 2 (Rds/perph2) promoter (Cai et al, Exp Eye Res. 2010 August;91(2):186-94); and the VMD2 promoter (Kachi et al, Human Gene Therapy, 2009 (20:31-9)). Each of these documents is incorporated by reference herein in its entirety. In another embodiment, the promoter is selected from human human EF1α promoter, rhodopsin promoter, rhodopsin kinase, interphotoreceptor binding protein (IRBP), cone opsin promoters (red-green, blue), cone opsin upstream sequences containing the red-green cone locus control region, cone transducing, and transcription factor promoters (neural retina leucine zipper (Nr1) and photoreceptor-specific nuclear receptor Nr2e3, bZIP).

In another embodiment, the promoter is a ubiquitous or constitutive promoter. An example of a suitable promoter is a hybrid chicken β-actin (CBA) promoter with cytomegalovirus (CMV) enhancer elements, such as the sequence shown in nt 1443-3104 of SEQ ID NO: 5. In another embodiment, the promoter is the CB7 promoter. Other suitable promoters include the human β-actin promoter, the human elongation factor-1α promoter, the cytomegalovirus (CMV) promoter, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PLoS ONE 9(8): e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. Other promoters may be selected by one of skill in the art.

In a further embodiment, the promoter is selected from SV40 promoter, the dihydrofolate reductase promoter, and the phosphoglycerol kinase (PGK) promoter, rhodopsin kinase promoter, the rod opsin promoter, the red-green opsin promoter, the blue opsin promoter, the inter photoreceptor binding protein (IRBP) promoter and the cGMP-β-phosphodiesterase promoter, a phage lambda (PL) promoter, a herpes simplex viral (HSV) promoter, a tetracycline-controlled trans-activator-responsive promoter (tet) system, a long terminal repeat (LTR) promoter, such as a RSV LTR, MoMLV LTR, BIV LTR or an HIV LTR, a U3 region promoter of Moloney murine sarcoma virus, a Granzyme A promoter, a regulatory sequence(s) of the metallothionein gene, a CD34 promoter, a CD8 promoter, a thymidine kinase (TK) promoter, a B19 parvovirus promoter, a PGK promoter, a glucocorticoid promoter, a heat shock protein (HSP) promoter, such as HSP65 and HSP70 promoters, an immunoglobulin promoter, an MMTV promoter, a Rous sarcoma virus (RSV) promoter, a lac promoter, a CaMV 35S promoter, a nopaline synthetase promoter, an MND promoter, or an MNC promoter. The promoter sequences thereof are known to one of skill in the art or available publically, such as in the literature or in databases, e.g., GenBank, PubMed, or the like.

In another embodiment, the promoter is an inducible promoter. The inducible promoter may be selected from known promoters including the rapamycin/rapalog promoter, the ecdysone promoter, the estrogen-responsive promoter, and the tetracycline-responsive promoter, or heterodimeric repressor switch. See, Sochor et al, An Autogenously Regulated Expression System for Gene Therapeutic Ocular Applications. Scientific Reports, 2015 Nov. 24;5:17105 and Daber R, Lewis M., A novel molecular switch. J Mol Biol. 2009 Aug. 28;391(4):661-70, Epub 2009 Jun. 21 which are both incorporated herein by reference in their entirety.

In a further embodiment, the promoter is a chicken beta-actin promoter with a nucleic acid sequence from nt 1443-3104 of SEQ ID NO: 5.

In one embodiment, the promoter is a human gamma-synuclein gene (i.e., human gamma-synuclein, human SNCG, hSNCG) promoter, such as the sequence shown in nt 1433 to nt 2362 of SEQ ID NO: 28. Also see, e.g., Chaffiol A et al. A New Promoter Allows Optogenetic Vision Restoration with Enhanced Sensitivity in Macaque Retina. Mol Ther. 2017 Nov. 1;25(11):2546-2560. doi: 10.1016/j.ymthe.2017.07.011. Epub 2017 Jul. 20.

In other embodiments, the expression cassette, vector, plasmid and virus described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein.

Examples of suitable polyA sequences include, e.g., a synthetic polyA or from bovine growth hormone (bGH), human growth hormone (hGH), SV40, rabbit β-globin (RGB), or modified RGB (mRGB). In a further embodiment, the poly A has a nucleic acid sequence from nt 5039 to nt 5246 of SEQ ID NO: 5.

In one embodiment, he expression cassette, vector, plasmid and virus described herein comprise a post-transcriptional regulatory element. In one embodiment, the post-transcriptional regulatory element is Woodchuck Hepatitis Virus (WHP) Posttranscriptional Regulatory Element (WPRE). Examples of sequence encoding a suitable WPRE are shown in SEQ ID NOs: 18, 19, 20, 25, 26, 27, and 28, e.g., nt 4279 to nt 4820 of SEQ ID NO: 28.

Examples of suitable enhancers include, e.g., the CMV enhancer, the RSV enhancer, the alpha fetoprotein enhancer, the TTR minimal promoter/enhancer, LSP (TH-binding globulin promoter/alphal-microglobulin/bikunin enhancer), an APB enhancer, ABPS enhancer, an alpha mic/bik enhancer, TTR enhancer, en34, ApoE amongst others.

In one embodiment, a Kozak sequence is included upstream of the hNRF2 or hSIRT1 coding sequence to enhance translation from the correct initiation codon. In one embodiment, the hNRF2 or hSIRT1 coding sequence is placed under the control of a hybrid chicken β actin (CBA) promoter. This promoter consists of the cytomegalovirus (CMV) immediate early enhancer, the proximal chicken β actin promoter, and optionally, the CBA exon 1 flanked by intron 1 sequences. In another embodiment, the intron is selected from CBA, human beta globin, IVS2, SV40, bGH, alpha-globulin, beta-globulin, collagen, ovalbumin, p53, or a fragment thereof.

In one embodiment, the expression cassette, the vector, the plasmid and the virus contain a 5' ITR, chicken beta-actin (CBA) promoter, CMV enhancer, human NRF2 coding sequence, bGH poly A and 3' ITR. In a further embodiment, the vector genome includes nt 1253 to 5425 of SEQ ID NO: 5. In yet a further embodiment, the 5' ITR has a nucleic acid sequence from nt 1253 to nt 1382 of SEQ ID NO: 5 and the 3' ITR has a nucleic acid sequence from nt 5296 to nt 5425 of SEQ ID NO: 5. In a further embodiment, the production plasmid has a sequence of SEQ ID NO: 5, also shown in FIG. 1. In a further embodiment, the production plasmid has a sequence of SEQ ID NO: 8. In a further embodiment, the production plasmid has a sequence of SEQ ID NO: 10. In a further embodiment, the production plasmid has a sequence of SEQ ID NO: 21. In a further embodiment, the production plasmid has a sequence of SEQ ID NO: 22. In a further embodiment, the production plasmid has a sequence of SEQ ID NO: 23. In a further embodiment, the production plasmid has a sequence of SEQ ID NO: 24. In a further embodiment, the vector genome includes nt 1253 to 5351 of SEQ ID NO: 8. In a further embodiment, the vector genome includes nt 1253 to 5359 of SEQ ID NO: 10. In a further embodiment, the vector genome comprises nt 1253 to nt 5359 of SEQ ID NO: 21. In a further embodiment, the vector genome comprises nt 1253 to nt 5425 of SEQ ID NO: 22. In a further embodiment, the vector genome comprises nt 1253 to nt 5351 of SEQ ID NO: 23. In a further embodiment, the vector genome comprises nt 1253 to nt 5378 of SEQ ID NO: 24.

In one embodiment, the expression cassette, the vector, the plasmid and the virus contain a 5' ITR, a hSNCG promoter, human NRF2 coding sequence, bGH poly A and 3' ITR. In one embodiment, the expression cassette, the vector, the plasmid and the virus contain a 5' ITR, a hSNCG promoter, human NRF2 coding sequence, a WPRE sequence, bGH poly A and 3' ITR. In a further embodiment, the vector genome comprises nt 1253 to nt 5253 of SEQ ID NO: 27. In yet a further embodiment, the 5' ITR has a nucleic acid sequence from nt 1253 to nt 1382 of SEQ ID NO: 27 and the 3' ITR has a nucleic acid sequence from nt 5124 to nt 5253 of SEQ ID NO: 27. In a further embodiment, the production plasmid has a sequence of SEQ ID NO: 25. In a further embodiment, the production plasmid has a sequence of SEQ ID NO: 26. In a further embodiment, the production plasmid has a sequence of SEQ ID NO: 27. In a further embodiment, the production plasmid has a sequence of SEQ ID NO: 28. In a further embodiment, the vector genome comprises nt 1253 to nt 5253 of SEQ ID NO: 25. In a further embodiment, the vector genome comprises nt 1253 to nt 5280 of SEQ ID NO: 26. In a further embodiment, the vector genome comprises nt 1253 to nt 5280 of SEQ ID NO: 28.

In one embodiment, the expression cassette, the vector, the plasmid and the virus contain a 5' ITR, chicken beta-actin (CBA) promoter, CMV enhancer, human SIRT1 coding sequence, bGH poly A and 3' ITR. In a further embodiment, the expression cassette includes nt 1253 to 5854 of SEQ ID NO: 6. In yet a further embodiment, the 5' ITR has a nucleic acid sequence from nt 1253 to nt 1382 of SEQ ID NO: 6 and the 3' ITR has a nucleic acid sequence from nt 5725 to nt 5854 of SEQ ID NO: 6. In a further embodiment, the production plasmid has a sequence of SEQ ID NO: 6, also shown in FIG. 2. In a further embodiment, the production plasmid has a sequence of SEQ ID NO: 9. In a further embodiment, the production plasmid has a sequence of SEQ ID NO: 11. In a further embodiment, the production plasmid has a sequence of SEQ ID NO: 13. In a further embodiment, the production plasmid has a sequence of SEQ ID NO: 14. In a further embodiment, the production plasmid has a sequence of SEQ ID NO: 15. In a further embodiment, the production plasmid has a sequence of SEQ ID NO: 16. In a further embodiment, the production plasmid has a sequence of SEQ ID NO: 17. In a further embodiment, the expression cassette includes nt 1253 to 5788 of SEQ ID NO: 9. In a further embodiment, the expression cassette comprises nt 1253 to 5792 of SEQ ID NO: 11. In a further embodiment, the expression cassette comprises nt 1253 to nt 5777 of SEQ ID NO: 13. In a further embodiment, the expression cassette comprises nt 1253 to nt 5854 of SEQ ID NO: 14. In a further embodiment, the expression cassette comprises nt 1253 to nt 5792 of SEQ ID NO: 15. In a further embodiment, the expression cassette comprises nt 1253 to nt 5819 of SEQ ID NO: 16. In a further embodiment, the expression cassette comprises nt 1253 to nt 5777 of SEQ ID NO: 17.

In one embodiment, the expression cassette, the vector, the plasmid and the virus contain a 5' ITR, a hSNCG promoter, human SIRT1 coding sequence, bGH poly A and 3' ITR. In one embodiment, the expression cassette, the vector, the plasmid and the virus contain a 5' ITR, a hSNCG promoter, human SIRT1 coding sequence, a WPRE sequence, bGH poly A and 3' ITR. In a further embodiment, the expression cassette comprises nt 1253 to nt 5694 of SEQ ID NO: 19. In yet a further embodiment, the 5' ITR has a nucleic acid sequence from nt 1253 to nt 1382 of SEQ ID NO: 19 and the 3' ITR has a nucleic acid sequence from nt 5565 to nt 5694 of SEQ ID NO: 19. In a further embodiment, the production plasmid has a sequence of SEQ ID NO: 19. In a further embodiment, the production plasmid has a sequence of SEQ ID NO: 18. In a further embodiment, the production plasmid has a sequence of SEQ ID NO: 20. In a further embodiment, the expression cassette comprises nt 1253 to nt 5706 of SEQ ID NO: 18. In a further embodiment, the expression cassette comprises nt 1253 to nt 5721 of SEQ ID NO: 20.

In certain embodiments, provided herein are the vector genome, the vector (such as rAAV vector), the virus (such as rAAV), or the production plasmid, as shown in FIGS. 1, 2, and 10 to 25.

In some embodiments, where a WPRE sequence is included in the vector genome, an alternate embodiment is contemplated wherein the WPRE is absent.

In another aspect, a method for treating ocular neuropathy and/or restoring visual function in a subject having in need thereof comprises delivering to a subject in need thereof a vector (such as rAAV) which encodes hNRF2, as described herein. In one embodiment, a method of treating a subject having ocular neuropathy with a rAAV described herein is provided.

In another aspect, a method for treating ocular neuropathy and/or restoring visual function in a subject having in need thereof comprises delivering to a subject in need thereof a vector (such as rAAV) which encodes hSIRT1, as described herein. In one embodiment, a method of treating a subject having ocular neuropathy with a rAAV described herein is provided.

In another aspect, a method of preserving retinal ganglion cell (RGC) function in a subject, comprising administering the an rAAV as described herein, is provided.

By "administering" as used in the methods means delivering the composition to the target cell. In one embodiment, the method involves delivering the composition by subretinal injection to the ganglion or other ocular cells. In another embodiment, intravitreal injection to the subject is employed. In another embodiment, subretinal injection to the subject is employed. In still another method, intravascular injections, such as injection via the palpebral vein may be employed. Still other methods of administration may be selected by one of skill in the art given this disclosure.

By "administering" or "route of administration" is meant delivery of a composition described herein, with or without a pharmaceutical carrier or excipient, to the subject. Routes of administration may be combined, if desired. In some embodiments, the administration is repeated periodically. The pharmaceutical compositions described herein are designed for delivery to subjects in need thereof by any suitable route or a combination of different routes. In some embodiments, direct delivery to the eye (optionally via ocular delivery, subretinal injection, intra-retinal injection, intravitreal, topical), or delivery via systemic routes is employed, e.g., intravascular, intraarterial, intraocular, intravenous, intramuscular, subcutaneous, intradermal, and other parental routes of administration. The nucleic acid molecules, the expression cassette and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

Also provided herein are pharmaceutical compositions. The pharmaceutical compositions described herein are designed for delivery to subjects in need thereof by any suitable route or a combination of different routes. In some embodiments, these delivery means are designed to avoid direct systemic delivery of the suspension containing the AAV composition(s) described herein. Suitably, this may have the benefit of reducing dose as compared to systemic administration, reducing toxicity and/or reducing undesirable immune responses to the AAV and/or transgene product.

In yet other aspects, these nucleic acid sequences, vectors, expression cassettes and rAAV viral vectors are useful in a pharmaceutical composition, which also comprises a pharmaceutically acceptable carrier, excipient, buffer, diluent, surfactant, preservative and/or adjuvant, etc. Such pharmaceutical compositions are used to express the NRF2 or SIRT1 in the host cells through delivery by such recombinantly engineered AAVs or artificial AAVs.

To prepare these pharmaceutical compositions containing the nucleic acid sequences, vectors, expression cassettes and rAAV viral vectors, the sequences or vectors or viral vector is preferably assessed for contamination by conventional methods and then formulated into a pharmaceutical composition suitable for administration to the eye. Such formulation involves the use of a pharmaceutically and/or physiologically acceptable vehicle or carrier, particularly one suitable for administration to the eye, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, surfactant, or excipient etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Patent Publication No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravitreal or subretinal delivery, a pH of 6.8 to about 7.2 may be desired. However, other pHs within the broadest ranges and these subranges may be selected for other route of delivery.

A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate .7H2O), potassium chloride, calcium chloride (e.g., calcium chloride .2H2O), dibasic sodium phosphate, and mixtures thereof, in water. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intravitreal delivery. In one example, the composition is formulated for subretinal delivery.

In one exemplary specific embodiment, the composition of the carrier or excipient contains 180 mM NaCl, 10 mM NaPi, pH7.3 with 0.0001% -0.01% Pluronic F68 (PF68). The exact composition of the saline component of the buffer ranges from 160 mM to 180 mM NaCl. Optionally, a different pH buffer (potentially HEPES, sodium bicarbonate, TRIS) is used in place of the buffer specifically described. Still alternatively, a buffer containing 0.9% NaCl is useful.

In the case of AAV viral vectors, quantification of the genome copies ("GC"), vector genomes ("VG"), or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). In another method the effective dose of a recombinant adeno-associated virus carrying a nucleic acid sequence encoding the NRF2 or SIRT1 coding sequence is measured as described in S. K. McLaughlin et al, 1988 J. Virol., 62:1963, which is incorporated by reference in its entirety.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the nucleic acid sequences encoding NRF2 or SIRT1 as described herein that is in the range of about $1.0\times10^9$ GC to about $1.0\times10^{15}$ GC per dose including all integers or fractional amounts within the range. In one embodiment, the compositions are formulated to contain at least $1\times10^9$, $2\times10^9$, $3\times10^9$, $4\times10^9$, $5\times10^9$, $6\times10^9$, $7\times10^9$, $8\times10^9$, or $9\times10^9$ GC per dose including all integers or fractional amounts within the range. In another embodiment, the compositions are formulated to contain at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per dose including all integers or fractional amounts within the range. In another embodiment, the compositions are formulated to contain at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per dose including all integers or fractional amounts within the range. In another embodiment, the compositions are formulated to contain at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, for human application the dose can range from $1\times10^{10}$ to about $1\times10^{12}$ GC per dose including all integers or fractional amounts within the range. All dosages may be measured by any known method, including as measured by oqPCR or digital droplet PCR (ddPCR) as described in, e.g., M. Lock et al, Hum Gene Ther Methods. 2014 April;25(2):115-25. doi: 10.1089/hgtb.2013.131, which is incorporated herein by reference.

In one embodiment, an aqueous suspension suitable for administration to a patient with an ocular disorder is provided. The suspension comprises an aqueous suspending liquid and about $1\times10^9$ GC or viral particles to about $1\times10^{11}$ GC or viral particles per eye of a recombinant adeno-associated virus (rAAV) described herein useful as a therapeutic for an ocular disorder described herein. In one embodiment, the ocular disorder is optic neuritis.

It may also be desirable to administer multiple "booster" dosages of the pharmaceutical compositions of this invention. For example, depending upon the duration of the transgene within the ocular target cell, one may deliver booster dosages at 6 month intervals, or yearly following the first administration. The fact that AAV-neutralizing antibodies were not generated by administration of the rAAV vector should allow additional booster administrations.

Such booster dosages and the need therefor can be monitored by the attending physicians, using, for example, the retinal and visual function tests and the visual behavior tests described in the examples below. Other similar tests may be used to determine the status of the treated subject over time. Selection of the appropriate tests may be made by the attending physician. Still alternatively, the method of this invention may also involve injection of a larger volume of virus-containing solution in a single or multiple injection to allow levels of visual function close to those found in wildtype retinas.

In another embodiment, the amount of the vectors, the virus and the replication-defective virus described herein carrying the codon optimized nucleic acid sequences encoding SIRT1 or NRF2 are in the range of about $1.0\times10^7$ VG per eye to about $1.0\times10^{15}$ VG per eye including all integers or fractional amounts within the range. In one embodiment, the amount thereof is at least $1\times10^7$, $2\times10^7$, $3\times10^7$, $4\times10^7$, $5\times10^7$, $6\times10^7$, $7\times10^7$, $8\times10^7$, or $9\times10^7$ VG per eye including all integers or fractional amounts within the range. In one embodiment, the amount thereof is at least $1\times10^8$, $2\times10^8$, $3\times10^8$, $4\times10^8$, $5\times10^8$, $6\times10^8$, $7\times10^8$, $8\times10^8$, or $9\times10^8$ VG per eye including all integers or fractional amounts within the range. In one embodiment, the amount thereof is at least $1\times10^9$, $2\times10^9$, $3\times10^9$, $4\times10^9$, $5\times10^9$, $6\times10^9$, $7\times10^9$, $8\times10^9$, or $9\times10^9$ VG per eye including all integers or fractional amounts within the range. In one embodiment, the amount thereof is at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ VG per eye including all integers or fractional amounts within the range. In one embodiment, the amount thereof is at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ VG per eye including all integers or fractional amounts within the range. In one embodiment, the amount thereof is at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ VG per eye including all integers or fractional amounts within the range. In one embodiment, the amount thereof is at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ VG per eye including all integers or fractional amounts within the range. In one embodiment, the amount thereof is at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ VG per eye including all integers or fractional amounts within the range. In one embodiment, the amount thereof is at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, the methods comprises dose ranging from $1\times10^9$to about $1\times10^{13}$ VG per eye per dose including all integers or fractional amounts within the range. In another embodiment, the method comprises delivery of the vector in an aqueous suspension. In another embodiment, the method comprises administering the rAAV described herein in a dosage of from $1\times10^9$ to $1\times10^{13}$ GC in a volume about or at least 150 microliters, thereby restoring visual function in said subject. All dosages may be measured by any known method, including as measured by oqPCR or digital droplet PCR (ddPCR) as described in, e.g., M. Lock et al, Hum Gene Ther Methods. 2014 April;25(2):115-25. doi: 10.1089/hgtb.2013.131, which is incorporated herein by reference.

These above doses may be administered in a variety of volumes of carrier, excipient or buffer formulation, ranging from about 25 to about 1000 microliters, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 kμL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is about 800 μL. In another embodiment, the volume is between about 150 and 800 μL. In another embodiment, the volume is between about 700 and 1000 μL. In another embodiment, the volume is between about 250 and 500 μL.

In one embodiment, the viral constructs may be delivered in doses of from at least $1\times10^9$ to about least $1\times10^{11}$ GCs in volumes of about 14, to about 3 μL for small animal subjects, such as mice. For larger veterinary subjects having eyes about the same size as human eyes, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the ocular condition and the degree to which the disorder, if progressive, has developed.

Yet another aspect described herein is a method for treating, retarding or halting progression of optic neuropathy or optic neuritis in a mammalian subject. In one embodiment, an rAAV carrying the SIRT1 or NRF2 native, modified or codon optimized sequence, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of optic neuropathy or optic neuritis, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. The dosages, administrations and regimens may be determined by the attending physician given the teachings of this specification. In one embodiment, the composition is administered in a single dosage selected from those above listed in an affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages). In another embodiment, multiple injections are made in different portions of the same eye. In another embodiment, a second administration of an rAAV including the selected expression cassette (e.g., SIRT1 or NRF2 containing cassette) is performed at a later time point. Such time point may be weeks, months or years following the first administration. Such second administration is, in one embodiment, performed with an rAAV having a different capsid than the rAAV from the first administration. In another embodiment, the rAAV from the first and second administration have the same capsid.

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention, it is desirable to perform non-invasive retinal imaging and functional studies to identify areas of the ganglion cells to be targeted for therapy as well as to test the efficacy of treatment. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, Multi-electrode array (MEA), Pupillary Light Responses, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described herein, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged ocular cells is impacted. In another embodiment, the volume and/or concentration of the rAAV composition is a greater amount, in order reach larger portions of the eye, including non-damaged ganglion cells.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference, optical coherence tomography (to measure thickness of various layers of the retina), histology (retinal thickness, rows of nuclei in the outer nuclear layer, immunofluorescence to document transgene expression, cone photoreceptor counting, staining of retinal sections with peanut agglutinin—which identifies cone photoreceptor sheaths).

Specifically for human subjects, following administration of a dosage of a composition described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics laser scanning ophthalmoscopy, mobility testing, test of reading speed and accuracy, microperimetry and/or ophthalmoscopy. These and other efficacy tests are described in U.S. Pat. No. 8,147,823; in co-pending International patent application publication WO 2014/011210 or WO 2014/124282, incorporated by reference.

In one embodiment of the methods described herein, a one-time intra-ocular delivery of a composition as described herein, e.g., an AAV delivery of an hNRF2 cassette, is useful in treating optic neuropathy or optic neuritis in a subject. In another embodiment of the methods described herein, a one-time intra-ocular delivery of a composition as described herein, e.g., an AAV delivery of an hNRF2 cassette, is useful in treating optic neuropathy or optic neuritis in a subject at risk.

In one embodiment of the methods described herein, a one-time intra-ocular delivery of a composition as described herein, e.g., an AAV delivery of an hSIRT1 cassette, is useful in treating optic neuropathy or optic neuritis in a subject. In another embodiment of the methods described herein, a one-time intra-ocular delivery of a composition as described herein, e.g., an AAV delivery of an hSIRT1 cassette, is useful in treating optic neuropathy or optic neuritis in a subject at risk.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the RGCs are functioning or remaining, as compared to a non-diseased eye. In one embodiment, neonatal treatment is defined as being administered a SIRT1 or NRF2 coding sequence, expression cassette or vector as described herein within 8 hours, the first 12 hours, the first 24 hours, or the first 48 hours of delivery. In another embodiment, particularly for a primate (human or non-human), neonatal delivery is within the period of about 12 hours to about 1 week, 2 weeks, 3 weeks, or about 1 month, or after about 24 hours to about 48 hours. In another embodiment, the composition is delivered after onset of symptoms. In one embodiment, treatment of the patient (e.g., a first injection) is initiated prior to the first year of life. In another embodiment, treatment is initiated after the first 1 year, or after the first 2 to 3 years of age, after 5 years of age, after 11 years of age, or at an older age. In one embodiment, treatment is initiated from ages about 4 years of age to about 12 years of age. In one embodiment, treatment is initiated on or after about 4 years of age. In one embodiment, treatment is initiated on or after about 5 years of age. In one embodiment, treatment is initiated on or after about 6 years of age. In one embodiment, treatment is initiated on or after about 7 years of age. In one embodiment, treatment is initiated on or after about 8 years of age. In one embodiment, treatment is initiated on or after about 9 years of age. In one embodiment, treatment is initiated on or after about 10 years of age. In one embodiment, treatment is initiated on or after about 11 years of age. In one embodiment, treatment is initiated on or after about 12 years of age. However, treatment can be initiated on or after about 15, about 20, about 25, about 30, about 35, about 40, about 45, about 50, about 55, about 60, about 65 or about 70 years of age. In one embodiment, treatment in utero is defined as administering the composition as described herein in the fetus. See, e.g., David et al, Recombinant adeno-associated virus-mediated in utero gene transfer gives therapeutic transgene expression in the sheep, Hum Gene Ther. 2011 April;

22(4):419-26. doi: 10.1089/hum.2010.007. Epub 2011 Feb. 2, which is incorporated herein by reference.

In another embodiment, the composition is readministered at a later date. Optionally, more than one readministration is permitted. Such readministration may be with the same type of vector, a different viral vector, or via non-viral delivery as described herein. In one embodiment, the vector is readministered to the patient to a different portion of the initially injected retina. In one embodiment, the vector is readministered to the patient to the same portion of the initially injected retina.

In yet another embodiment, any of the above described methods is performed in combination with another, or secondary, therapy. The secondary therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In one embodiment, a method of generating a recombinant rAAV comprises obtaining a plasmid containing an AAV expression cassette as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver the SIRT1 or NRF2 coding sequence in the expression cassettes and genomes described above and in the examples below.

In certain embodiments of this invention, a subject has optic neuropathy or optic neuritis or other ocular condition described herein, for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

As used herein, the term "treatment" or "treating" is defined encompassing administering to a subject one or more compounds or compositions described herein for the purposes of amelioration of one or more symptoms of the ocular disorders described herein. "Treatment" can thus include one or more of reducing onset or progression of the ocular disorders described herein, preventing disease, reducing the severity of the disease symptoms, or retarding their progression, including the progression of blindness, removing the disease symptoms, delaying onset of disease or monitoring progression of disease or efficacy of therapy in a given subject.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, "disease", "disorder" and "condition" are used interchangeably, to indicate an abnormal state in a subject.

As used herein, the term "about" or "~" means a variability of 10% from the reference given, unless otherwise specified.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

EXAMPLE

The following examples are illustrative only and are not intended to limit the present invention.

Example 1

Recombinant rAAV and In Vitro Expression Studies

Here we describe several agents which can be delivered to retinal ganglion cells and potentially prevent permanent vision loss. The agents, NRF2 and Sirtuins (SIRT1, 2, 3, 4 5, 6, 7) act by decreasing oxidative or metabolic stress and thus by providing neurotrophic support. Sirtuins are NAD-dependent protein deacetylases. Intravitreal delivery of sirtuin activators such as resveratrol have been shown to reduce deficits from optic neuritis and optic crush injury in mouse models. (Shindler et al. Invest Ophthalmol Vis Sci 48(8):3602 (2007); Zuo et al Invest Ophthalmol Vis Sci 54(7):5097-102 (2013)). Nuclear factor-like 2 (NRF2) is a transcription factor that regulates a pathway of genes that decrease oxidative and other forms of stress.

We have generated rAAV vectors capable of delivering NRF2 (FIG. 1) and sirtuins (SIRT1; FIG. 2) to diseased tissue, including retinal cells in the eye. The vectors are used to treat a wide variety of genetic and acquired optic nerve disorders. Our results indicate that delivery of the proviral plasmid or of a recombinant adeno-associated virus (AAV) containing the NRF2 cDNA to eyes of mice leads to expression of NRF2 and in animals with optic neuritis, can ameliorate the disorder.

Example 2

Vector Design

Figure 3:
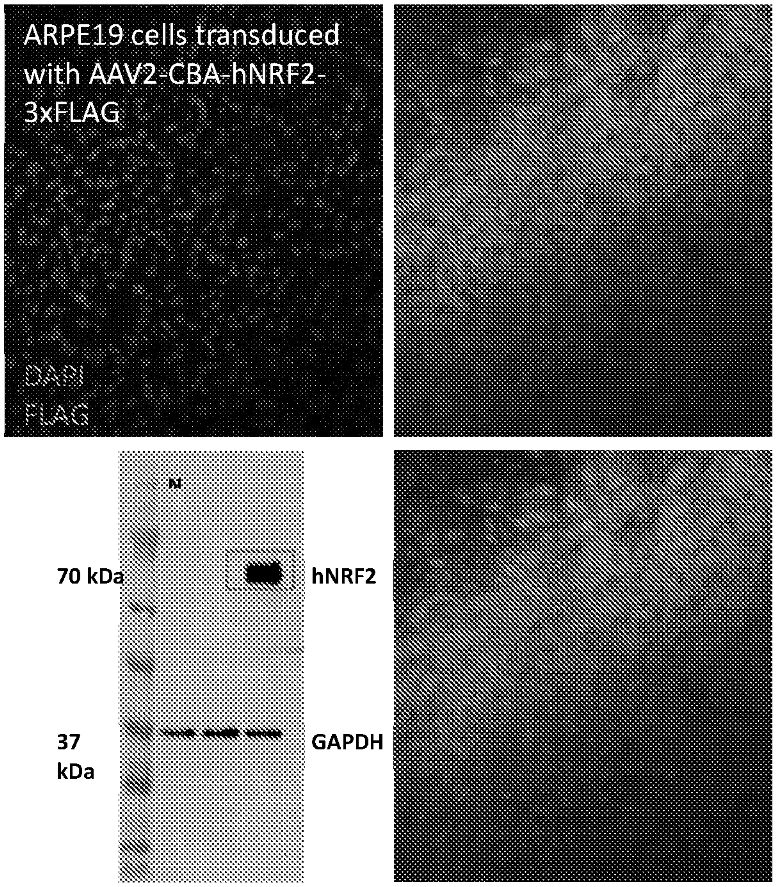
FIG. 3 shows 3 photomicrographs of ARPE19 cells transduced with AAV2-CBA-hNRF2-3xFLAG vector. pAAV-CMV/CBA-hNRF2-3xFLAG uses the chicken beta actin (CBA) promoter plus cytomegalovirus (CMV) enhancer to drive expression of the human NRF2 cDNA with a C-terminal 3xFLAG epitope tag. (CBA) promoter. The NRF2 sequence terminates into a bovine growth hormone (bGH) polyadenylation signal. The entire AAV expression cassette is flanked by the AAV2 inverted terminal repeats (ITRs). Transfection of ARPE19 cells resulted in both immunohistochemically detectable transgene expression and production of NRF2 protein of the predicted size (bottom left).
Figure 4:
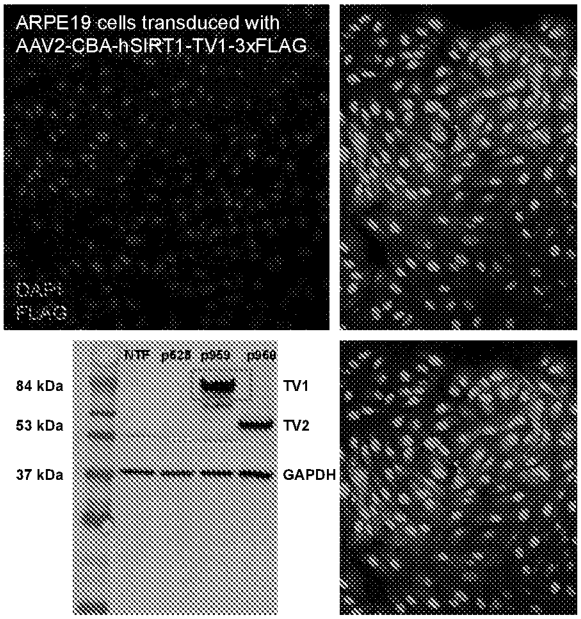
FIG. 4 shows 3 photomicrographs of ARPE19 cells transduced with AAV2-CBA-hSIRT1-3xFLAG vector. hSIRT1-3xFLAG uses the chicken beta actin (CBA) promoter plus cytomegalovirus (CMV) enhancer to drive expression of the human SIRT1 cDNA with a C-terminal 3xFLAG epitope tag. (CBA) promoter. The SIRT1 sequence terminates into a bovine growth hormone (bGH) polyadenylation signal. The entire AAV expression cassette is flanked by the AAV2 inverted terminal repeats (ITRs). Transfection of ARPE19 cells resulted in both immunohistochemically detectable transgene expression and production of SIRT1 protein of the predicted size (bottom left).

Cis plasmids including the hNRF2 (FIG. 1) or hSIRT1 (FIG. 2) coding sequences were designed. pAAV-CMV/CBA-hNRF2-3xFLAG (SEQ ID NO: 5) uses the chicken beta actin (CBA) promoter plus cytomegalovirus (CMV) enhancer to drive expression of the human NRF2 cDNA with a C-terminal 3xFLAG epitope tag. (CBA) promoter. The NRF2 sequence terminates into a bovine growth hormone (bGH) polyadenylation signal. The entire AAV expression cassette is flanked by the AAV2 inverted terminal repeats (ITRs). Transfection of ARPE19 cells resulted in both immunohistochemically detectable transgene expression and production of NRF2 protein of the predicted size. FIG. 3.

pAAV-CMV/CBA-hSIRT1-3xFLAG (SEQ ID NO: 6) uses the chicken beta actin (CBA) promoter plus cytomegalovirus (CMV) enhancer to drive expression of the human SIRT1 cDNA with a C-terminal 3xFLAG epitope tag. (CBA) promoter. The SIRT1 sequence terminates into a bovine growth hormone (bGH) polyadenylation signal. The entire AAV expression cassette is flanked by the AAV2 inverted terminal repeats (ITRs). Transfection of ARPE19 cells resulted in both immunohistochemically detectable transgene expression and production of SIRT1 protein of the predicted size. FIG. 4.

Example 3

Transfection of Neuro2a Cells

Figure 5:
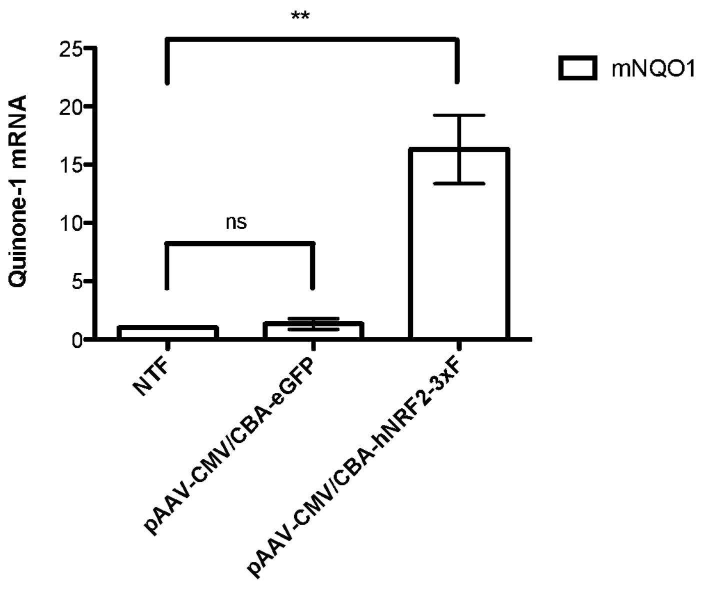
FIG. 5 demonstrates that transfection with pAAV-CMV/CBA-hNRF2-3XFLAG results in gene activation in Neuro2a cells. pAAV-CMV/CBA-eGFP was transfected as control in a second cohort of cells. RNA was extracted at 48 hours post-transfection and synthesized into cDNA. qRT-PCR analysis of quinone-1 (mNQO1) mRNA (a major downstream transcriptional target of NRF2) reveals enriched transcripts levels (**=P<0.01) in the pAAV-CMV/CBA-hNRF2-3xFLAG-treated cells compared to nontransfected and reporter transfected cells.

Transfection with pAAV-CMV/CBA-hNRF2-3XFLAG results in gene activation in Neuro2a cells (a neuroblastoma cell line). pAAV-CMV/CBA-eGFP was transfected as control in a second cohort of cells. RNA was extracted at 48 hours post-transfection and synthesized into cDNA. qRT-PCR analysis of quinone-1 (mNQO1) mRNA (a major downstream transcriptional target of NRF2) reveals enriched transcripts levels (=P<0.01) in the pAAV-CMV/CBA-hNRF2-3xFLAG-treated cells compared to nontransfected and reporter transfected cells. FIG. 5**.

Example 4

Injection of Mouse Model

A mouse model of experimental optic neuritis was tested to see if injection with AAV-hNRF2 or AAVhSIRT1 vectors preserved RGC function.

Wild-type mice receive intravitreal injection of AAV2 or AAV7m8 vectors at P30 (2 uL, 2E10 vg). EAE phenotype induced by injection of MOG35-39 emulsified in CFA at two sites on the back followed by IP injection of pertussis toxin. MOG+CFA induces autoimmune response while PT degrades blood-brain barrier, allowing immune entry to the CNS.

Sham-induced animals receive injections of PBS+CFA and PT. Baseline OKR measured prior to EAE induction (week 0) and once a week for 7 weeks.

Cohort 1=10 control mice (sham-induced) were injected as follows: OD=AAV2-CAG-eGFP and OS=vehicle.

Cohort 2=10 control mice (EAE-induced) were injected as follows: OD=AAV2-CAG-eGFP and OS=vehicle.

Figure 6A:
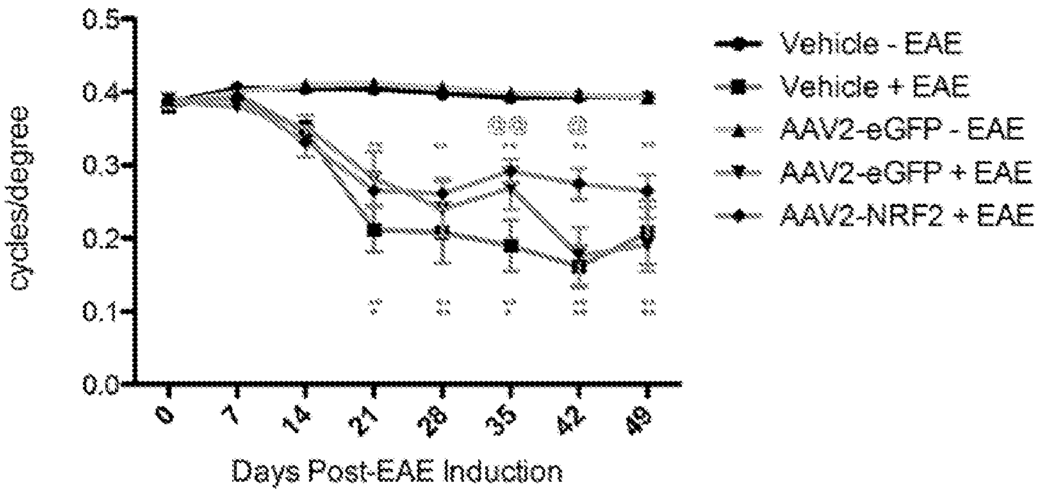
FIG. 6A demonstrates that intravitreal injection of AAV2-CMV/CBA-hNRF2 in a mouse model of experimental optic neuritis results in preservation of retinal ganglion cell (RGC) function compared to controls. Retinal function was assessed in a masked fashion by measuring the optokinetic reflex (OKR), a measure of visual acuity. The greater the cycles/degree, the better the visual acuity. Sham-induced mice treated with vehicle or AAV2-eGFP exhibit robust OKR scores throughout the experiment. EAE-induced mice show a significant decline in visual function at experimental day 21 and throughout the remainder of the experiment, mirroring the inflammation and cell death occurring in the optic nerve. However, EAE-induced animals treated with AAV2-NRF2 exhibit significantly enhanced OKR scores at day 35 (@@:P<0.01) and day 42 (@:P<0.05) and demonstrate a trend towards improvement at days 21, 28, and 49 compared to EAE-induced animals treated with vehicle.
Figure 6B:
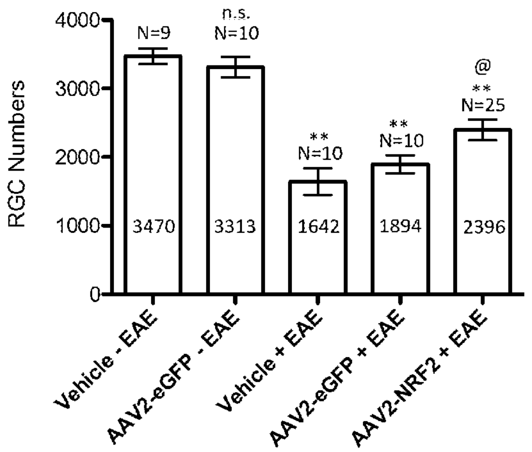
FIG. 6B demonstrates that intravitreal injection of AAV2-CMV/CBA-hNRF2 in a mouse model of experimental optic neuritis results in preservation of retinal ganglion cell (RGC) numbers compared to controls. Retinal ganglion cell numbers were assessed in a masked fashion by histology. EAE immunized animals exhibit significantly reduced RGC numbers compared to non-induced controls injected with vehicle (**=P<0.01). However, treatment with AAV2-CMV/CBA-hNRF2-3xFLAG provides significantly enhanced RGC survival compared to EAE immunized controls injected with vehicle (@=P<0.05).
Figure 6C:
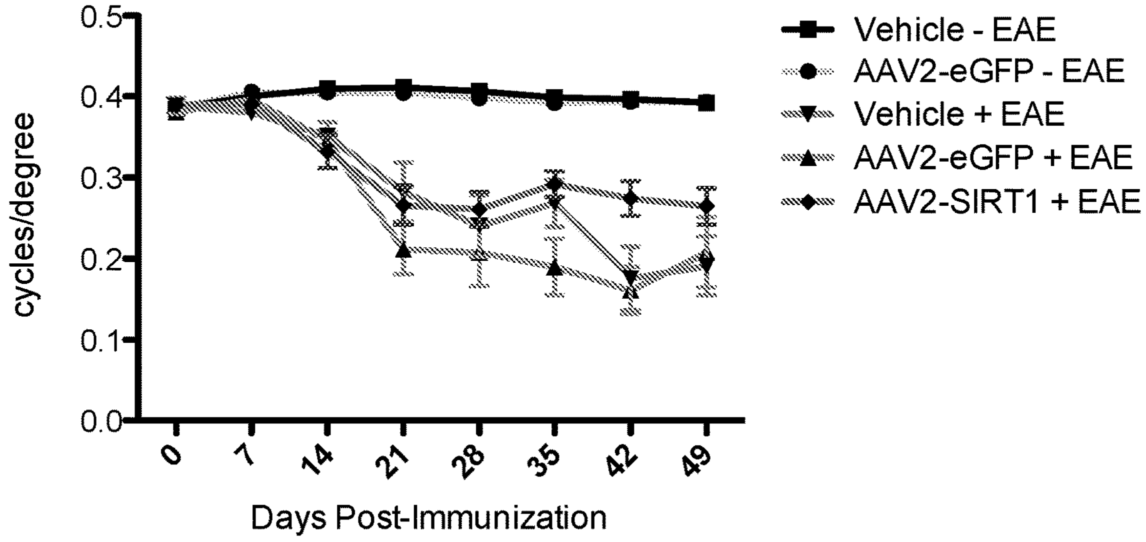
FIG. 6C demonstrates that intravitreal injection of AAV2-CMV/CBA-hSIRT1 in a mouse model of experimental optic neuritis results in preservation of retinal ganglion cell (RGC) function compared to controls. Retinal function was assessed in a masked fashion by measuring the optokinetic reflex (OKR), a measure of visual acuity. The greater the cycles/degree, the better the visual acuity. Sham-induced mice treated with vehicle or AAV2-eGFP exhibit robust OKR scores throughout the experiment. EAE-induced mice show a significant decline in visual function at experimental day 21 and throughout the remainder of the experiment, mirroring the inflammation and cell death occurring in the optic nerve. However, EAE-induced animals treated with AAV2-SIRT1 exhibit statistically significant preservation in OKR compared to AAV2-eGFP+EAE at day 35 (P<0.01) and day 42 (P<0.05) and compared to EAE-induced animals treated with vehicle. Data represented as mean +/−SEM. Differences in OKR compared using one-way ANOVA followed by Turkey's HSD test. Differences considered statistically significantly at P<0.05.
Figure 6D:
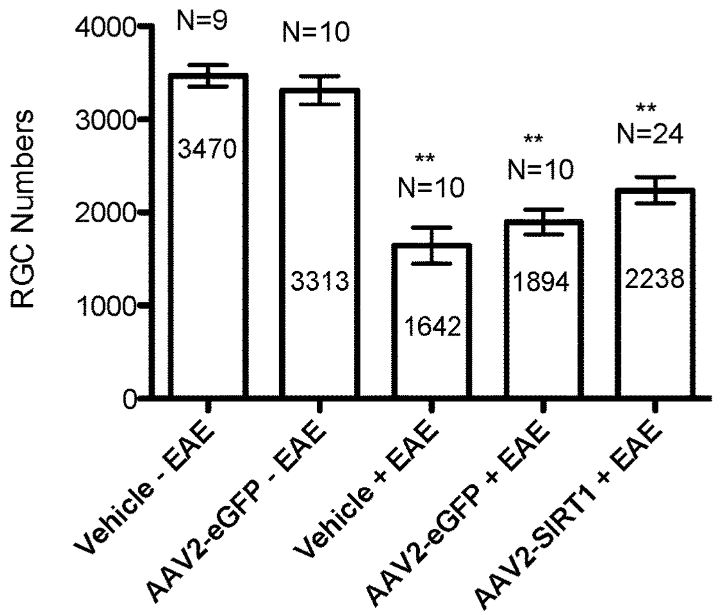
FIG. 6D demonstrates that intravitreal injection of AAV2-CMV/CBA-hSIRT1 in a mouse model of experimental optic neuritis results in preservation of retinal ganglion cell (RGC) numbers compared to controls. Retinal ganglion cell numbers were assessed in a masked fashion by histology. EAE immunized animals exhibit significantly reduced RGC numbers compared to non-induced controls injected with vehicle (**=P<0.01). However, treatment with AAV2-CMV/CBA-hNRF2-3xSIRT1 provides significantly enhanced RGC survival compared to EAE immunized controls injected with vehicle.
Figure 7:
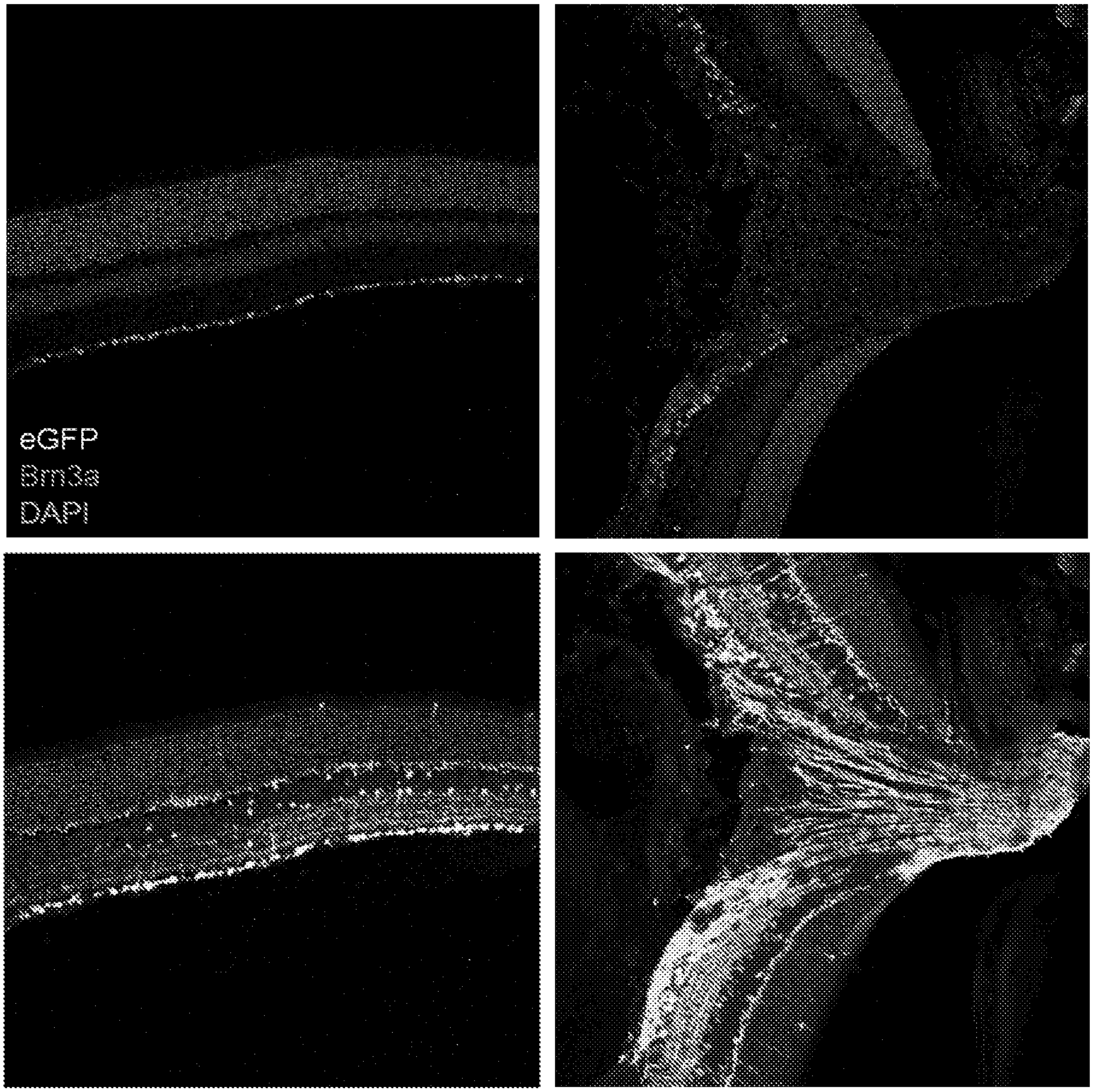
FIG. 7 are 4 photographs showing that AAV2 efficiently targets RGCs with intravitreal injection.

Cohort 3: 25 mice (EAE-induced) were injected as follows: OD (oculus dextrus)=AAV2-CAG-hNRF2-3xFLAG and OS (oculus sinister) =AAV2-CAG-hSIRT1-3xFLAG Intravitreal injection of AAV2-CMV/CBA-hNRF2 or AAV2-CMV/CBA-hSIRT1 resulted in preservation of retinal ganglion cell (RGC) function compared to controls. Retinal function was assessed in a masked fashion by measuring the optokinetic reflex (OKR), a measure of visual acuity. The greater the cycles/degree, the better the visual acuity. Sham-induced mice treated with vehicle or AAV2-eGFP exhibit robust OKR scores throughout the experiment. EAE-induced mice show a significant decline in visual function at experimental day 21 and throughout the remainder of the experiment, mirroring the inflammation and cell death occurring in the optic nerve. However, EAE-induced animals treated with AAV2-NRF2 exhibit significantly enhanced OKR scores at day 35 (@@:P<0.01) and day 42 (@:P<0.05) and demonstrate a trend towards improvement at days 21, 28, and 49 compared to EAE-induced animals treated with vehicle. FIG. 6A. EAE-induced animals treated with AAV2-SIRT1 exhibit statistically significant preservation in OKR compared to AAV2-eGFP +EAE at day 35 (P<0.01) and day 42 (P<0.05) and compared to EAE-induced animals treated with vehicle. FIG. 6C.

Intravitreal injection of AAV2-CMV/CBA-hNRF2 or AAV2-CMV/CBA-hSIRT1 in a mouse model of experimental optic neuritis results in preservation of retinal ganglion cell (RGC) numbers compared to controls. Retinal ganglion cell numbers were assessed in a masked fashion by histology. EAE immunized animals exhibit significantly reduced RGC numbers compared to non-induced controls injected with vehicle (=P<0.01). However, treatment with AAV2-CMV/CBA-hNRF2-3xFLAG or AAV2-CMV/CBA-hNRF2-3xSIRT1 provides significantly enhanced RGC survival compared to EAE immunized controls injected with vehicle (@=P<0.05). FIG. 6B, 6**D.

Neither NRF2 nor SIRT1 overexpression can halt optic nerve demyelination.

Example 5

SIRT1 Gene Transfer Promotes Retinal Ganglion Cell Neuroprotection in Experimental Optic Neuritis The following describes experiments detailed in McDougald et al, Investigative Ophthalmology & Visual Science March 2018, Vol.59, 1212-1220, which is incorporated herein by reference in its entirety.

Multiple sclerosis (MS) is a chronic, inflammatory disease characterized by activation of CD4+ T cells that infiltrate the central nervous system (CNS) and mount an autoimmune response against myelin. Optic neuritis is a condition commonly observed in MS patients that leads to temporary or permanent visual decline following demyelination of the optic nerve and loss of retinal ganglion cells. Current therapies for MS and ON include immunosuppressive agents that mitigate the inflammatory component of disease. Unfortunately, these treatments provide temporary symptomatic relief and, moreover, do not attenuate further neuronal loss. Therefore, it is critical to identify alternative treatment strategies that address underlying mechanisms of neuropathology. The conserved role of oxidative injury in MS and other forms of neurodegenerative disease is an attractive therapeutic target to delay or halt disease progression. Here we describe an approach that preserves retinal ganglion cell numbers and function during experimental optic neuritis following SIRT1 gene augmentation. SIRT1 is an NAD-dependent deacetylase that activates numerous cytoprotective mechanisms that suppress ROS activity, improve mitochondrial function, and inhibit apoptosis. We generated and characterized adeno-associated virus (AAV) vectors that drive constitutive expression of human SIRT1 using retinal-derived cell lines and in vivo models. Wild-type mice received intravitreal injections of AAV-SIRT1, AAV-eGFP, or vehicle. Afterwards, mice were vaccinated with myelin antigen to induce experimental autoimmune encephalomyelitis (EAE), an established model of MS that recapitulates the clinical features of optic neuritis including reduced visual acuity, optic nerve atrophy, and death of retinal ganglion cells (RGCs). Ganglion cell function was evaluated following EAE induction by measuring the optokinetic response (OKR). All EAE induced animals exhibited severely reduced OKR scores compared to sham immunized controls. However, treatment with AAV-SIRT1 improved visual acuity compared to vehicle and reporter injected animals also subjected to EAE. To examine the effect of SIRT1 gene augmentation on neuronal survival, retinae were harvested and stained with antibodies to label and quantify ganglion cells. Treatment with AAV-SIRT1 increased RGC survival compared to vehicle and reporter treated controls. Ongoing experiments will examine the contribution of SIRT1 gene augmentation in mitigating optic nerve atrophy as well as restricting oxidative damage in affected cell types. Collectively, this investigation suggests AAV-mediated SIRT1 gene augmentation can mediate neuroprotection in optic neuritis and MS pathogenesis.

A. Current understanding of MS pathogenesis has benefited from studies of experimental autoimmune encephalomyelitis (EAE).6 Manifestations of optic neuritis in EAE include optic nerve thinning, RGC loss, and reduced visual function, similar to the human disease, thus providing an in vivo system for characterization of neurodegenerative processes and a platform for interrogating neuroprotective strategies.7-9 Prior studies suggest oxidative stress and mitochondrial injury are central mediators of MS pathology.1 Accumulation of reactive oxygen and nitrogen species (ROS/RNS) within MS lesions leads to damage of cellular components including proteins, lipids, and DNA. Fortunately, eukaryotic cells are equipped with a collection of defense systems to combat oxidative injury and maintain redox homeostasis.10,11 We hypothesized that amplifying such mechanisms within RGCs using a conventional gene transfer approach may promote neuroprotection in experimental optic neuritis.

Nuclear factor (erythroid-derived 2)-like 2 (NRF2) is a basic leucine zipper transcription factor that activates a network of genes associated with antioxidant defense and cellular detoxification.11 Transgenic ablation of NRF2 during EAE development generates a phenotype of accelerated demyelination, immune cell infiltration, and proinflammatory cytokine signaling compared to wild-type animals also subjected to EAE.12 In addition, Nrf2 knockout mice demonstrate enhanced decline in visual function, loss of RGCs, and exacerbated optic nerve atrophy.13 Accumulating evidence supports therapeutic modulation of NRF2 activity via small molecule activation or transgenic overexpression in neurodegenerative diseases driven by oxidation.14-17 A gene augmentation strategy demonstrated a transient increase in survival of RGCs targeted with NRF2 expression vectors following optic nerve crush.17 Based on the collective data, we reasoned that stimulation of NRF2 activity may provide an effective means to protect RGCs in optic neuritis.

Sirtuin 1 (SIRT1) is an evolutionarily conserved NAD+-dependent deacetylase that regulates various components of cellular metabolism with respect to aging, DNA repair, mitochondrial biogenesis, and apoptosis.18 Accumulating evidence suggests modulation of SIRT1 activity via pharmacologic induction or transgenic overexpression may offer therapeutic value in several forms of neurodegenerative disease.19-27 In experimental optic neuritis, small molecule activators of SIRT1, including resveratrol and related polyphenolic compounds, are effective in preserving visual acuity and RGC survival during EAE and viral-induced demyelinating disease.19,21 In addition, Nimmagadda et al.24 demonstrated suppression of inflammation and demyelination following EAE sensitization using a transgenic mouse containing neural-restricted overexpression of SIRT1. However, the study design was limited to MS lesions localized to the spinal cord and did not examine the contribution of SIRT1 overexpression in ameliorating ocular disease manifestations.24 Potential neuroprotective effects of SIRT1 overexpression specifically in RGCs need to be examined In the present study, we interrogated the effects of SIRT1 or NRF2 overexpression in experimental optic neuritis via adeno-associated virus (AAV) gene transfer to RGCs. We developed and characterized AAV serotype 2 (AAV2) vectors that drive constitutive expression of human NRF2 and SIRT1 in vitro and in the mouse retina. We examined the neuroprotective contribution of SIRT1 and NRF2 gene augmentation in suppressing RGC death, optic nerve inflammation and demyelination, and vision loss in EAE mice.

B. Methods

Animals

C57B1/6J mice were obtained from the Jackson Laboratory and raised in a 12-hour light/dark cycle. Animals were housed at the University of Pennsylvania in compliance with ARVO Statement for the Use of Animals in Ophthalmic and Vision Research as well as with institutional and federal regulations.

AAV Vector Design and Production

Human SIRT1 (transcript variant 1) and human NRF2 (transcript variant 1) cDNA clones were obtained from Origene. Sequences were amplified with Q5 DNA polymerase (NEB) and cloned into an AAV expression plasmid using a commercial cloning kit (In-Fusion HD; Clontech Laboratories, Mountain View, Calif., USA). Transgene expression was driven by a CAG promoter derived from pDRIVE-CAG (InvivoGen, San Diego, Calif., USA). Both cDNA sequences contained a C-terminal 3xFLAG epitope tag that terminates into a bovine growth hormone (bGH) polyadenylation sequence. AAV expression cassettes were flanked by the AAV2 inverted terminal repeats. A proviral plasmid driving expression of enhanced green fluorescent protein (eGFP) was obtained from Jean Bennett, Md., PhD (University of Pennsylvania) and contains identical cis regulatory elements. AAV2-NRF2, AAV2-SIRT1, and AAV2-eGFP vectors were generated using previously described methods and purified with CsCl gradient by the CAROT research vector core at the University of Pennsylvania.

Cell Culture

ARPE-19 cells were supplied by ATCC (Manassas, Va., USA) and grown at 37° C. with 5% CO2. Cells were maintained in Dulbecco's modified Eagle's medium: nutrient mixture F-12 (DMEM/F12; Gibco Laboratories, Gaithersburg, Md., USA) and supplemented with 10% fetal bovine serum (FBS) and 1% penicillin-streptomycin. 84-31 cells were provided by James Wilson, Md., PhD (University of Pennsylvania) and were cultured in medium (DMEM-GlutaMax; Gibco Laboratories) and supplemented with 10% FBS and 1% penicillin-streptomycin. We seeded 84-31 cells at a density of 350,000 cells and transduced with AAV2 vectors at a multiplicity of infection (MOI) of 100,000. Cells were harvested for expression analysis at 48 hours post-transduction. For AAV transduction in ARPE-19 cells, 150,000 cells were plated and transduced with AAV2 vectors at an MOI of 100,000. Cells were harvested for expression analysis at 72 hours posttransduction. Cells were rinsed with PBS and fixed in 4% paraformaldehyde for 15 minutes at room temperature. Afterwards, cells were blocked in 0.1% Triton X-100 and 1% bovine serum albumin (BSA) for 30 minutes at room temperature. Cells were incubated with primary antibody solution containing 1% BSA and rabbit anti-FLAG antibody (CST #14793; 1:200) for 1 hour at room temperature. Cells were washed with PBS and incubated in secondary antibody solution containing 1% BSA and goat anti-rabbit AlexaFluor-594 antibodies (1:500) for 1 hour at room temperature. Cells were removed from secondary incubation, washed in PBS, and mounted with (Fluoromount-G; Southern Biotech; Birmingham, Ala., USA) containing DAPI.

Quantitative Real-Time PCR (RT-qPCR)

RNA was isolated from 84-31 cells (provided by James Wilson) using the RNA kit (Macherey-Nagel Nucleospin RNA kit; Thermo Fisher Scientific, Waltham, Mass., USA). First-strand cDNA synthesis was performed using 500 ng of total RNA with the first-strand synthesis system (SuperScript III; Thermo Fisher Scientific) according to manufacturer's protocol. Real-time PCR was performed with a commercial system (7500 Fast; Applied Biosystems, Foster City, Calif., USA) using a PCR master mix (Power SYBR green; Invitrogen). The following primer sequences were used: 5' CCACTCCTCCACCTTTGAC 3' (human GAPDH Forward); 5' ACCCTGTTGCTGTAGCCA 3' (human GAPDH Reverse); GAGCTGGGGTGTCTGTTTCA (human SIRT1 Forward); GGAAGTCTACAGCAAGGCGA (human SIRT1 Reverse); GTCACATCGAGAGCCCAGTC (human NRF2 Forward); and AGCTCCTCCCAAACTTGCTC (human NRF2 Reverse). Relative gene expression was quantified with the ΔΔCT method and normalized to GAPDH.

Intravitreal Injections

We anesthetized 4-week-old mice by isoflurane inhalation. A 33'/2 gauge needle was used to create a small incision at the limbus. Afterward, a 10-μL Hamilton syringe (701 RN; Hamilton Company, Reno, NV, USA) attached to a 33-gauge blunt-end needle was inserted into the vitreous cavity with the needle tip placed directly above the optic nerve head. We dispensed 2 μL of AAV preparation containing approximately 1×1010 vector genomes were dispensed into each eye bilaterally. Vehicle treated eyes were injected with an equivalent volume of vector dilution buffer (0.001% Pluronic F68 in PBS). The two eyes of each mouse received different injections (vehicle, AAV2-NRF2, AAV2-SIRT1, or AAV2-eGFP) allowing each eye to serve as an independent experimental end point.

Induction and Score of EAE

We anesthetized 8-week-old C57B1/6 mice by isoflurane inhalation and injected at two sites subcutaneously with 200 μg of myelin oligodendrocyte glycoprotein peptide (MOG35-55; GenScript, Piscataway, N.J., USA) emulsified in antigen solution (Complete Freund's Adjuvant [CFA]; Difco Laboratories, Inc., Detroit, MI, USA) with 2.5 mg/mL mycobacterium tuberculosis (Difco Laboratories, Inc.). Control mice that were not induced for EAE were injected with an equal volume of PBS and CFA. All mice were given 200 ng pertussis toxin (List Biological, Campbell, Calif., USA) in 0.1 mL of PBS by intraperitoneal injection at 0 hours and 48 hours postimmunization with MOG35-55. Clinical EAE was assessed using a previously described five-point scale19: no disease=0; partial tail paralysis=0.5; tail paralysis or waddling gait=1.0; partial tail paralysis and waddling gait=1.5; tail paralysis and waddling gait=2.0; partial limb paralysis=2.5; paralysis of one limb=3.0; paralysis of one limb and partial paralysis of another=3.5; paralysis of two limbs=4.0; moribund state=4.5; death=5.0.

Optokinetic Response Recordings (OKRs)

Visual function was assessed by measuring the OKR using commercial software and apparatus (OptoMotry; CerebralMechanics, Inc., Medicine Hat, AB, Canada) as previously described.28 OKR was determined as the highest spatial frequency where mice track a 100% contract grating that is projected at different spatial frequencies. Measurements were performed by an investigator blinded to the experimental treatments.

Retinal Histology and RGC Quantification

Eyes were harvested and placed in 4% paraformaldehyde (PFA) overnight at 4° C. Eyes were washed in PBS followed by dissection of retinal cups. Tissues were permeabilized and blocked in 2% Triton X-100, 10% normal donkey serum, and PBS and then incubated with goat anti-Brn3a antibody (Santa Cruz Biotechnology, Dallas, Tex., USA) diluted 1:100 at 4° C. Retinal cups were washed and then incubated in secondary antibody solution containing 2% Triton X-100, 10% normal donkey serum, and donkey anti-goat AlexaFluor 594 antibody (1:500 dilution). After washing, samples were prepared as flatmounts and mounted onto glass slides with an aqueous mounting medium (SouthernBiotech) containing 4',6-diamidino-2-phenylindole (DAPI). RGCs were quantified as previously described.7, 19,25,26 Briefly, retinal micrographs were recorded at ×40 magnification in 12 standard fields (1/6, 3/6, and 5/6 of the retinal radius from the center of the retina in each quadrant). Total RGC counts from the 12 fields per retinal sample covering a total area of 0.45 mm2/retina were recorded by an investigator masked to the experimental conditions using ImageJ software (avaiable at imagej.nih.gov/ij/; provided in the public domain by the National Institutes of Health, Bethesda, MD, USA). Retinal cross-sections were incubated in blocking buffer containing PBS, 2% Triton X-100, and 10% normal donkey serum for 1 hour at room temperature. Next, sections were incubated in primary antibody solution containing the previously described components and a rabbit anti-FLAG antibody (CST #14793) at 1:100 dilutions overnight in a humidified chamber at room temperature. Sections were washed in PBS three times and incubated in secondary antibody solution containing donkey anti-rabbit AlexaFluor 488 antibody diluted at 1:200 for 2 hours at room temperature. Slides were then washed in PBS three times and mounted with aqueous mounting medium (SouthernBiotech) containing DAPI.

Optic Nerve Histology and Scoring

Histologic staining and scoring was performed as in prior studies.7-9,19-25 Optic nerves were harvested, fixed in 4% PFA, and embedded in paraffin. Nerves were subsequently cut into 5-μm longitudinal sections. To examine immune cell infiltration, sections were stained with hematoxylin and eosin (H&E). Inflammation was scored by an investigator blinded to the experimental treatments, and nerves were graded on a 0 to 4 point scale: no infiltration=0; mild cellular infiltration=1; moderate infiltration=2; severe infiltration=3; massive infiltration =4. Sections were stained with luxol fast blue (LFB) to assess myelination. These sections were graded on a 0 to 3 point scale: 0=no demyelination; 1=scattered foci of demyelination; 2=prominent foci of demyelination; and 3=large (confluent) areas of demyelination.

Statistics

All data are represented as means±SEM. Differences between treatment groups with respect to OKR responses, RGC quantification, and optic nerve histopathology were compared using a 1-way ANOVA followed by Tukey's honest significant difference test using statistical software (GraphPad Prism 7.0; GraphPad Software, Inc., La Jolla, CA, USA). Differences were considered statistically significant at $P<0.05$.

C. Results

Design and Characterization of AAV2 Vectors

Figure 26A:
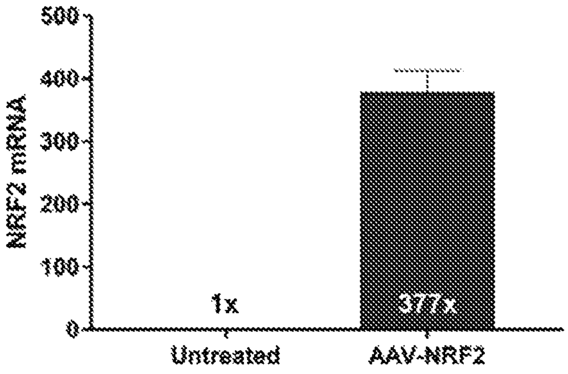
FIG. 26A and 26B shows in vitro characterization of AAV2 vectors. RT-qPCR analysis of relative quantities of human NRF2 or human SIRT1 mRNA in 84-31 cells treated with (A) AAV2-NRF2 and (B) AAV2-SIRT1 compared to nontransduced cells.
Figure 26B:
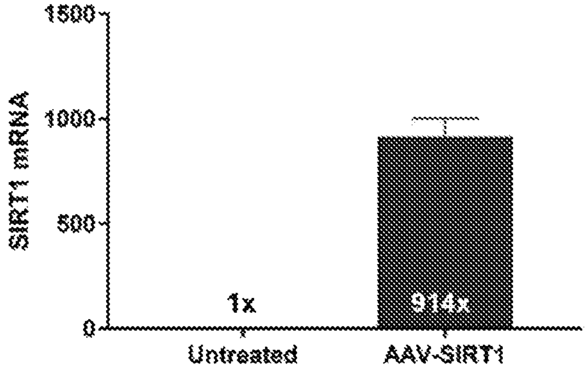
Figure 27:
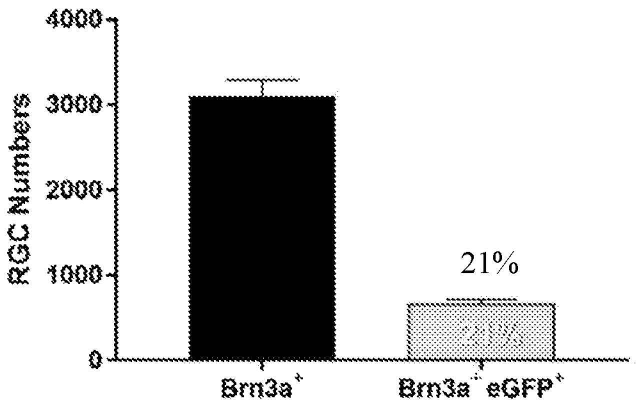
FIG. 27 shows AAV2 RGC transduction efficiency following intravitreal delivery. Quantification of RGC transduction (n=5 retina) following intravitreal injection of AAV2-eGFP.

Vectors based upon recombinant adeno-associated virus (AAV) have emerged as the current standard for achieving safe and stable gene transfer directed to nondividing cells such as neurons. AAV serotype 2 (AAV2) demonstrates a robust safety profile following subretinal delivery in clinical trials for Leber congenital amaurosis type 2.29-32 We generated AAV2 vectors expressing eGFP, human NRF2, or human SIRT1 driven by a ubiquitous promoter (FIGS. 1 and 2). Vector expression was examined in vitro with RT-qPCR and immunofluorescence (Data not shown.). RT-qPCR revealed robust levels of transgene expression in 84-31 cells treated with the designated vector compared to untreated controls (FIGS. 26A and 26B). Immunofluorescent labeling of ARPE-19 cells transduced with AAV2-SIRT1 demonstrates strong nuclear localization of the transgene product (Data not shown), while cells transduced with AAV2-NRF2 display robust cytoplasmic and nuclear distribution of the tagged protein (Data not shown). Next, we examined the retinal transduction profile of AAV2 following intravitreal delivery with a vector expressing enhanced green fluorescent protein in a cohort of wild-type mice. Similar to previously described reports,33-38 AAV2-eGFP displayed transduction of the ganglion cell layer and optic nerve head Data not shown). This vector achieved approximately 21% RGC transduction by quantifying the number of eGFP positive RGCs labeled with Brn3a antibody (FIG. 27). AAV2 vectors driving expression of NRF2 or SIRT1 were injected into the right and left eyes, respectively, of wild-type mice display similar transduction profiles in vivo (Data not shown).

SIRT1 Gene Transfer Preserves RGC Function During EAE

Figures 28A, 28B:
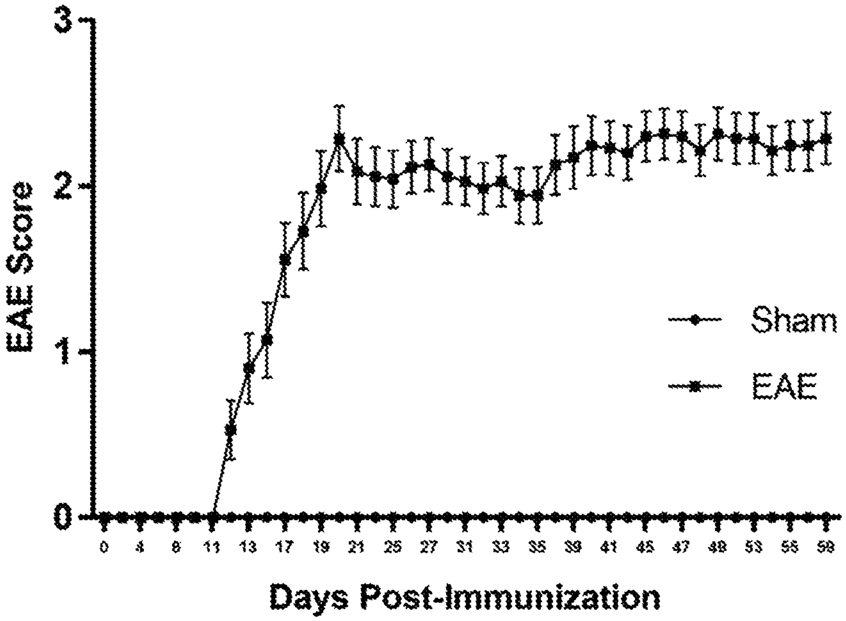
FIG. 28A and 28B demonstrates experimental groups and clinical scoring of EAE. (A) Outline of the experimental groups used in the study. (B) Clinical scores of sham (n=10) and EAE-induced (n=35) animals. Data represented as mean±SEM.

C57B16/J mice received intravitreal injections of AAV2 vectors or vehicle at postnatal week 4 followed by EAE/sham induction at postnatal week 8 (FIG. 28A). Following MOG35-55 immunization, animals displayed phenotypic features of EAE beginning near day 12 post-immunization (FIG. 28B) similar to prior studies.7,19,25 We measured visual function in response to gene transfer by recording the OKR prior to EAE/sham immunization and once every 7 days postimmunization. Earlier reports demonstrate a marked reduction in the OKR throughout the course of EAE.7 Sham-induced animals treated with intravitreal injections of vehicle or AAV2-eGFP exhibit robust OKR scores throughout the experimental timeline, suggesting minimal adverse effects associated with intravitreal delivery, vector recruitment, and transgene overexpression. Similarly, animals injected with AAV2-NRF2 or AAV2-SIRT1 displayed strong responses prior to induction. Following EAE sensitization, MOG-induced animals exhibit a decline in OKR scores beginning by day 21 postinduction. However, eyes treated with AAV2-SIRT1 demonstrate an upward trend in functional responses throughout the experimental timeline. In addition, the AAV2-SIRT1 treatment group achieves statistically significant preservation at days 35 (AAV2-SIRT1=0.292±0.016; AAV2-eGFP=0.19±0.035; P=0.032) and 42 (AAV2-SIRT1=0.274±0.022; AAV2-eGFP=0.161±0.029; P=0.049) when compared to the EAE-induced control group treated with AAV2-eGFP. NRF2 augmentation did not provide statistically meaningful preservation of visual acuity throughout the experimental timeline.

NRF2 Gene Transfer Improves RGC Survival During EAE

Figure 29:
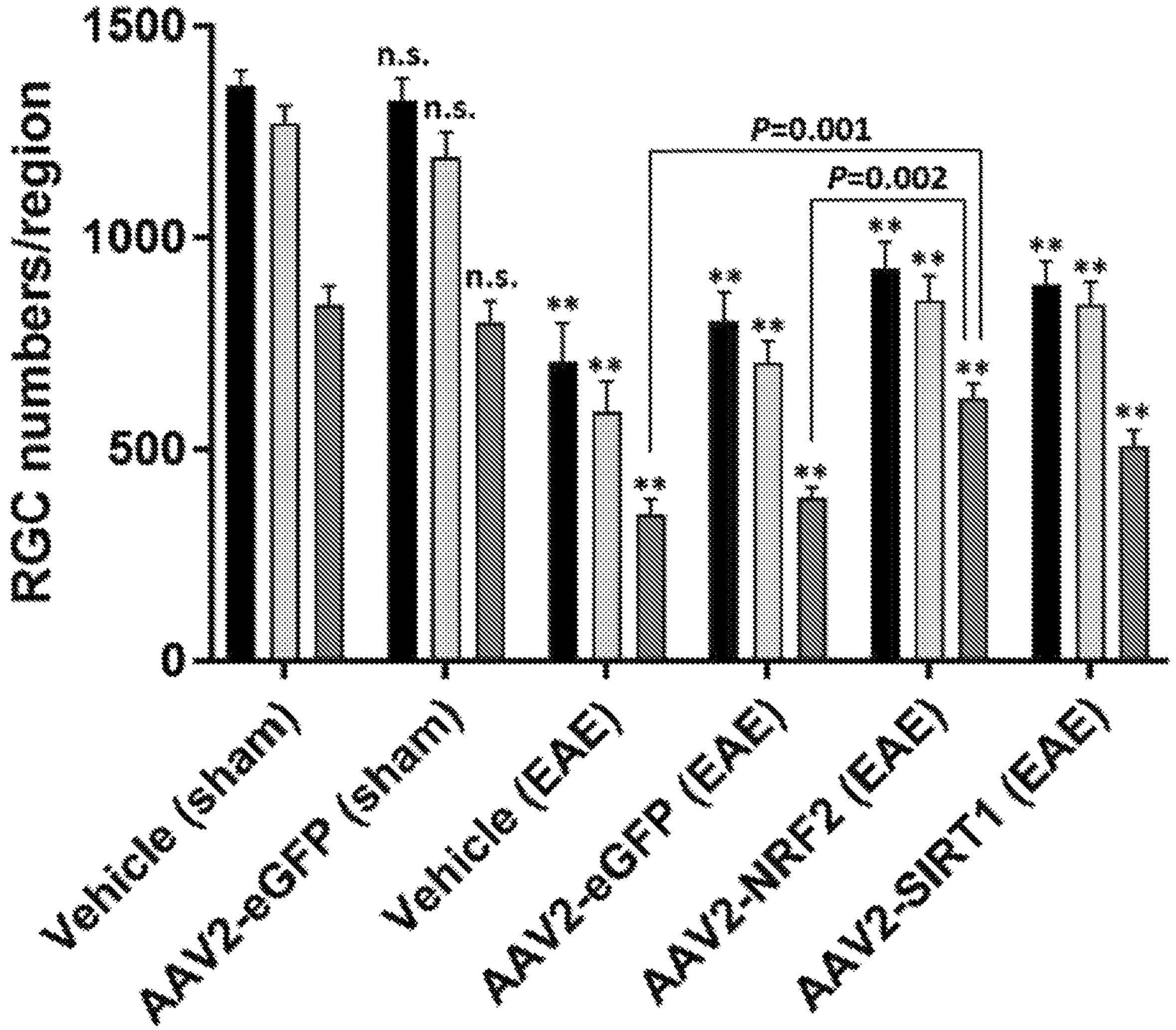
FIG. 29 demonstrates the effect of gene transfer on RGC survival during EAE. RGC numbers quantified per retinal region. Left bars: central. Middle bars: midperipheral. Right bars: peripheral. Data represented as mean±SEM. *P<0.05, **P<0.01 by 1-way ANOVA and Tukey's HSD post-test.

Permanent visual decline in optic neuritis coincides with the loss of RGCs.7 Retinas from each treatment group were isolated and stained with antibodies directed against Brn3a, a marker of RGCs, to determine whether SIRT1 or NRF2 gene augmentation conferred a protective advantage upon RGCs during EAE (FIG. 29). Intravitreal injection of AAV2 was well tolerated as indicated by comparative total RGC counts in sham-induced animals treated with vehicle. In mice sensitized to EAE, RGC numbers were significantly reduced in all treatment groups compared to sham-induced controls injected with vehicle or AAV2-eGFP (P<0.01). Treatment with AAV2-SIRT1 showed an upward trend in total RGC survival compared to control eyes, although this effect was not statistically significant. NRF2 gene transfer did provide a statistically significant increase in RGC survival compared to eyes treated with vehicle (P=0.027; FIG. 6B). We also examined the effect of NRF2 or SIRT1 gene transfer upon regional RGC density in the mouse retina (central, midperipheral, and peripheral; FIG. 29). NRF2 augmentation promoted survival of RGCs located within peripheral regions of the retina compared to both vehicle (P=0.001) and AAV2-eGFP (P=0.002) treatment groups sensitized to EAE. We observed a nonsignificant but trending increase in regional RGC density in retinas treated with AAV2-SIRT1.

Figure 8A:
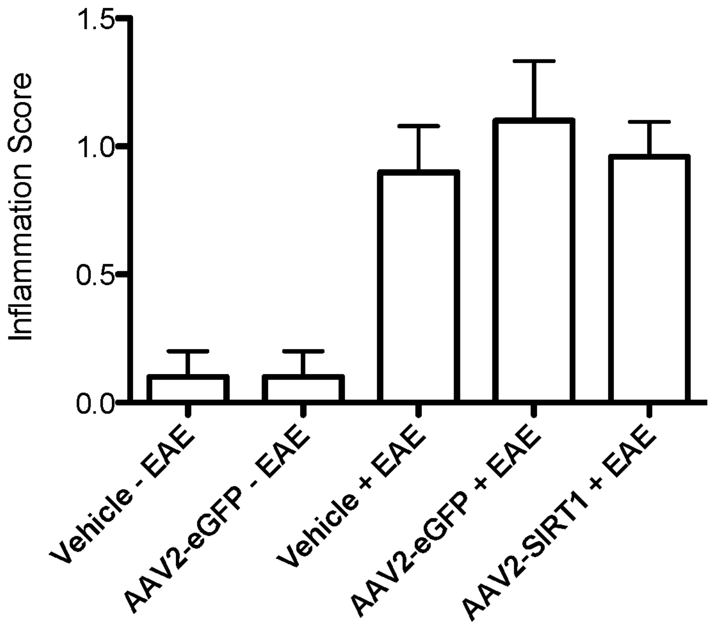
FIG. 8A is a graph demonstrating that SIRT1 does not affect inflammation. Scoring scale: no infiltration=0; mild=1; moderate=2; severe=3; nodular=4.
Figure 8B:
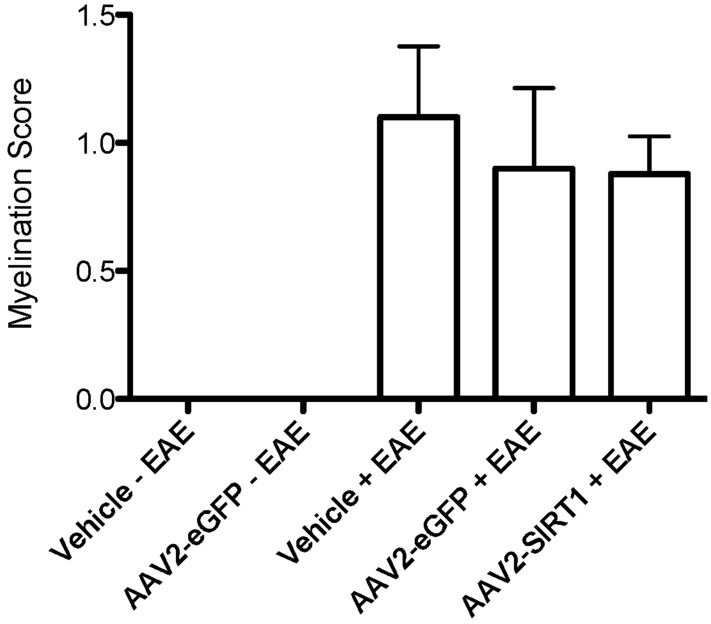
FIG. 8B is a graph demonstrating that SIRT1 does not affect demyelination. Scoring scale: no demyelination=0; mild=1; moderate=2; severe=3; massive=4.
Figure 8C:
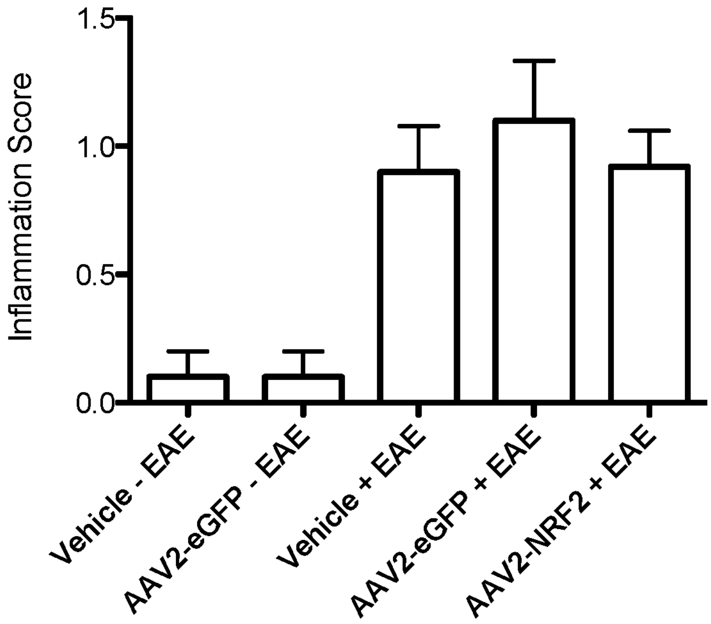
FIG. 8C is a graph demonstrating that NRF2 does not affect inflammation. Scoring scale: no infiltration=0; mild=1; moderate=2; severe=3; nodular=4.
Figure 8D:
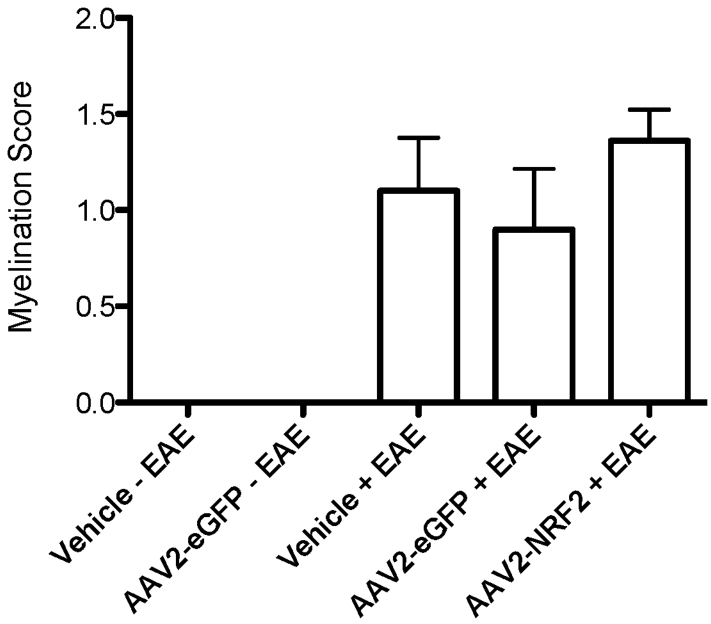
FIG. 8D is a graph demonstrating that NRF2 does not affect demyelination. Scoring scale: no demyelination=0; mild=1; moderate=2; severe=3; massive=4.
Figure 10:
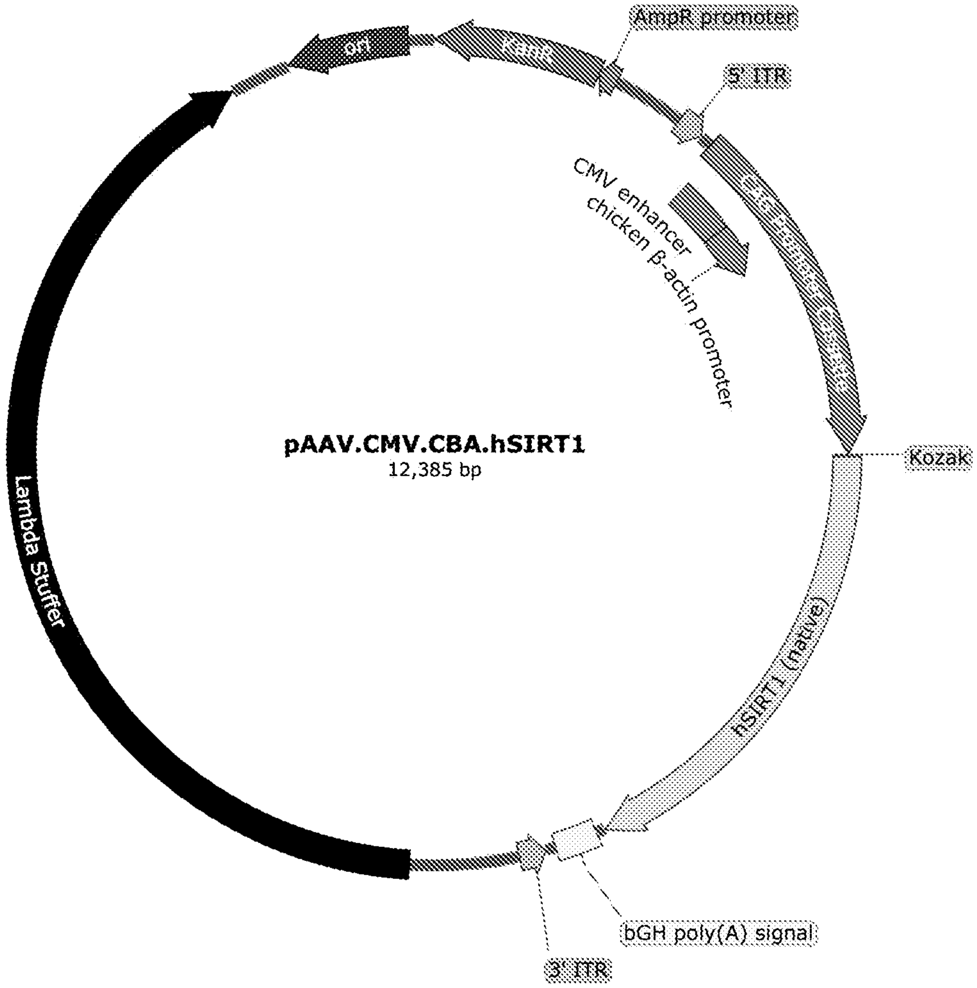
FIG. 10 provides a plasmid map of the pAAV.CMV.CBA.hSIRT1 vector.
Figure 11:
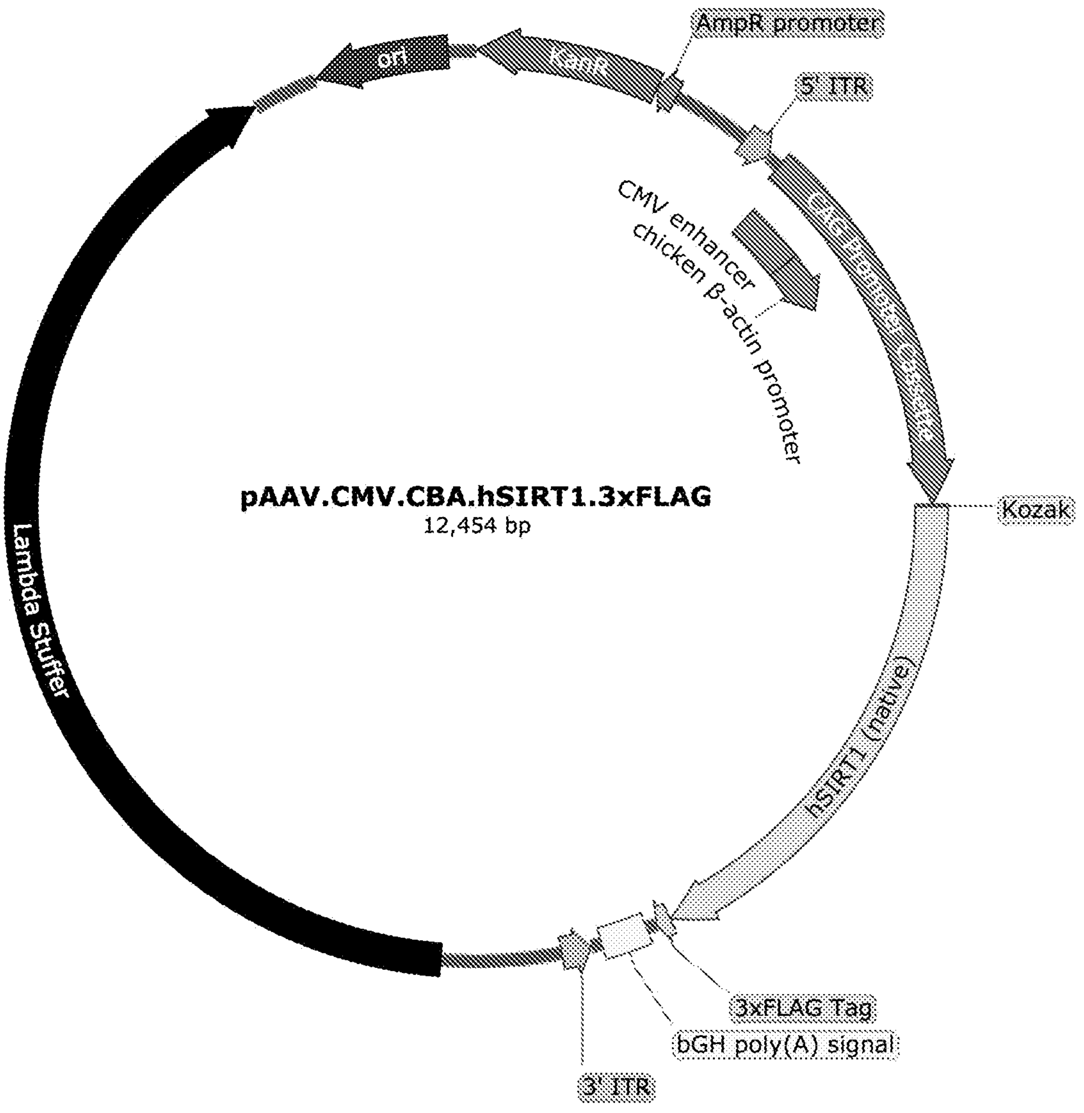
FIG. 11 provides a plasmid map of the pAAV.CMV.CBA.hSIRT1.3xFLAG vector.
Figure 12:
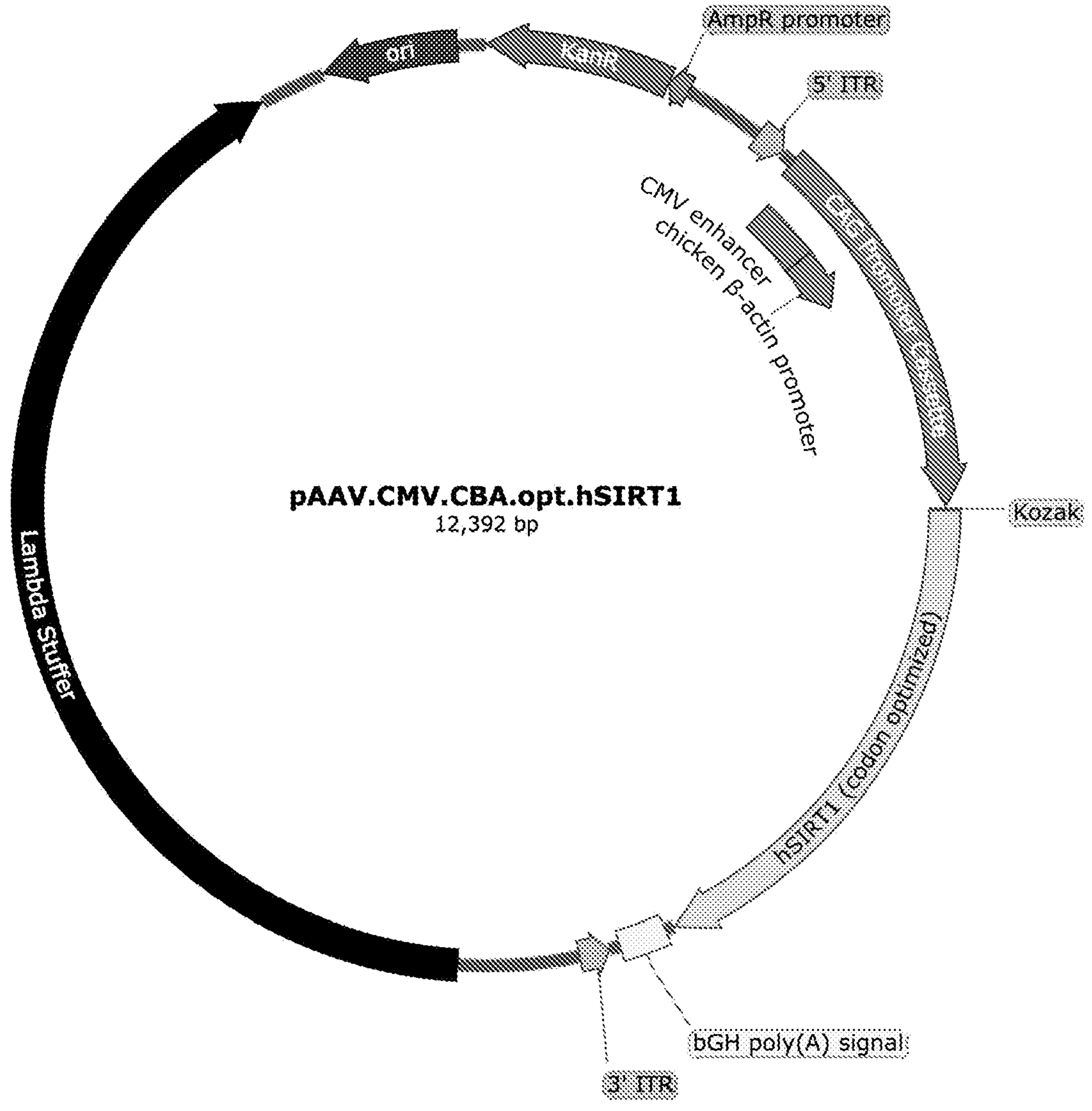
FIG. 12 provides a plasmid map of the pAAV.pAAV.CMV.CBA.opt.hSIRT1 vector.
Figure 13:
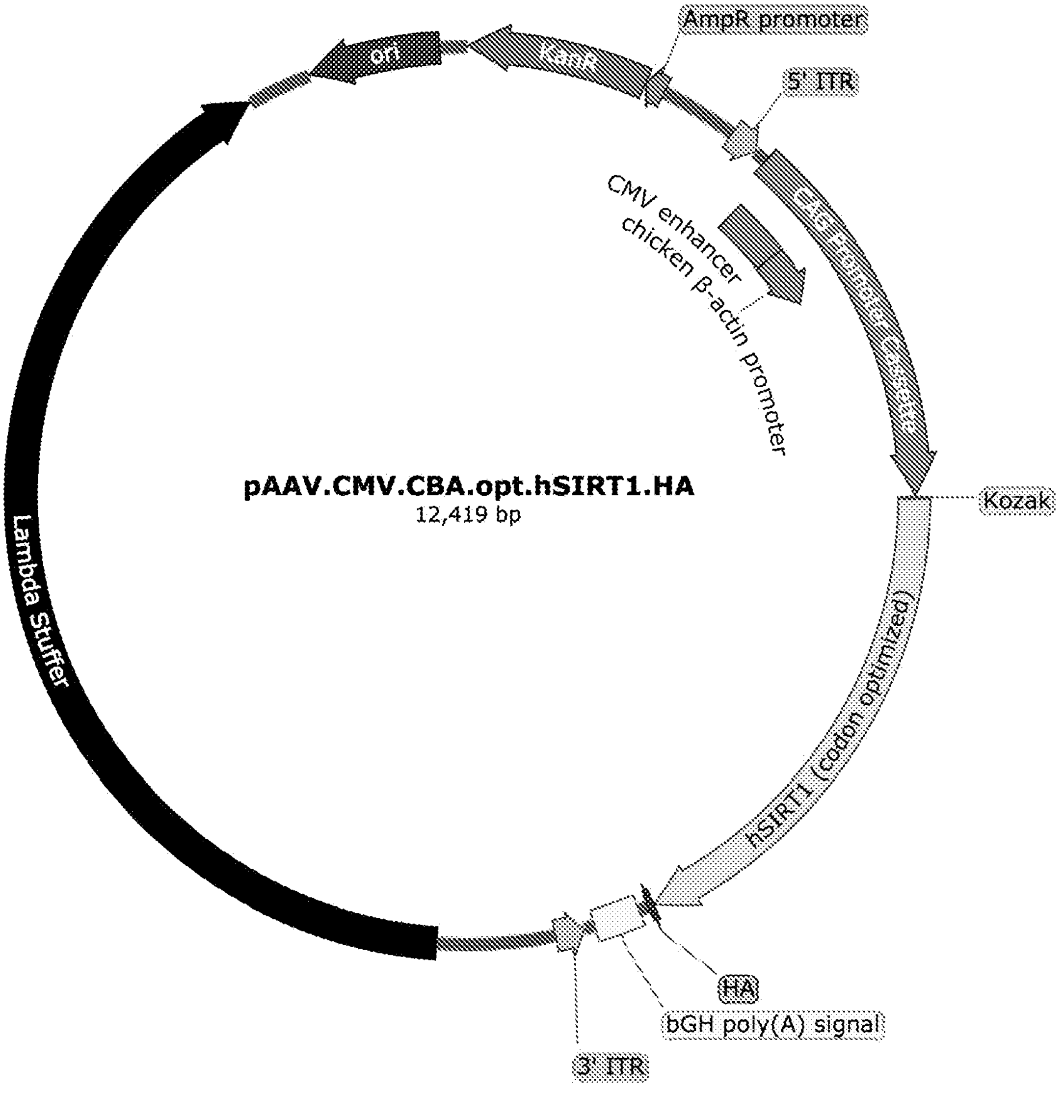
FIG. 13 provides a plasmid map of the pAAV.CMV.CBA.opt.hSIRT1.HA vector.
Figure 14:
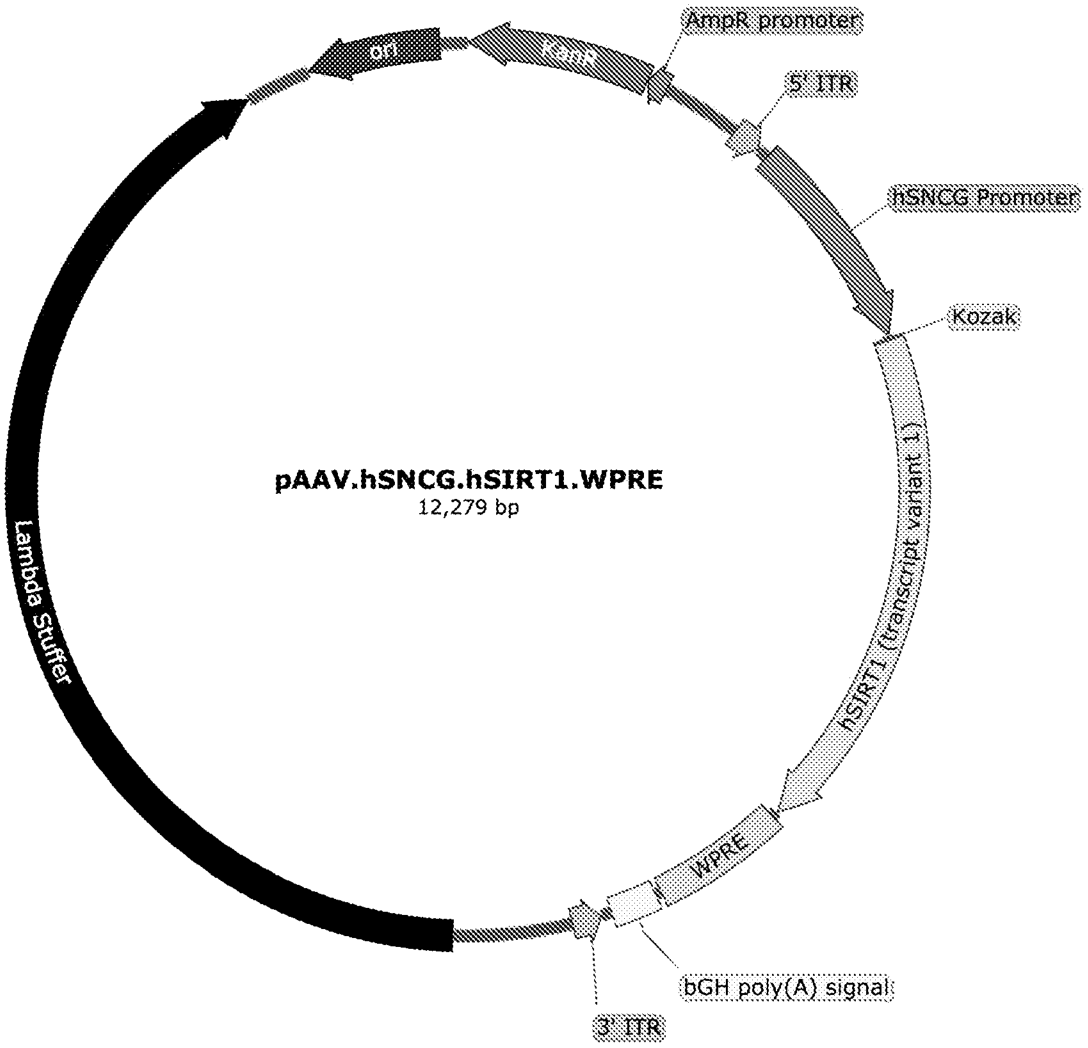
FIG. 14 provides a plasmid map of the pAAV.hSNCG.hSIRT1.WPRE vector.
Figure 15:
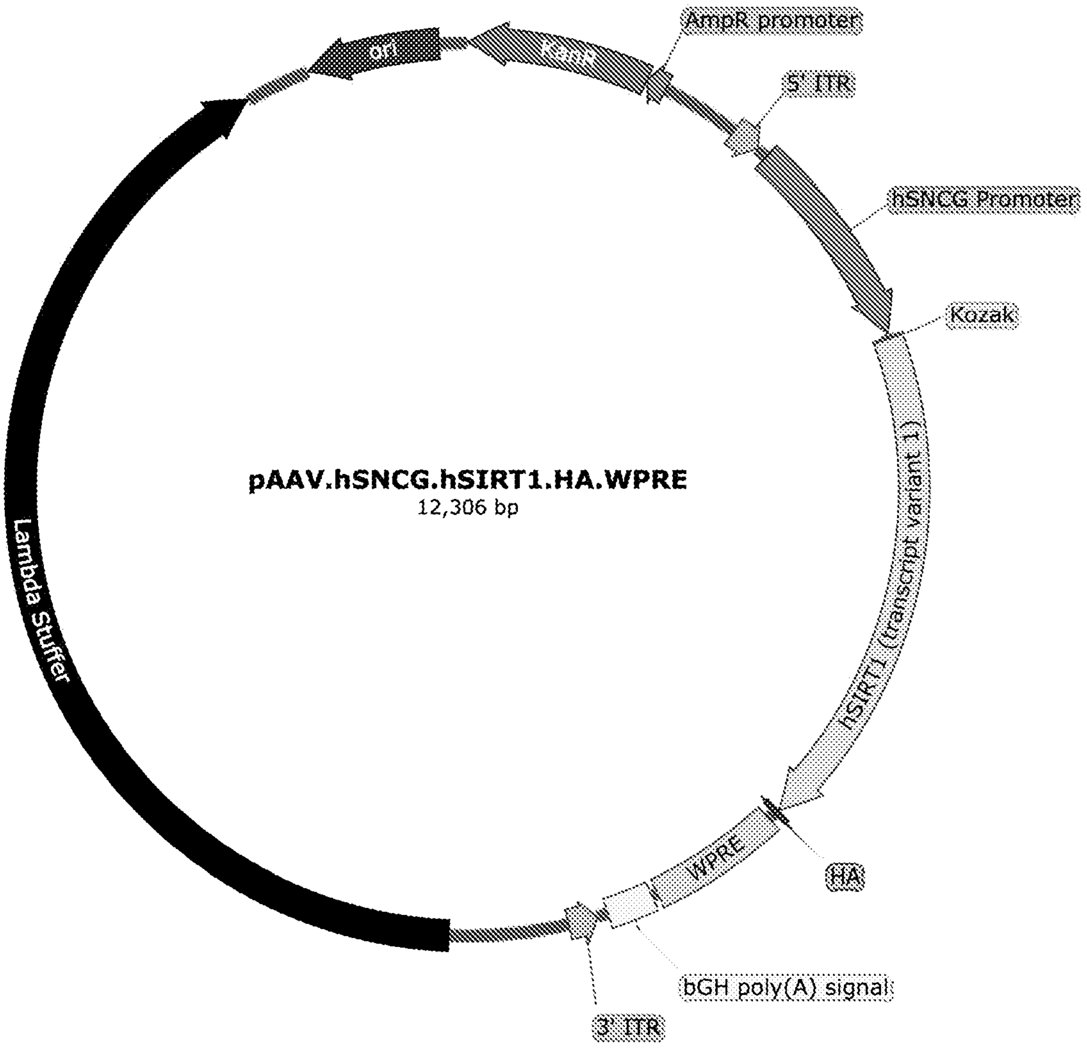
FIG. 15 provides a plasmid map of the pAAV.hSNCG.hSIRT1.HA.WPRE vector.
Figure 16:
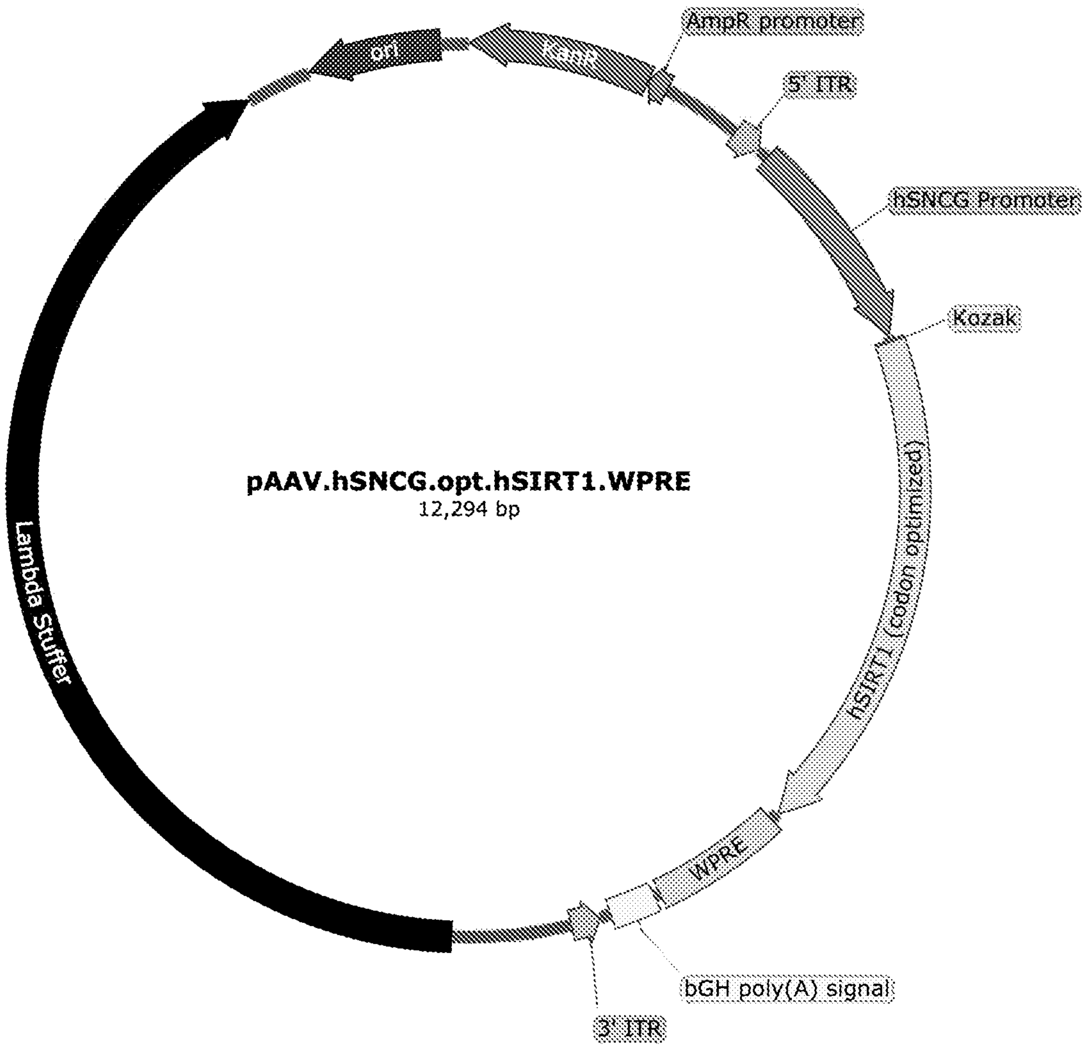
FIG. 16 provides a plasmid map of the pAAV.hSNCG.opt.hSIRT1.WPRE vector.
Figure 17:
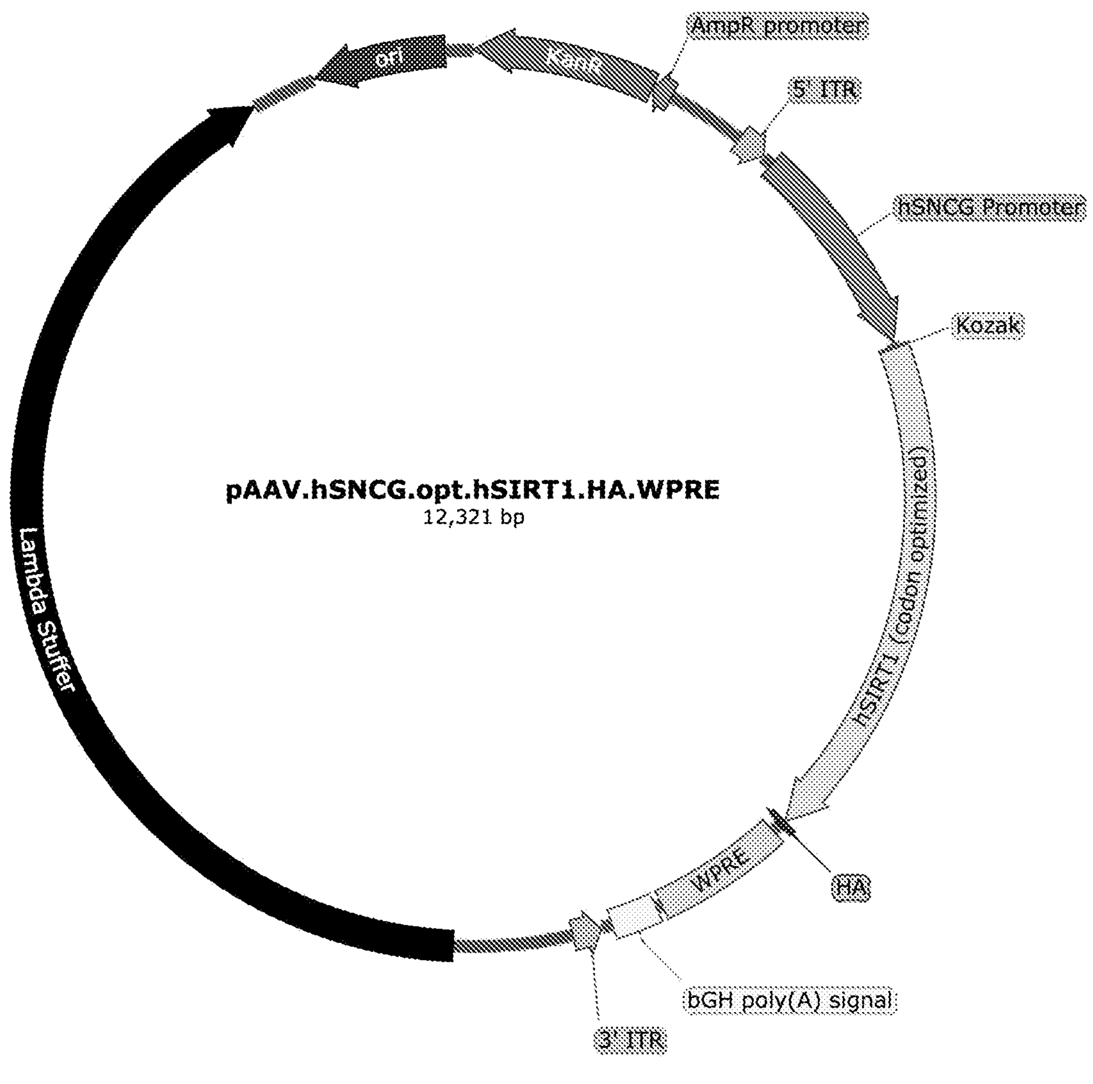
FIG. 17 provides a plasmid map of the pAAV.hSNCG.opt.hSIRT1.HA.WPRE vector.
Figure 18:
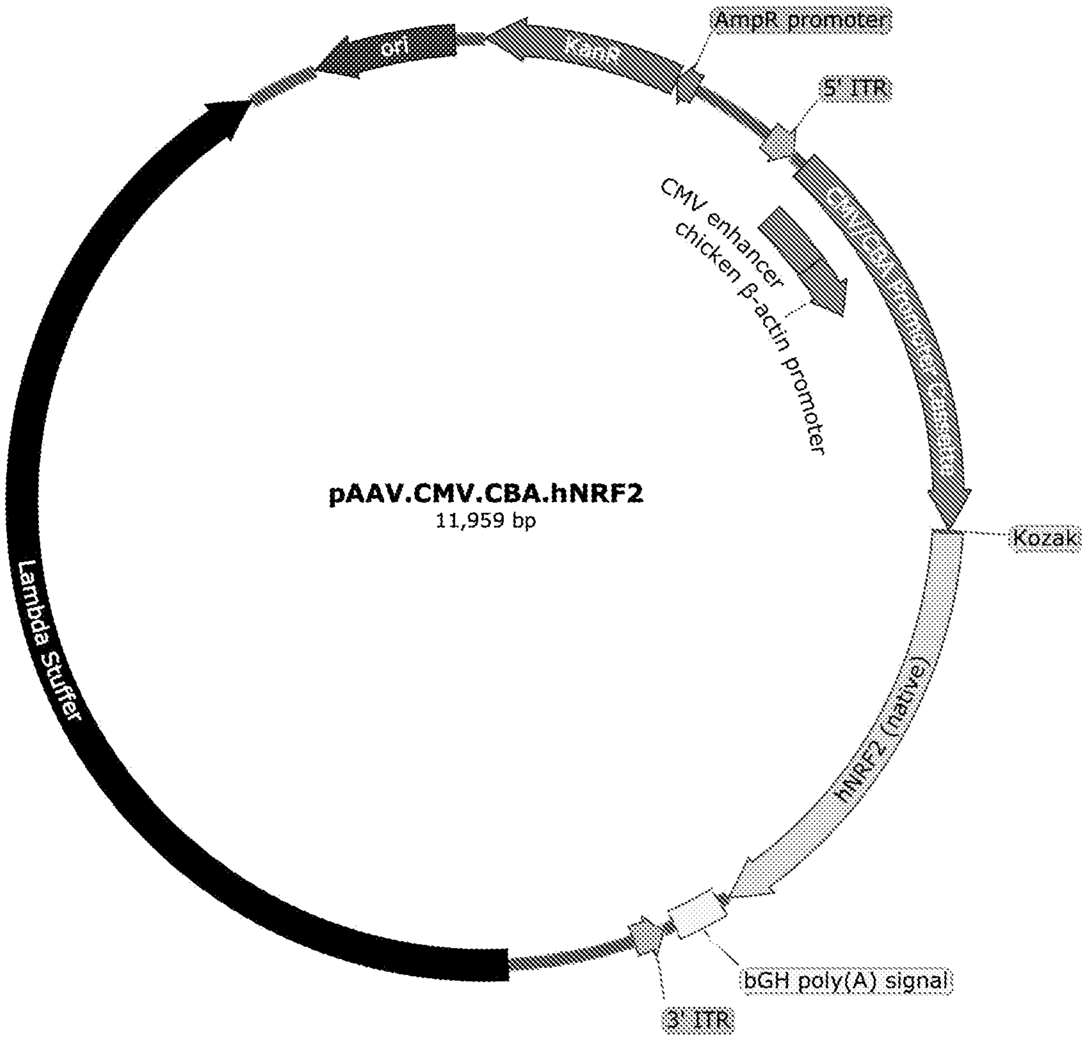
FIG. 18 provides a plasmid map of the pAAV.CMV.CBA.hNRF2 vector.
Figure 19:
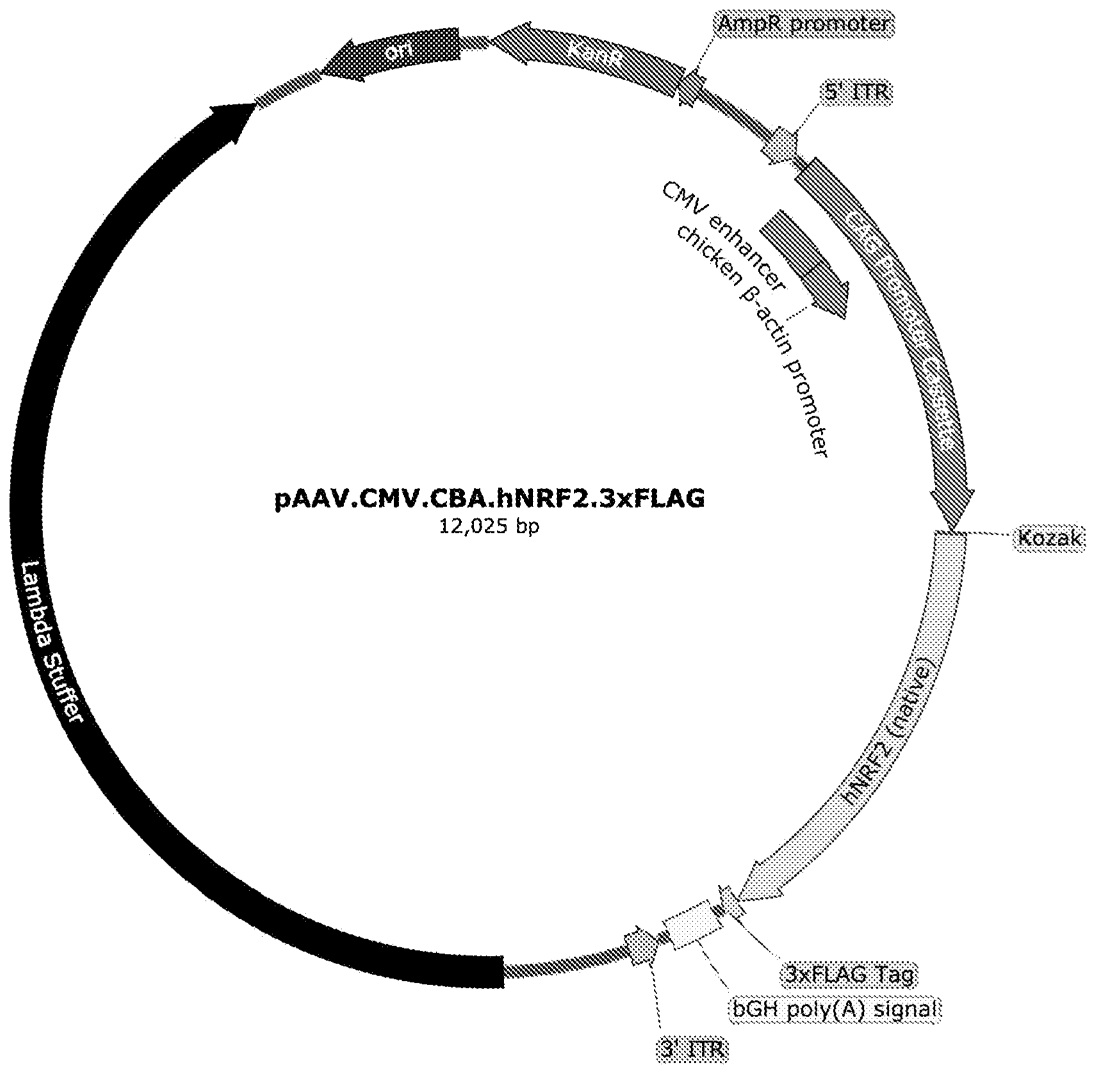
FIG. 19 provides a plasmid map of the pAAV.CMV.CBA.hNRF2.3xFLAG vector.
Figure 20:
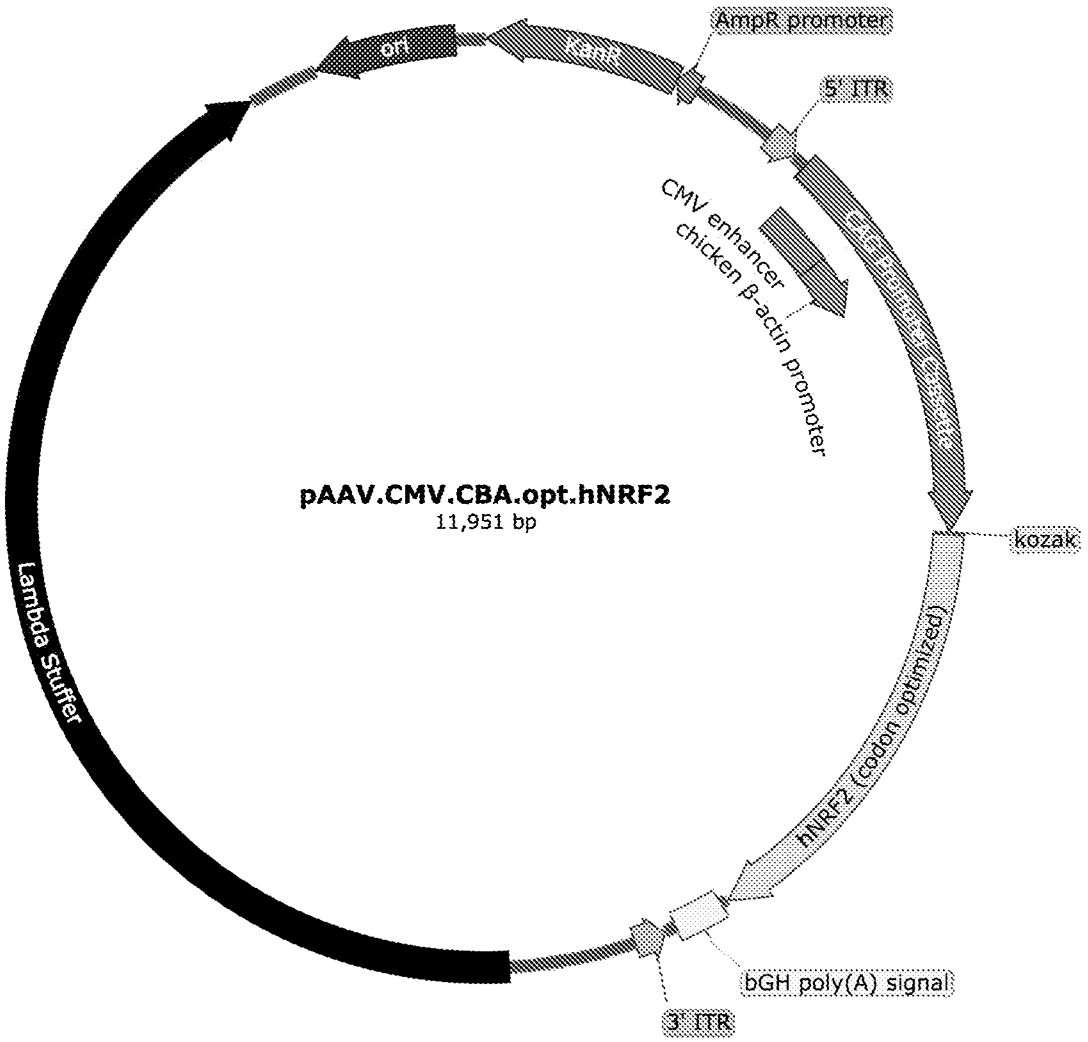
FIG. 20 provides a plasmid map of the pAAV.CMV.CBA.opt.hNRF2 vector.
Figure 21:
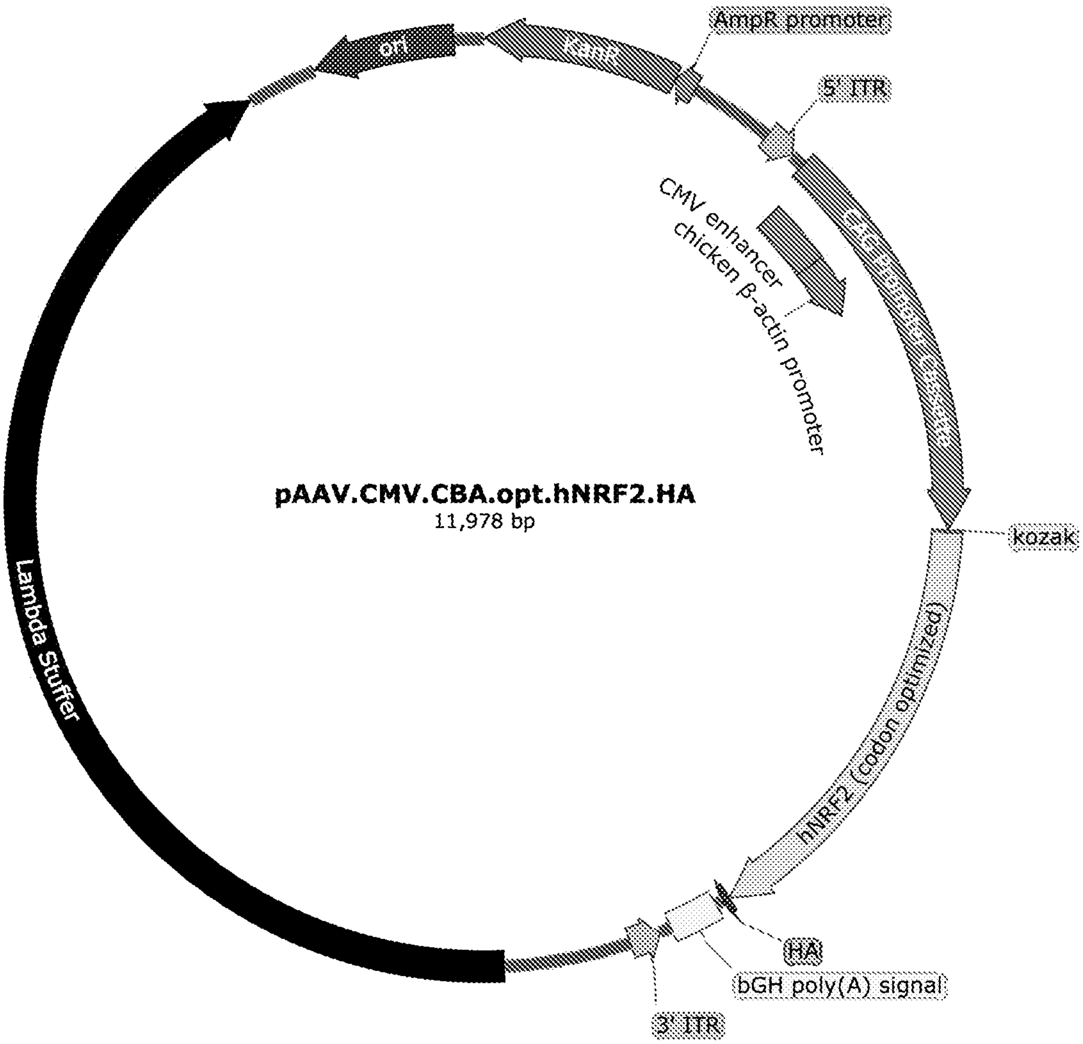
FIG. 21 provides a plasmid map of the pAAV.CMV.CBA.opt.hNRF2.HA vector.
Figure 22:
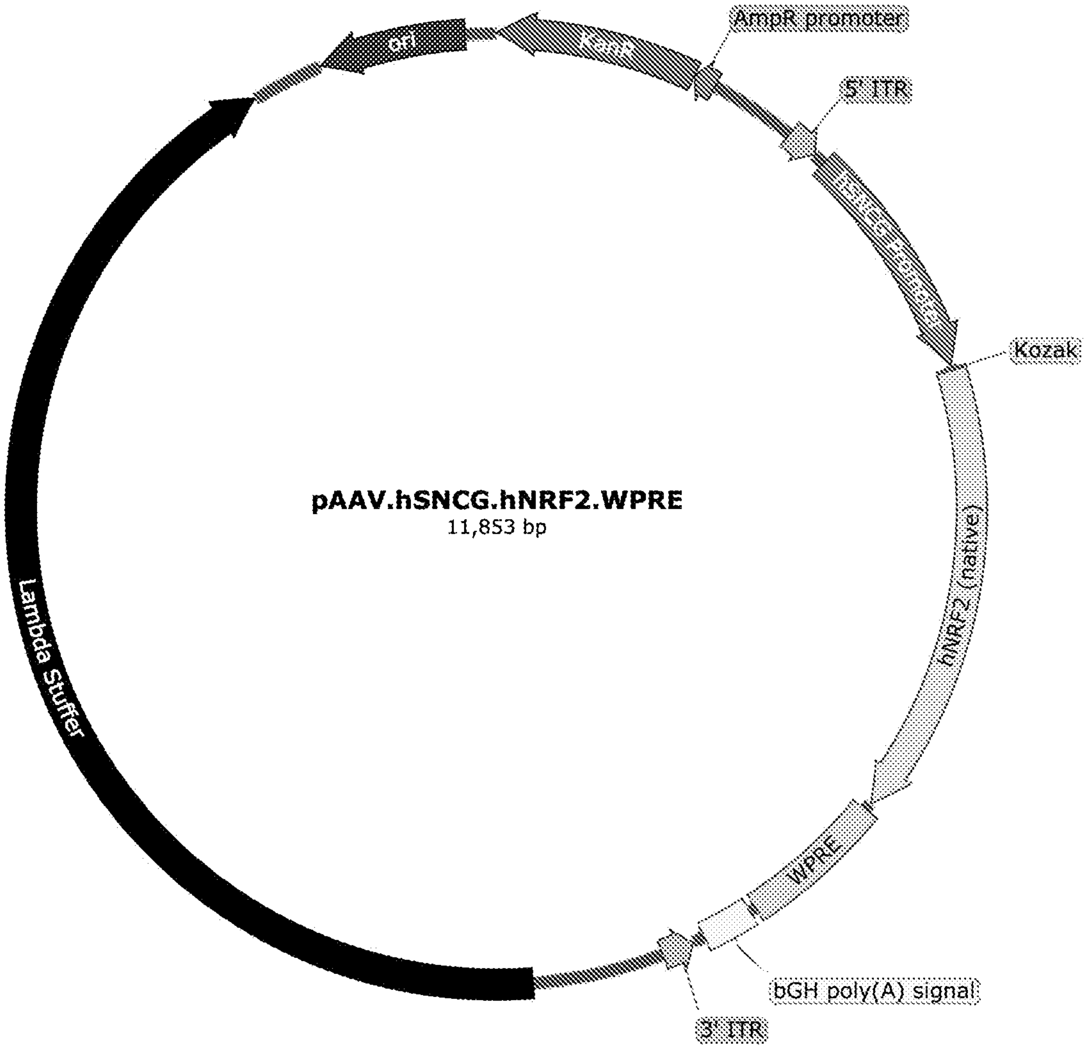
FIG. 22 provides a plasmid map of the pAAV.hSNCG.hNRF2.WPRE vector.
Figure 23:
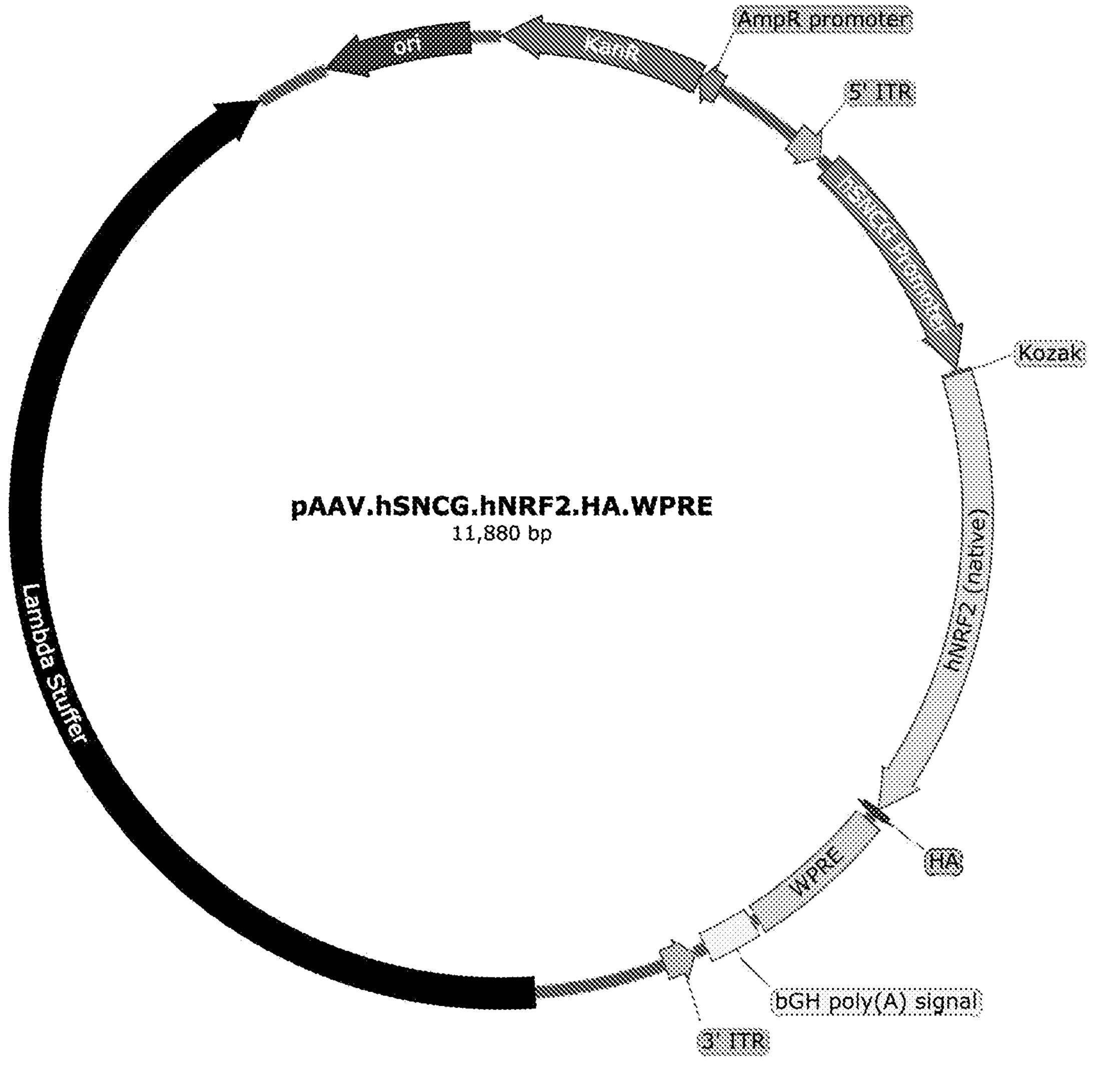
FIG. 23 provides a plasmid map of the pAAV.hSNCG.hNRF2.HA.WPRE vector.
Figure 24:
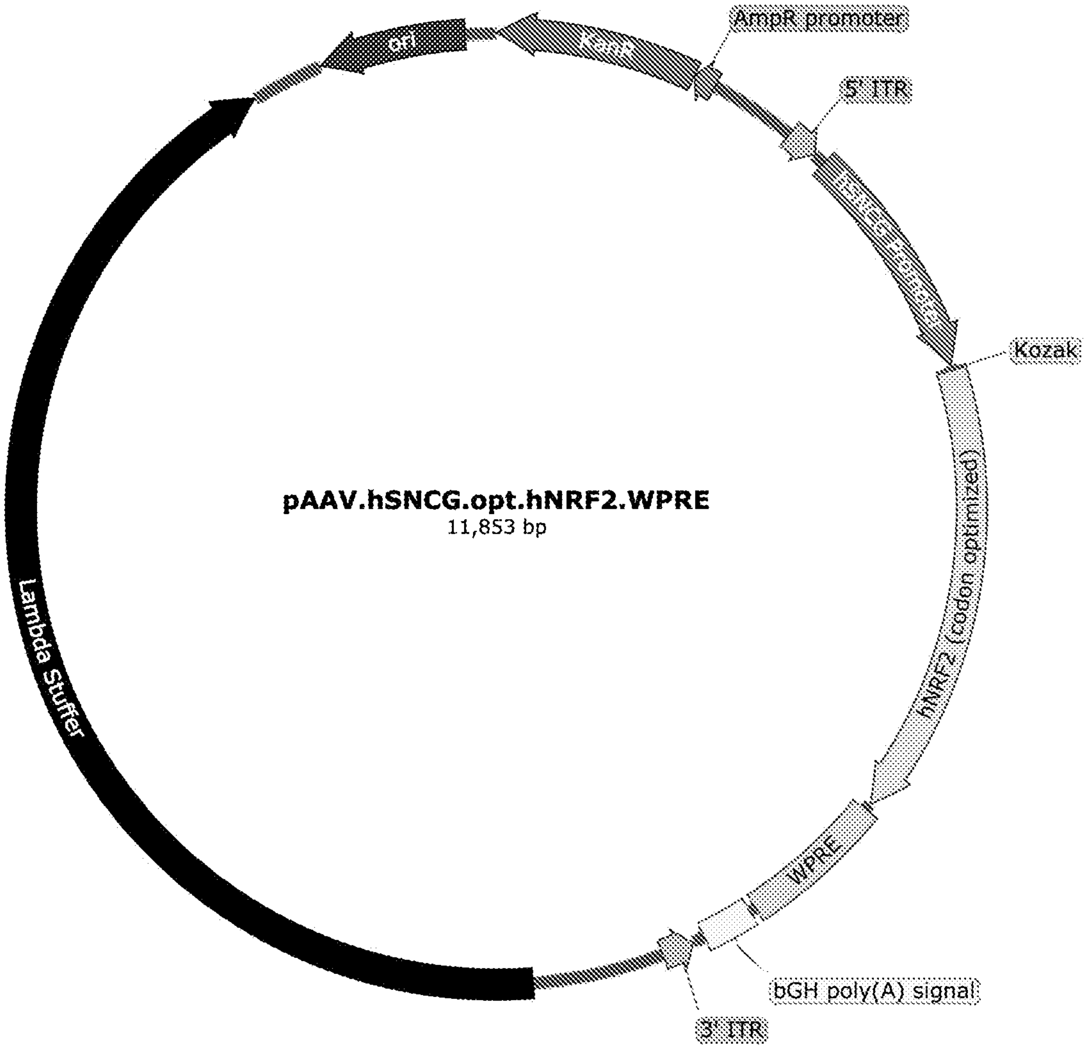
FIG. 24 provides a plasmid map of the pAAV.hSNCG.opt.hNRF2.WPRE vector.
Figure 25:
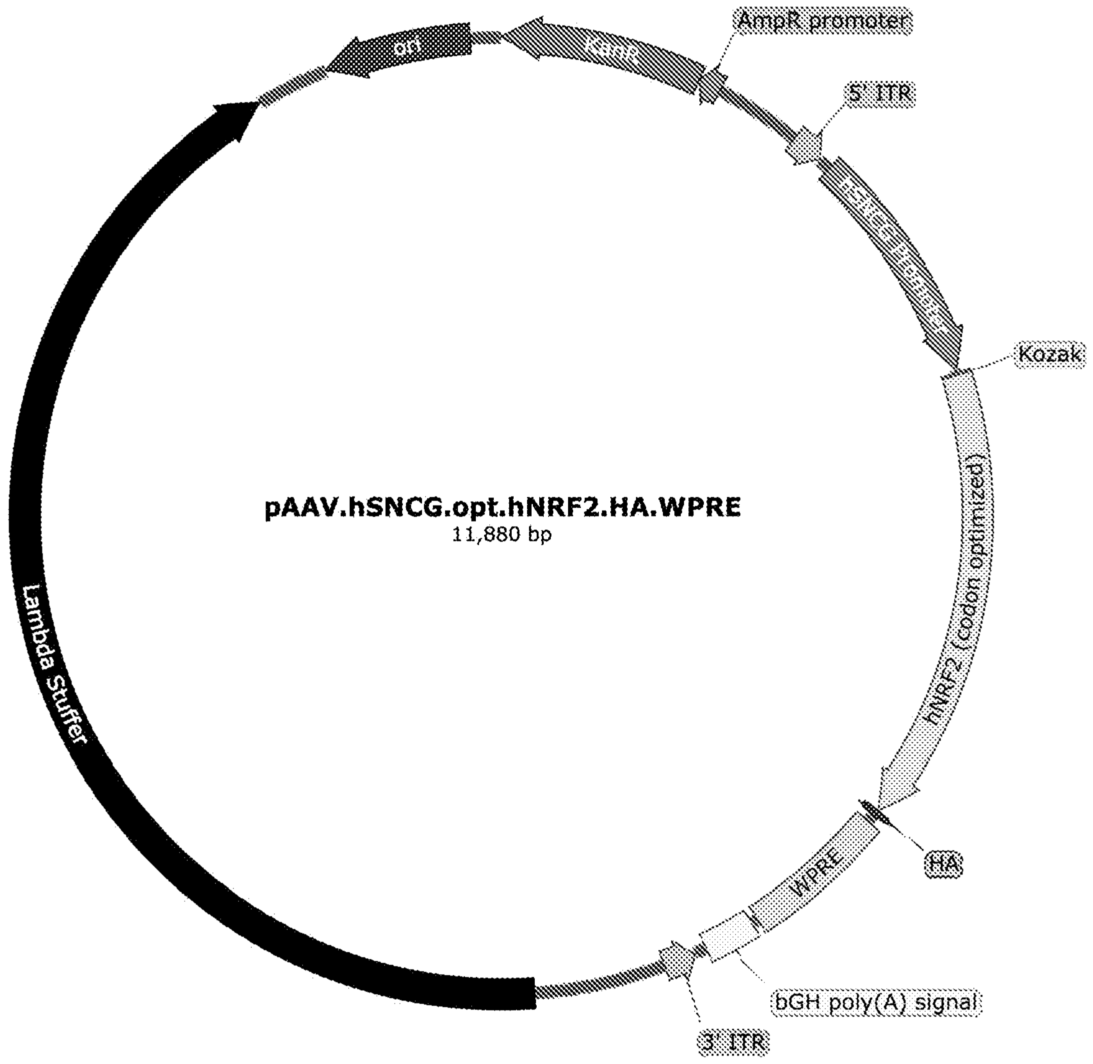
FIG. 25 provides a plasmid map of the pAAV.hSNCG.opt.hNRF2.HA.WPRE vector.

Gene Transfer With NRF2 or SIRT1 Fails to Attenuate Optic Nerve Inflammation and Demyelination We investigated immune infiltration of the optic nerve in response to SIRT1 or NRF2 gene therapy. Optic nerve sections were subjected to H&E staining for evidence of immune cell infiltration. Optic nerves from sham-induced animals that received intravitreal injection of vehicle or AAV2-eGFP displayed minimal evidence of immune recruitment. However, all EAE-sensitized animal cohorts demonstrated enhanced infiltration. Optic nerves derived from animals dosed with NRF2 or SIRT1 vectors did not show a difference in immune recruitment compared to the vehicle and AAV2-eGFP treated animals undergoing EAE (FIGS. 8A, C). We examined the effect of gene transfer on EAE-induced optic nerve demyelination by staining optic nerve sections with LFB. Sections from sham-induced animals injected with vehicle or AAV2-eGFP exhibited robust LFB labeling indicative of healthy nerves not subject to the immune-mediated demyelination of EAE. EAE animals treated with vehicle or AAV2-eGFP demonstrated decreased LFB staining compared to sham-induced animals. Gene transfer with SIRT1 or NRF2 did not prevent demyelination as these animals demonstrated similar myelination scores as EAE induced controls (FIGS. 8B, D).

D. Discussion

The present study explored the effects of SIRT1 or NRF2 gene transfer in experimental optic neuritis. Under cellular conditions of redox equilibrium, NRF2 is sequestered within the cytoplasm and subject to proteasomal-mediated degradation.10,39,40 During oxidative challenge, modifications to critical binding proteins free NRF2 to translocate into the nucleus, recruit transcriptional machinery to antioxidant response elements (AREs), and stimulate transcription of target genes associated with antioxidant defense and cellular detoxification.11 SIRT1 is recruited to the nucleus and other cellular compartments where it modulates the activity of various protein targets. SIRT1 is known to deacetylate and inhibit the transcription factor, p53, thereby downregulating apoptotic gene expression and thus improving cell viability.41 SIRT1 promotes mitochondrial function and antioxidant metabolism by activating PGC-1$\alpha$, a master transcriptional regulator of these responses.42 While SIRT1 and NRF2 are typically believed to function via separate pathways, recent evidence suggests SIRT1 involvement in regulating the expression and activation of NRF2.43 In addition, treatment with pharmacologic agents such as resveratrol, a known activator of SIRT1, was shown to enhance NRF2 expression and activity of its downstream effectors.44,45 We hypothesized that gene augmentation of NRF2 or SIRT1 within RGCs could ameliorate pathologic features of experimental optic neuritis. Our data demonstrate distinct effects upon RGC survival and function following AAV2-mediated overexpression of NRF2 or SIRT1, suggesting these candidate factors promote neuroprotective mechanisms that may modify MS pathogenesis.

RGC-directed gene therapy with SIRT1 and NRF2 vectors revealed differential effects upon visual acuity during EAE. Visual acuity was not affected prior to EAE development with any of the vectors tested, suggesting vector delivery or transgene overexpression did not mediate unintended toxicity on retinal function. We observed a statistically significant decline in visual acuity beginning at day 21 postimmunization with all AAV2 and vehicle-treated animals subjected to EAE, whereas sham-induced cohorts presented robust responses throughout the experimental timeline. While Larabee et al.13 reported that NRF2 knockout mice exhibit increased visual decline compared to wild-type cohorts during EAE, augmenting NRF2 activity with AAV2 gene transfer was unable to preserve visual acuity in the current study. Failure to reverse effects of knockout studies may be due to the limited number of RGCs (21%) infected with the AAV2 vectors in this study. However, interestingly, overexpression of SIRT1 mediated a trending increase in functional recovery beginning at day 28 postinduction compared to vehicle and AAV2-eGFP control groups subjected to EAE. This protective effect achieved statistical significance compared to the AAV2-eGFP control group at 35 and 42 days postinduction, which is remarkable given that only a subset of RGCs were transfected. This finding also correlates with prior investigations utilizing compounds that stimulate SIRT1 activity and demonstrate varying degrees of OKR preservation in the context of experimental optic neuritis as well as optic nerve crush.19, 26,27

RGC numbers were significantly reduced in all animal groups sensitized to EAE. However, we observed increased RGC numbers with SIRT1 and NRF2 gene augmentation compared to the AAV2-eGFP and vehicle treatment groups. SIRT1 gene transfer did not mediate a statistically significant increase in RGC numbers but only a positive trend in survival compared to EAE-induced controls. NRF2 gene transfer provided the most robust protective response with respect to total and regional RGC survival. This outcome is particularly interesting as NRF2 augmentation did not correlate with an improvement in retinal function as shown by OKR recordings. However, disparities between OKR and RGC survival have been previously documented in this mode1.27 Another explanation for this finding could be that NRF2 overexpression is simply supporting survival of the RGC cells bodies but unable to sustain function. This interpretation is consistent with findings by Xiong et al. 17 where NRF2 gene transfer-mediated transient yet significant preservation of RGCs following optic nerve crush without promoting axonal regeneration required for functional retention. Importantly, as indicated above, we only achieved approximately 21% RGC transduction with the AAV2 vector and previously described dose. Regarding the discrepancy between OKR preservation and RGC survival following AAV2-SIRT1 treatment, it is also possible that SIRT1 augmentation may influence the survival of ON direction-selective ganglion cells, which is the subset of cells that contribute to the OKR, but not mediate a statistically significant effect upon total RGC survival.46 Moreover, selection of a vector platform with enhanced capabilities for RGC transduction may provide a more potent means of cellular protection and functional preservation in this model. Recent developments utilizing rational design and in vivo selection have generated novel AAV capsids with improved potency and tropism for retinal cell types compared to naturally isolated serotypes such as AAV2.47-51 Further investigation into SIRT1 or NRF2-mediated neuroprotection in this model with an improved vector system is certainly warranted. The differential effects observed here also suggest a potential role for combined therapy with overexpression of both SIRT1 and NRF2. Due to limitations of the current transduction efficiency and the total volume that can be injected in the eye, coinjection of both vectors is not feasible, but future development of improved vector systems may allow investigation of a dual therapy.

While we did observe evidence of neuroprotection upon RGC function and viability, overexpression of neither NRF2 nor SIRT1 was able to suppress the inflammatory and demyelinating phenotype associated with optic neuritis. RGC-directed gene therapy did not influence immune recruitment to the optic nerve as shown by H&E histological analysis. This observation correlates with previous studies that examined small molecule-mediated neuroprotection during EAE. Specifically, pharmacologic activators of SIRT1, including resveratrol and related compounds, did not suppress inflammation in the spinal cord or optic nerve when administered at various doses in the same EAE model 19 used in the current study. Interestingly, transgenic overexpression of human SIRT1 within neurons was able to reduce inflammation within spinal cord lesions.24 Similar to the effects on immunomodulation, AAV2-mediated expression of NRF2 or SIRT1 did not alleviate optic nerve demyelination. While these approaches did not attenuate demyelination, other studies that examined antioxidant or mitochondrial-directed gene therapy strategies during EAE have shown preserved myelin in the optic nerve.34-38 However, discrepancies in animal models, EAE immunization protocols, and other components of study design limit a direct comparison with these reports. In addition, our findings with respect to inflammation and myelination may once again reflect the limited transduction efficiency of the AAV2 vector.

Collectively, this study demonstrates at least partial neuroprotective effects of NRF2 and SIRT1 gene augmentation in the context of experimental optic neuritis, and suggests an important role of these signals in MS pathogenesis. Moreover, it underscores the therapeutic potential of targeting conserved cell survival pathways or mechanisms to impede progression of complex neurodegenerative disease.

All publications cited in this specification are incorporated herein by reference, including McDougald et al, Investigative Ophthalmology & Visual Science March 2018, Vol.59, 1212-1220. Similarly, the SEQ ID NOs which are referenced herein and which appear in the appended Sequence Listing are incorporated by reference, as is U.S. Provisional Patent Application No. 62/488,989, filed Apr. 24, 2017. While the invention has been described with reference to particular embodiments, it will be appreciated that modifications can be made without departing from the spirit of the invention. Such modifications are intended to fall within the scope of the appended claims.

(Sequence Listing Free Text)

The following information is provided for sequences containing free text under numeric identifier <223>.

| SEQ ID NO: (containing free text) | Free text under <223> |
|---|---|
| 5 | <223> constructed sequence |
| 6 | <223> constructed sequence |
| 7 | <223> constructed sequence |
| 8 | <223> constructed sequence |
| 9 | <223> constructed sequence |
| 10 | <223> constructed sequence |
| 11 | <223> constructed sequence |
| 12 | <223> constructed sequence |
| 13 | <223> constructed sequence |
| 14 | <223> constructed sequence |
| 15 | <223> constructed sequence |
| 16 | <223> constructed sequence |
| 17 | <223> constructed sequence |
| 18 | <223> constructed sequence |
| 19 | <223> constructed sequence |
| 20 | <223> constructed sequence |
| 21 | <223> constructed sequence |
| 22 | <223> constructed sequence |
| 23 | <223> constructed sequence |
| 24 | <223> constructed sequence |
| 25 | <223> constructed sequence |
| 26 | <223> constructed sequence |
| 27 | <223> constructed sequence |
| 28 | <223> constructed sequence |

REFERENCE

1. Lassmann H, Horssen J V, Mahad D. Progressive multiple sclerosis: pathology and pathogenesis. Nat Rev Neurol. 2012; 8: 647-656.

2. Costello F, Coupland S, Hodge W, et al. Quantifying axonal loss after optic neuritis with optical coherence tomography. Ann Neurol. 2006; 59: 963-969.

3. Fisher J B, Jacobs D A, Markowitz C E, et al. Relation of visual function to retinal nerve fiber layer thickness in multiple sclerosis. Ophthalmol 2006; 113: 324-332.

4. Trip S A, Schlottmann P G, Jones S J, et al. Retinal nerve fiber layer axonal loss and visual dysfunction in optic neuritis. Ann Neurol. 2005; 58: 383-391.

5. Beck R W, Cleary P A, Anderson M M Jr, et al. A randomized controlled trial of corticosteroids in the treatment of acute optic neuritis. The optic neuritis study group. N Engl J Med. 1992; 326: 581-588.

6. Lublin F D. Role of myelin antigens in murine relapsing experimental allergic encephalomyelitis. J Clin Lab Immunol. 1984; 13: 179-182.

7. Quinn T A, Dutt M, Shindler K S. Optic neuritis and retinal ganglion cell loss in a chronic murine model of multiple sclerosis. Front Neurol. 2011; 2.

8. Shindler K S, Guan Y, Ventura E, et al. Retinal ganglion cell loss induced by acute optic neuritis in a relapsing model of multiple sclerosis. Mult Scler. 2006; 12: 526-532.

9. Shindler K S, Ventura E, Dutt M, et al. Inflammatory demyelination induces axonal injury and retinal ganglion cell apoptosis in experimental optic neuritis. Exp Eye Res. 2008; 87: 208-213.

10. Dinkova-Kostova A T, Holtzclaw W D, Cole R N, et al. Direct evidence of sulfhydryl groups of KEAP1 are the sensors regulating induction of phase 2 enzymes that protect against carcinogens and oxidants. Proc Natl Acad Sci USA. 2002; 99: 11908-11913.

11. Johnson D A, Johnson J A. NRF2—a therapeutic target for the treatment of neurodegenerative diseases. Free Radic Biol Med. 2015; 88: 253-267.

12. Johnson D A, Amirahmadi S, Ward C, et al. The absence of the pro-antioxidant transcription factor NRF2 exacerbates experimental autoimmune encephalomyelitis. Toxicol Sci. 2010; 114: 237-246.

13. Larabee C M, Desai S, Agasing A, et al. Loss of Nrf2 exacerbates the visual deficits and optic neuritis elicited by experimental autoimmune encephalomyelitis. Mol Vis. 2016; 22: 1503-1513.

14. Li B, Cui W, Liu J, et al. Sulforaphane ameliorates the development of experimental autoimmune encephalomyelitis by antagonizing oxidative stress and Th17-related inflammation in mice. Exp Neurol. 2013; 250: 239-249.

15.Liang K J, Woodard K T, Weaver M A, et al. AAV-NRF2 promotes protection and recovery in animal models of oxidative stress. Mol Ther. 2017; 25: 765-779.

16. Linker R A, Lee D H, Ryan S, et al. Fumaric acid esters exert neuroprotective effects in neuroinflammation via activation of the Nrf2 antioxidant pathway. Brain. 2011; 134 (part 3): 678-692.

17. Xiong W, MacColl Garfinkel A E, Li Y, et al. NRF2 promotes neuronal survival in neurodegeneration and acute nerve damage. J Clin Invest. 2015; 125: 1433-1445.

18. Martin A, Tegla C A, Cudrici C D, et al. Role of SIRT1 in autoimmune demyelination and neurodegeneration. Immunol Res. 2015; 61: 187-197.

19. Fonseca-Kelly Z, Nassrallah M, Uribe J, et al. Resveratrol neuroprotection in a chronic mouse model of multiple sclerosis. Front Neurol. 2012; 3:84.

20. Jeong H, Cohen DE, Cui L, et al. SIRT1 mediates neuroprotection from mutant huntingtin by activation of the TORC1 and CREB transcriptional pathway. Nat Med. 2011; 18: 159-165.

21. Khan R S, Dine K, Das Sarma J, et al. SIRT1 activating compounds reduce oxidative stress mediated neuronal loss in viral induced CNS demyelinating disease. Acta Neuropathol Commun 2014; 2:3.

22. Khan R S, Fonseca-Kelly Z, Callinan C, et al. SIRT1 activating compounds reduce oxidative stress and prevent cell death in neuronal cells. Front Cell Neurosci. 2012; 6: 63.

23. Kim D, Nguyen M D, Dobbin M M, et al. SIRT1 deacetylase protects against neurodegeneration in models for Alzheimer's disease and amyotrophic lateral sclerosis. EMBO J. 2007; 26: 3169-3179.

24. Nimmagadda V K, Bever C T, Vattikunta N R, et al. Overexpression of SIRT1 protein in neurons protects against experimental autoimmune encephalomyelitis through activation of multiple SIRT1 targets. J Immunol 2013; 190: 4595-4607.

25. Shindler K S, Ventura E, Dutt M, et al. Oral resveratrol reduces neuronal damage in a model of multiple sclerosis. J Neuroophthalmol 2010; 30: 328-339.

26. Shindler K S, Ventura E, Rex T S, et al. SIRT1 activation confers neuroprotection in experimental optic neuritis. Invest Ophthalmol Vis Sci. 2007; 48: 3602-3609.

27. Zuo L, Khan R S, Lee V, et al. SIRT1 promotes RGC survival and delays loss of function following optic nerve crush. Invest Ophthalmol Vis Sci. 2013; 54: 5097-5102.

28. Prusky G T, Alam N M, Beekman S, et al. Rapid quantification of adult and developing mouse spatial vision using a virtual optomotor system. Invest Ophthalmol Vis Sci. 2004; 45: 4611-4616.

29. Bennett J, Wellman J, Marshall K A, et al. Safety and durability of effect of contralateral-eye administration of AAV2 gene therapy in patients with childhood-onset blindness caused by RPE65 mutations: a follow-on phase 1 trial. Lancet. 2016; 388: 661-672.

30. Bennicelli J, Wright J F, Komaromy A, et al. Reversal of blindness in animal models of Leber congenital amaurosis using optimized AAV2-mediated gene transfer. Mol Ther. 2008; 16: 458-465.

31. Maguire A M, Simonelli F, Pierce E A, et al. Safety and efficacy of gene transfer for Leber's congenital amaurosis. N Engl J Med. 2008; 358: 2240-2248.

32. Pierce E A, Bennett J. The status of the RPE65 gene therapy trials: safety and efficacy. Cold Spring Harb Perspect Med. 2015; 5: a017285.

33. Dudus L, Anand V, Acland G M, et al. Persistent transgene product in retina, optic nerve and brain after intraocular injection of rAAV. Vision Res. 1999; 39: 2545-2553.

34. Qi X, Hauswirth W W, Guy J. Dual gene therapy with extracellular superoxide dismutase and catalase attenuates experimental optic neuritis. Mol Vis. 2007; 13: 1-11.

35. Qi X, Lewin As, Sun L, et al. Suppression of mitochondrial oxidative stress provides long-term neuroprotection in experimental optic neuritis. Invest Ophthalmol Vis Sci. 2007; 48: 681-691.

36. Talla V, Koilkonda R, Porciatti V, et al. Complex I subunit gene therapy with NDUFA6 ameliorates neurodegeneration in EAE. Invest Ophthalmol Vis Sci. 2015; 56: 1129-1140.

37. Talla V, Porciatti V, Chiodo V, et al. Gene therapy with mitochondrial heat shock protein 70 suppresses visual loss and optic atrophy in experimental autoimmune encephalomyelitis. Invest Ophthalmol Vis Sci. 2014; 55: 5214-5226.

38. Talla V, Yu H, Chou T H, et al. NADH-dehydrogenase type-2 suppresses irreversible visual loss and neurodegeneration in the EAE animal model of MS. Mol Ther. 2013; 21: 1876-1888.

39. Itoh K, Wakabayashi N, Katoh Y, et al. Keapl regulates both cytoplasmic-nuclear shuttling and degradation of NRF2 in response to electrophiles. Genes Cells. 2003; 8: 379-391.

40. McMahon M, Itoh K, Yamamoto M, et al. Keapl-dependent proteasomal degradation of transcription factor NRF2 contributes to negative regulation of antioxidant response element-driven gene expression. J Biol Chem. 2003; 278: 21592-21600.

41. Luo J, Nikolaev A Y, Imai S, et al. Negative control of p53 by Sir2alpha promotes cell survival under stress. Cell. 2001; 107: 137-148.

42. Nemoto S, Fergusson M M, Finkel T. SIRT1 functionally interacts with the metabolic regulator and transcriptional coactivator PGC-1α. J Biol Chem. 2005; 280: 16456-16460.

43. Ding Y W, Zhao G J, Li X L, et al. SIRT1 exerts protective effects against paraquat-induced injury in mouse type II alveolar epithelial cells by deacetylating NRF2 in vitro. Int J Mol Med. 2016; 37: 1049-1058.

44. Xia X, Qu B, Li Y M, et al. NFAT5 protects astrocytes against oxygen-glucose-serum deprivation/restoration damage via the SIRT1/Nrf2 pathway. J Mol Neurosci. 2017; 61: 96-104.

45. Zhang P, Li Y, Du Y, et al. Resveratrol ameliorated vascular calcification by regulating Sirt-1 and Nrf2. Transplant Proc. 2016; 48: 3378-3386.

46. Sugita Y, Miura K, Araki F, et al. Contributions of retinal direction-selective ganglion cells to optokinetic responses in mice. Eur J Neurosci. 2013; 38: 2823-2831.

47. Choudhury S R, Fitzpatrick Z, Harris A F, et al. In vivo selection yields AAV-B1 capsid for central nervous system and muscle gene therapy. Mol Ther. 2016; 1247-1257.

48. Cronin T, Vandenberghe L H, Hantz P, et al. Efficient transduction and optogenetic stimulation of retinal bipolar cells by a synthetic adeno-associated virus capsid and promoter. EMBO Mol Med. 2014; 6: 1175-1190.

49. Dalkara D, Byrne L C, Klimczak R R, et al. In vivo-directed evolution of a new adeno-associated virus for therapeutic outer retinal gene delivery from the vitreous. Sci Transl Med. 2013; 5: 189.

50. Deverman B E, Pravdo P L, Simpson B P, et al. Cre-dependent selection yields AAV variants for widespread gene transfer to the adult brain. Nat Biotechnol. 2016; 34: 204-209.

51. Zinn E, Pacouret S, Khaychuk V, et al. In silico reconstruction of the viral evolutionary lineage yields a potent gene therapy vector. Cell Rep. 2015; 12: 1056-1068.

What is claimed is:

1. A recombinant adeno-associated virus (fAAV) comprising an AAV capsid, and a vector genome packaged therein, the vector genome comprising:

(a) an AAV5' inverted terminal repeat (ITR) sequence;

(b) a promoter sequence;

(c) a sequence encoding human Sirtuin 1 (SIRT1); and (d) an AAV3' ITR sequence, wherein the sequence encoding human SIRT1 comprises SEQ ID NO: 12 and is operably linked to the promoter sequence.

2. The recombinant AAV according to claim 1, wherein the AAV capsid is an AAV2 capsid or variant thereof, an AAV7m8 capsid or variant thereof, an AAV8 capsid, an AAV6 capsid or variant thereof, an AAV9 capsid or variant thereof, an AAV7 capsid or variant thereof, an AAV5 capsid or variant thereof, an AAV1 capsid or variant thereof, an AAV3 capsid or variant thereof, or an AAV4 capsid or variant thereof.

3. The recombinant AAV according to claim 1, wherein the promoter sequence comprises a cytomegalovirus (CMV) promoter0 or a hybrid promoter comprising a CMV enhancer sequence and a chicken-beta actin (CBA) promoter sequence.

4. The recombinant AAV according to claim 1, wherein the AAV5' ITR sequence and/or the AAV3' ITR sequence is from AAV2.

5. A composition comprising the recombinant AAV according to claim 1 and a pharmaceutically acceptable carrier or excipient suitable for delivery to thcan eye.

6. The recombinant AAV according to claim 1, wherein the vector genome further comprises a woodchuck hepatitis virus post-transcriptional regulatory element (WPRE).

7. A method of treating optic neuropathy in a subject in need thereof, the method comprising delivery of the recombinant AAV according to claim 1 to an eye of the subject.

8. The method according to claim 7, wherein about $1\times10^9$ to about $1\times10^{13}$ vector genomes in an aqueous suspension are delivered to the eye of the subject.

9. The method according to claim 7, wherein the human SIRT1 is expressed in retinal ganglion cells of the eye of the subject, the method preserving function of the retinal ganglion cells.

10. The recombinant AAV according to claim 1, wherein the promoter sequence comprises nucleotides 1433 to 2362 of SEQ ID NO: 28.

11. The recombinant AAV according to claim 1, wherein the promoter sequence comprises a human gamma-synuclein gene promoter sequence.

12. A method of treating optic neuropathy in a subject in need thereof, the method comprising delivery of a recombinant AAV to an eye of the subject, the recombinant AAV comprising an AAV capsid, and a vector genome packaged therein, the vector genome comprising:

(a) an AAV5' ITR sequence;

(b) a promoter sequence;

(c) a sequence encoding human SIRT1; and (d) an AAV3' ITR sequence, wherein the sequence encoding human SIRT1 comprises SEQ ID NO: 12 and is operably linked to the promoter sequence, and wherein delivery of the recombinant AAV results in transduction and preservation of retinal ganglions cells in the eye to treat optic neuropathy.

13. The method according to claim 12, wherein about $1\times10^9$ 'o about $1\times10^{13}$ vector genomes of the recombinant AAV in an aqueous suspension are delivered to the eye of the subject.

14. The method according to claim 12, wherein the promoter sequence comprises a cytomegalovirus (CMV) promoter sequence or a hybrid promoter comprising a CMV enhancer sequence and a chicken-beta actin (CBA) promoter sequence.

15. A plasmid comprising an expression cassette comprising a sequence encoding human SIRT1 operably linked to a promoter sequence, wherein the sequence encoding human SIRT1 comprises SEQ ID NO: 12.

16. The plasmid according to claim 15, wherein the promoter sequence comprises a cytomegalovirus (CMV) promoter sequence or a hybrid promoter comprising a CMV enhancer sequence and a chicken-beta actin (CBA) promoter sequence.

17. The plasmid according to claim 15, wherein the expression cassette further comprises one or more of an intron, a Kozak sequence, a polyA, and a post-transcriptional regulatory element.

18. The plasmid according to claim 15, wherein the expression cassette further comprises a WPRE.

19. The plasmid according to claim 15, wherein the expression cassette is flanked by a 5' ITR sequence and a 3' ITR sequence.

20. A packaging cell comprising the plasmid according to claim 15.

21. The plasmid according to claim 15, wherein the promoter sequence comprises a human gamma-synuclein gene promoter sequence.

* * * * *

UNITED STATES PATENT AND TRADEMARK OFFICE
CERTIFICATE OF CORRECTION

PATENT NO. : 11,879,133 B2
APPLICATION NO. : 16/607834
DATED : January 23, 2024
INVENTOR(S) : Jean Bennett et al.

It is certified that error appears in the above-identified patent and that said Letters Patent is hereby corrected as shown below:

In the Claims

Column 295 Line 2 Claim 1, should read as follows:
-- 1. A recombinant adeno-associated virus (rAAV) comprising an AAV capsid, and a vector genome packaged therein, the vector genome comprising:

(a) an AAV 5' inverted terminal repeat (ITR) sequence;
(b) a promoter sequence;
(c) a sequence encoding human Sirtuin 1 (SIRT1); and
(d) an AAV 3' ITR sequence, wherein the sequence encoding human SIRT1 comprises SEQ ID NO: 12 and is operably linked to the promoter sequence. --

Column 295 Line 22 Claim 3, should read as follows:
-- 3. The recombinant AAV according to claim 1, wherein the promoter sequence comprises a cytomegalovirus (CMV) promoter or a hybrid promoter comprising a CMV enhancer sequence and a chicken-beta actin (CBA) promoter sequence. --

Column 295 Line 30 Claim 5, should read as follows:
-- 5. A composition comprising the recombinant AAV according to claim 1 and a pharmaceutically acceptable carrier or excipient suitable for delivery to an eye. --

Column 296 line 17 Claim 13, should read as follows:
-- 13. The method according to claim 12, wherein about $1 \times 10^9$ to about $1 \times 10^{13}$ vector genomes of the recombinant AAV in an aqueous suspension are delivered to the eye of the subject. --

Signed and Sealed this
Fourteenth Day of May, 2024

Katherine Kelly Vidal

Katherine Kelly Vidal
*Director of the United States Patent and Trademark Office*